(12) United States Patent
Hoffmann et al.

(10) Patent No.: US 7,939,533 B2
(45) Date of Patent: May 10, 2011

(54) DUAL NK1/NK3 RECEPTOR ANTAGONISTS

(75) Inventors: Torsten Hoffmann, Weil am Rhein (DE); Andreas Koblet, Binningen (CH); Jens-Uwe Peters, Grenzach-Wyhlen (DE); Patrick Schnider, Oberwil (CH); Andrew Sleight, Riedisheim (FR); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 155 days.

(21) Appl. No.: 12/361,569

(22) Filed: Jan. 29, 2009

(65) Prior Publication Data

US 2009/0137806 A1 May 28, 2009

Related U.S. Application Data

(63) Continuation of application No. 10/884,707, filed on Jul. 2, 2004, now abandoned.

(30) Foreign Application Priority Data

Jul. 3, 2003 (EP) .................................... 03014513

(51) Int. Cl.
   *A61K 31/497* (2006.01)
   *A61K 31/44* (2006.01)
(52) U.S. Cl. ............... 514/253.13; 514/332; 514/343
(58) Field of Classification Search .......... 514/253.13, 514/332, 343
   See application file for complete search history.

(56) References Cited

U.S. PATENT DOCUMENTS 5,972,938 A    10/1999   Rupniak et al.

FOREIGN PATENT DOCUMENTS

| | | |
|---|---|---|
| EP | 1 035 115 | 9/2000 |
| EP | 1103545 | 5/2001 |
| EP | 1 192 952 | 4/2002 |
| WO | WO 95/16679 | 6/1995 |
| WO | WO 95/18124 | 7/1995 |
| WO | WO 95/23798 | 9/1995 |
| WO | WO 98/24445 | 6/1998 |
| WO | WO 00/50398 | 8/2000 |
| WO | WO 02/06236 | 1/2002 |
| WO | WO 02/08232 | 1/2002 |
| WO | WO 02/016324 | 2/2002 |
| WO | WO 03/006016 | 1/2003 |

OTHER PUBLICATIONS

Kamali, F., Current Opinion in Investigational Drugs, 2001 vol. 2(7) pp. 950-956.
Giardina, G. A. M., et al., Expert Opinion on Therapeutic Patents, 2000 vol. 10(6) pp. 939-960.
Barker, R., Reviews in the Neurosciences, 1996, vol. 7, pp. 187-214.
Longmore, J. et al., Can. J. Physiol, Pharmacol. 1997, vol. 75 pp. 612-621.
Shotyk, W. et al., Science, 1998, vol. 281, pp. 1635-1640.
Maggi, C. A. et al., J. Auton. Pharmacol., 1993, vol. 13, pp. 23-93.
Navari, R. M. et al., The New England Journal of Medicine, 1999, vol. 340, No. 3, pp. 190-195.
ChemIDplus Advanced, : RN 148296-18-8, 2007.

*Primary Examiner* — Sreeni Padmanabhan
*Assistant Examiner* — Renee Claytor
(74) *Attorney, Agent, or Firm* — George W. Johnston; Patricia S. Rocha-Tramaloni; Kimberly J. Prior

(57) ABSTRACT

The present invention provides a method for the treatment of schizophrenia which comprises administering a compound of formula

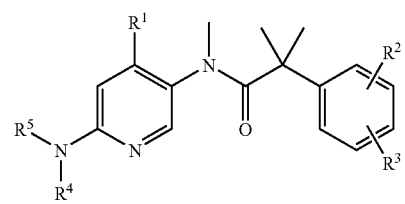

wherein the substituents are as described herein or a pharmaceutically active acid-addition salt thereof. In particular, the invention provides methods for treating both positive and negative symptoms of schizophrenia through dual inhibition of NK1 and NK3 receptors. The invention also provides novel compounds with formula I and methods for preparing compounds of the invention.

8 Claims, No Drawings

DUAL NK1/NK3 RECEPTOR ANTAGONISTS

PRIORITY TO RELATED APPLICATIONS

This application is a continuation of U.S. application Ser. No. 10/884,707, filed Jul. 2, 2004, now pending; which claims the benefit of European Application No. 03014513.0, filed Jul. 3, 2003. The entire contents of the above-identified applications are hereby incorporated by reference.

BACKGROUND OF THE INVENTION

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Resources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956956 and *Psychiatric Disorders Study* 4, *Schizophrenia*, June 2003, Decision Resources, Inc., Waltham, Mass.).

In addition, EP 1 192 952 describes a pharmaceutical composition containing a combination of a NK3 receptor antagonist and a CNS penetrant NK1 receptor antagonist for the treatment of depression and anxiety.

Now it has been found that the combination of the antidepressant, mood enhancing properties of NK1 receptor antagonism and the antipsychotic symptoms of NK3 receptor antagonism are suitable to treat both positive and negative symptoms in schizophrenia.

This advantage may be realized in the administration of an ideal drug against schizophrenia.

Some of the compounds of formula I are described in EP 1035115, WO 02/08232 or WO 02/16324.

They have been described as active at the NK1 receptor for the treatment of diseases related to this receptor, such as inflammatory conditions including migraine, rheumatoid arthritis, asthma, and inflammatory bowel disease as well as mediation of the emetic reflex and the modulation of central nervous system (CNS) disorders such as Parkinson's disease, anxiety, pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

The neurokinin-1 receptor antagonists are further useful for the treatment of motion sickness, for treatment induced vomiting or for the treatment of psychoimmunologic or psychosomatic disorders, see *Neurosci. Res.*, 1996, 7, 187-214, *Can. J. Phys.*, 1997, 75, 612-621, *Science*, 1998, 281, 1640-1645, *Anton. Pharmacol.*, 13, 23-93, 1993, WO 95/16679, WO 95/18124 and WO 95/23798, *The New England Journal of Medicine*, Vol. 340, No. 3 190-195, 1999, U.S. Pat. No. 5,972,938.

SUMMARY OF THE INVENTION

The present invention relates to the use of compounds of formula I and pharmaceutically acceptable salts thereof for the treatment of positive and negative symptoms in schizophrenia, novel compounds of formulas I, pharmaceutically active acid-addition salts thereof, all stereoisomeric forms of the compounds of formula I, including each of the individual enantiomers and mixtures thereof, the preparation of the above-mentioned novel compounds, medicaments containing them and their manufacture as well as the use of the above-mentioned compounds in the control or prevention of illnesses, especially of illnesses and disorders of the kind referred to earlier or in the manufacture of corresponding medicaments.

Thus, in one embodiment the invention provides a method of treating schizophrenia which comprises administering a compound of formula ![Structure I showing pyridine with R¹, R⁵N(R⁴)-, and N-methyl amide with gem-dimethyl linked to aryl bearing R² and R³]

I wherein

R¹ is aryl, unsubstituted or substituted by one or more substituents selected from the group consisting of alkyl, alkoxy, halogen, —(CH$_2$)$_d$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl, or is heteroaryl, selected from the group consisting of pyridin-2- or 3-yl, imidazolyl and oxazolyl, each of which is unsubstituted or substituted by alkyl, halogen or alkoxy;

R² and R³ are each independently hydrogen, halogen, alkyl, alkoxy, OCHF$_2$, OCH$_2$F, OCF$_3$ or CF$_3$;

R⁴ and R⁵ are each independently hydrogen,

—(CR'R")$_1$—(CR'R")$_1$—(CR'R")$_a$—OH or —(CR'R")$_1$—(CR'R")$_1$—(CR'R")$_a$-alkyl, wherein R' and R" on each carbon atom may be the same or different from each other, —C$_b$-alkyl,

—C(O)H,

—(CH$_2$)$_d$cycloalkyl, unsubstituted or substituted by hydroxy,

—(CH$_2$)$_c$NR'R",

—(CH$_2$)$_c$NR'C(O)-alkyl,

—(CH$_2$)$_d$NR'S(O)$_2$-alkyl,

—(CH$_2$)$_d$S(O)-alkyl,

—(CH$_2$)$_d$S-alkyl,

—(CH$_2$)$_d$S(O)$_2$-alkyl;

—(CH$_2$)$_d$S(O)$_2$—NR'R"

R' is hydrogen, alkyl, —(CH$_2$)$_d$OH, —C(O)H, —C(O)-alkyl, —C(O)-cycloalkyl, —S(O)$_2$-alkyl, —S(O)$_2$-halogenalkyl, —S(O)-alkyl, —S-alkyl or —S(O)$_2$—N-di-alkyl;

R" is hydrogen or alkyl; or

R⁴ and R⁵ form together with the N-atom to which they are attached a ring with —(CH$_2$)$_e$—, which is unsubstituted or substituted by one or more substituents selected from the group consisting of alkyl, halogen, CF$_3$, —(CR'R")$_d$OH, =O, —CHO, and —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl, or —C(O)NR'R", or with —(CH$_2$)$_c$—NR'—(CH$_2$)$_2$—, which is unsubstituted or substituted by one or more substituents, selected from the group consisting of alkyl, halogen, CF$_3$, —(CR'R")$_d$OH, =O, —CHO, —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R", or with —(CH$_2$)$_c$—O—(CH$_2$)$_2$—, which is unsubstituted or substituted by one or more substituents, selected from the group consisting of alkyl, halogen, CF$_3$, —(CR'R")$_d$OH, =O, —CHO, —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R", or with —(CH$_2$)$_c$—S(O)$_f$—(CH$_2$)$_c$—, which is unsubstituted or substituted by one or more substituents selected from the group consisting of alkyl, halogen, CF$_3$, —(CR'R")$_d$OH, =O, —CHO, and —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R", or with —CH$_2$CH=CH—CH$_2$—, which is unsubstituted or substituted by one or more substituents selected from the group consisting of alkyl, halogen, CF$_3$, —(CR'R")$_d$OH, =O, —CHO, and —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R";

or with

—(CH$_2$)$_2$—S(O)$_2$N(CH$_3$)—CH$_2$, or with

—S(O)—O—(CH$_2$)$_g$— or —NR⁴R⁵ is

![Two bicyclic amine structures: an azabicyclic ring with R' substituent, and an azabicyclic ring containing O]

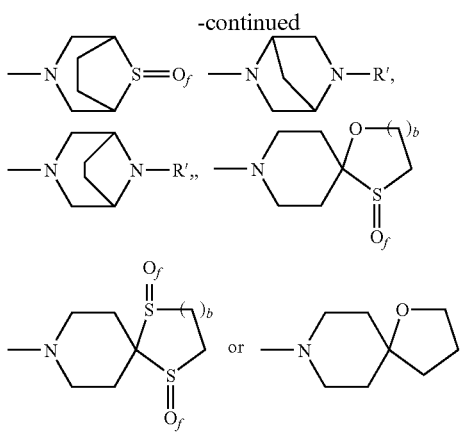

a is 0 or 1;
b is 1 or 2;
c is 1, 2, or 3;
d is 0, 1, 2, or 3;
e is 3, 4, or 5;
f is 0, 1, or 2; and
g is 2 or 3;
or a pharmaceutically active acid-addition salt thereof.

The compounds of formula I may contain some asymmetric carbon atoms. Accordingly, the present invention includes all stereoisomeric forms of the compounds of formula I, including each of the individual enantiomers and mixtures thereof.

The compounds of formula I and their salts are characterized by valuable therapeutic properties. It has surprisingly been found that the compounds of formula I show a high affinity simultaneously to both the NK1 and the NK3 receptors (dual NK1/NK3 receptor antagonists), useful in the treatment of schizophrenia.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1-4 carbon atoms, for example, methyl, ethyl, propyl, isopropyl, n-butyl, i-butyl, t-butyl and the like. The term "alkyl" denotes a straight- or branched-chain alkyl group containing from 1-7 carbon atoms.

The terms "lower alkoxy" and "alkoxy" denote a group wherein the alkyl residues are as defined above, and which is attached via an oxygen atom.

The term "halogen" denotes chlorine, iodine, fluorine and bromine.

The term "cycloalkyl" denotes a saturated carbocyclic group containing 3-6 carbon atoms.

The term "aryl" means a monovalent cyclic aromatic hydrocarbon group consisting of one or more fused rings in which at least one ring is aromatic in nature. Examples of aryl radicals include, but are not limited to, phenyl, naphthyl, biphenyl, indanyl, anthraquinolyl, and the like. The preferred aryl group is phenyl.

"Heteroaryl" means a monovalent aromatic carbocyclic group having one or more rings incorporating one, two, or three heteroatoms within the ring wherein the heteroatoms are chosen from nitrogen, oxygen, or sulfur. Examples of heteroaryl radicals include, but are not limited to, imidazolyl, isoxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphtyridinyl, and the like. Preferred heteroaryl groups are isoxazolyl and pyridinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

In one embodiment the invention provides a method of treating schizophrenia which comprises administering a compound of formula

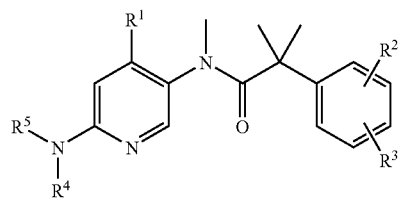

I wherein
$R^1$ is aryl, unsubstituted or substituted by one or more substituents selected from the group consisting of alkyl, alkoxy, halogen, —(CH$_2$)$_d$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl,
or
is heteroaryl, selected from the group consisting of pyridin-2- or 3-yl, imidazolyl and oxazolyl, each of which is unsubstituted or substituted by alkyl, halogen or alkoxy;
$R^2$ and $R^3$ are each independently hydrogen, halogen, alkyl, alkoxy, OCHF$_2$, OCH$_2$F, OCF$_3$ or CF$_3$;
$R^4$ and $R^5$ are each independently hydrogen,
—(CR'R")$_1$—(CR'R")$_1$—(CR'R")$_a$—OH or
—(CR'R")$_1$—(CR'R")$_1$—(CR'R")$_a$-alkyl, wherein R' and R" on each carbon atom may be the same or different from each other,
—C$_b$-alkyl,
—C(O)H,
—(CH$_2$)$_d$cycloalkyl, unsubstituted or substituted by hydroxy,
—(CH$_2$)$_c$NR'R",
—(CH$_2$)$_c$NR'C(O)-alkyl,
—(CH$_2$)$_c$NR'S(O)$_2$-alkyl,
—(CH$_2$)$_a$S(O)-alkyl,
—(CH$_2$)$_a$S-alkyl,
—(CH$_2$)$_a$S(O)$_2$-alkyl, or
—(CH$_2$)$_a$S(O)$_2$—NR'R";
R' is hydrogen, alkyl, —(CH$_2$)$_d$OH, —C(O)H, —C(O)-alkyl, —C(O)-cycloalkyl, —S(O)$_2$-alkyl, —S(O)$_2$-halogen-alkyl, —S(O)-alkyl, —S-alkyl or —S(O)$_2$—N-di-alkyl;

R" is hydrogen or alkyl; or

R⁴ and R⁵ form together with the N-atom to which they are attached a ring
with —(CH₂)ₑ—, which is unsubstituted or substituted
by one or more substituents, selected from the group consisting of alkyl, halogen, CF₃, —(CR'R")_dOH, =O, —CHO, and —NR'R", wherein R' and R" are as described above or may form together with the N-atom to which they are attached a ring with —(CH₂)ₑ,
or
by —(CH₂)_dNR'—C(O)-alkyl, —(CH₂)_d—C(O)-alkyl, —(CH₂)_d—C(O)-cycloalkyl, —(CH₂)_dOC(O)NR'R", —(CH₂)_d—S(O)₂-alkyl, —(CH₂)_d—S(O)-alkyl, —(CH₂)_d—S-alkyl, —(CH₂)_d—S(O)₂—NR'R", —(CH₂)_d-pyrrolidinyl, or —C(O)NR'R",
or with
—(CH₂)_c—NR'—(CH₂)₂—, which is unsubstituted or substituted
by one or more substituents, selected from the group consisting of alkyl, halogen, CF₃, —(CR'R")_dOH, =O, —CHO, and —NR'R", wherein R' and R" are as described above or may form together with the N-atom to which they are attached a ring with —(CH₂)ₑ,
or
by —(CH₂)_dNR'—C(O)-alkyl, —(CH₂)_d—C(O)-alkyl, —(CH₂)_d—C(O)-cycloalkyl, —(CH₂)_dOC(O)NR'R", —(CH₂)_d—S(O)₂-alkyl, —(CH₂)_d—S(O)-alkyl, —(CH₂)_d—S-alkyl, —(CH₂)_d—S(O)₂—NR'R", —(CH₂)_d-pyrrolidinyl or —C(O)NR'R",
or with
—(CH₂)_c—O—(CH₂)₂—, which is unsubstituted or substituted
by one or more substituents, selected from the group consisting of alkyl, halogen, CF₃, —(CR'R")_dOH, =O, —CHO, and —NR'R", wherein R' and R" are as described above or may form together with the N-atom to which they are attached a ring with —(CH₂)ₑ,
or
by —(CH₂)_dNR'—C(O)-alkyl, —(CH₂)_d—C(O)-alkyl, —(CH₂)_d—C(O)-cycloalkyl, —(CH₂)_dOC(O)NR'R", —(CH₂)_d—S(O)₂-alkyl, —(CH₂)_d—S(O)-alkyl, —(CH₂)_d—S-alkyl, —(CH₂)_d—S(O)₂—NR'R", —(CH₂)_d-pyrrolidinyl or —C(O)NR'R",
or with
—(CH₂)_c—S(O)_f—(CH₂)_c—, which is unsubstituted or substituted
by one or more substituents, selected from the group consisting of alkyl, halogen, CF₃, —(CR'R")_dOH, =O, —CHO, and —NR'R", wherein R' and R" are as described above or may form together with the N-atom to which they are attached a ring with —(CH₂)ₑ,
or
by —(CH₂)_dNR'—C(O)-alkyl, —(CH₂)_d—C(O)-alkyl, —(CH₂)_d—C(O)-cycloalkyl, —(CH₂)_oOC(O)NR'R", —(CH₂)_d—S(O)₂-alkyl, —(CH₂)_d—S(O)-alkyl, —(CH₂)_d—S-alkyl, —(CH₂)_d—S(O)₂—NR'R", —(CH₂)_d-pyrrolidinyl or —C(O)NR'R",
or with
—CH₂CH=CH—CH₂—, which is unsubstituted or substituted
by one or more substituents, selected from the group consisting of alkyl, halogen, CF₃, —(CR'R")_dOH, =O, —CHO, and —NR'R", wherein R' and R" are as described above or may form together with the N-atom to which they are attached a ring with —(CH₂)ₑ,
or
by —(CH₂)_dNR'—C(O)-alkyl, —(CH₂)_d—C(O)-alkyl, —(CH₂)_d—C(O)-cycloalkyl, —(CH₂)_dOC(O)NR'R", —(CH₂)_d—S(O)₂-alkyl, —(CH₂)_d—S(O)-alkyl, —(CH₂)_d—S-alkyl, —(CH₂)_d—S(O)₂—NR'R", —(CH₂)_d-pyrrolidinyl or —C(O)NR'R"; or
with —(CH₂)₂—S(O)₂N(CH₃)—CH₂, or with —S(O)—O—(CH₂)_g—;

or —NR⁴R⁵ is

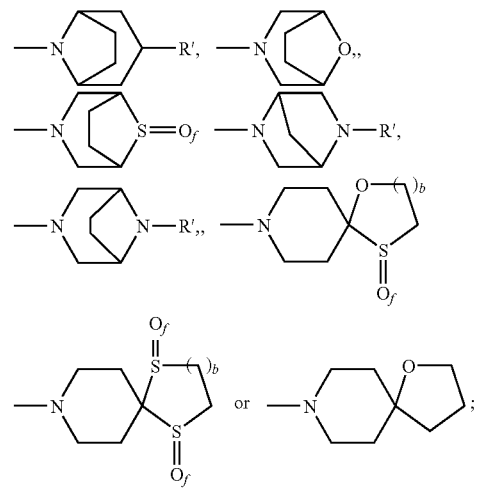

a is 0 or 1;
b is 1 or 2;
c is 1, 2, or 3;
d is 0, 1, 2, or 3;
e is 3, 4, or 5;
f is 0, 1, or 2; and
g is 2 or 3;
or a pharmaceutically active acid-addition salt thereof.

In another embodiment, the invention provides a method of treating schizophrenia which comprises administering a compound of 1 formula

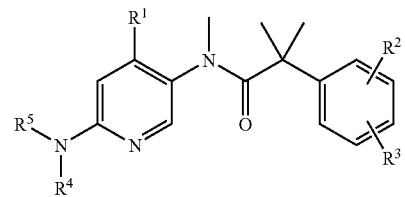

I-1 wherein
R¹ is aryl, unsubstituted or substituted by one or more substituents selected from the group consisting of lower alkyl, lower alkoxy, halogen, —(CH₂)_dOH, —C(O)H, CF₃, CN, S-lower alkyl, —S(O)₂-lower alkyl, —C(O)NR'R", —NR'R", —NR'C(O)-lower alkyl, and —NR'S(O)₂-lower alkyl,
or
is heteroaryl, selected from the group consisting of pyridin-2- or 3-yl, imidazolyl, and oxazolyl, each of which is unsubstituted or substituted by lower alkyl, halogen or lower alkoxy;

$R^2$ and $R^3$ are each independently hydrogen, halogen, lower alkyl, lower alkoxy, $OCHF_2$, $OCH_2F$, $OCF_3$ or $CF_3$;

$R^4$ and $R^5$ are each independently hydrogen,
—$(CR'R'')_1$—$(CR'R'')_1$—$(CR'R'')_a$—OH or
—$(CR'R'')_1$—$(CR'R'')_1$—$(CR'R'')_a$-lower alkyl,
wherein R' and R'' on each carbon atom may be the same or different from each other,
—$C_b$-alkyl,
—C(O)H, —$(CH_2)_d$cycloalkyl, unsubstituted or substituted by hydroxy,
—$(CH_2)_c$NR'C(O)-lower alkyl, —$(CH_2)_c$NR'S(O)$_2$-lower alkyl, or
—$(CH_2)_d$S(O)$_2$-lower alkyl;

R' is hydrogen, lower alkyl, —$(CH_2)_d$OH, —C(O)H, —C(O)-lower alkyl, —C(O)-cycloalkyl or S(O)$_2$-lower alkyl;

R'' is hydrogen or lower alkyl;

or $R^4$ and $R^5$ form together with the N-atom to which they are attached a ring with
—$(CH_2)_e$—, which is unsubstituted or substituted
by one or more substituents, selected from the group consisting of lower alkyl, halogen, $CF_3$, —$(CR'R'')_d$OH, =O, and —NR'R'', wherein R' and R'' may form together with the N-atom to which they are attached a ring with —$(CH_2)_e$,
or
by —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)_d$-pyrrolidinyl, or —C(O)NR'R'',
or with
—$(CH_2)_c$—NR'—$(CH_2)_2$—, which is unsubstituted or substituted
by one or more substituents, selected from the group consisting of lower alkyl, halogen, —$(CR'R'')_d$OH, =O, and —NR'R'', wherein R' and R'' may form together with the N-atom to which they are attached a ring with —$(CH_2)_e$,
or
by —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)_d$-pyrrolidinyl or —C(O)NR'R'',
or with
—$(CH_2)_c$—O—$(CH_2)_2$—, which is unsubstituted or substituted
by one or more substituents, selected from the group consisting of lower alkyl, halogen, —$(CR'R'')_d$OH, =O, and —NR'R'', wherein R' and R'' may form together with the N-atom to which they are attached a ring with —$(CH_2)_e$,
or
by —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)_d$-pyrrolidinyl or —C(O)NR'R'', or with
—$(CH_2)_c$—S(O)$_f$—$(CH_2)_2$—, which is unsubstituted or substituted
by one or more substituents, selected from the group consisting of lower alkyl, halogen, —$(CR'R'')_d$OH, =O, and —NR'R'', wherein R' and R'' may form together with the N-atom to which they are attached a ring with —$(CH_2)_e$,
or
by —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)_d$-pyrrolidinyl or —C(O)NR'R'',
or with
—$CH_2CH=CH-CH_2$—, which is unsubstituted or substituted
by one or more substituents, selected from the group consisting of lower alkyl, halogen, —$(CR'R'')_d$OH, =O, and —NR'R'', wherein R' and R'' may form together with the N-atom to which they are attached a ring with —$(CH_2)_e$,
or
by —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)$ d-pyrrolidinyl or —C(O)NR'R'';

a is 0 or 1;
b is 1 or 2;
c is 1, 2, or 3;
d is 0, 1, 2, or 3;
e is 3, 4 or 5;
f is 0, 1, or 2; and
g is 2 or 3;

or a pharmaceutically active acid-addition salts thereof as described above.

In another embodiment of the invention, the method employs a compound of formula I-1, wherein $R^1$, $R^4$ and $R^5$ have the definitions as described in formula I-1 and $R^2$ and $R^3$ are both $CF_3$.

In another embodiment of the invention, the method employs a compound of formula I-1, wherein $R^4$ and $R^5$ form together with the N-atom to which they are attached a ring with —$(CH_2)_e$—, which is unsubstituted or substituted by one or more substituents selected from the group consisting of lower alkyl, halogen, —$(CR'R'')_d$OH, =O, —NR'R'', —$(CH_2)_d$NR'—C(O)-lower alkyl, —$(CH_2)_d$—C(O)-lower alkyl, —$(CH_2)_d$—C(O)-cycloalkyl, —$(CH_2)_d$OC(O)NR'R'', —$(CH_2)_d$—S(O)$_2$-lower alkyl, —$(CH_2)_d$—pyrrolidinyl, and —C(O)NR'R''.

In another embodiment of the invention, the method employs a compound of formula I-1, wherein $R^4$ and $R^5$ form together with the N-atom to which they are attached a ring with —$(CH_2)_4$—, wherein the ring is mono substituted by —$CH_2OH$ or disubstituted by hydroxy and —$CH_2OH$. Examples of such compounds include (S)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide, (2S,4R)-2-(3,5-bis-trifluoromethyl-phenyl)-N-[4-(2-chlorophenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2-bromophenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-bromophenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-chlorophenyl)-6-(3-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-chlorophenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide, (2R,3R)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(5-fluoro-2-methyl-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(3-fluoro-2-methyl-phenyl)-6-(2-hydroxymethyl-pyrrolidin-1-yl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2S,4R)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-hydroxymethyl-phenyl)-pyridin-3-yl]-N-methyl-isobutyramide, (2S,4R)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[4-(4-fluoro-2-hydroxymethyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(5-fluoro-2-methyl-phenyl)-6-(3-hydroxy-2-hydroxymethyl-pyrrolidin-1-yl)-pyridin-3-yl]-N-methyl-isobutyramide, (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide and (S)-2-(3,5-bis-trifluoromethyl-phenyl)-N-[4-(2-bromo-phenyl)-6-(2-hydroxymethyl-pyrrolidin-1-yl)-pyridin-3-yl]-N-methyl-isobutyramide.

In another embodiment of the invention, the method employs a compound of formula I-1, wherein $R^4$ and $R^5$ form together with the N-atom to which they are attached a ring with —(CH$_2$)$_4$—, wherein the ring is disubstituted by NHC(O)CH$_3$ and —CH$_2$OH. An example of such compounds is (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

In another embodiment of the invention, the method employs a compound of formula I-1, wherein $R^4$ and $R^5$ form together with the N-atom to which they are attached a ring with —(CH$_2$)$_4$—, wherein the ring is disubstituted by =O and —CH$_2$OH. Examples of such compounds are (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide and (S)-2-(3,5-bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide.

In another embodiment of the invention, the method employs a compound of formula I-1 wherein $R^4$ and $R^5$ form together with the N-atom to which they are attached a ring with —(CH$_2$)$_4$—, wherein the ring is di- or tri-substituted by halogen and —CH$_2$OH. Examples of such compounds are (2S,4S)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[6-(4-fluoro-2-hydroxymethyl-pyrrolidin-1-yl)-4-(4-fluoro-2-methyl-phenyl)-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-(4-fluoro-2-methyl-phenyl)-pyridin-3-yl]-N-methyl-isobutyramide and (2S,4R)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide.

In another embodiment of the invention, the method employs a compound of formula I-1, wherein $R^4$ and $R^5$ are each independently hydrogen, —(CR'R")$_1$—(CR'R")$_1$—(CR'R")$_a$—OH or —(CR'R")$_1$—(CR'R")$_1$—(CR'R")$_a$-lower alkyl, wherein R' and R" on each carbon atom may be the same or different from each other, or are —C$_b$-alkyl, —C(O)H, —(CH$_2$)$_d$cycloalkyl which is unsubstituted or substituted by hydroxy, —(CH$_2$)$_c$NR'C(O)-lower alkyl, —(CH$_2$)$_c$NR'S(O)$_2$-lower alkyl, —(CH$_2$)$_d$S(O)$_2$-lower alkyl, C(O)(CH$_2$)$_d$OH; R' is hydrogen, lower alkyl, —(CH$_2$)$_d$OH, —C(O)-lower alkyl, —C(O)-cycloalkyl or S(O)$_2$-lower alkyl; and R" is hydrogen or lower alkyl.

In another embodiment of the invention, the method employs a compound of formula I-1, wherein $R^4$ and $R^5$ are each independently hydrogen, —CH(CH$_2$OH)CH$_2$OH or —(CH$_2$)$_c$OH. Examples of such compounds are 2-(3,5-bis-trifluoromethyl-phenyl)-N-[4-(2-chloro-phenyl)-6-(2-hydroxy-1-hydroxymethyl-ethylamino)-pyridin-3-yl]-N-methyl-isobutyramide, N-[6-[bis-(2-hydroxy-ethyl)-amino]-4-(2-chloro-phenyl)-pyridin-3-yl]-2-(3,5-bis-trifluoromethyl-phenyl)-N-methyl-isobutyramide, N-{6-[bis-(2-hydroxy-ethyl)-amino]-4-o-tolyl-pyridin-3-yl}-2-(3,5-bis-trifluoromethyl-phenyl)-N-methyl-isobutyramide, N-[6-[bis-(2-hydroxy-ethyl)-amino]-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-{4-(4-fluoro-2-methyl-phenyl)-6-[(2-hydroxy-ethyl)-(3-hydroxy-propyl)-amino]-pyridin-3-yl}-N-methyl-isobutyramide, N-[6-[bis-(2-hydroxy-ethyl)-amino]-4-(3-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(5-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(2-bromo-phenyl)-pyridin-3-yl]-2-(3,5-bis-trifluoromethyl-phenyl)-N-methyl-isobutyramide, (2S,4S)-2-(3,5-bis-trifluoromethyl-phenyl)-N-[4-(2-fluoro-phenyl)-6-(4-hydroxy-2-hydroxymethyl-pyrrolidin-1-yl)-pyridin-3-yl]-N-methyl-isobutyramide and (2S,4S)-2-(3,5-bis-trifluoromethyl-phenyl)-N-[6-(4-hydroxy-2-hydroxymethyl-pyrrolidin-1-yl)-4-(2-trifluoromethyl-phenyl)-pyridin-3-yl]-N-methyl-isobutyramide.

In another embodiment of the invention, the method employs a compound of formula I-1, wherein $R^4$ and $R^5$ form together with the N-atom to which they are attached a ring with $-(CH_2)_c-O-(CH_2)_2-$, which is unsubstituted or substituted by one or more substituents selected from the group consisting of lower alkyl, halogen, $(CR'R'')_dOH$, $=O$, $-NR'R''$, $-(CH_2)_dNR'-C(O)$-lower alkyl, $-(CH_2)_d-C(O)$-lower alkyl, $-(CH_2)_d-C(O)$-cycloalkyl, $-(CH_2)_dOC(O)NR'R''$, $-(CH_2)_d-S(O)_2$-lower alkyl, $-(CH_2)_d-$ pyrrolidinyl and $-C(O)NR'R''$.

In another embodiment of the invention, the method employs a compound of formula I-1, wherein $R^4$ and $R^5$ form together with the N-atom to which they are attached a ring with $-(CH_2)_2-O-(CH_2)_2-$, wherein the ring is substituted by $-CH_2OH$. Examples of such compounds are (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide and (R)-(2-(3,5-bis-trifluoromethyl-phenyl)-N-[6-(3-hydroxymethyl-morpholin-4-yl)-4-o-tolyl-pyridin-3-yl]-N-methyl-isobutyramide.

In another embodiment of the invention, the method employs a compound of formula I-1, wherein $R^4$ and $R^5$ form together with the N-atom to which they are attached a ring with $-(CH_2)C-S(O)_f-(CH_2)_2-$, which is unsubstituted or substituted by one or more substituents selected from the group consisting of lower alkyl, halogen, $-(CR'R'')_dOH$, $=O$, $-NR'R''$, $-(CH_2)_dNR'-C(O)$-lower alkyl, $-(CH_2)_d-C(O)$-lower alkyl, $-(CH_2)_d-C(O)$-cycloalkyl, $-(CH_2)_dOC(O)NR'R''$, $-(CH_2)_d-S(O)_2$-lower alkyl, $-(CH_2)_d-$ pyrrolidinyl and $-C(O)NR'R''$.

In another embodiment of the invention, the method employs a compound of formula I-1, wherein $R^4$ and $R^5$ form together with the N-atom to which they are attached a ring with $-(CH_2)_2-S(O)_2-(CH_2)_2-$, wherein the ring is mono-substituted by $-CH_2OH$. Examples of such compounds are (RS)-2-(3,5-bis-trifluoromethyl-phenyl)-N-[4-(4-fluoro-2-methyl-phenyl)-6-(3-hydroxymethyl-1,1-dioxo-1$\lambda^6$-thiomorpholin-4-yl)-pyridin-3-yl]-N-methyl-isobutyramide and (RS)-2-(3,5-bis-trifluoromethyl-phenyl)-N-[6-(3-hydroxymethyl-1,1-dioxo-1$\lambda^6$-thiomorpholin-4-yl)-4-o-tolyl-pyridin-3-yl]-N-methyl-isobutyramide.

In another embodiment of the invention, the method employs a compound of formula I-1, wherein $R^1$, $R^4$ and $R^5$ have the definitions as described above and $R^2$ and $R^3$ are other than di-$CF_3$.

In another embodiment of the invention, the method employs a compound of formula I-1, wherein $R^4$ and $R^5$ form together with the N-atom to which they are attached a ring with $-(CH_2)_4-$ wherein the ring is mono substituted by $-CH_2OH$ or disubstituted by OH and $-CH_2OH$. Examples of such compounds are (2S,4R)—N-[4-(2-chloro-phenyl)-6-(4-hydroxy-2-hydroxymethyl-pyrrolidin-1-yl)-pyridin-3-yl]-2-(3,5-dichloro-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide, (2S,4R)-2-(3-chloro-5-methoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)-2-(3,5-dichloro-phenyl)-N-[6-(2-hydroxymethyl-pyrrolidin-1-yl)-4-o-tolyl-pyridin-3-yl]-N-methyl-isobutyramide, (2S,4R)-2-(3,5-dichloro-phenyl)-N-[6-(4-hydroxy-2-hydroxymethyl-pyrrolidin-1-yl)-4-o-tolyl-pyridin-3-yl]-N-methyl-isobutyramide, (2S,4R)-2-(3,5-dichloro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)—N-[4-(4-fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide, (2S,4R)—N-[4-(4-fluoro-2-methyl-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide, (2S,4R)-2-(3-chloro-5-methoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4R)-2-(3-chloro-5-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide, (2S,4R)-2-(3-Chloro-5-difluoromethoxy-phenyl)-N-[6-(4-hydroxy-2-hydroxymethyl-pyrrolidin-1-yl)-4-o-tolyl-pyridin-3-yl]-N-methyl-isobutyramide and (2S,4R)-2-(3-Chloro-5-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide.

In another embodiment, the invention provides a compound of formula

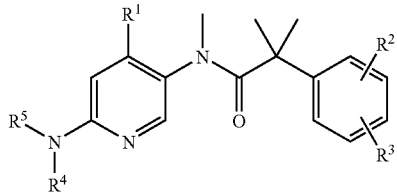

I-1 wherein
R$^1$ is aryl, unsubstituted or substituted by one or more substituents selected from the group consisting of lower alkyl, lower alkoxy, halogen, —(CH$_2$)$_a$OH, —C(O)H, CF$_3$, CN, S-lower alkyl, —S(O)$_2$-lower alkyl, —C(O)NR'R", —NR'R", —NR'C(O)-lower alkyl, and —NR'S(O)$_2$-lower alkyl,
or
is heteroaryl, selected from the group consisting of pyridin-2- or 3-yl, imidazolyl, and oxazolyl, each of which is unsubstituted or substituted by lower alkyl, halogen or lower alkoxy;
R$^2$ and R$^3$ are each independently hydrogen, halogen, lower alkyl, lower alkoxy, OCHF$_2$, OCH$_2$F, OCF$_3$ or CF$_3$;
R$^4$ and R$^5$ are each independently hydrogen,
— (CR'R")$_1$—(CR'R")$_1$—(CR'R")$_a$—OH  or
—(CR'R")$_1$—(CR'R")—(CR'R")$_a$-lower alkyl, wherein R' and R" on each carbon atom may be the same or different from each other,
—C$_b$-alkyl,
—C(O)H, —(CH$_2$)$_d$cycloalkyl, unsubstituted or substituted by hydroxy,
—(CH$_2$)$_c$NR'C(O)-lower alkyl, —(CH$_2$)$_c$NR'S(O)$_2$-lower alkyl, or
—(CH$_2$)$_d$S(O)$_2$-lower alkyl;
R' is hydrogen, lower alkyl, —(CH$_2$)$_d$OH, —C(O)H, —C(O)-lower alkyl, —C(O)-cycloalkyl or S(O)$_2$-lower alkyl;
R" is hydrogen or lower alkyl;
or
R$^4$ and R$^5$ form together with the N-atom to which they are attached a ring with
—(CH$_2$)$_e$—, which is unsubstituted or substituted
   by one or more substituents, selected from the group consisting of lower alkyl, halogen, CF$_3$, —(CR'R")$_d$OH, =O, and —NR'R", wherein R' and R" may form together with the N-atom to which they are attached a ring with —(CH$_2$)$_e$,
or
by —(CH$_2$)$_d$NR'—C(O)-lower alkyl, —(CH$_2$)$_d$—C(O)-lower alkyl, —(CH$_2$)$_d$—C(O)-cycloalkyl, —(CH$_2$)$_d$OC(O)NR'R", —(CH$_2$)$_d$—S(O)$_2$-lower alkyl, —(CH$_2$)$_d$-pyrrolidinyl, or —C(O)NR'R",
or with
—(CH$_2$)$_c$—NR'—(CH$_2$)$_2$—, which is unsubstituted or substituted
   by one or more substituents, selected from the group consisting of lower alkyl, halogen, —(CR'R")$_d$OH, =O, and —NR'R", wherein R' and R" may form together with the N-atom to which they are attached a ring with —(CH$_2$)$_e$,
or
by —(CH$_2$)$_d$NR'—C(O)-lower alkyl, —(CH$_2$)$_d$—C(O)-lower alkyl, —(CH$_2$)$_d$—C(O)-cycloalkyl, —(CH$_2$)$_d$OC(O)NR'R", —(CH$_2$)$_d$—S(O)$_2$-lower alkyl, —(CH$_2$)$_d$-pyrrolidinyl or —C(O)NR'R",
or with
—(CH$_2$)$_c$—O—(CH$_2$)$_2$—, which is unsubstituted or substituted
   by one or more substituents, selected from the group consisting of lower alkyl, halogen, —(CR'R")$_d$OH, =O, and —NR'R", wherein R' and R" may form together with the N-atom to which they are attached a ring with —(CH$_2$)$_e$,
or
by —(CH$_2$)$_d$NR'—C(O)-lower alkyl, —(CH$_2$)$_d$—C(O)-lower alkyl, —(CH$_2$)$_d$—C(O)-cycloalkyl, —(CH$_2$)$_d$OC(O)NR'R", —(CH$_2$)$_d$—S(O)$_2$-lower alkyl, —(CH$_2$)$_d$-pyrrolidinyl or —C(O)NR'R",
or with
—(CH$_2$)$_c$—S(O)$_f$—(CH$_2$)$_2$—, which is unsubstituted or substituted
   by one or more substituents, selected from the group consisting of lower alkyl, halogen, —(CR'R")$_d$OH, =O, and —NR'R", wherein R' and R" may form together with the N-atom to which they are attached a ring with —(CH$_2$)$_e$,
or
by —(CH$_2$)$_d$NR'—C(O)-lower alkyl, —(CH$_2$)$_d$—C(O)-lower alkyl, —(CH$_2$)$_d$—C(O)-cycloalkyl, —(CH$_2$)$_d$OC(O)NR'R", —(CH$_2$)$_d$—S(O)$_2$-lower alkyl, —(CH$_2$)$_d$-pyrrolidinyl or —C(O)NR'R",
or with
—CH$_2$CH=CH—CH$_2$—, which is unsubstituted or substituted
   by one or more substituents, selected from the group consisting of lower alkyl, halogen, —(CR'R")$_d$OH, =O, and —NR'R", wherein R' and R" may form together with the N-atom to which they are attached a ring with —(CH$_2$)$_e$,
or
by —(CH$_2$)$_d$NR'—C(O)-lower alkyl, —(CH$_2$)$_d$—C(O)-lower alkyl, —(CH$_2$)$_d$—C(O)-cycloalkyl, —(CH$_2$)$_d$OC(O)NR'R", —(CH$_2$)$_d$—S(O)$_2$-lower alkyl, —(CH$_2$)$_d$-pyrrolidinyl or —C(O)NR'R";
a is 0 or 1;
b is 1 or 2;
c is 1, 2, or 3;
d is 0, 1, 2, or 3;
e is 3, 4 or 5;
f is 0, 1, or 2; and
g is 2 or 3;
or a pharmaceutically active acid-addition salts thereof as described above.

In another embodiment, the invention is a compound of formula I-1, wherein R$^1$ is unsubstituted or substituted phenyl and R$^4$ and R$^5$ are each independently hydrogen, —(CR'R")$_1$—(CR'R")$_1$—(CR'R")$_a$—OH, or —(CR'R")$_1$—(CR'R")$_1$—(CR'R")$_a$-lower alkyl, wherein R' and R" on each carbon atom may be the same or different from each other, or are C$_b$-alkyl. Examples of these compounds are
N-[4-(2-chloro-phenyl)-6-(2-hydroxy-ethylamino)-pyridin-3-yl]-2-(3,5-dichloro-phenyl)-N-methyl-isobutyramide,
2-(3,5-dichloro-phenyl)-N-[4-(4-fluoro-2-methyl-phenyl)-6-(2-hydroxy-ethylamino)-pyridin-3-yl]-N-methyl-isobutyramide, 2-(3,5-bis-trifluoromethyl-phenyl)-N-[4-(2-chloro-phenyl)-6-[(2-hydroxy-ethyl)-methyl-amino]-pyridin-3-yl]-N-methyl-isobutyramide, 2-(3,5-bis-trifluoromethyl-phenyl)-N-[4-(2-chloro-phenyl)-6-[ethyl-(2-hydroxy-ethyl)-amino]-pyridin-3-yl]-N-methyl-isobutyramide, 2-(3,5-bis-trifluoromethyl-phenyl)-N-[4-(2-chloro-phenyl)-6-[(2-hydroxy-ethyl)-propyl-amino]-pyridin-3-yl]-N-methyl-isobutyramide, 2-(3,5-bis-trifluoromethyl-phenyl)-N-[6-[butyl-(2-hydroxy-ethyl)-amino]-4-(2-chloro-phenyl)-pyridin-3-yl]-N-methyl-isobutyramide, (RS)-2-(3,5-bis-trifluoromethyl-phenyl)-N-[4-(2-chloro-phenyl)-6-[(2,3-dihydroxy-propyl)-methyl-amino]-pyridin-3-yl]-N-methyl-isobutyramide, (S)-2-(3,5-bis-trifluoromethyl-phenyl)-N-[4-(2-chloro-phenyl)-6-(1-hydroxymethyl-3-methyl-butylamino)-pyridin-3-yl]-N-methyl-isobutyramide, 2-(3,5-bis-trifluoromethyl-phenyl)-N-[4-(4-fluoro-2-methyl-phenyl)-6-(2-hydroxy-ethylamino)-pyridin-3-yl]-N-methyl-isobutyramide, 2-(3,5-bis-trifluoromethyl-phenyl)-N-[4-(2-chloro-4-fluoro-phenyl)-6-(2-hydroxy-ethylamino)-pyridin-3-yl]-N-methyl-isobutyramide, 2-(3,5-bis-trifluoromethyl-phenyl)-N-[4-(2,4-dichloro-phenyl)-6-(2-hydroxy-ethylamino)-pyridin-3-yl]-N-methyl-isobutyramide, (S)-2-(3,5-bis-trifluoromethyl-phenyl)-N-[4-(2,4-dichloro-phenyl)-6-(2-hydroxy-propylamino)-pyridin-3-yl]-N-methyl-isobutyramide, (S)-2-(3,5-bis-trifluoromethyl-phenyl)-N-[4-(2-chloro-phenyl)-6-(2-hydroxy-propylamino)-pyridin-3-yl]-N-methyl-isobutyramide, (R)-2-(3,5-bis-trifluoromethyl-phenyl)-N-[4-(2-chloro-phenyl)-6-(2-hydroxy-propylamino)-pyridin-3-yl]-N-methyl-isobutyramide, (RS)-2-(3,5-bis-trifluoromethyl-phenyl)-N-[4-(2-chloro-phenyl)-6-(2-hydroxy-propylamino)-pyridin-3-yl]-N-methyl-isobutyramide, 2-(3,5-bis-trifluoromethyl-phenyl)-N-[4-(2-chloro-phenyl)-6-(2-hydroxy-2-methyl-propylamino)-pyridin-3-yl]-N-methyl-isobutyramide, 2-(3,5-bis-trifluoromethyl-phenyl)-N-[4-(2-chloro-phenyl)-6-(2-hydroxy-butylamino)-pyridin-3-yl]-N-methyl-isobutyramide, (S)-2-(3,5-bis-trifluoromethyl-phenyl)-N-[4-(4-fluoro-2-methyl-phenyl)-6-(2-hydroxy-propylamino)-pyridin-3-yl]-N-methyl-isobutyramide, (RS)-2-(3,5-bis-trifluoromethyl-phenyl)-N-[4-(2-chloro-phenyl)-6-(2,3-dihydroxy-propylamino)-pyridin-3-yl]-N-methyl-isobutyramide, (S)-2-(3,5-bis-trifluoromethyl-phenyl)-N-[4-(2-chloro-phenyl)-6-(2-hydroxy-1-methyl-ethylamino)-pyridin-3-yl]-N-methyl-isobutyramide, (R)-2-(3,5-bis-trifluoromethyl-phenyl)-N-[4-(2-chloro-phenyl)-6-(2-hydroxy-1-methyl-ethylamino)-pyridin-3-yl]-N-methyl-isobutyramide, 2-(3,5-bis-trifluoromethyl-phenyl)-N-[4-(2-chloro-phenyl)-6-(2-hydroxy-1-hydroxymethyl-ethylamino)-pyridin-3-yl]-N-methyl-isobutyramide, N-[6-[bis-(2-hydroxy-ethyl)-amino]-4-(2-chloro-phenyl)-pyridin-3-yl]-2-(3,5-bis-trifluoromethyl-phenyl)-N-methyl-isobutyramide, N-{6-[bis-(2-hydroxy-ethyl)-amino]-4-o-tolyl-pyridin-3-yl]-2-(3,5-bis-trifluoromethyl-phenyl)-N-methyl-isobutyramide, N-[6-[bis-(2-hydroxy-ethyl)-amino]-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-[(2-hydroxy-ethyl)-(3-hydroxy-propyl)-amino]-pyridin-3-yl]-N-methyl-isobutyramide, N-[6-[bis-(2-hydroxy-ethyl)-amino]-4-(2,4-dichloro-phenyl)-pyridin-3-yl]-2-(3,5-bis-trifluoromethyl-phenyl)-N-methyl-isobutyramide, N-[6-[bis-(2-hydroxy-ethyl)-amino]-4-(3,4-dichloro-phenyl)-pyridin-3-yl]-2-(3,5-bis-trifluoromethyl-phenyl)-N-methyl-isobutyramide, N-[6-[bis-(2-hydroxy-ethyl)-amino]-4-(4-fluoro-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-phenyl)-6-[(2-hydroxy-ethyl)-methyl-amino]-pyridin-3-yl]-N-methyl-isobutyramide, 2-(3,5-bis-trifluoromethyl-phenyl)-N-[6-[ethyl-(2-hydroxy-ethyl)-amino]-4-(4-fluoro-phenyl)-pyridin-3-yl]-N-methyl-isobutyramide, 2-(3,5-bis-trifluoromethyl-phenyl)-N-[6-[ethyl-(2-hydroxy-ethyl)-amino]-4-o-tolyl-pyridin-3-yl]-N-methyl-isobutyramide, 2-(3,5-bis-trifluoromethyl-phenyl)-N-[6-[(2-hydroxy-ethyl)-propyl-amino]-4-o-tolyl-pyridin-3-yl]-N-methyl-isobutyramide, (S)-2-(3,5-bis-trifluoromethyl-phenyl)-N-[6-(2-hydroxy-propylamino)-4-o-tolyl-pyridin-3-yl]-N-methyl-isobutyramide, N-[6-[bis-(2-hydroxy-propyl)-amino]-4-o-tolyl-pyridin-3-yl]-2-(3,5-bis-trifluoromethyl-phenyl)-N-methyl-isobutyramide, (S)-2-(3,5-bis-trifluoromethyl-phenyl)-N-[6-(2,3-dihydroxy-propylamino)-4-o-tolyl-pyridin-3-yl]-N-methyl-isobutyramide, (R)-2-(3,5-bis-trifluoromethyl-phenyl)-N-[6-(2,3-dihydroxy-propylamino)-4-o-tolyl-pyridin-3-yl]-N-methyl-isobutyramide, N-[6-[bis-(2-hydroxy-propyl)-amino]-4-(2-chloro-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-chloro-phenyl)-6-(2,3-dihydroxy-propylamino)-pyridin-3-yl]-N-methyl-isobutyramide, (R)-2-(3,5-bis-trifluoromethyl-phenyl)-N-[4-(2-chloro-phenyl)-6-(2,3-dihydroxy-propylamino)-pyridin-3-yl]-N-methyl-isobutyramide, N-[6-[bis-(2-hydroxy-ethyl)-amino]-4-(3-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(5-fluoro-2-methyl-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-bromo-phenyl)-6-(2-hydroxy-propylamino)-pyridin-3-yl]-N-methyl-isobutyramide, N-[6-[bis-(2-hydroxy-ethyl)-amino]-4-(2-bromo-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide, 2-(3,5-bis-trifluoromethyl-phenyl)-N-[6-(2-hydroxy-1-hydroxymethyl-ethylamino)-4-o-tolyl-pyridin-3-yl]-N-methyl-isobutyramide, (1R,2R)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1R,2S)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1S,2R)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1S,2S)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, 2-(3,5-bis-trifluoromethyl-phenyl)-N-[4-(2-chloro-phenyl)-6-[hexyl-(2-hydroxy-ethyl)-amino]-pyridin-3-yl]-N-methyl-isobutyramide, 2-(3,5-bis-trifluoromethyl-phenyl)-N-[4-(2-chloro-phenyl)-6-[(2-hydroxy-ethyl)-pentyl-amino]-pyridin-3-yl]-N-methyl-isobutyramide, 2-(3,5-bis-trifluoromethyl-phenyl)-N-[4-(2-chloro-phenyl)-6-[(2-hydroxy-ethyl)-(3-hydroxy-propyl)-amino]-pyridin-3-yl]-N-methyl-isobutyramide, (R)-2-(3,5-bis-trifluoromethyl-phenyl)-N-[6-(2-hydroxy-propylamino)-4-o-tolyl-pyridin-3-yl]-N-methyl-isobutyramide and 2-(3,5-bis-trifluoromethyl-phenyl)-N-[4-(4-fluoro-2-methyl-phenyl)-6-[(2-hydroxy-1-hydroxymethyl-ethyl)-methyl-amino]-pyridin-3-yl]-N-methyl-isobutyramide.

In another embodiment, the invention is a compound of formula I-1, wherein $R^1$ is unsubstituted or substituted phenyl, $R^4$ is hydrogen and $R^5$ is —$(CH_2)_d$-cycloalkyl, unsubstituted or substituted by hydroxy. Examples of these compounds are trans-2-(3,5-bis-trifluoromethyl-phenyl)-N-[4-(2-chloro-phenyl)-6-(4-hydroxy-cyclohexylamino)-pyridin-3-yl]-N-methyl-isobutyramide, trans-2-(3,5-bis-trifluoromethyl-phenyl)-N-[4-(2,4-dichloro-phenyl)-6-(4-hydroxy-cyclohexylamino)-pyridin-3-yl]-N-methyl-isobutyramide, trans-2-(3,5-bis-trifluoromethyl-phenyl)-N-[4-(4-fluoro-2-methyl-phenyl)-6-(4-hydroxy-cyclohexylamino)-pyridin-3-yl]-N-methyl-isobutyramide, trans-2-(3,5-bis-trifluoromethyl-phenyl)-N-[4-(2-bromo-phenyl)-6-(4-hydroxy-cyclohexylamino)-pyridin-3-yl]-N-methyl-isobutyramide, (1RS,2RS)-2-(3,5-bis-trifluoromethyl-phenyl)-N-[4-(2-chloro-phenyl)-6-(2-hydroxy-cyclohexylamino)-pyridin-3-yl]-N-methyl-isobutyramide, (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide, (1S,2S)-2-(3,5-bis-trifluoromethyl-phenyl)-N-[4-(2-chloro-phenyl)-6-(2-hydroxy-cyclopentylamino)-pyridin-3-yl]-N-methyl-isobutyramide and (1S,2S)-2-(3,5-bis-trifluoromethyl-phenyl)-N-[4-(4-fluoro-2-methyl-phenyl)-6-(2-hydroxy-cyclopentylamino)-pyridin-3-yl]-N-methyl-isobutyramide.

In another embodiment, the invention is a compound of formula I-1, wherein $R^1$ is unsubstituted or substituted phenyl, $R^4$ is hydrogen and $R^5$ is —$(CH_2)_c$NR'C(O)-lower alkyl or —$(CH_2)_d$S(O)$_2$-lower alkyl. Examples of such compounds are 2-(3,5-bis-trifluoromethyl-phenyl)-N-[4-(2-chloro-phenyl)-6-(2-methanesulfonyl-ethylamino)-pyridin-3-yl]-N-methyl-isobutyramide and N-[6-(2-acetylamino-ethylamino)-4-(2-chloro-phenyl)-pyridin-3-yl]-2-(3,5-bis-trifluoromethyl-phenyl)-N-methyl-isobutyramide.

In another embodiment, the invention is a compound of formula I-1, wherein $R^1$ is unsubstituted or substituted phenyl and $R^4$ and $R^5$ form together with the N-atom to which they are attached a ring with —$(CH_2)_4$—, which ring is substituted by one or two groups —$(CR'R'')_d$OH. Examples of such compounds are (S)—N-[4-(2-chloro-phenyl)-6-(2-hydroxymethyl-pyrrolidin-1-yl)-pyridin-3-yl]-2-(3,5-dichloro-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-dichloro-phenyl)-N-methyl-isobutyramide, (S)—N-[4-(2-chloro-phenyl)-6-(2-hydroxymethyl-pyrrolidin-1-yl)-pyridin-3-yl]-2-(3-fluoro-5-trifluoromethyl-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-difluoro-phenyl)-N-methyl-isobutyramide, (S)-2-(3-chloro-5-methoxy-phenyl)-N-[4-(2-chloro-phenyl)-6-(2-hydroxymethyl-pyrrolidin-1-yl)-pyridin-3-yl]-N-methyl-isobutyramide, (2S,4R)-2-(3-chloro-5-methoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)—N-[4-(2-chloro-phenyl)-6-(2-hydroxymethyl-pyrrolidin-1-yl)-pyridin-3-yl]-2-(3,5-dimethyl-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-dimethyl-phenyl)-N-methyl-isobutyramide, (S)-2-(3,5-dichloro-phenyl)-N-[6-(2-hydroxymethyl-pyrrolidin-1-yl)-4-o-tolyl-pyridin-3-yl]-N-methyl-isobutyramide, (2S,4R)-2-(3,5-dichloro-phenyl)-N-[6-(4-hydroxy-2-hydroxymethyl-pyrrolidin-1-yl)-4-o-tolyl-pyridin-3-yl]-N-methyl-isobutyramide, (S)-2-(3-fluoro-5-trifluoromethyl-phenyl)-N-[6-(2-hydroxymethyl-pyrrolidin-1-yl)-4-o-tolyl-pyridin-3-yl]-N-methyl-isobutyramide, (2R,4S)-2-(3-fluoro-5-trifluoromethyl-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-difluoro-phenyl)-N-[6-(2-hydroxymethyl-pyrrolidin-1-yl)-4-o-tolyl-pyridin-3-yl]-N-methyl-isobutyramide, (2S,4R)-2-(3,5-difluoro-phenyl)-N-[6-(4-hydroxy-2-hydroxymethyl-pyrrolidin-1-yl)-4-o-tolyl-pyridin-3-yl]-N-methyl-isobutyramide, (S)-2-(3-chloro-5-methoxy-phenyl)-N-[6-(2-hydroxymethyl-pyrrolidin-1-yl)-4-o-tolyl-pyridin-3-yl]-N-methyl-isobutyramide, (2S,4R)-2-(3-chloro-5-methoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dimethyl-phenyl)-N-[6-(2-hydroxymethyl-pyrrolidin-1-yl)-4-o-tolyl-pyridin-3-yl]-N-methyl-isobutyramide, (2S,4R)-2-(3,5-dimethyl-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dichloro-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-dichloro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)—N-[4-(4-fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide,
(2S,4R)—N-[4-(4-fluoro-2-methyl-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide,
(S)—N-[4-(4-fluoro-2-methyl-phenyl)-6-(2-hydroxymethyl-pyrrolidin-1-yl)-pyridin-3-yl]-N-methyl-2-(3-trifluoromethyl-phenyl)-isobutyramide,
(2S,4R)—N-[4-(4-fluoro-2-methyl-phenyl)-6-(4-hydroxy-2-hydroxymethyl-pyrrolidin-1-yl)-pyridin-3-yl]-N-methyl-2-(3-trifluoromethyl-phenyl)-isobutyramide,
(S)-2-(3,5-difluoro-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3,5-difluoro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-2-(3-chloro-5-methoxy-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3-chloro-5-methoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-(3,5-dimethyl-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3,5-dimethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-2-(3-chloro-5-difluoromethoxy-phenyl)-N-[4-(2-chloro-phenyl)-6-(2-hydroxymethyl-pyrrolidin-1-yl)-pyridin-3-yl]-N-methyl-isobutyramide,
(2S,4R)-2-(3-chloro-5-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide,
(S)-2-(3-chloro-5-difluoromethoxy-phenyl)-N-[6-(2-hydroxymethyl-pyrrolidin-1-yl)-4-o-tolyl-pyridin-3-yl]-N-methyl-isobutyramide,
(2S,4R)-2-(3-chloro-5-difluoromethoxy-phenyl)-N-[6-(4-hydroxy-2-hydroxymethyl-pyrrolidin-1-yl)-4-o-tolyl-pyridin-3-yl]-N-methyl-isobutyramide,
(S)-2-(3-chloro-5-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3-chloro-5-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide,
(R)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(2-chloro-phenyl)-6-(3-hydroxy-pyrrolidin-1-yl)-pyridin-3-yl]-N-methyl-isobutyramide,
(R)-2-(3,5-bis-trifluoromethyl-phenyl)-N-[4-(2-chloro-phenyl)-6-(3-hydroxy-pyrrolidin-1-yl)-pyridin-3-yl]-N-methyl-isobutyramide,
(3R,4S)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide,
(3R,4R)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide,
(R)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide,
(R)-2-(3,5-bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide,
(R)-2-(3,5-bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide,
(2R,4R)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide,
(S)-2-(3,5-bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide,
(RS)-2-(3,5-bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide,
(2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(2-bromo-phenyl)-6-(3-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(2,4-dichloro-phenyl)-6-(3-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(2-chloro-phenyl)-6-(3-hydroxy-2-hydroxymethyl-pyrrolidin-1-yl)-pyridin-3-yl]-N-methyl-isobutyramide,
(2R,4S)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide,
(2R,3R)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-2-(3,5-bis-trifluoromethyl-phenyl)-N-{4-(4-fluoro-2-methyl-phenyl)-6-[2-(1-hydroxy-1-methyl-ethyl)-pyrrolidin-1-yl]-pyridin-3-yl}-N-methyl-isobutyramide, (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(5-fluoro-2-methyl-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(3-fluoro-2-methyl-phenyl)-6-(2-hydroxymethyl-pyrrolidin-1-yl)-pyridin-3-yl]-N-methyl-isobutyramide,
(R)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide,
(RS)-2-(3,5-bis-trifluoromethyl-phenyl)-N-[4-(2-chloro-phenyl)-6-(3-hydroxymethyl-pyrrolidin-1-yl)-pyridin-3-yl]-N-methyl-isobutyramide,
(3S,4S)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide,
(3S,4S)-2-(3,5-bis-trifluoromethyl-phenyl)-N-[6-(3,4-dihydroxy-pyrrolidin-1-yl)-4-o-tolyl-pyridin-3-yl]-N-methyl-isobutyramide,
(3R,4S)-2-(3,5-bis-trifluoromethyl-phenyl)-N-[6-(3,4-dihydroxy-pyrrolidin-1-yl)-4-o-tolyl-pyridin-3-yl]-N-methyl-isobutyramide,
(2R,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide,
(2S,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide,
(2R,5R)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide,
(2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-phenyl-pyridin-3-yl]-N-methyl-isobutyramide,
(2S,4R)-2-(3,5-bis-trifluoromethyl-phenyl)-N-[4-(4-fluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-chloro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-dimethylamino-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-bromo-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-chloro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3,5-difluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3,4-difluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-fluoro-4-methyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-chloro-4-fluoro-phenyl)-6-(4-hydroxy-2-hydroxymethyl-pyrrolidin-1-yl)-pyridin-3-yl]-N-methyl-isobutyramide,
(2S,4R)—N-[4-(2-amino-phenyl)-6-(4-hydroxy-2-hydroxymethyl-pyrrolidin-1-yl)-pyridin-3-yl]-2-(3,5-bis-trifluoromethyl-phenyl)-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-methoxy-phenyl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-hydroxy-phenyl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-methylsulfanyl-phenyl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-methanesulfonyl-phenyl)-pyridin-3-yl]-N-methyl-isobutyramide,
(2S,4R)-2-[5-{[2-(3,5-bis-trifluoromethyl-phenyl)-2-methyl-propionyl]-methyl-amino}-2-(4-hydroxy-2-hydroxymethyl-pyrrolidin-1-yl)-pyridin-4-yl]-benzamide,
(2S,4R)-2-(3,5-bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2-formyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-hydroxymethyl-phenyl)-pyridin-3-yl]-N-methyl-isobutyramide,
(2S,4R)-2-(3,5-bis-trifluoromethyl-phenyl)-N-[4-(2,5-dichloro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[4-(2-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-(2-trifluoromethyl-phenyl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-(2-methoxy-phenyl)-pyridin-3-yl]-N-methyl-isobutyramide, (2S,4S)-2-(3,5-bis-trifluoromethyl-phenyl)-N-[4-(2-cyano-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-phenyl-pyridin-3-yl]-N-methyl-isobutyramide, (2S,4S)-2-(3,5-bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide, (2R,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2R,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2R,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2R,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-(2-trifluoromethyl-phenyl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-(2-methoxy-phenyl)-pyridin-3-yl]-N-methyl-isobutyramide, (2R,3S)-2-(3,5-bis-trifluoromethyl-phenyl)-N-[4-(2-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-phenyl-pyridin-3-yl]-N-methyl-isobutyramide, (2R,3S)-2-(3,5-bis-trifluoromethyl-phenyl)-N-[4-(4-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-p-tolyl-pyridin-3-yl]-N-methyl-isobutyramide, (2R,3S)-2-(3,5-bis-trifluoromethyl-phenyl)-N-[4-(3,4-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-chloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,5-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,3-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-chloro-4-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-formyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-hydroxymethyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(5-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,5-difluoro-phenyl)-6-(3-hydroxy-2-hydroxymethyl-pyrrolidin-1-yl)-pyridin-3-yl]-N-methyl-isobutyramide, (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide, (S)-2-(3,5-bis-trifluoromethyl-phenyl)-N-[6-(2-hydroxymethyl-pyrrolidin-1-yl)-4-(2-methoxy-phenyl)-pyridin-3-yl]-N-methyl-isobutyramide, (S)-2-(3,5-bis-trifluoromethyl-phenyl)-N-[4-(2-bromo-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2-fluoro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,5-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,3-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(4-chloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(4-fluoro-phenyl)-6-(2-hydroxymethyl-pyrrolidin-1-yl)-pyridin-3-yl]-N-methyl-isobutyramide and (S)-2-(3,5-bis-trifluoromethyl-phenyl)-N-[6-(2-hydroxymethyl-pyrrolidin-1-yl)-4-phenyl-pyridin-3-yl]-N-methyl-isobutyramide.

In another embodiment, the invention is a compound of formula I-1, wherein $R^1$ is unsubstituted or substituted phenyl and $R^4$ and $R^5$ form together with the N-atom to which they are attached a ring with —$(CH_2)_4$—, which ring is substituted by one to three substituents selected from the group consisting of —NR'R", —$(CH_2)_d$—C(O)-lower alkyl, $CH_2OH$, —$(CH_2)_d$-pyrrolidinyl, —$(CH_2)_d$—S(O)$_2$-lower alkyl, =O, halogen and —$(CH_2)_d$OC(O)NR'R". Examples of such compounds are (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide, (S)—N-[6-(3-acetylamino-pyrrolidin-1-yl)-4-(2-chloro-phenyl)-pyridin-3-yl]-2-(3,5-bis-trifluoromethyl-phenyl)-N-methyl-isobutyramide, (R)—N-[6-(3-acetylamino-pyrrolidin-1-yl)-4-(2-chloro-phenyl)-pyridin-3-yl]-2-(3,5-bis-trifluoromethyl-phenyl)-N-methyl-isobutyramide, (RS)—N-[6-[3-(acetyl-ethyl-amino)-pyrrolidin-1-yl]-4-(2-chloro-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-chloro-phenyl)-6-(−2-pyrrolidin-1-ylmethyl-pyrrolidin-1-yl)-pyridin-3-yl]-N-methyl-isobutyramide, (S)-2-(3,5-bis-trifluoromethyl-phenyl)-N-[4-(2-chloro-phenyl)-6-(3-dimethylamino-pyrrolidin-1-yl)-pyridin-3-yl]-N-methyl-isobutyramide, (RS)-2-(3,5-bis-trifluoromethyl-phenyl)-N-[4-(2-chloro-phenyl)-6-(3-methanesulfonyl-pyrrolidin-1-yl)-pyridin-3-yl]-N-methyl-isobutyramide, (S)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide, (R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide, (R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide, (R)—N-[6-[3-(acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide, (S)—N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide, (S)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide, (S)-(2-(3,5-bis-trifluoromethyl-phenyl)-N-[6-[3-(ethyl-methanesulfonyl-amino)-pyrrolidin-1-yl]-4-(4-fluoro-2-methyl-phenyl)-pyridin-3-yl]-N-methyl-isobutyramide, (S)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide, (S)—N-[6-[3-(acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(3-oxo-pyrrolidin-1-yl)-pyridin-3-yl]-N-methyl-isobutyramide, (S)—N-[6-(3-acetylamino-pyrrolidin-1-yl)-4-(2-bromo-phenyl)-pyridin-3-yl]-2-(3,5-bis-trifluoromethyl-phenyl)-N-methyl-isobutyramide, (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide, (S)-2-(3,5-bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide, (2S,4S)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[6-(4-fluoro-2-hydroxymethyl-pyrrolidin-1-yl)-4-(4-fluoro-2-methyl-phenyl)-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-(4-fluoro-2-methyl-phenyl)-pyridin-3-yl]-N-methyl-isobutyramide, (2S,4R)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide, (S)—N-[6-[2-(acetylamino-methyl)-pyrrolidin-1-yl]-4-(4-fluoro-2-methyl-phenyl)-pyridin-3-yl]-2-(3,5-bis-trifluoromethyl-phenyl)-N-methyl-isobutyramide or (S)-dimethyl-carbamic acid 1-[5-{[2-(3,5-bis-trifluoromethyl-phenyl)-2-methyl-propionyl]-methyl-amino}-4-(4-fluoro-2-methyl-phenyl)-pyridin-2-yl]-pyrrolidin-2-ylmethyl ester.

In another embodiment, the invention is a compound of formula I-1, wherein $R^1$ is unsubstituted or substituted phenyl and $R^4$ and $R^5$ form together with the N-atom to which they are attached a ring with —$(CH_2)_h$—, which ring is mono- or di-substituted by —$(CH_2)_d$OH or —NR'R", wherein h is 3 or 5. Examples of such compounds are (RS)-2-(3,5-bis-trifluoromethyl-phenyl)-N-[4'-(2-chloro-phenyl)-3-hydroxy-3,4,5,6-tetrahydro-2H-[1,2']bipyridinyl-5'-yl]-N-methyl-isobutyramide, 2-(3,5-bis-trifluoromethyl-phenyl)-N-[4'-(2-chloro-phenyl)-4-hydroxy-3,4,5,6-tetrahydro-2H-[1,2']bipyridinyl-5'-yl]-N-methyl-isobutyramide, 2-(3,5-bis-trifluoromethyl-phenyl)-N-[4'-(2-chloro-phenyl)-4-hydroxymethyl-3,4,5,6-tetrahydro-2H-[1,2']bipyridinyl-5'-yl]-N-methyl-isobutyramide, (RS)-2-(3,5-bis-trifluoromethyl-phenyl)-N-[4'-(2-chloro-phenyl)-2-(2-hydroxy-ethyl)-3,4,5,6-tetrahydro-2H-[1,2']bipyridinyl-5'-yl]-N-methyl-isobutyramide, 2-(3,5-bis-trifluoromethyl-phenyl)-N-[4-(2-chloro-phenyl)-6-(3-hydroxy-azetidin-1-yl)-pyridin-3-yl]-N-methyl-isobutyramide, N-[4-amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide, 2-(3,5-bis-trifluoromethyl-phenyl)-N-[4'-(2-chloro-phenyl)-4-methanesulfonylamino-3,4,5,6-tetrahydro-2H-[1,2']bipyridinyl-5'-yl]-N-methyl-isobutyramide, N-[4-acetylamino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide,
(RS)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
(R)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
(S)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
2-(3,5-bis-trifluoromethyl-phenyl)-N-[4-(4-fluoro-2-methyl-phenyl)-6-(3-hydroxy-azetidin-1-yl)-pyridin-3-yl]-N-methyl-isobutyramide,
2-(3,5-bis-trifluoromethyl-phenyl)-N-[6-(3-hydroxy-azetidin-1-yl)-4-o-tolyl-pyridin-3-yl]-N-methyl-isobutyramide,
2-(3,5-bis-trifluoromethyl-phenyl)-N-(4-hydroxymethyl-4'-o-tolyl-3,4,5,6-tetrahydro-2H-[1,2']bipyridinyl-5'-yl)-N-methyl-isobutyramide,
(3R,5R)-2-(3,5-bis-trifluoromethyl-phenyl)-N-(3,5-dihydroxy-4'-o-tolyl-3,4,5,6-tetrahydro-2H-[1,2']bipyridinyl-5'-yl)-N-methyl-isobutyramide,
(3R,5R)-2-(3,5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide,
(3S,5R)-5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide,
(3RS,4SR)-2-(3,5-bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide,
(3RS,4RS)-2-(3,5-bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide,
(3RS,4SR)-2-(3,5-bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide,
(3RS,4RS)-2-(3,5-bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide,
(2RS,4SR)-2-(3,5-bis-trifluoromethyl-phenyl)-N-[4'-(2-chloro-phenyl)-4-hydroxy-2-hydroxymethyl-3,4,5,6-tetrahydro-2H-[1,2']bipyridinyl-5'-yl]-N-methyl-isobutyramide,
(2RS,4SR)-2-(3,5-bis-trifluoromethyl-phenyl)-N-(4-hydroxy-2-hydroxymethyl-4'-o-tolyl-3,4,5,6-tetrahydro-2H-[1,2']bipyridinyl-5'-yl)-N-methyl-isobutyramide,
(3RS,4SR)-2-(3,5-bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide,
(3RS,4RS)-2-(3,5-bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide,
(3RS,4SR)-2-(3,5-bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide,
(3RS,4RS)-2-(3,5-bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide and
(2RS,3RS)-2-(3,5-bis-trifluoromethyl-phenyl)-N-[4'-(2-chloro-phenyl)-3-hydroxy-2-hydroxymethyl-3,4,5,6-tetrahydro-2H-[1,2']bipyridinyl-5'-yl]-N-methyl-isobutyramide.

In another embodiment, the invention is a compound of formula I-1, wherein $R^1$ is unsubstituted or substituted phenyl and $R^4$ and $R^5$ form together with the N-atom to which they are attached a ring with —$(CH_2)_g$—NR'—$(CH_2)_2$—, which is unsubstituted or mono- or di-substituted by —$(CH_2)_d$—C(O)-lower alkyl, —$(CH_2)_d$—C(O)-cycloalkyl, —NR'R" or =O. Examples of such compounds are
N-[6-(4-acetyl-piperazin-1-yl)-4-(2-chloro-phenyl)-pyridin-3-yl]-2-(3,5-bis-trifluoromethyl-phenyl)-N-methyl-isobutyramide,
2-(3,5-bis-trifluoromethyl-phenyl)-N-[4-(2-chloro-phenyl)-6-(4-cyclopropanecarbonyl-piperazin-1-yl)-pyridin-3-yl]-N-methyl-isobutyramide,
N-[6-(4-acetyl-[1,4]diazepan-1-yl)-4-(2-chloro-phenyl)-pyridin-3-yl]-2-(3,5-bis-trifluoromethyl-phenyl)-N-methyl-isobutyramide and
2-(3,5-bis-trifluoromethyl-phenyl)-N-[4-(4-fluoro-2-methyl-phenyl)-6-(5-oxo-[1,4]diazepan-1-yl)-pyridin-3-yl]-N-methyl-isobutyramide.

In another embodiment, the invention is a compound of formula I-1, wherein $R^1$ is unsubstituted or substituted phenyl and $R^4$ and $R^5$ form together with the N-atom to which they are attached a ring with —$(CH_2)_2$, —O—$(CH_2)_2$—, which is unsubstituted or mono- or -di-substituted by —$(CR'R")_d$OH. Examples of such compounds are
(R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide,
(R)-(2-(3,5-bis-trifluoromethyl-phenyl)-N-[6-(3-hydroxymethyl-morpholin-4-yl)-4-o-tolyl-pyridin-3-yl]-N-methyl-isobutyramide and
(RS)-2-(3,5-bis-trifluoromethyl-phenyl)-N-[6-(2-hydroxymethyl-morpholin-4-yl)-4-o-tolyl-pyridin-3-yl]-N-methyl-isobutyramide.

In another embodiment, the invention is a compound of formula I-1, wherein $R^1$ is unsubstituted or substituted phenyl and $R^4$ and $R^5$ form together with the N-atom to which they are attached a ring with —$(CH_2)_c$—S(O)$_f$—$(CH_2)_2$—, which is unsubstituted or mono- or di-substituted by —$(CR'R")_d$OH Examples of such compounds are
(RS)-2-(3,5-bis-trifluoromethyl-phenyl)-N-[4-(4-fluoro-2-methyl-phenyl)-6-(3-hydroxymethyl-1,1-dioxo-1$\lambda^6$-thiomorpholin-4-yl)-pyridin-3-yl]-N-methyl-isobutyramide and
(RS)-2-(3,5-bis-trifluoromethyl-phenyl)-N-[6-(3-hydroxymethyl-1,1-dioxo-1$\lambda^6$_thiomorpholin-4-yl)-4-o-tolyl-pyridin-3-yl]-N-methyl-isobutyramide.

In another embodiment, the invention is a compound of formula I-1, wherein $R^1$ is unsubstituted or substituted phenyl as described above and $R^4$ and $R^5$ form together with the N-atom to which they are attached a ring with —$CH_2CH=CH$—$CH_2$—, which is unsubstituted or mono-substituted by, —$(CR'R")_d$OH. One such compound is
(S)-2-(3,5-bis-trifluoromethyl-phenyl)-N-[4-(4-fluoro-2-methyl-phenyl)-6-(2-hydroxymethyl-2,5-dihydro-pyrrol-1-yl)-pyridin-3-yl]-N-methyl-isobutyramide.

In another embodiment, the invention is a compound of formula I-1, wherein $R^1$ is unsubstituted or substituted heteroaryl as described above. Examples of such compounds are
(2S,4R)-2-(3,5-bis-trifluoromethyl-phenyl)-N-[4-(3,5-dimethyl-isoxazol-4-yl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[6'-(4-hydroxy-2-hydroxymethyl-pyrrolidin-1-yl)-2,6-dimethoxy-[3,4']bipyridinyl-3'-yl]-N-methyl-isobutyramide, (2S,4R)-2-(3,5-bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide,
(2S,4R)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide,
(2S,4R)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide,
(2S,4S)-2-(3,5-bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide,
(2S,4S)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide,
(2S,4S)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide,
(2R,3S)-2-(3,5-bis-trifluoromethyl-phenyl)-N-[6'-(3-hydroxy-2-hydroxymethyl-pyrrolidin-1-yl)-2-methyl-[3,4']bipyridinyl-3'-yl]-N-methyl-isobutyramide,
(S)-2-(3,5-bis-trifluoromethyl-phenyl)-N-[6'-(2-hydroxymethyl-pyrrolidin-1-yl)-2-methyl-[3,4']bipyridinyl-3'-yl]-N-methyl-isobutyramide,
N-{6'-[bis-(2-hydroxy-ethyl)-amino]-2-methyl-[3,4']bipyridinyl-3'-yl}-2-(3,5-bis-trifluoromethyl-phenyl)-N-methyl-isobutyramide,
(S)-2-(3,5-bis-trifluoromethyl-phenyl)-N-[6'-(2-hydroxymethyl-pyrrolidin-1-yl)-4-methyl-[3,4']bipyridinyl-3'-yl]-N-methyl-isobutyramide,
N-{6'-[bis-(2-hydroxy-ethyl)-amino]-4-methyl-[3,4']bipyridinyl-3'-yl}-2-(3,5-bis-trifluoromethyl-phenyl)-N-methyl-isobutyramide and
2-(3,5-bis-trifluoromethyl-phenyl)-N-{6'-[(2-hydroxyethyl)-methyl-amino]-4-methyl-[3,4']bipyridinyl-3'-yl}-N-methyl-isobutyramide.

Preferred is the use of compounds of formula I, wherein $R^1$, $R^4$ and $R^5$ have the definitions as described above and $R^2$ and $R^3$ are both $CF_3$.

Further preferred is the use of compounds of formula I, wherein $R^4$ and $R^5$ form together with the N-atom to which they are attached a ring with —$(CH_2)_e$—, which ring is unsubstituted or substituted by one or more substituents selected from the group consisting of alkyl, halogen, $CF_3$, —$(CR'R'')_d$OH, =O, and —NR'R'', wherein R' and R'' may form together with the N-atom to which they are attached a ring with —$(CH_2)_e$, or substituted by —$(CH_2)_d$NR'—C(O)-alkyl, —$(CH_2)_d$—C(O)-alkyl, —$(CH_2)_d$—C(O)-cycloalkyl, —$(CH_2)_d$OC(O)NR'R'', —$(CH_2)_d$—S(O)_2$— alkyl, —$(CH_2)_d$-pyrrolidinyl or —C(O)NR'R''.

Preferred is also the use of compounds of formula I, wherein $R^4$ and $R^5$ form together with the N-atom to which they are attached a ring with —$(CH_2)_e$—, wherein the ring is mono or di-substituted by hydroxy, —$CH_2OH$ or —C(O)H. Examples of such compounds are
(S)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2-chlorophenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(2-bromophenyl)-6-(4-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(2-bromophenyl)-6-(3-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(2-chlorophenyl)-6-(3-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2-chlorophenyl)-6-(4-hydroxy-2-hydroxymethyl-pyrrolidin-1-yl)-pyridin-3-yl]-N-methyl-isobutyramide,
(2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide,
(2R,3R)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(5-fluoro-2-methyl-phenyl)-6-(2-hydroxymethyl-pyrrolidin-1-yl)-pyridin-3-yl]-N-methyl-isobutyramide,
(S)-2-(3,5-bis-trifluoromethyl-phenyl)-N-[4-(3-fluoro-2-methyl-phenyl)-6-(2-hydroxymethyl-pyrrolidin-1-yl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide,
(2S,4R)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[6-(4-hydroxy-2-hydroxymethyl-pyrrolidin-1-yl)-4-(2-hydroxymethyl-phenyl)-pyridin-3-yl]-N-methyl-isobutyramide,
(2S,4R)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide,
(2S,4S)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide,
(2S,4S)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[4-(4-fluoro-2-hydroxymethyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(5-fluoro-2-methyl-phenyl)-6-(3-hydroxy-2-hydroxymethyl-pyrrolidin-1-yl)-pyridin-3-yl]-N-methyl-isobutyramide, (S)-2-(3,5-bis-trifluoromethyl-phenyl)-N-[6-(2-hydroxyethyl-pyrrolidin-1-yl)-4-o-tolyl-pyridin-3-yl]-N-methyl-isobutyramide, (S)-2-(3,5-bis-trifluoromethyl-phenyl)-N-[4-(2-bromo-phenyl)-6-(2-hydroxymethyl-pyrrolidin-1-yl)-pyridin-3-yl]-N-methyl-isobutyramide, (3R,5S)-2-(3,5-bis-trifluoromethyl-phenyl)-N-[4'-(4-fluoro-2-methyl-phenyl)-3,5-dihydroxy-3,4,5,6-tetrahydro-2H-[1,2']bipyridinyl-5'-yl]-N-methyl-isobutyramide, (3S,5S)-2-(3,5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide, (S)-2-(3,5-bis-trifluoromethyl-phenyl)-N-[6-(2-formyl-pyrrolidin-1-yl)-4-o-tolyl-pyridin-3-yl]-N-methyl-isobutyramide, 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide, (RS)-2-(3,5-bis-trifluoromethyl-phenyl)-N-[4-(4-fluoro-2-methyl-phenyl)-6-(3-hydroxymethyl-pyrrolidin-1-yl)-pyridin-3-yl]-N-methyl-isobutyramide, (S)-2-(3,5-dimethoxy-phenyl)-N-[6-(2-hydroxymethyl-pyrrolidin-1-yl)-4-o-tolyl-pyridin-3-yl]-N-methyl-isobutyramide, (2S,4R)-2-(3,5-dimethoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dimethoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-dimethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-dimethoxy-phenyl)-N-methyl-isobutyramide, (2S,4R)-2-(3,5-bis-difluoromethoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-bis-difluoromethoxy-phenyl)-N-[6-(2-hydroxymethyl-pyrrolidin-1-yl)-4-o-tolyl-pyridin-3-yl]-N-methyl-isobutyramide, (S)-2-(3,5-bis-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-bis-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)-2-(3,5-bis-difluoromethoxy-phenyl)-N-[4-(2-chloro-phenyl)-6-(2-hydroxymethyl-pyrrolidin-1-yl)-pyridin-3-yl]-N-methyl-isobutyramide, (2S,4R)-2-(3,5-bis-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4R)—N-[6-(4-hydroxy-2-hydroxymethyl-pyrrolidin-1-yl)-4-o-tolyl-pyridin-3-yl]-N-methyl-2-(3-trifluoromethoxy-phenyl)-isobutyramide and (2S,4R)—N-[4-(4-fluoro-2-methyl-phenyl)-6-(4-hydroxy-2-hydroxymethyl-pyrrolidin-1-yl)-pyridin-3-yl]-N-methyl-2-(3-trifluoromethoxy-phenyl)-isobutyramide.

Preferred are further compounds of formula I, wherein $R^4$ and $R^5$ form together with the N-atom to which they are attached a ring with —$(CH_2)_e$—, wherein the ring is mono or di-substituted by $NH_2$, $NHS(O)_2CH_3$, $NCH_3S(O)_2CH_3$, $N(CH_2CH_3)S(O)_2CH_3$, $NHC(O)CH_3$ and —$CH_2OH$. Examples of such compounds are (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide, (R)—N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide, (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide, (R)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide, (R)-2-(3,5-bis-trifluoromethyl-phenyl)-N-[6-[3-(ethyl-methanesulfonyl-amino)-pyrrolidin-1-yl]-4-(4-fluoro-2-methyl-phenyl)-pyridin-3-yl]-N-methyl-isobutyramide, 2-(3,5-bis-trifluoromethyl-phenyl)-N-[4'-(4-fluoro-2-methyl-phenyl)-4-methanesulfonylamino-3,4,5,6-tetrahydro-2H-[1,2']bipyridinyl-5'-yl]-N-methyl-isobutyramide, 2-(3,5-bis-trifluoromethyl-phenyl)-N-[4'-(4-fluoro-2-methyl-phenyl)-4-(methanesulfonyl-methyl-amino)-3,4,5,6-tetrahydro-2H-[1,2']bipyridinyl-5'-yl]-N-methyl-isobutyramide and 2-(3,5-bis-trifluoromethyl-phenyl)-N-[4-(ethyl-methanesulfonyl-amino)-4'-(4-fluoro-2-methyl-phenyl)-3,4,5,6-tetrahydro-2H-[1,2']bipyridinyl-5'-yl]-N-methyl-isobutyramide.

A further preferred group of compounds are further those, wherein $R^4$ and $R^5$ form together with the N-atom to which they are attached a ring with —$(CH_2)_4$— and wherein the ring is disubstituted by =O and —$CH_2OH$, for example the following compounds:

(S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide and (S)-2-(3,5-bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide.

Compounds of formula I, wherein $R^4$ and $R^5$ form together with the N-atom to which they are attached a ring with —$(CH_2)_4$—, wherein the ring is di- or tri-substituted by halogen and —$CH_2OH$, are also preferred. The following compounds relate to this group:

(2S,4S)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[6-(4-fluoro-2-hydroxymethyl-pyrrolidin-1-yl)-4-(4-fluoro-2-methyl-phenyl)-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide, (S)-2-(3,5-bis-trifluoromethyl-phenyl)-N-[6-(4,4-difluoro-2-hydroxymethyl-pyrrolidin-1-yl)-4-(4-fluoro-2-methyl-phenyl)-pyridin-3-yl]-N-methyl-isobutyramide and (2S,4R)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide.

A further preferred group of compounds are those, wherein $R^4$ and $R^5$ form together with the N-atom to which they are attached a ring with —$(CH_2)_e$—, wherein the ring is substituted by $CH_2S(O)_2CH_3$, $CH_2SCH_3$ or $CH_2S(O)CH_3$. Examples of such compounds are (S)-2-(3,5-bis-trifluoromethyl-phenyl)-N-[4-(4-fluoro-2-methyl-phenyl)-6-(2-methanesulfonylmethyl-pyrrolidin-1-yl)-pyridin-3-yl]-N-methyl-isobutyramide, 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide, (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide, 2-(3,5-bis-trifluoromethyl-phenyl)-N-[4'-(4-fluoro-2-methyl-phenyl)-4-methanesulfonylmethyl-3,4,5,6-tetrahydro-2H-[1,2']bipyridinyl-5'-yl]-N-methyl-isobutyramide, (RS)-2-(3,5-bis-trifluoromethyl-phenyl)-N-[4-(4-fluoro-2-methyl-phenyl)-6-(3-methylsulfanylmethyl-pyrrolidin-1-yl)-pyridin-3-yl]-N-methyl-isobutyramide, 2-(3,5-bis-trifluoromethyl-phenyl)-N-{4-(4-fluoro-2-methyl-phenyl)-6-[(RS)-3-((RS)-methanesulfinylmethyl)-pyrrolidin-1-yl]-pyridin-3-yl}-N-methyl-isobutyramide and (RS)-2-(3,5-bis-trifluoromethyl-phenyl)-N-[4-(4-fluoro-2-methyl-phenyl)-6-(3-methanesulfonylmethyl-pyrrolidin-1-yl)-pyridin-3-yl]-N-methyl-isobutyramide.

Other preferred compounds of formula I are those, wherein $R^4$ and $R^5$ form together with the N-atom to which they are attached a ring with —$(CH_2)_e$—, wherein the ring is substituted by $S(O)_2CH_3$, $SCH_3$, $S(O)CH_3$ or $S(O)_2N(CH_3)_2$, for example the following compounds:

2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide, (RS)-2-(3,5-bis-trifluoromethyl-phenyl)-N-[4'-(4-fluoro-2-methyl-phenyl)-3-methanesulfonyl-3,4,5,6-tetrahydro-2H-[1,2']bipyridinyl-5'-yl]-N-methyl-isobutyramide, 2-(3,5-bis-trifluoromethyl-phenyl)-N-[4'-(4-fluoro-2-methyl-phenyl)-4-methanesulfonyl-3,4,5,6-tetrahydro-2H-[1,2']bipyridinyl-5'-yl]-N-methyl-isobutyramide, 2-(3,5-bis-trifluoromethyl-phenyl)-N-[4-dimethylsulfamoyl-4'-(4-fluoro-2-methyl-phenyl)-3,4,5,6-tetrahydro-2H-[1,2']bipyridinyl-5'-yl]-N-methyl-isobutyramide, 2-(3,5-bis-trifluoromethyl-phenyl)-N-[4'-(2-chloro-phenyl)-4-methylsulfanyl-3,4,5,6-tetrahydro-2H-[1,2']bipyridinyl-5'-yl]-N-methyl-isobutyramide, (RS)-2-(3,5-bis-trifluoromethyl-phenyl)-N-[4'-(2-chloro-phenyl)-4-methanesulfinyl-3,4,5,6-tetrahydro-2H-[1,2']bipyridinyl-5'-yl]-N-methyl-isobutyramide and 2-(3,5-bis-trifluoromethyl-phenyl)-N-[4'-(2-chloro-phenyl)-4-methanesulfonyl-3,4,5,6-tetrahydro-2H-[1,2']bipyridinyl-5'-yl]-N-methyl-isobutyramide.

Compounds, wherein —$NR^4R^5$ is and R' is as described in claim 1, are further preferred, which compounds are (1S,3R,5R)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide, (1R,3S,5S)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide, (rac)-(1R,3R,5S)-2-(3,5-bis-trifluoromethyl-phenyl)-N-[4-(4-fluoro-2-methyl-phenyl)-6-(3-methanesulfinyl-8-aza-bicyclo[3.2.1]oct-8-yl)-pyridin-3-yl]-N-methyl-isobutyramide, (1R,3R,5S)-2-(3,5-bis-trifluoromethyl-phenyl)-N-[4-(4-fluoro-2-methyl-phenyl)-6-(3-methanesulfonyl-8-aza-bicyclo[3.2.1]oct-8-yl)-pyridin-3-yl]-N-methyl-isobutyramide, 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide, 2-(3,5-bis-trifluoromethyl-phenyl)-N-[6-(4,4-dioxo-1-oxa-$4\lambda^6$-thia-8-aza-spiro[4.5]dec-8-yl)-4-(4-fluoro-2-methyl-phenyl)-pyridin-3-yl]-N-methyl-isobutyramide, 2-(3,5-bis-trifluoromethyl-phenyl)-N-[4-(4-fluoro-2-methyl-phenyl)-6-(1-oxa-5-thia-9-aza-spiro[5.5]undec-9-yl)-pyridin-3-yl]-N-methyl-isobutyramide, 2-(3,5-bis-trifluoromethyl-phenyl)-N-[6-(5,5-dioxo-1-oxa-$5\lambda^6$-thia-9-aza-spiro[5.5]undec-9-yl)-4-(4-fluoro-2-methyl-phenyl)-pyridin-3-yl]-N-methyl-isobutyramide, 2-(3,5-bis-trifluoromethyl-phenyl)-N-[4-(4-fluoro-2-methyl-phenyl)-6-(1,1,4,4-tetraoxo-$1\lambda^6,4\lambda^6$-dithia-8-aza-spiro[4.5]dec-8-yl)-pyridin-3-yl]-N-methyl-isobutyramide, 2-(3,5-bis-trifluoromethyl-phenyl)-N-[4-(4-fluoro-2-methyl-phenyl)-6-(1,1,5,5-tetraoxo-$1\lambda^6$, $5\lambda^6$-dithia-9-aza-spiro[5.5]undec-9-yl)-pyridin-3-yl]-N-methyl-isobutyramide, 2-(3,5-bis-trifluoromethyl-phenyl)-N-[4-(4-fluoro-2-methyl-phenyl)-6-(1-oxa-8-aza-spiro[4.5]dec-8-yl)-pyridin-3-yl]-N-methyl-isobutyramide, 2-(3,5-bis-trifluoromethyl-phenyl)-N-[(1S,5R)-4-(4-fluoro-2-methyl-phenyl)-6-8-oxa-3-aza-bicyclo[3.2.1]oct-3-yl-pyridin-3-yl]-N-methyl-isobutyramide, (1S,5R)-2-(3,5-bis-trifluoromethyl-phenyl)-N-[6-(8,8-dioxo-$8\lambda^6$-thia-3-aza-bicyclo[3.2.1]oct-3-yl)-4-(4-fluoro-2-methyl-phenyl)-pyridin-3-yl]-N-methyl-isobutyramide, (1S,4S)-2-(3,5-bis-trifluoromethyl-phenyl)-N-[4-(4-fluoro-2-methyl-phenyl)-6-((1S,4S)-5-methanesulfonyl-2,5-diaza-bicyclo[2.2.1]hept-2-yl)-pyridin-3-yl]-N-methyl-isobutyramide and (1R,5S)-2-(3,5-bis-trifluoromethyl-phenyl)-N-[4-(4-fluoro-2-methyl-phenyl)-6-(8-methanesulfonyl-3,8-diaza-bicyclo[3.2.1]oct-3-yl)-pyridin-3-yl]-N-methyl-isobutyramide.

Another group of preferred compounds of formula I are those wherein $R^4$ and $R^5$ are each independently hydrogen; —(CR'R")$_1$—(CR'R")$_1$—(CR'R")$_a$—OH or —(CR'R")$_1$—(CR'R")$_1$—(CR'R")$_a$-alkyl, wherein R' and R" on each carbon atom may be the same or different from each other; —C$_b$-alkyl; —C(O)H; —(CH$_2$)$_d$cycloalkyl, unsubstituted or substituted by hydroxy; or is —(CH$_2$)$_c$NR'R", —(CH$_2$)$_c$NR'C(O)-alkyl, —(CH$_2$)$_c$NR'S(O)$_2$-alkyl, —(CH$_2$)$_d$S(O)-alkyl, —(CH$_2$)$_d$S-alkyl, —(CH$_2$)$_f$S(O)$_2$-alkyl or —(CH$_2$)$_d$S(O)$_2$—NR'R".

Especially preferred compounds from this group are those, wherein $R^4$ and $R^5$ are each independently hydrogen, —CH(CH$_2$OH)CH$_2$OH or —(CH$_2$)$_c$OH, for example, 2-(3,5-bis-trifluoromethyl-phenyl)-N-[4-(2-chloro-phenyl)-6-(2-hydroxy-1-hydroxymethyl-ethylamino)-pyridin-3-yl]-N-methyl-isobutyramide, N-[6-[bis-(2-hydroxy-ethyl)-amino]-4-(2-chloro-phenyl)-pyridin-3-yl]-2-(3,5-bis-trifluoromethyl-phenyl)-N-methyl-isobutyramide, N-{6-[bis-(2-hydroxy-ethyl)-amino]-4-o-tolyl-pyridin-3-yl}-2-(3,5-bis-trifluoromethyl-phenyl)-N-methyl-isobutyramide, N-[6-[bis-(2-hydroxy-ethyl)-amino]-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-{4-(4-fluoro-2-methyl-phenyl)-6-[(2-hydroxy-ethyl)-(3-hydroxy-propyl)-amino]-pyridin-3-yl}-N-methyl-isobutyramide, N-[6-[bis-(2-hydroxy-ethyl)-amino]-4-(3-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(5-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(2-bromo-phenyl)-pyridin-3-yl]-2-(3,5-bis-trifluoromethyl-phenyl)-N-methyl-isobutyramide, (2S,4S)-2-(3,5-bis-trifluoromethyl-phenyl)-N-[4-(2-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-(2-trifluoromethyl-phenyl)-pyridin-3-yl]-N-methyl-isobutyramide, (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide, 2-(3,5-bis-difluoromethoxy-phenyl)-N-[6-(2-hydroxy-ethylamino)-4-o-tolyl-pyridin-3-yl]-N-methyl-isobutyramide, 2-(3,5-bis-difluoromethoxy-phenyl)-N-[4-(4-fluoro-2-methyl-phenyl)-6-(2-hydroxy-ethylamino)-pyridin-3-yl]-N-methyl-isobutyramide and 2-(3,5-bis-difluoromethoxy-phenyl)-N-[4-(2-chloro-phenyl)-6-(2-hydroxy-ethylamino)-pyridin-3-yl]-N-methyl-isobutyramide.

Compounds of formula I, wherein $R^4$ and $R^5$ are each independently hydrogen, (CH$_2$)$_2$SCH$_3$, (CH$_2$)$_2$S(O)$_2$CH$_3$ or (CH$_2$)$_2$S(O)$_2$NHCH$_3$ are also preferred. Examples of such compounds are 2-(3,5-bis-trifluoromethyl-phenyl)-N-[4-(4-fluoro-2-methyl-phenyl)-6-(2-methylsulfanyl-ethylamino)-pyridin-3-yl]-N-methyl-isobutyramide, 2-(3,5-bis-trifluoromethyl-phenyl)-N-[4-(4-fluoro-2-methyl-phenyl)-6-(2-methanesulfonyl-ethylamino)-pyridin-3-yl]-N-methyl-isobutyramide and 2-(3,5-bis-trifluoromethyl-phenyl)-N-[4-(2-chloro-phenyl)-6-(2-methylsulfamoyl-ethylamino)-pyridin-3-yl]-N-methyl-isobutyramide.

Other preferred compounds are those, wherein $R^4$ and $R^5$ are each independently hydrogen, (CH$_2$)$_2$NH$_2$, (CH$_2$)$_2$NHS(O)$_2$CH$_3$ or (CH$_2$)$_2$NHC(O)CH$_3$, for example, N-[6-(2-amino-ethylamino)-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(2-methanesulfonylamino-ethylamino)-pyridin-3-yl]-N-methyl-isobutyramide and N-[6-(2-acetylamino-ethylamino)-4-(4-fluoro-2-methyl-phenyl)-pyridin-3-yl]-2-(3,5-bis-trifluoromethyl-phenyl)-N-methyl-isobutyramide.

Preferred are further compounds of formula I, wherein $R^4$ and $R^5$ form together with the N-atom to which they are attached a ring with —(CH$_2$)$_c$—O—(CH$_2$)$_2$—, which is unsubstituted or substituted by one or more substituent selected from the group consisting of alkyl, halogen, CF$_3$, —(CR'R")$_d$OH, =O, —CHO, and —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R".

To this group relate compounds, wherein $R^4$ and $R^5$ form together with the N-atom to which they are attached a ring with —(CH$_2$)$_2$—O—(CH$_2$)$_2$—, wherein the ring is unsubstituted or substituted by —CH$_2$OH, for example, (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide, (R)-(2-(3,5-bis-trifluoromethyl-phenyl)-N-[6-(3-hydroxymethyl-morpholin-4-yl)-4-o-tolyl-pyridin-3-yl]-N-methyl-isobutyramide, (RS)-2-(3,5-Bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide and 2-(3,5-Bis-trifluoromethyl-phenyl)-N-[4-(4-fluoro-2-methyl-phenyl)-6-morpholin-4-yl-pyridin-3-yl]-N-methyl-isobutyramide.

Another preferred group are compounds of formula I, wherein $R^4$ and $R^5$ form together with the N-atom to which they are attached a ring with —(CH$_2$)$_c$—S(O)$_f$—(CH$_2$)$_v$—, which is unsubstituted or substituted by one or more substituents selected from the group consisting of alkyl, halogen, CF$_3$, —(CR'R")$_d$OH, =O, —CHO, and —NR'R", wherein R' and R" are as described above or may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$—S(O)-alkyl, —(CH$_2$)$_d$—S-alkyl, —(CH$_2$)$_d$—S(O)$_2$—NR'R", —(CH$_2$)$_d$-pyrrolidinyl or —C(O)NR'R".

Especially preferred compounds from this group are those wherein $R^4$ and $R^5$ form together with the N-atom to which they are attached a ring with —(CH$_2$)$_2$—S(O)$_2$—(CH$_2$)$_2$—, wherein the ring is unsubstituted or substituted by —CH₂OH or methyl. Examples of such compounds are
(RS)-2-(3,5-bis-trifluoromethyl-phenyl)-N-[4-(4-fluoro-2-methyl-phenyl)-6-(3-hydroxymethyl-1,1-dioxo-1λ⁶-thiomorpholin-4-yl)-pyridin-3-yl]-N-methyl-isobutyramide,
(RS)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
2-(3,5-Bis-trifluoromethyl-phenyl)-N-[4-(4-fluoro-2-methyl-phenyl)-6-thiazolidin-3-yl-pyridin-3-yl]-N-methyl-isobutyramide,
(1RS,4RS)- or (1RS,4SR)-2-(3,5-bis-trifluoromethyl-phenyl)-N-[4-(4-fluoro-2-methyl-phenyl)-6-(4-hydroxymethyl-1-oxo-1λ⁴-thiazolidin-3-yl)-pyridin-3-yl]-N-methyl-isobutyramide (Diastereomeric racemate of Example 349),
(1RS,4SR)- or (1RS,4RS)-2-(3,5-bis-trifluoromethyl-phenyl)-N-[4-(4-fluoro-2-methyl-phenyl)-6-(4-hydroxymethyl-1-oxo-1λ⁴-thiazolidin-3-yl)-pyridin-3-yl]-N-methyl-isobutyramide (Diastereomeric racemate of Example 348),
(RS)-2-(3,5-bis-trifluoromethyl-phenyl)-N-[4-(4-fluoro-2-methyl-phenyl)-6-(4-hydroxymethyl-1,1-dioxo-1λ⁶-thiazolidin-3-yl)-pyridin-3-yl]-N-methyl-isobutyramide,
(+)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
(−)-2-(3,5-Bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
(RS)-2-(3,5-bis-trifluoromethyl-phenyl)-N-[4-(4-fluoro-2-methyl-phenyl)-6-(1-oxo-1λ⁴-[1,4]thiazepan-4-yl)-pyridin-3-yl]-N-methyl-isobutyramide,
2-(3,5-bis-trifluoromethyl-phenyl)-N-[6-(1,1-dioxo-1λ⁶-[1,4]thiazepan-4-yl)-4-(4-fluoro-2-methyl-phenyl)-pyridin-3-yl]-N-methyl-isobutyramide,
2-(3,5-bis-trifluoromethyl-phenyl)-N-[6-(1,1-dioxo-1λ⁶-[1,3]thiazinan-3-yl)-4-(4-fluoro-2-methyl-phenyl)-pyridin-3-yl]-N-methyl-isobutyramide and
2-(3,5-bis-trifluoromethyl-phenyl)-N-[4-(2-chloro-phenyl)-6-(2-methyl-1,1-dioxo-1λ⁶-[1,2,4]thiadiazinan-4-yl)-pyridin-3-yl]-N-methyl-isobutyramide.

Preferred are also compounds wherein R¹, R⁴ and R⁵ have the definitions as describe above and R² and R³ are other than di-CF₃. Examples of such compounds are
(2S,4R)—N-[4-(2-chloro-phenyl)-6-(4-hydroxy-2-hydroxymethyl-pyrrolidin-1-yl)-pyridin-3-yl]-2-(3,5-dichloro-phenyl)-N-methyl-isobutyramide,
(2S,4R)—N-[4-(2-chloro-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide,
(2S,4R)-2-(3-chloro-5-methoxy-phenyl)-N-[4-(2-chloro-phenyl)-6-(4-hydroxy-2-hydroxymethyl-pyrrolidin-1-yl)-pyridin-3-yl]-N-methyl-isobutyramide,
(S)-2-(3,5-dichloro-phenyl)-N-[6-(2-hydroxymethyl-pyrrolidin-1-yl)-4-o-tolyl-pyridin-3-yl]-N-methyl-isobutyramide,
(2S,4R)-2-(3,5-dichloro-phenyl)-N-[6-(4-hydroxy-2-hydroxymethyl-pyrrolidin-1-yl)-4-o-tolyl-pyridin-3-yl]-N-methyl-isobutyramide,
(2S,4R)-2-(3,5-dichloro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)—N-[4-(4-fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide,
(2S,4R)—N-[4-(4-fluoro-2-methyl-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide,
(2S,4R)-2-(3-chloro-5-methoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(2S,4R)-2-(3-chloro-5-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide,
(2S,4R)-2-(3-chloro-5-difluoromethoxy-phenyl)-N-[6-(4-hydroxy-2-hydroxymethyl-pyrrolidin-1-yl)-4-o-tolyl-pyridin-3-yl]-N-methyl-isobutyramide,
(2S,4R)-2-(3-chloro-5-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(S)-2-(3,5-dimethoxy-phenyl)-N-[6-(2-hydroxymethyl-pyrrolidin-1-yl)-4-o-tolyl-pyridin-3-yl]-N-methyl-isobutyramide,
(2S,4R)-2-(3,5-dimethoxy-phenyl)-N-[6-(4-hydroxy-2-hydroxymethyl-pyrrolidin-1-yl)-4-o-tolyl-pyridin-3-yl]-N-methyl-isobutyramide,
2-(3,5-dimethoxy-phenyl)-N-[4-(4-fluoro-2-methyl-phenyl)-6-(2-hydroxy-ethylamino)-pyridin-3-yl]-N-methyl-isobutyramide,
(S)-2-(3,5-dimethoxy-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3,5-dimethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(2S,4R)—N-[4-(2-chloro-phenyl)-6-(4-hydroxy-2-hydroxymethyl-pyrrolidin-1-yl)-pyridin-3-yl]-2-(3,5-dimethoxy-phenyl)-N-methyl-isobutyramide,
2-(3,5-bis-difluoromethoxy-phenyl)-N-[6-(2-hydroxy-ethylamino)-4-o-tolyl-pyridin-3-yl]-N-methyl-isobutyramide,
(2S,4R)-2-(3,5-bis-difluoromethoxy-phenyl)-N-[6-(4-hydroxy-2-hydroxymethyl-pyrrolidin-1-yl)-4-o-tolyl-pyridin-3-yl]-N-methyl-isobutyramide,
(S)-2-(3,5-bis-difluoromethoxy-phenyl)-N-[6-(2-hydroxymethyl-pyrrolidin-1-yl)-4-o-tolyl-pyridin-3-yl]-N-methyl-isobutyramide,
2-(3,5-bis-difluoromethoxy-phenyl)-N-[4-(4-fluoro-2-methyl-phenyl)-6-(2-hydroxy-ethylamino)-pyridin-3-yl]-N-methyl-isobutyramide,
(S)-2-(3,5-bis-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide,
(2S,4R)-2-(3,5-bis-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide,
(S)-2-(3,5-bis-difluoromethoxy-phenyl)-N-[4-(2-chloro-phenyl)-6-(2-hydroxymethyl-pyrrolidin-1-yl)-pyridin-3-yl]-N-methyl-isobutyramide,
2-(3,5-bis-difluoromethoxy-phenyl)-N-[4-(2-chloro-phenyl)-6-(2-hydroxy-ethylamino)-pyridin-3-yl]-N-methyl-isobutyramide,
(2S,4R)-2-(3,5-bis-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide,
(2S,4R)—N-[6-(4-hydroxy-2-hydroxymethyl-pyrrolidin-1-yl)-4-o-tolyl-pyridin-3-yl]-N-methyl-2-(3-trifluoromethoxy-phenyl)-isobutyramide, (2S,4R)—N-[4-(4-fluoro-2-methyl-phenyl)-6-(4-hydroxy-2-hydroxymethyl-pyrrolidin-1-yl)-pyridin-3-yl]-N-methyl-2-(3-trifluoromethoxy-phenyl)-isobutyramide, 2-(3,5-bis-difluoromethoxy-phenyl)-N-[4-(2-chloro-phenyl)-6-piperazin-1-yl-pyridin-3-yl]-N-methyl-isobutyramide, 2-(3,5-bis-difluoromethoxy-phenyl)-N-[4-(4-fluoro-2-methyl-phenyl)-6-piperazin-1-yl-pyridin-3-yl]-N-methyl-isobutyramide, 2-(3,5-bis-difluoromethoxy-phenyl)-N-[4-(2-chloro-phenyl)-6-(4-methanesulfonyl-piperazin-1-yl)-pyridin-3-yl]-N-methyl-isobutyramide, 2-(3,5-bis-difluoromethoxy-phenyl)-N-[4-(4-fluoro-2-methyl-phenyl)-6-(4-methanesulfonyl-piperazin-1-yl)-pyridin-3-yl]-N-methyl-isobutyramide, 2-(3,5-bis-difluoromethoxy-phenyl)-N-methyl-N-(6-piperazin-1-yl-4-o-tolyl-pyridin-3-yl)-isobutyramide and 2-(3,5-bis-difluoromethoxy-phenyl)-N-[6-(4-methanesulfonyl-piperazin-1-yl)-4-o-tolyl-pyridin-3-yl]-N-methyl-isobutyramide.

A preferred group of compounds of formula I are compounds wherein $R^4$ and $R^5$ form together with the N-atom to which they are attached a ring with —$(CH_2)_c$—NR'—$(CH_2)_2$—, which is unsubstituted or substituted by one or more substituents selected from the group consisting of alkyl, halogen, $CF_3$, —$(CR'R'')_d$OH, =O, —CHO, and —NR'R'', wherein R' and R'' are as described above or may form together with the N-atom to which they are attached a ring with —$(CH_2)_e$, or by —$(CH_2)_d$NR'—C(O)-alkyl, —$(CH_2)_d$—C(O)-alkyl, —$(CH_2)_d$—C(O)-cycloalkyl, —$(CH_2)_d$OC(O)NR'R'', —$(CH_2)_d$—S(O)$_2$-alkyl, —$(CH_2)_d$—S(O)-alkyl, —$(CH_2)_d$—S-alkyl, —$(CH_2)_d$—S(O)$_2$—NR'R'', —$(CH_2)_d$-pyrrolidinyl or —C(O)NR'R''.

Preferred from this group are those compounds wherein $R^4$ and $R^5$ form together with the N-atom to which they are attached a ring with —$(CH_2)_c$—NR'—$(CH_2)_2$—, and wherein R' on the N-atom is hydrogen, lower alkyl, C(O)H, C(O)CH$_3$, C(O)-cyclopropyl, S(O)$_2$-alkyl, S(O)$_2$—CH$_2$Cl or S(O)$_2$—N(CH$_3$)$_2$. Examples of such compounds are N-[6-(4-acetyl-piperazin-1-yl)-4-(2-chloro-phenyl)-pyridin-3-yl]-2-(3,5-bis-trifluoromethyl-phenyl)-N-methyl-isobutyramide, 2-(3,5-bis-trifluoromethyl-phenyl)-N-[4-(2-chloro-phenyl)-6-(4-cyclopropanecarbonyl-piperazin-1-yl)-pyridin-3-yl]-N-methyl-isobutyramide, N-[6-(4-acetyl-[1,4]diazepan-1-yl)-4-(2-chloro-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(5-oxo-[1,4]diazepan-1-yl)-pyridin-3-yl]-N-methyl-isobutyramide, 2-(3,5-bis-trifluoromethyl-phenyl)-N-[4-(4-fluoro-2-methyl-phenyl)-6-(3-methanesulfonyl-imidazolidin-1-yl)-pyridin-3-yl]-N-methyl-isobutyramide, N-[6-(3-acetyl-imidazolidin-1-yl)-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[6-(4-methanesulfonyl-piperazin-1-yl)-4-o-tolyl-pyridin-3-yl]-N-methyl-isobutyramide, 2-(3,5-bis-trifluoromethyl-phenyl)-N-[4-(2-chloro-phenyl)-6-(4-methanesulfonyl-piperazin-1-yl)-pyridin-3-yl]-N-methyl-isobutyramide, 2-(3,5-bis-trifluoromethyl-phenyl)-N-[4-(3-chloro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[4-(3-fluoro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[4-(4-fluoro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[6-(4-ethanesulfonyl-piperazin-1-yl)-4-(4-fluoro-2-methyl-phenyl)-pyridin-3-yl]-N-methyl-isobutyramide, 2-(3,5-bis-trifluoromethyl-phenyl)-N-[6-(4-chloromethanesulfonyl-piperazin-1-yl)-4-(4-fluoro-2-methyl-phenyl)-pyridin-3-yl]-N-methyl-isobutyramide, 2-(3,5-bis-trifluoromethyl-phenyl)-N-[6-(4-dimethylsulfamoyl-piperazin-1-yl)-4-(4-fluoro-2-methyl-phenyl)-pyridin-3-yl]-N-methyl-isobutyramide, (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide, (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide, (R)-2-(3,5-bis-trifluoromethyl-phenyl)-N-[4-(2-chloro-phenyl)-6-(4-methanesulfonyl-2-methyl-piperazin-1-yl)-pyridin-3-yl]-N-methyl-isobutyramide, (R)-2-(3,5-bis-trifluoromethyl-phenyl)-N-[6-(4-methanesulfonyl-2-methyl-piperazin-1-yl)-4-o-tolyl-pyridin-3-yl]-N-methyl-isobutyramide, (S)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide, (S)-2-(3,5-bis-trifluoromethyl-phenyl)-N-[4-(2-chloro-phenyl)-6-(–4-methanesulfonyl-3-methyl-piperazin-1-yl)-pyridin-3-yl]-N-methyl-isobutyramide, (S)-2-(3,5-bis-trifluoromethyl-phenyl)-N-[6-(–4-methanesulfonyl-3-methyl-piperazin-1-yl)-4-o-tolyl-pyridin-3-yl]-N-methyl-isobutyramide, (S)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide, (2RS,5SR)-2-(3,5-bis-trifluoromethyl-phenyl)-N-[4-(4-fluoro-2-methyl-phenyl)-6-(4-methanesulfonyl-2,5-dimethyl-piperazin-1-yl)-pyridin-3-yl]-N-methyl-isobutyramide, (2S,6R)-2-(3,5-bis-trifluoromethyl-phenyl)-N-[4-(4-fluoro-2-methyl-phenyl)-6-(4-methanesulfonyl-2,6-dimethyl-piperazin-1-yl)-pyridin-3-yl]-N-methyl-isobutyramide, (3S,5R)-2-(3,5-bis-trifluoromethyl-phenyl)-N-[4-(4-fluoro-2-methyl-phenyl)-6-(4-methanesulfonyl-3,5-dimethyl-piperazin-1-yl)-pyridin-3-yl]-N-methyl-isobutyramide, (S)-2-(3,5-bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide, (S)-2-(3,5-bis-trifluoromethyl-phenyl)-N-[4-(4-fluoro-2-methyl-phenyl)-6-(4-formyl-2-hydroxymethyl-piperazin-1-yl)-pyridin-3-yl]-N-methyl-isobutyramide, (S)-2-(3,5-bis-trifluoromethyl-phenyl)-N-[6-(4-cyclopropanecarbonyl-2-hydroxymethyl-piperazin-1-yl)-4-(4-fluoro-2-methyl-phenyl)-pyridin-3-yl]-N-methyl-isobutyramide, (S)—N-[6-(4-acetyl-2-hydroxymethyl-piperazin-1-yl)-4-(4-fluoro-2-methyl-phenyl)-pyridin-3-yl]-2-(3,5-bis-trifluoromethyl-phenyl)-N-methyl-isobutyramide, (S)-2-(3,5-bis-trifluoromethyl-phenyl)-N-[6-(4-ethyl-2-hydroxymethyl-piperazin-1-yl)-4-(4-fluoro-2-methyl-phenyl)-pyridin-3-yl]-N-methyl-isobutyramide, (S)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide,
(R)-2-(3,5-bis-trifluoromethyl-phenyl)-N-[6-(3-hydroxymethyl-4-methanesulfonyl-piperazin-1-yl)-4-o-tolyl-pyridin-3-yl]-N-methyl-isobutyramide,
(R)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide,
2-(3,5-bis-trifluoromethyl-phenyl)-N-[4-(4-fluoro-2-methyl-phenyl)-6-(4-methanesulfonyl-3,3-dimethyl-piperazin-1-yl)-pyridin-3-yl]-N-methyl-isobutyramide,
2-(3,5-bis-trifluoromethyl-phenyl)-N-[6-(4-methanesulfonyl-3,3-dimethyl-piperazin-1-yl)-4-o-tolyl-pyridin-3-yl]-N-methyl-isobutyramide,
(S)-2-(3,5-bis-trifluoromethyl-phenyl)-N-[4-(2-hydroxymethyl-phenyl)-6-(–4-methanesulfonyl-3-methyl-piperazin-1-yl)-pyridin-3-yl]-N-methyl-isobutyramide,
2-(3,5-bis-trifluoromethyl-phenyl)-N-[4-(4-fluoro-2-methyl-phenyl)-6-(4-methanesulfonyl-2,2-dimethyl-piperazin-1-yl)-pyridin-3-yl]-N-methyl-isobutyramide,
2-(3,5-bis-trifluoromethyl-phenyl)-N-[6-(4-methanesulfonyl-2,2-dimethyl-piperazin-1-yl)-4-o-tolyl-pyridin-3-yl]-N-methyl-isobutyramide,
2-(3,5-bis-difluoromethoxy-phenyl)-N-[4-(2-chloro-phenyl)-6-piperazin-1-yl-pyridin-3-yl]-N-methyl-isobutyramide,
2-(3,5-bis-difluoromethoxy-phenyl)-N-[4-(4-fluoro-2-methyl-phenyl)-6-piperazin-1-yl-pyridin-3-yl]-N-methyl-isobutyramide,
2-(3,5-bis-difluoromethoxy-phenyl)-N-[4-(2-chloro-phenyl)-6-(4-methanesulfonyl-piperazin-1-yl)-pyridin-3-yl]-N-methyl-isobutyramide,
2-(3,5-bis-difluoromethoxy-phenyl)-N-[4-(4-fluoro-2-methyl-phenyl)-6-(4-methanesulfonyl-piperazin-1-yl)-pyridin-3-yl]-N-methyl-isobutyramide,
2-(3,5-bis-difluoromethoxy-phenyl)-N-methyl-N-(6-piperazin-1-yl-4-o-tolyl-pyridin-3-yl)-isobutyramide and
2-(3,5-bis-difluoromethoxy-phenyl)-N-[6-(4-methanesulfonyl-piperazin-1-yl)-4-o-tolyl-pyridin-3-yl]-N-methyl-isobutyramide.

The following compounds of formulas IA to IJ, are novel. Encompassed by formula I are compounds of formula IA

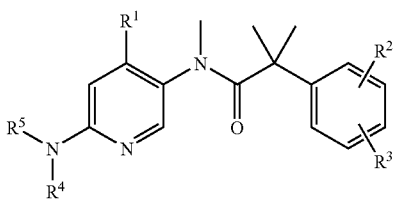

IA wherein
$R^1$ is phenyl, unsubstituted or substituted by one or more substituents selected from the group consisting of alkyl, alkoxy, halogen, —(CH$_2$)$_d$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl;
$R^2$ and $R^3$ are each independently hydrogen, halogen, alkyl, alkoxy, OCHF$_2$, OCH$_2$F, OCF$_3$ or CF$_3$;
$R^4$ and $R^5$ are each independently
hydrogen,
—(CR'R")$_1$—(CR'R")$_1$—(CR'R")$_a$—OH, or
—(CR'R")$_1$—(CR'R")$_1$—(CR'R")$_a$-alkyl, wherein R' and R" on each carbon atom may be the same or different from each other and are hydrogen
or C$_b$-alkyl;
R' is hydrogen, alkyl, —(CH$_2$)$_d$OH, —C(O)H, —C(O)-alkyl, —C(O)-cycloalkyl, —S(O)$_2$-alkyl, —S(O)$_2$-halogen-alkyl, —S(O)-alkyl, —S-alkyl or —S(O)$_2$—N-di-alkyl,
R" is hydrogen or alkyl;
a is 0 or 1;
b is 1 or 2; and
d is 0, 1, 2 or 3;
or a pharmaceutically active acid-addition salt thereof.
Some specific compounds of formula IA are
N-[4-(2-chloro-phenyl)-6-(2-hydroxy-ethylamino)-pyridin-3-yl]-2-(3,5-dichloro-phenyl)-N-methyl-isobutyramide,
2-(3,5-dichloro-phenyl)-N-[4-(4-fluoro-2-methyl-phenyl)-6-(2-hydroxy-ethylamino)-pyridin-3-yl]-N-methyl-isobutyramide,
2-(3,5-bis-trifluoromethyl-phenyl)-N-[4-(2-chloro-phenyl)-6-[(2-hydroxy-ethyl)-methyl-amino]-pyridin-3-yl]-N-methyl-isobutyramide,
2-(3,5-bis-trifluoromethyl-phenyl)-N-[4-(2-chloro-phenyl)-6-[ethyl-(2-hydroxy-ethyl)-amino]-pyridin-3-yl]-N-methyl-isobutyramide,
2-(3,5-bis-trifluoromethyl-phenyl)-N-[4-(2-chloro-phenyl)-6-[(2-hydroxy-ethyl)-propyl-amino]-pyridin-3-yl]-N-methyl-isobutyramide,
2-(3,5-bis-trifluoromethyl-phenyl)-N-[6-[butyl-(2-hydroxy-ethyl)-amino]-4-(2-chloro-phenyl)-pyridin-3-yl]-N-methyl-isobutyramide,
(RS)-2-(3,5-bis-trifluoromethyl-phenyl)-N-[4-(2-chloro-phenyl)-6-[(2,3-dihydroxy-propyl)-methyl-amino]-pyridin-3-yl]-N-methyl-isobutyramide,
(S)-2-(3,5-bis-trifluoromethyl-phenyl)-N-[4-(2-chloro-phenyl)-6-(1-hydroxymethyl-3-methyl-butylamino)-pyridin-3-yl]-N-methyl-isobutyramide,
2-(3,5-bis-trifluoromethyl-phenyl)-N-[4-(4-fluoro-2-methyl-phenyl)-6-(2-hydroxy-ethylamino)-pyridin-3-yl]-N-methyl-isobutyramide,
2-(3,5-bis-trifluoromethyl-phenyl)-N-[4-(2-chloro-4-fluoro-phenyl)-6-(2-hydroxy-ethylamino)-pyridin-3-yl]-N-methyl-isobutyramide,
2-(3,5-bis-trifluoromethyl-phenyl)-N-[4-(2,4-dichloro-phenyl)-6-(2-hydroxy-ethylamino)-pyridin-3-yl]-N-methyl-isobutyramide,
(S)-2-(3,5-bis-trifluoromethyl-phenyl)-N-[4-(2,4-dichloro-phenyl)-6-(2-hydroxy-propylamino)-pyridin-3-yl]-N-methyl-isobutyramide,
(S)-2-(3,5-bis-trifluoromethyl-phenyl)-N-[4-(2-chloro-phenyl)-6-(2-hydroxy-propylamino)-pyridin-3-yl]-N-methyl-isobutyramide,
(R)-2-(3,5-bis-trifluoromethyl-phenyl)-N-[4-(2-chloro-phenyl)-6-(2-hydroxy-propylamino)-pyridin-3-yl]-N-methyl-isobutyramide,
(RS)-2-(3,5-bis-trifluoromethyl-phenyl)-N-[4-(2-chloro-phenyl)-6-(2-hydroxy-propylamino)-pyridin-3-yl]-N-methyl-isobutyramide,
2-(3,5-bis-trifluoromethyl-phenyl)-N-[4-(2-chloro-phenyl)-6-(2-hydroxy-2-methyl-propylamino)-pyridin-3-yl]-N-methyl-isobutyramide,
2-(3,5-bis-trifluoromethyl-phenyl)-N-[4-(2-chloro-phenyl)-6-(2-hydroxy-butylamino)-pyridin-3-yl]-N-methyl-isobutyramide,
(S)-2-(3,5-bis-trifluoromethyl-phenyl)-N-[4-(4-fluoro-2-methyl-phenyl)-6-(2-hydroxy-propylamino)-pyridin-3-yl]-N-methyl-isobutyramide, (RS)-2-(3,5-bis-trifluoromethyl-phenyl)-N-[4-(2-chloro-phenyl)-6-(2,3-dihydroxy-propylamino)-pyridin-3-yl]-N-methyl-isobutyramide, (S)-2-(3,5-bis-trifluoromethyl-phenyl)-N-[4-(2-chloro-phenyl)-6-(2-hydroxy-1-methyl-ethylamino)-pyridin-3-yl]-N-methyl-isobutyramide, (R)-2-(3,5-bis-trifluoromethyl-phenyl)-N-[4-(2-chloro-phenyl)-6-(2-hydroxy-1-methyl-ethylamino)-pyridin-3-yl]-N-methyl-isobutyramide, 2-(3,5-bis-trifluoromethyl-phenyl)-N-[4-(2-chloro-phenyl)-6-(2-hydroxy-1-hydroxymethyl-ethylamino)-pyridin-3-yl]-N-methyl-isobutyramide, N-[6-[bis-(2-hydroxy-ethyl)-amino]-4-(2-chloro-phenyl)-pyridin-3-yl]-2-(3,5-bis-trifluoromethyl-phenyl)-N-methyl-isobutyramide, N-{6-[bis-(2-hydroxy-ethyl)-amino]-4-o-tolyl-pyridin-3-yl]-2-(3,5-bis-trifluoromethyl-phenyl)-N-methyl-isobutyramide, N-[6-[bis-(2-hydroxy-ethyl)-amino]-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-[(2-hydroxy-ethyl)-(3-hydroxy-propyl)-amino]-pyridin-3-yl]-N-methyl-isobutyramide, N-[6-[bis-(2-hydroxy-ethyl)-amino]-4-(2,4-dichloro-phenyl)-pyridin-3-yl]-2-(3,5-bis-trifluoromethyl-phenyl)-N-methyl-isobutyramide, N-[6-[bis-(2-hydroxy-ethyl)-amino]-4-(3,4-dichloro-phenyl)-pyridin-3-yl]-2-(3,5-bis-trifluoromethyl-phenyl)-N-methyl-isobutyramide, N-[6-[bis-(2-hydroxy-ethyl)-amino]-4-(4-fluoro-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-phenyl)-6-[(2-hydroxy-ethyl)-methyl-amino]-pyridin-3-yl]-N-methyl-isobutyramide, 2-(3,5-bis-trifluoromethyl-phenyl)-N-[6-[ethyl-(2-hydroxy-ethyl)-amino]-4-(4-fluoro-phenyl)-pyridin-3-yl]-N-methyl-isobutyramide, 2-(3,5-bis-trifluoromethyl-phenyl)-N-[6-[ethyl-(2-hydroxy-ethyl)-amino]-4-o-tolyl-pyridin-3-yl]-N-methyl-isobutyramide, 2-(3,5-bis-trifluoromethyl-phenyl)-N-[6-[(2-hydroxy-ethyl)-propyl-amino]-4-o-tolyl-pyridin-3-yl]-N-methyl-isobutyramide, (S)-2-(3,5-bis-trifluoromethyl-phenyl)-N-[6-(2-hydroxy-propylamino)-4-o-tolyl-pyridin-3-yl]-N-methyl-isobutyramide, N-[6-[bis-(2-hydroxy-propyl)-amino]-4-o-tolyl-pyridin-3-yl]-2-(3,5-bis-trifluoromethyl-phenyl)-N-methyl-isobutyramide, (S)-2-(3,5-bis-trifluoromethyl-phenyl)-N-[6-(2,3-dihydroxy-propylamino)-4-o-tolyl-pyridin-3-yl]-N-methyl-isobutyramide, (R)-2-(3,5-bis-trifluoromethyl-phenyl)-N-[6-(2,3-dihydroxy-propylamino)-4-o-tolyl-pyridin-3-yl]-N-methyl-isobutyramide, N-[6-[bis-(2-hydroxy-propyl)-amino]-4-(2-chloro-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-chloro-phenyl)-6-(2,3-dihydroxy-propylamino)-pyridin-3-yl]-N-methyl-isobutyramide, (R)-2-(3,5-bis-trifluoromethyl-phenyl)-N-[4-(2-chloro-phenyl)-6-(2,3-dihydroxy-propylamino)-pyridin-3-yl]-N-methyl-isobutyramide, N-[6-[bis-(2-hydroxy-ethyl)-amino]-4-(3-fluoro-2-methyl-phenyl)-pyridin-3-yl]-2-(3,5-bis-trifluoromethyl-phenyl)-N-methyl-isobutyramide, N-[6-[bis-(2-hydroxy-ethyl)-amino]-4-(5-fluoro-2-methyl-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-bromo-phenyl)-6-(2-hydroxy-propylamino)-pyridin-3-yl]-N-methyl-isobutyramide, N-[6-[bis-(2-hydroxy-ethyl)-amino]-4-(2-bromo-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide, 2-(3,5-bis-trifluoromethyl-phenyl)-N-[6-(2-hydroxy-1-hydroxymethyl-ethylamino)-4-o-tolyl-pyridin-3-yl]-N-methyl-isobutyramide, (1R,2R)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1R,2S)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1S,2R)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, (1S,2S)-2-(3,5-bis-trifluoromethyl-phenyl)-N-[4-(2-chloro-phenyl)-6-(2-hydroxy-1-hydroxymethyl-propylamino)-pyridin-3-yl]-N-methyl-isobutyramide, 2-(3,5-bis-trifluoromethyl-phenyl)-N-[4-(2-chloro-phenyl)-6-[hexyl-(2-hydroxy-ethyl)-amino]-pyridin-3-yl]-N-methyl-isobutyramide, 2-(3,5-bis-trifluoromethyl-phenyl)-N-[4-(2-chloro-phenyl)-6-[(2-hydroxy-ethyl)-pentyl-amino]-pyridin-3-yl]-N-methyl-isobutyramide, 2-(3,5-bis-trifluoromethyl-phenyl)-N-[4-(2-chloro-phenyl)-6-[(2-hydroxy-ethyl)-(3-hydroxy-propyl)-amino]-pyridin-3-yl]-N-methyl-isobutyramide, (R)-2-(3,5-bis-trifluoromethyl-phenyl)-N-[6-(2-hydroxy-propylamino)-4-o-tolyl-pyridin-3-yl]-N-methyl-isobutyramide and 2-(3,5-bis-trifluoromethyl-phenyl)-N-[4-(4-fluoro-2-methyl-phenyl)-6-[(2-hydroxy-1-hydroxymethyl-ethyl)-methyl-amino]-pyridin-3-yl]-N-methyl-isobutyramide.

Other compounds of formula I are compounds of formula IB

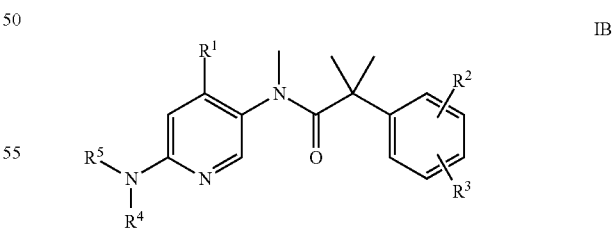

wherein

R$^1$ is phenyl, unsubstituted or substituted by one or more substituents selected from the group consisting of alkyl, alkoxy, halogen, —(CH$_2$)$_a$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl;

R$^2$ and R$^3$ are each independently hydrogen, halogen, alkyl, alkoxy, OCHF$_2$, OCH$_2$F, OCF$_3$ or CF$_3$;

R⁴ and R⁵ are each independently hydrogen, —(CH₂)₂SCH₃, —(CH₂)₂S(O)₂CH₃, —(CH₂)₂S(O)NHCH₃, —(CH₂)₂NH₂, —(CH₂)₂NHS(O)₂CH₃ or —(CH₂)₂NHC(O)CH₃;
R' is hydrogen, alkyl, —(CH₂)ₐOH, —C(O)H, —C(O)-alkyl, —C(O)-cycloalkyl, —S(O)₂-alkyl, —S(O)₂-halogen-alkyl, —S(O)-alkyl, —S-alkyl or —S(O)₂—N-di-alkyl;
R" is hydrogen or alkyl;
b is 1 or 2; and
d is 0, 1, 2, or 3;
or a pharmaceutically active acid-addition salt thereof.

Some specific compounds of formula IB are
2-(3,5-bis-trifluoromethyl-phenyl)-N-[4-(2-chloro-phenyl)-6-(2-methanesulfonyl-ethylamino)-pyridin-3-yl]-N-methyl-isobutyramide,
2-(3,5-bis-trifluoromethyl-phenyl)-N-[4-(4-fluoro-2-methyl-phenyl)-6-(2-methylsulfanyl-ethylamino)-pyridin-3-yl]-N-methyl-isobutyramide,
2-(3,5-bis-trifluoromethyl-phenyl)-N-[4-(4-fluoro-2-methyl-phenyl)-6-(2-methanesulfonyl-ethylamino)-pyridin-3-yl]-N-methyl-isobutyramide,
N-[6-(2-amino-ethylamino)-4-(4-fluoro-2-methyl-phenyl)-pyridin-3-yl]-2-(3,5-bis-trifluoromethyl-phenyl)-N-methyl-isobutyramide,
2-(3,5-bis-trifluoromethyl-phenyl)-N-[4-(4-fluoro-2-methyl-phenyl)-6-(2-methanesulfonylamino-ethylamino)-pyridin-3-yl]-N-methyl-isobutyramide and 2-(3,5-bis-trifluoromethyl-phenyl)-N-[4-(2-chloro-phenyl)-6-(2-methylsulfamoyl-ethylamino)-pyridin-3-yl]-N-methyl-isobutyramide.

Also encompassed by formula I are compounds of formula IC

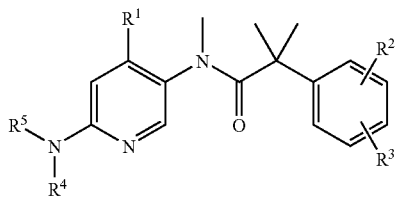

IC wherein
R¹ is phenyl, unsubstituted or substituted by one or more substituents selected from the group consisting of alkyl, alkoxy, halogen, —(CH₂)ₐOH, —C(O)H, CF₃, CN, S-alkyl, —S(O)ᵦ-alkyl, —C(O)NR'R", —NR'R", —NR'C(O)-alkyl and —NR'S(O)₂-alkyl;
R² and R³ are each independently hydrogen, halogen, alkyl, alkoxy, OCHF₂, OCH₂F, OCF₃ or CF₃;
R⁴ is hydrogen;
R⁵ is —(CH₂)ₒ-cycloalkyl, unsubstituted or substituted by hydroxy;
R' is hydrogen, alkyl, —(CH₂)ₐOH, —C(O)H, —C(O)-alkyl, —C(O)-cycloalkyl, —S(O)₂-alkyl, —S(O)₂-halogen-alkyl, —S(O)-alkyl, —S-alkyl or —S(O)₂—N-di-alkyl;
R" is hydrogen or alkyl;
b is 1 or 2; and
d is 0, 1, 2, or 3;
or a pharmaceutically active acid-addition salt thereof.

Some compounds of formula IC are trans-2-(3,5-bis-trifluoromethyl-phenyl)-N-[4-(2-chloro-phenyl)-6-(4-hydroxy-cyclohexylamino)-pyridin-3-yl]-N-methyl-isobutyramide,
trans-2-(3,5-bis-trifluoromethyl-phenyl)-N-[4-(2,4-dichloro-phenyl)-6-(4-hydroxy-cyclohexylamino)-pyridin-3-yl]-N-methyl-isobutyramide,
trans-2-(3,5-bis-trifluoromethyl-phenyl)-N-[4-(4-fluoro-2-methyl-phenyl)-6-(4-hydroxy-cyclohexylamino)-pyridin-3-yl]-N-methyl-isobutyramide,
trans-2-(3,5-bis-trifluoromethyl-phenyl)-N-[4-(2-bromo-phenyl)-6-(4-hydroxy-cyclohexylamino)-pyridin-3-yl]-N-methyl-isobutyramide,
(1RS,2RS)-2-(3,5-bis-trifluoromethyl-phenyl)-N-[4-(2-chloro-phenyl)-6-(2-hydroxy-cyclohexylamino)-pyridin-3-yl]-N-methyl-isobutyramide,
(1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide,
(1S,2S)-2-(3,5-bis-trifluoromethyl-phenyl)-N-[4-(2-chloro-phenyl)-6-(2-hydroxy-cyclopentylamino)-pyridin-3-yl]-N-methyl-isobutyramide and
(1S,2S)-2-(3,5-bis-trifluoromethyl-phenyl)-N-[4-(4-fluoro-2-methyl-phenyl)-6-(2-hydroxy-cyclopentylamino)-pyridin-3-yl]-N-methyl-isobutyramide.

Other compounds encompassed by formula I are compounds of formula ID

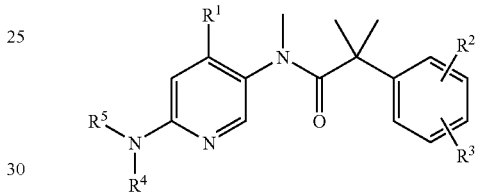

ID wherein
R¹ is phenyl, unsubstituted or substituted by one or more substituents selected from the group consisting of alkyl, alkoxy, halogen, —(CH₂)ₐOH, —C(O)H, CF₃, CN, S-alkyl, —S(O)ᵦ-alkyl, —C(O)NR'R", —NR'R", —NR'C(O)-alkyl and —NR'S(O)₂-alkyl;
R² and R³ are each independently hydrogen, halogen, alkyl, alkoxy, OCHF₂, OCH₂F, OCF₃ or CF₃;
R⁴ and R⁵ form together with the N-atom to which they are attached a ring with —(CH₂)ₑ—, which is unsubstituted or substituted by one or more substituents selected from the group consisting of —(CR'R")ₐOH;
R' is hydrogen, alkyl, —(CH₂)ₐOH, —C(O)H, —C(O)-alkyl, —C(O)-cycloalkyl, —S(O)₂-alkyl, —S(O)₂-halogen-alkyl, —S(O)-alkyl, —S-alkyl or —S(O)₂—N-di-alkyl;
R" is hydrogen or alkyl;
b is 1 or 2;
d is 0, 1, 2, or 3; and
e is 3, 4, or 5;
or a pharmaceutically active acid-addition salt thereof.

Examples of compounds of formula ID are
wherein the compounds are selected from the group consisting of
(S)—N-[4-(2-chloro-phenyl)-6-(2-hydroxymethyl-pyrrolidin-1-yl)-pyridin-3-yl]-2-(3,5-dichloro-phenyl)-N-methyl-isobutyramide,
(2S,4R)—N-[4-(2-chloro-phenyl)-6-(4-hydroxy-2-hydroxymethyl-pyrrolidin-1-yl)-pyridin-3-yl]-2-(3,5-dichloro-phenyl)-N-methyl-isobutyramide,
(S)—N-[4-(2-chloro-phenyl)-6-(2-hydroxymethyl-pyrrolidin-1-yl)-pyridin-3-yl]-2-(3-fluoro-5-trifluoromethyl-phenyl)-N-methyl-isobutyramide,
(2S,4R)—N-[4-(2-chloro-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-difluoro-phenyl)-N-methyl-isobutyramide, (S)-2-(3-chloro-5-methoxy-phenyl)-N-[4-(2-chloro-phenyl)-6-(2-hydroxymethyl-pyrrolidin-1-yl)-pyridin-3-yl]-N-methyl-isobutyramide, (2S,4R)-2-(3-chloro-5-methoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)—N-[4-(2-chloro-phenyl)-6-(2-hydroxymethyl-pyrrolidin-1-yl)-pyridin-3-yl]-2-(3,5-dimethyl-phenyl)-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-dimethyl-phenyl)-N-methyl-isobutyramide, (S)-2-(3,5-dichloro-phenyl)-N-[6-(2-hydroxymethyl-pyrrolidin-1-yl)-4-o-tolyl-pyridin-3-yl]-N-methyl-isobutyramide, (2S,4R)-2-(3,5-dichloro-phenyl)-N-[6-(4-hydroxy-2-hydroxymethyl-pyrrolidin-1-yl)-4-o-tolyl-pyridin-3-yl]-N-methyl-isobutyramide, (S)-2-(3-fluoro-5-trifluoromethyl-phenyl)-N-[6-(2-hydroxymethyl-pyrrolidin-1-yl)-4-o-tolyl-pyridin-3-yl]-N-methyl-isobutyramide, (2R,4S)-2-(3-fluoro-5-trifluoromethyl-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-difluoro-phenyl)-N-[6-(2-hydroxymethyl-pyrrolidin-1-yl)-4-o-tolyl-pyridin-3-yl]-N-methyl-isobutyramide, (2S,4R)-2-(3,5-difluoro-phenyl)-N-[6-(4-hydroxy-2-hydroxymethyl-pyrrolidin-1-yl)-4-o-tolyl-pyridin-3-yl]-N-methyl-isobutyramide, (S)-2-(3-chloro-5-methoxy-phenyl)-N-[6-(2-hydroxymethyl-pyrrolidin-1-yl)-4-o-tolyl-pyridin-3-yl]-N-methyl-isobutyramide, (2S,4R)-2-(3-chloro-5-methoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dimethyl-phenyl)-N-[6-(2-hydroxymethyl-pyrrolidin-1-yl)-4-o-tolyl-pyridin-3-yl]-N-methyl-isobutyramide, (2S,4R)-2-(3,5-dimethyl-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dichloro-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-dichloro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)—N-[4-(4-fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide, (2S,4R)—N-[4-(4-fluoro-2-methyl-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide, (S)—N-[4-(4-fluoro-2-methyl-phenyl)-6-(2-hydroxymethyl-pyrrolidin-1-yl)-pyridin-3-yl]-N-methyl-2-(3-trifluoromethyl-phenyl)-isobutyramide, (2S,4R)—N-[4-(4-fluoro-2-methyl-phenyl)-6-(4-hydroxy-2-hydroxymethyl-pyrrolidin-1-yl)-pyridin-3-yl]-N-methyl-2-(3-trifluoromethyl-phenyl)-isobutyramide, (S)-2-(3,5-difluoro-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-difluoro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)-2-(3-chloro-5-methoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3-chloro-5-methoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)-(3,5-dimethyl-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-dimethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)-2-(3-chloro-5-difluoromethoxy-phenyl)-N-[4-(2-chloro-phenyl)-6-(2-hydroxymethyl-pyrrolidin-1-yl)-pyridin-3-yl]-N-methyl-isobutyramide, (2S,4R)-2-(3-chloro-5-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)-2-(3-chloro-5-difluoromethoxy-phenyl)-N-[6-(2-hydroxymethyl-pyrrolidin-1-yl)-4-o-tolyl-pyridin-3-yl]-N-methyl-isobutyramide, (2S,4R)-2-(3-chloro-5-difluoromethoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3-chloro-5-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3-chloro-5-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide, (R)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2-chloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2-chloro-phenyl)-6-(3-hydroxy-pyrrolidin-1-yl)-pyridin-3-yl]-N-methyl-isobutyramide, (R)-2-(3,5-bis-trifluoromethyl-phenyl)-N-[4-(2-chloro-phenyl)-6-(3-hydroxy-pyrrolidin-1-yl)-pyridin-3-yl]-N-methyl-isobutyramide, (3R,4S)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide, (3R,4R)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide, (R)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide, (R)-2-(3,5-bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide, (R)-2-(3,5-bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide, (2R,4R)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide, (S)-2-(3,5-bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide, (RS)-2-(3,5-bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide, (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-bromo-phenyl)-6-(3-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,4-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-chloro-phenyl)-6-(3-hydroxy-2-hydroxymethyl-pyrrolidin-1-yl)-pyridin-3-yl]-N-methyl-isobutyramide, (2R,4S)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide, (2R,3R)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (S)-2-(3,5-bis-trifluoromethyl-phenyl)-N-{4-(4-fluoro-2-methyl-phenyl)-6-[2-(1-hydroxy-1-methyl-ethyl)-pyrrolidin-1-yl]-pyridin-3-yl}-N-methyl-isobutyramide, (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(5-fluoro-2-methyl-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(3-fluoro-2-methyl-phenyl)-6-(2-hydroxymethyl-pyrrolidin-1-yl)-pyridin-3-yl]-N-methyl-isobutyramide, (R)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide, (RS)-2-(3,5-bis-trifluoromethyl-phenyl)-N-[4-(2-chloro-phenyl)-6-(3-hydroxymethyl-pyrrolidin-1-yl)-pyridin-3-yl]-N-methyl-isobutyramide, (3S,4S)-2-(3,5-bis-trifluoromethyl-phenyl)-N-[4-(2-chloro-phenyl)-6-(3,4-dihydroxy-pyrrolidin-1-yl)-pyridin-3-yl]-N-methyl-isobutyramide, (3S,4S)-2-(3,5-bis-trifluoromethyl-phenyl)-N-[6-(3,4-dihydroxy-pyrrolidin-1-yl)-4-o-tolyl-pyridin-3-yl]-N-methyl-isobutyramide, (3R,4S)-2-(3,5-bis-trifluoromethyl-phenyl)-N-[6-(3,4-dihydroxy-pyrrolidin-1-yl)-4-o-tolyl-pyridin-3-yl]-N-methyl-isobutyramide, (2R,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide, (2S,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide, (2R,5R)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide, (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-phenyl-pyridin-3-yl]-N-methyl-isobutyramide, (2S,4R)-2-(3,5-bis-trifluoromethyl-phenyl)-N-[4-(4-fluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-chloro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-dimethylamino-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-bromo-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-chloro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3,5-difluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3,4-difluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-fluoro-4-methyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-chloro-4-fluoro-phenyl)-6-(4-hydroxy-2-hydroxymethyl-pyrrolidin-1-yl)-pyridin-3-yl]-N-methyl-isobutyramide, (2S,4R)—N-[4-(2-amino-phenyl)-6-(4-hydroxy-2-hydroxymethyl-pyrrolidin-1-yl)-pyridin-3-yl]-2-(3,5-bis-trifluoromethyl-phenyl)-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-methoxyphenyl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-hydroxyphenyl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-methylsulfanyl-phenyl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-methanesulfonyl-phenyl)-pyridin-3-yl]-N-methyl-isobutyramide, (2S,4R)-2-[5-{[2-(3,5-bis-trifluoromethyl-phenyl)-2-methyl-propionyl]-methyl-amino}-2-(4-hydroxy-2-hydroxymethyl-pyrrolidin-1-yl)-pyridin-4-yl]-benzamide, (2S,4R)-2-(3,5-bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2-formyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[6-(4-hydroxy-2-hydroxymethyl-pyrrolidin-1-yl)-4-(2-hydroxymethyl-phenyl)-pyridin-3-yl]-N-methyl-isobutyramide, (2S,4R)-2-(3,5-bis-trifluoromethyl-phenyl)-N-[4-(2,5-dichloro-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide, (2S,4R)-2-(3,5-bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2S,4S)-2-(3,5-bis-trifluoromethyl-phenyl)-N-[4-(2-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-(2-trifluoromethyl-phenyl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-(2-methoxyphenyl)-pyridin-3-yl]-N-methyl-isobutyramide, (2S,4S)-2-(3,5-bis-trifluoromethyl-phenyl)-N-[4-(2-cyanophenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2-bromophenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[6-(4-hydroxy-2-hydroxymethyl-pyrrolidin-1-yl)-4-phenyl-pyridin-3-yl]-N-methyl-isobutyramide, (2S,4S)-2-(3,5-bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide, (2S,4S)-2-(3,5-bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide, (2R,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2R,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2R,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2R,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-(2-trifluoromethyl-phenyl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-(2-methoxyphenyl)-pyridin-3-yl]-N-methyl-isobutyramide, (2R,3S)-2-(3,5-bis-trifluoromethyl-phenyl)-N-[4-(2-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-phenyl-pyridin-3-yl]-N-methyl-isobutyramide, (2R,3S)-2-(3,5-bis-trifluoromethyl-phenyl)-N-[4-(4-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[6-(3-hydroxy-2-hydroxymethyl-pyrrolidin-1-yl)-4-p-tolyl-pyridin-3-yl]-N-methyl-isobutyramide, (2R,3S)-2-(3,5-bis-trifluoromethyl-phenyl)-N-[4-(3,4-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-chloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,5-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,3-dichloro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2-chloro-4-fluoro-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-formyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(4-fluoro-2-hydroxymethyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(3-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(5-fluoro-2-methyl-phenyl)-6-(3-hydroxy-2-hydroxymethyl-pyrrolidin-1-yl)-pyridin-3-yl]-N-methyl-isobutyramide, (2R,3S)-2-(3,5-bis-trifluoromethyl-phenyl)-N-[4-(2,5-difluoro-phenyl)-6-(3-hydroxy-2-hydroxymethyl-pyrrolidin-1-yl)-pyridin-3-yl]-N-methyl-isobutyramide, (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide, (S)-2-(3,5-bis-trifluoromethyl-phenyl)-N-[6-(2-hydroxymethyl-pyrrolidin-1-yl)-4-(2-methoxy-phenyl)-pyridin-3-yl]-N-methyl-isobutyramide, (S)-2-(3,5-bis-trifluoromethyl-phenyl)-N-[4-(2-bromo-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2-fluoro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,5-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(2,3-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(4-chloro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[4-(4-fluoro-phenyl)-6-(2-hydroxymethyl-pyrrolidin-1-yl)-pyridin-3-yl]-N-methyl-isobutyramide, (S)-2-(3,5-bis-trifluoromethyl-phenyl)-N-[6-(2-hydroxymethyl-pyrrolidin-1-yl)-4-phenyl-pyridin-3-yl]-N-methyl-isobutyramide, (3R,5S)-2-(3,5-bis-trifluoromethyl-phenyl)-N-[4'-(4-fluoro-2-methyl-phenyl)-3,5-dihydroxy-3,4,5,6-tetrahydro-2H-[1,2']bipyridinyl-5'-yl]-N-methyl-isobutyramide, (3S,5S)-2-(3,5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide, 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide, (RS)-2-(3,5-bis-trifluoromethyl-phenyl)-N-[4-(4-fluoro-2-methyl-phenyl)-6-(3-hydroxymethyl-pyrrolidin-1-yl)-pyridin-3-yl]-N-methyl-isobutyramide, (S)-2-(3,5-dimethoxy-phenyl)-N-[6-(2-hydroxymethyl-pyrrolidin-1-yl)-4-o-tolyl-pyridin-3-yl]-N-methyl-isobutyramide, (2S,4R)-2-(3,5-dimethoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-dimethoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-dimethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4R)—N-[4-(2-chloro-phenyl)-6-(4-hydroxy-2-hydroxymethyl-pyrrolidin-1-yl)-pyridin-3-yl]-2-(3,5-dimethoxy-phenyl)-N-methyl-isobutyramide, (2S,4R)-2-(3,5-bis-difluoromethoxy-phenyl)-N-[6-(4-hydroxy-2-hydroxymethyl-pyrrolidin-1-yl)-4-o-tolyl-pyridin-3-yl]-N-methyl-isobutyramide, (S)-2-(3,5-bis-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide, (2S,4R)-2-(3,5-bis-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide, (S)-2-(3,5-bis-difluoromethoxy-phenyl)-N-[4-(2-chloro-phenyl)-6-(2-hydroxymethyl-pyrrolidin-1-yl)-pyridin-3-yl]-N-methyl-isobutyramide, (2S,4R)-2-(3,5-bis-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide, (2S,4R)—N-[6-(4-hydroxy-2-hydroxymethyl-pyrrolidin-1-yl)-4-o-tolyl-pyridin-3-yl]-N-methyl-2-(3-trifluoromethoxy-phenyl)-isobutyramide and (2S,4R)—N-[4-(4-fluoro-2-methyl-phenyl)-6-(4-hydroxy-2-hydroxymethyl-pyrrolidin-1-yl)-pyridin-3-yl]-N-methyl-2-(3-trifluoromethoxy-phenyl)-isobutyramide.

Specific compounds of formula ID, encompassed by formula I, which ring is substituted by one to three substituents, selected from the group consisting of —NR'R", —$(CH_2)_d$—C(O)-lower alkyl, —$CH_2OH$, —$(CH_2)_d$-pyrrolidinyl, —$(CH_2)_d$—$S(O)_2$-alkyl, =O, halogen or —$(CH_2)_d$OC(O)NR'R", are the followings (2S,4S)—N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide, (S)—N-[6-(3-acetylamino-pyrrolidin-1-yl)-4-(2-chloro-phenyl)-pyridin-3-yl]-2-(3,5-bis-trifluoromethyl-phenyl)-N-methyl-isobutyramide, (R)—N-[6-(3-acetylamino-pyrrolidin-1-yl)-4-(2-chloro-phenyl)-pyridin-3-yl]-2-(3,5-bis-trifluoromethyl-phenyl)-N-methyl-isobutyramide, (RS)—N-[6-[3-(acetyl-ethyl-amino)-pyrrolidin-1-yl]-4-(2-chloro-phenyl)-pyridin-3-yl]-2-(3,5-bis-trifluoromethyl-phenyl)-N-methyl-isobutyramide, (S)-2-(3,5-bis-trifluoromethyl-phenyl)-N-[4-(2-chloro-phenyl)-6-(–2-pyrrolidin-1-ylmethyl-pyrrolidin-1-yl)-pyridin-3-yl]-N-methyl-isobutyramide, (S)-2-(3,5-bis-trifluoromethyl-phenyl)-N-[4-(2-chloro-phenyl)-6-(3-dimethylamino-pyrrolidin-1-yl)-pyridin-3-yl]-N-methyl-isobutyramide, (RS)-2-(3,5-bis-trifluoromethyl-phenyl)-N-[4-(2-chloro-phenyl)-6-(3-methanesulfonyl-pyrrolidin-1-yl)-pyridin-3-yl]-N-methyl-isobutyramide,
(S)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide,
(R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide,
(R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide,
(R)—N-[6-[3-(acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide,
(S)—N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide,
(S)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide,
(S)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide,
(S)-(2-(3,5-bis-trifluoromethyl-phenyl)-N-[6-[3-(ethyl-methanesulfonyl-amino)-pyrrolidin-1-yl]-4-(4-fluoro-2-methyl-phenyl)-pyridin-3-yl]-N-methyl-isobutyramide,
(S)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide,
(S)—N-[6-[3-(acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide,
2-(3,5-bis-trifluoromethyl-phenyl)-N-[4-(4-fluoro-2-methyl-phenyl)-6-(3-oxo-pyrrolidin-1-yl)-pyridin-3-yl]-N-methyl-isobutyramide,
(S)—N-[6-(3-acetylamino-pyrrolidin-1-yl)-4-(2-bromo-phenyl)-pyridin-3-yl]-2-(3,5-bis-trifluoromethyl-phenyl)-N-methyl-isobutyramide,
(S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide,
(S)-2-(3,5-bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide,
(2S,4S)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide,
(2S,4S)-2-(3,5-bis-trifluoromethyl-phenyl)-N-[6-(4-fluoro-2-hydroxymethyl-pyrrolidin-1-yl)-4-(4-fluoro-2-methyl-phenyl)-pyridin-3-yl]-N-methyl-isobutyramide,
(S)-2-(3,5-bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide,
(S)-2-(3,5-bis-trifluoromethyl-phenyl)-N-[6-(4,4-difluoro-2-hydroxymethyl-pyrrolidin-1-yl)-4-(4-fluoro-2-methyl-phenyl)-pyridin-3-yl]-N-methyl-isobutyramide,
(2S,4R)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide,
(S)—N-[6-[2-(acetylamino-methyl)-pyrrolidin-1-yl]-4-(4-fluoro-2-methyl-phenyl)-pyridin-3-yl]-2-(3,5-bis-trifluoromethyl-phenyl)-N-methyl-isobutyramide or
(S)-dimethyl-carbamic acid 1-[5-{[2-(3,5-bis-trifluoromethyl-phenyl)-2-methyl-propionyl]-methyl-amino}-4-(4-fluoro-2-methyl-phenyl)-pyridin-2-yl]-pyrrolidin-2-ylmethyl ester.

(RS)-2-(3,5-bis-trifluoromethyl-phenyl)-N-[4'-(2-chloro-phenyl)-3-hydroxy-3,4,5,6-tetrahydro-2H-[1,2']bipyridinyl-5'-yl]-N-methyl-isobutyramide,
2-(3,5-bis-trifluoromethyl-phenyl)-N-[4'-(2-chloro-phenyl)-4-hydroxy-3,4,5,6-tetrahydro-2H-[1,2']bipyridinyl-5'-yl]-N-methyl-isobutyramide,
2-(3,5-bis-trifluoromethyl-phenyl)-N-[4'-(2-chloro-phenyl)-4-hydroxymethyl-3,4,5,6-tetrahydro-2H-[1,2']bipyridinyl-5'-yl]-N-methyl-isobutyramide,
(RS)-2-(3,5-bis-trifluoromethyl-phenyl)-N-[4'-(2-chloro-phenyl)-2-(2-hydroxy-ethyl)-3,4,5,6-tetrahydro-2H-[1,2']bipyridinyl-5'-yl]-N-methyl-isobutyramide,
2-(3,5-bis-trifluoromethyl-phenyl)-N-[4-(2-chloro-phenyl)-6-(3-hydroxy-azetidin-1-yl)-pyridin-3-yl]-N-methyl-isobutyramide,
N-[4-amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide,
2-(3,5-bis-trifluoromethyl-phenyl)-N-[4'-(2-chloro-phenyl)-4-methanesulfonylamino-3,4,5,6-tetrahydro-2H-[1,2']bipyridinyl-5'-yl]-N-methyl-isobutyramide,
N-[4-acetylamino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide,
(RS)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
(R)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
(S)-2-(3,5-bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide,
2-(3,5-bis-trifluoromethyl-phenyl)-N-[4-(4-fluoro-2-methyl-phenyl)-6-(3-hydroxy-azetidin-1-yl)-pyridin-3-yl]-N-methyl-isobutyramide,
2-(3,5-bis-trifluoromethyl-phenyl)-N-[6-(3-hydroxy-azetidin-1-yl)-4-o-tolyl-pyridin-3-yl]-N-methyl-isobutyramide,
2-(3,5-bis-trifluoromethyl-phenyl)-N-(4-hydroxymethyl-4'-o-tolyl-3,4,5,6-tetrahydro-2H-[1,2']bipyridinyl-5'-yl)-N-methyl-isobutyramide,
(3R,5R)-2-(3,5-bis-trifluoromethyl-phenyl)-N-(3,5-dihydroxy-4'-o-tolyl-3,4,5,6-tetrahydro-2H-[1,2']bipyridinyl-5'-yl)-N-methyl-isobutyramide,
(3R,5R)-2-(3,5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide,
(3S,5R)-5-bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide,
(3RS,4SR)-2-(3,5-bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide,
(3RS,4RS)-2-(3,5-bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide,
(3RS,4SR)-2-(3,5-bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide,
(3RS,4RS)-2-(3,5-bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide,
(2RS,4SR)-2-(3,5-bis-trifluoromethyl-phenyl)-N-[4'-(2-chloro-phenyl)-4-hydroxy-2-hydroxymethyl-3,4,5,6-tetrahydro-2H-[1,2']bipyridinyl-5'-yl]-N-methyl-isobutyramide, (2RS,4SR)-2-(3,5-bis-trifluoromethyl-phenyl)-N-(4-hydroxy-2-hydroxymethyl-4'-o-tolyl-3,4,5,6-tetrahydro-2H-[1,2']bipyridinyl-5'-yl)-N-methyl-isobutyramide, (3RS,4SR)-2-(3,5-bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide, (3RS,4RS)-2-(3,5-bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide, (3RS,4SR)-2-(3,5-bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide, (3RS,4RS)-2-(3,5-bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide and (2RS,3RS)-2-(3,5-bis-trifluoromethyl-phenyl)-N-[4'-(2-chloro-phenyl)-3-hydroxy-2-hydroxymethyl-3,4,5,6-tetrahydro-2H-[1,2']bipyridinyl-5'-yl]-N-methyl-isobutyramide.

Other compounds of formula I are specific compounds of formula IE

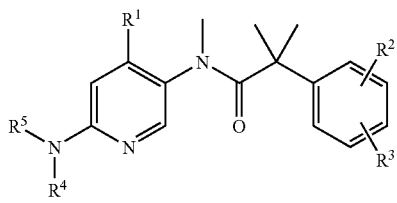

IE wherein $R^1$ is phenyl, unsubstituted or substituted by one or more substituents selected from the group consisting of alkyl, alkoxy, halogen, —$(CH_2)_d$OH, —C(O)H, $CF_3$, CN, S-alkyl, —$S(O)_b$-alkyl, —C(O)NR'R", —NR'R", —NR'C(O)-alkyl and —NR'S(O)$_2$-alkyl;

$R^2$ and $R^3$ are each independently hydrogen, halogen, alkyl, alkoxy, $OCHF_2$, $OCH_2F$, $OCF_3$ or $CF_3$;

$R^4$ and $R^5$ form together with the N-atom to which they are attached a ring with —$(CH_2)_c$—NR'—$(CH_2)_2$—, which is unsubstituted or substituted by one or more substituents selected from the group consisting of lower alkyl, halogen, —(CR'R")$_d$OH, =O, and —NR'R", wherein R' and R" may form together with the N-atom to which they are attached a ring with —$(CH_2)_e$, or by —$(CH_2)_d$NR'—C(O)-alkyl, —$(CH_2)_d$—C(O)-alkyl, —$(CH_2)_d$—C(O)-cycloalkyl, —$(CH_2)_d$OC(O)NR'R", —$(CH_2)_d$—S(O)$_2$-alkyl, —$(CH_2)_d$-pyrrolidinyl or —C(O)NR'R";

R' is hydrogen, alkyl, —$(CH_2)_d$OH, —C(O)H, —C(O)-alkyl, —C(O)-cycloalkyl, —S(O)$_2$-alkyl, —S(O)$_2$-halogen-alkyl, —S(O)-alkyl, —S-alkyl or —S(O)$_2$—N-di-alkyl;

R" is hydrogen or alkyl;

b is 1 or 2;

c is 1, 2, or 3;

d is 0, 1, 2, or 3; and e is 3, 4, or 5;

or a pharmaceutically active acid-addition salt thereof.

Examples of compounds of formula IE are

N-[6-(4-acetyl-piperazin-1-yl)-4-(2-chloro-phenyl)-pyridin-3-yl]-2-(3,5-bis-trifluoromethyl-phenyl)-N-methyl-isobutyramide, 2-(3,5-bis-trifluoromethyl-phenyl)-N-[4-(2-chloro-phenyl)-6-(4-cyclopropanecarbonyl-piperazin-1-yl)-pyridin-3-yl]-N-methyl-isobutyramide, N-[6-(4-acetyl-[1,4]diazepan-1-yl)-4-(2-chloro-phenyl)-pyridin-3-yl]-2-(3,5-bis-trifluoromethyl-phenyl)-N-methyl-isobutyramide, 2-(3,5-bis-trifluoromethyl-phenyl)-N-[4-(4-fluoro-2-methyl-phenyl)-6-(5-oxo-[1,4]diazepan-1-yl)-pyridin-3-yl]-N-methyl-isobutyramide, 2-(3,5-bis-trifluoromethyl-phenyl)-N-[4-(4-fluoro-2-methyl-phenyl)-6-(3-methanesulfonyl-imidazolidin-1-yl)-pyridin-3-yl]-N-methyl-isobutyramide, N-[6-(3-acetyl-imidazolidin-1-yl)-4-(4-fluoro-2-methyl-phenyl)-pyridin-3-yl]-2-(3,5-bis-trifluoromethyl-phenyl)-N-methyl-isobutyramide, 2-(3,5-bis-trifluoromethyl-phenyl)-N-[6-(4-methanesulfonyl-piperazin-1-yl)-4-o-tolyl-pyridin-3-yl]-N-methyl-isobutyramide, 2-(3,5-bis-trifluoromethyl-phenyl)-N-[4-(2-chloro-phenyl)-6-(4-methanesulfonyl-piperazin-1-yl)-pyridin-3-yl]-N-methyl-isobutyramide, 2-(3,5-bis-trifluoromethyl-phenyl)-N-[4-(3-chloro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[4-(3-fluoro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[4-(4-fluoro-2-methyl-phenyl)-6-(4-methanesulfonyl-piperazin-1-yl)-pyridin-3-yl]-N-methyl-isobutyramide, 2-(3,5-bis-trifluoromethyl-phenyl)-N-[6-(4-ethanesulfonyl-piperazin-1-yl)-4-(4-fluoro-2-methyl-phenyl)-pyridin-3-yl]-N-methyl-isobutyramide, 2-(3,5-bis-trifluoromethyl-phenyl)-N-[6-(4-chloromethanesulfonyl-piperazin-1-yl)-4-(4-fluoro-2-methyl-phenyl)-pyridin-3-yl]-N-methyl-isobutyramide, 2-(3,5-bis-trifluoromethyl-phenyl)-N-[6-(4-dimethylsulfamoyl-piperazin-1-yl)-4-(4-fluoro-2-methyl-phenyl)-pyridin-3-yl]-N-methyl-isobutyramide, (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide, (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide, (R)-2-(3,5-bis-trifluoromethyl-phenyl)-N-[4-(2-chloro-phenyl)-6-(4-methanesulfonyl-2-methyl-piperazin-1-yl)-pyridin-3-yl]-N-methyl-isobutyramide, (R)-2-(3,5-bis-trifluoromethyl-phenyl)-N-[6-(4-methanesulfonyl-2-methyl-piperazin-1-yl)-4-o-tolyl-pyridin-3-yl]-N-methyl-isobutyramide, (S)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide, (S)-2-(3,5-bis-trifluoromethyl-phenyl)-N-[4-(2-chloro-phenyl)-6-(–4-methanesulfonyl-3-methyl-piperazin-1-yl)-pyridin-3-yl]-N-methyl-isobutyramide, (S)-2-(3,5-bis-trifluoromethyl-phenyl)-N-[6-(–4-methanesulfonyl-3-methyl-piperazin-1-yl)-4-o-tolyl-pyridin-3-yl]-N-methyl-isobutyramide, (S)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide, (2RS,5SR)-2-(3,5-bis-trifluoromethyl-phenyl)-N-[4-(4-fluoro-2-methyl-phenyl)-6-(4-methanesulfonyl-2,5-dimethyl-piperazin-1-yl)-pyridin-3-yl]-N-methyl-isobutyramide, (2S,6R)-2-(3,5-bis-trifluoromethyl-phenyl)-N-[4-(4-fluoro-2-methyl-phenyl)-6-(4-methanesulfonyl-2,6-dimethyl-piperazin-1-yl)-pyridin-3-yl]-N-methyl-isobutyramide, (3S,5R)-2-(3,5-bis-trifluoromethyl-phenyl)-N-[4-(4-fluoro-2-methyl-phenyl)-6-(4-methanesulfonyl-3,5-dimethyl-piperazin-1-yl)-pyridin-3-yl]-N-methyl-isobutyramide, (S)-2-(3,5-bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide, (S)-2-(3,5-bis-trifluoromethyl-phenyl)-N-[4-(4-fluoro-2-methyl-phenyl)-6-(4-formyl-2-hydroxymethyl-piperazin-1-yl)-pyridin-3-yl]-N-methyl-isobutyramide, (S)-2-(3,5-bis-trifluoromethyl-phenyl)-N-[6-(4-cyclopropanecarbonyl-2-hydroxymethyl-piperazin-1-yl)-4-(4-fluoro-2-methyl-phenyl)-pyridin-3-yl]-N-methyl-isobutyramide, (S)—N-[6-(4-acetyl-2-hydroxymethyl-piperazin-1-yl)-4-(4-fluoro-2-methyl-phenyl)-pyridin-3-yl]-2-(3,5-bis-trifluoromethyl-phenyl)-N-methyl-isobutyramide, (S)-2-(3,5-bis-trifluoromethyl-phenyl)-N-[6-(4-ethyl-2-hydroxymethyl-piperazin-1-yl)-4-(4-fluoro-2-methyl-phenyl)-pyridin-3-yl]-N-methyl-isobutyramide, (S)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide, (R)-2-(3,5-bis-trifluoromethyl-phenyl)-N-[6-(3-hydroxymethyl-4-methanesulfonyl-piperazin-1-yl)-4-o-tolyl-pyridin-3-yl]-N-methyl-isobutyramide, (R)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide, 2-(3,5-bis-trifluoromethyl-phenyl)-N-[4-(4-fluoro-2-methyl-phenyl)-6-(4-methanesulfonyl-3,3-dimethyl-piperazin-1-yl)-pyridin-3-yl]-N-methyl-isobutyramide, 2-(3,5-bis-trifluoromethyl-phenyl)-N-[6-(4-methanesulfonyl-3,3-dimethyl-piperazin-1-yl)-4-o-tolyl-pyridin-3-yl]-N-methyl-isobutyramide, (S)-2-(3,5-bis-trifluoromethyl-phenyl)-N-[4-(2-hydroxymethyl-phenyl)-6-(-4-methanesulfonyl-3-methyl-piperazin-1-yl)-pyridin-3-yl]-N-methyl-isobutyramide, 2-(3,5-bis-trifluoromethyl-phenyl)-N-[4-(4-fluoro-2-methyl-phenyl)-6-(4-methanesulfonyl-2,2-dimethyl-piperazin-1-yl)-pyridin-3-yl]-N-methyl-isobutyramide, 2-(3,5-bis-trifluoromethyl-phenyl)-N-[6-(4-methanesulfonyl-2,2-dimethyl-piperazin-1-yl)-4-o-tolyl-pyridin-3-yl]-N-methyl-isobutyramide, 2-(3,5-bis-difluoromethoxy-phenyl)-N-[4-(2-chloro-phenyl)-6-piperazin-1-yl-pyridin-3-yl]-N-methyl-isobutyramide, 2-(3,5-bis-difluoromethoxy-phenyl)-N-[4-(4-fluoro-2-methyl-phenyl)-6-piperazin-1-yl-pyridin-3-yl]-N-methyl-isobutyramide, 2-(3,5-bis-difluoromethoxy-phenyl)-N-[4-(2-chloro-phenyl)-6-(4-methanesulfonyl-piperazin-1-yl)-pyridin-3-yl]-N-methyl-isobutyramide, 2-(3,5-bis-difluoromethoxy-phenyl)-N-[4-(4-fluoro-2-methyl-phenyl)-6-(4-methanesulfonyl-piperazin-1-yl)-pyridin-3-yl]-N-methyl-isobutyramide, 2-(3,5-bis-difluoromethoxy-phenyl)-N-methyl-N-(6-piperazin-1-yl-4-o-tolyl-pyridin-3-yl)-isobutyramide and 2-(3,5-bis-difluoromethoxy-phenyl)-N-[6-(4-methanesulfonyl-piperazin-1-yl)-4-o-tolyl-pyridin-3-yl]-N-methyl-isobutyramide.

Additional compounds of formula I are compounds of formula IF

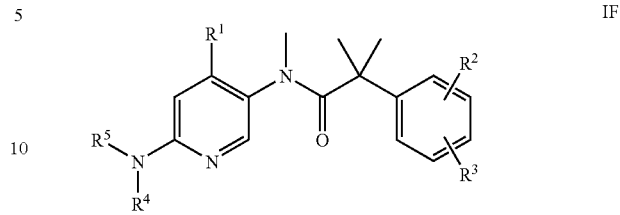

wherein $R^1$ is phenyl, unsubstituted or substituted by one or more substituents selected from the group consisting of alkyl, alkoxy, halogen, —(CH$_2$)$_d$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl, or is heteroaryl selected from the group consisting of pyridin-2- or 3-yl, imidazolyl and oxazolyl, each of which is unsubstituted or substituted by alkyl, halogen or alkoxy;

$R^2$ and $R^3$ are each independently hydrogen, halogen, alkyl, alkoxy, OCHF$_2$, OCH$_2$F, OCF$_3$ or CF$_3$; and $R^4$ and $R^5$ form together with the N-atom to which they are attached a ring with —(CH$_2$)$_c$—O—(CH$_2$)$_2$—, which is unsubstituted or substituted by one or more substituent selected from the group consisting of lower alkyl, halogen, —(CR'R")$_d$OH, ═O, —NR'R", wherein R' and R" may form together with the N-atom to which they are attached a ring with —(CH$_2$)$_e$, or by —(CH$_2$)$_d$NR'—C(O)-alkyl, —(CH$_2$)$_d$—C(O)-alkyl, —(CH$_2$)$_d$—C(O)-cycloalkyl, —(CH$_2$)$_d$OC(O)NR'R", —(CH$_2$)$_d$—S(O)$_2$-alkyl, —(CH$_2$)$_d$-pyrrolidinyl or —C(O)NR'R";

R' is hydrogen, alkyl, —(CH$_2$)$_d$OH, —C(O)H, —C(O)-alkyl, —C(O)-cycloalkyl, —S(O)$_2$-alkyl, —S(O)$_2$-halogenalkyl, —S(O)-alkyl, —S-alkyl or —S(O)$_2$—N-di-alkyl;

R" is hydrogen or alkyl;

b is 1 or 2;

c is 1, 2, or 3;

d is 0, 1, 2, or 3; and e is 3, 4, or 5;

or a pharmaceutically active acid-addition salt thereof.

Compounds of formula IF include (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide, (R)-(2-(3,5-bis-trifluoromethyl-phenyl)-N-[6-(3-hydroxymethyl-morpholin-4-yl)-4-o-tolyl-pyridin-3-yl]-N-methyl-isobutyramide, (RS)-2-(3,5-bis-trifluoromethyl-phenyl)-N-[6-(2-hydroxymethyl-morpholin-4-yl)-4-o-tolyl-pyridin-3-yl]-N-methyl-isobutyramide, (RS)-2-(3,5-bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide and 2-(3,5-bis-trifluoromethyl-phenyl)-N-[4-(4-fluoro-2-methyl-phenyl)-6-morpholin-4-yl-pyridin-3-yl]-N-methyl-isobutyramide.

Formula I also encompasses compounds of formula IG I

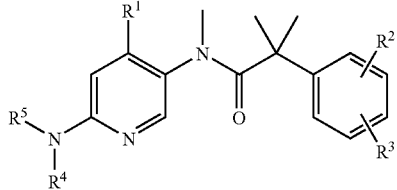

wherein
R¹ is phenyl, unsubstituted or substituted by one or more substituents selected from the group consisting of alkyl, alkoxy, halogen, —(CH₂)$_d$OH, —C(O)H, CF₃, CN, S-alkyl, —S(O)$_b$-alkyl, —C(O)NR'R", —NR'R", —NR'C(O)-alkyl and —NR'S(O)₂-alkyl;
R² and R³ are each independently hydrogen, halogen, alkyl, alkoxy, OCHF₂, OCH₂F, OCF₃ or CF₃;
R⁴ and R⁵ form together with the N-atom to which they are attached a ring with —(CH₂)$_c$—S(O)$_f$—(CH₂)₂—, which is unsubstituted or substituted
by one or more substituents selected from the group consisting of lower alkyl, halogen, —(CR'R")$_d$OH, ═O, and —NR'R", wherein R' and R" may form together with the N-atom to which they are attached a ring with —(CH₂)$_e$,
or
by —(CH₂)$_d$NR'—C(O)-alkyl, —(CH₂)$_d$—C(O)-alkyl, —(CH₂)$_d$—C(O)-cycloalkyl, —(CH₂)$_d$OC(O)NR'R", —(CH₂)$_d$—S(O)₂-alkyl, —(CH₂)$_d$-pyrrolidinyl or —C(O)NR'R";
R' is hydrogen, alkyl, —(CH₂)$_d$OH, —C(O)H, —C(O)-alkyl, —C(O)-cycloalkyl, —S(O)₂-alkyl, —S(O)₂-halogenalkyl, —S(O)-alkyl, —S-alkyl or —S(O)₂—N-di-alkyl;
R" is hydrogen or alkyl;
b is 1 or 2;
c is 1, 2, or 3;
d is 0, 1, 2, 3 or 4; and
e is 3, 4, or 5; and
f is 0, 1, or 2;
or a pharmaceutically active acid-addition salt thereof.
Examples of compounds of formula IG include
(RS)-2-(3,5-bis-trifluoromethyl-phenyl)-N-[4-(4-fluoro-2-methyl-phenyl)-6-(3-hydroxymethyl-1,1-dioxo-1λ⁶-thiomorpholin-4-yl)-pyridin-3-yl]-N-methyl-isobutyramide,
(RS)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
2-(3,5-bis-trifluoromethyl-phenyl)-N-[4-(4-fluoro-2-methyl-phenyl)-6-thiazolidin-3-yl-pyridin-3-yl]-N-methyl-isobutyramide,
(1RS,4RS)- or (1RS,4SR)-2-(3,5-bis-trifluoromethyl-phenyl)-N-[4-(4-fluoro-2-methyl-phenyl)-6-(4-hydroxymethyl-1-oxo-1λ⁴-thiazolidin-3-yl)-pyridin-3-yl]-N-methyl-isobutyramide (Diastereomeric racemate of Example 349),
(1RS,4SR)- or (1RS,4RS)-2-(3,5-bis-trifluoromethyl-phenyl)-N-[4-(4-fluoro-2-methyl-phenyl)-6-(4-hydroxymethyl-1-oxo-1λ⁴-thiazolidin-3-yl)-pyridin-3-yl]-N-methyl-isobutyramide (Diastereomeric racemate of Example 348),
(RS)-2-(3,5-bis-trifluoromethyl-phenyl)-N-[4-(4-fluoro-2-methyl-phenyl)-6-(4-hydroxymethyl-1,1-dioxo-1λ⁶-thiazolidin-3-yl)-pyridin-3-yl]-N-methyl-isobutyramide,
(+)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
(−)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide,
(RS)-2-(3,5-bis-trifluoromethyl-phenyl)-N-[4-(4-fluoro-2-methyl-phenyl)-6-(1-oxo-1λ⁴-[3,4]thiazepan-4-yl)-pyridin-3-yl]-N-methyl-isobutyramide,
2-(3,5-bis-trifluoromethyl-phenyl)-N-[6-(1,1-dioxo-1λ⁶-[1,4]thiazepan-4-yl)-4-(4-fluoro-2-methyl-phenyl)-pyridin-3-yl]-N-methyl-isobutyramide and
2-(3,5-bis-trifluoromethyl-phenyl)-N-[6-(1,1-dioxo-1λ⁶-[1,3]thiazinan-3-yl)-4-(4-fluoro-2-methyl-phenyl)-pyridin-3-yl]-N-methyl-isobutyramide.

The invention relates also to compounds of formula I, wherein R¹ is unsubstituted or substituted phenyl as described above and R⁴ and R⁵ form together with the N-atom to which they are attached a ring with —CH₂CH═CH—CH₂—, which is unsubstituted or mono-substituted by —(CR'R")$_d$OH. An example of such a compound is
(S)-2-(3,5-bis-trifluoromethyl-phenyl)-N-[4-(4-fluoro-2-methyl-phenyl)-6-(2-hydroxymethyl-2,5-dihydro-pyrrol-1-yl)-pyridin-3-yl]-N-methyl-isobutyramide.

Other compounds of formula I are compounds of formula IH

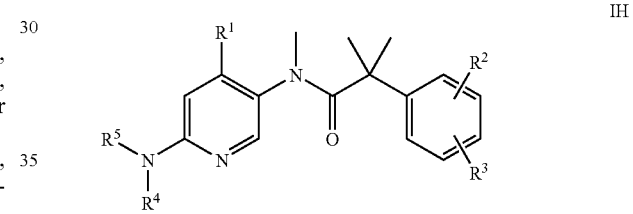

wherein
R¹ is heteroaryl selected from the group consisting of pyridin-2- or 3-yl, imidazolyl and oxazolyl, each of which is unsubstituted or substituted by alkyl, halogen or alkoxy;
R² and R³ are each independently hydrogen, halogen, alkyl, alkoxy, OCHF₂, OCH₂F, OCF₃ or CF₃;
and the other substituents are as described in formula I above.
Examples for compounds of formula IH are
(2S,4R)-2-(3,5-bis-trifluoromethyl-phenyl)-N-[4-(3,5-dimethyl-isoxazol-4-yl)-6-(4-hydroxy-2-hydroxymethyl-pyrrolidin-1-yl)-pyridin-3-yl]-N-methyl-isobutyramide,
(2S,4R)-2-(3,5-bis-trifluoromethyl-phenyl)-N-[6'-(4-hydroxy-2-hydroxymethyl-pyrrolidin-1-yl)-2,6-dimethoxy-[3,4']bipyridinyl-3'-yl]-N-methyl-isobutyramide,
(2S,4R)-2-(3,5-bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide,
(2S,4R)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide,
(2S,4R)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide,
(2S,4S)-2-(3,5-bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide,
(2S,4S)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide, (2S,4S)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide, (2R,3S)-2-(3,5-bis-trifluoromethyl-phenyl)-N-[6'-(3-hydroxy-2-hydroxymethyl-pyrrolidin-1-yl)-2-methyl-[3,4']bipyridinyl-3'-yl]-N-methyl-isobutyramide, (S)-2-(3,5-bis-trifluoromethyl-phenyl)-N-[6'-(2-hydroxymethyl-pyrrolidin-1-yl)-2-methyl-[3,4']bipyridinyl-3'-yl]-N-methyl-isobutyramide, N-{6'-[bis-(2-hydroxy-ethyl)-amino]-2-methyl-[3,4']bipyridinyl-3'-yl}-2-(3,5-bis-trifluoromethyl-phenyl)-N-methyl-isobutyramide, (S)-2-(3,5-bis-trifluoromethyl-phenyl)-N-[6'-(2-hydroxymethyl-pyrrolidin-1-yl)-4-methyl-[3,4']bipyridinyl-3'-yl]-N-methyl-isobutyramide, N-{6'-[bis-(2-hydroxy-ethyl)-amino]-4-methyl-[3,4']bipyridinyl-3'-yl}-2-(3,5-bis-trifluoromethyl-phenyl)-N-methyl-isobutyramide and 2-(3,5-bis-trifluoromethyl-phenyl)-N-{6'-[(2-hydroxy-ethyl)-methyl-amino]-4-methyl-[3,4']bipyridinyl-3'-yl}-N-methyl-isobutyramide.

Also encompassed by formula I are compounds of compounds of formula I J,

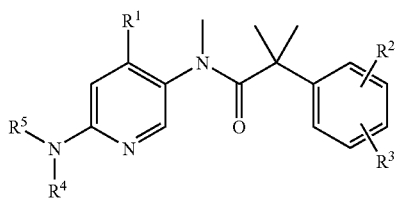

wherein

R¹ is aryl, unsubstituted or substituted by one or more substituents selected from the group consisting of alkyl, alkoxy, halogen, —(CH$_2$)$_d$OH, —C(O)H, CF$_3$, CN, S-alkyl, —S(O)$_b$-alkyl, —C(O)NR'R", —NR'R", —NR'C(O)-alkyl, and —NR'S(O)$_2$-alkyl, or is heteroaryl, selected from the group consisting of pyridin-2- or 3-yl, imidazolyl and oxazolyl, each of which is unsubstituted or substituted by alkyl, halogen or alkoxy;

R² and R³ are each independently hydrogen, halogen, alkyl, alkoxy, OCHF$_2$, OCH$_2$F, OCF$_3$ or CF$_3$;

—NR⁴R⁵ are

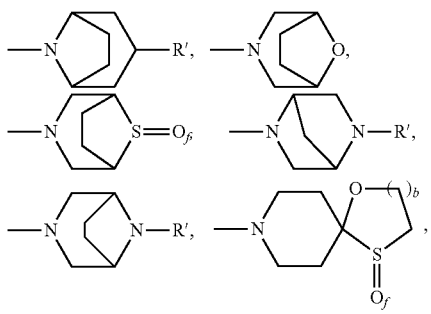

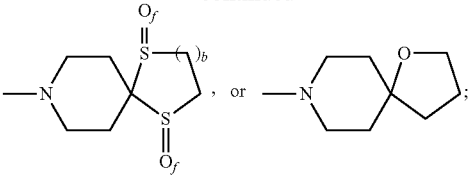

R' is hydrogen, alkyl, —(CH$_2$)$_d$OH, —C(O)H, —C(O)-alkyl, —C(O)-cycloalkyl, —S(O)$_2$-alkyl, —S(O)$_2$-halogenalkyl, —S(O)-alkyl, —S-alkyl or —S(O)$_2$—N-di-alkyl, R" is hydrogen or alkyl;

b is 1 or 2;

d is 0, 1, 2, or 3; and f is 0, 1, or 2;

or a pharmaceutically active acid-addition salt thereof.

Examples of such compounds are (1S,3R,5R)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide, (1R,3S,5S)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide, (rac)-(1R,3R,5S)-2-(3,5-bis-trifluoromethyl-phenyl)-N-[4-(4-fluoro-2-methyl-phenyl)-6-(3-methanesulfinyl-8-aza-bicyclo[3.2.1]oct-8-yl)-pyridin-3-yl]-N-methyl-isobutyramide, (1R,3S,5S)-2-(3,5-bis-trifluoromethyl-phenyl)-N-[4-(4-fluoro-2-methyl-phenyl)-6-(3-methanesulfonyl-8-aza-bicyclo[3.2.1]oct-8-yl)-pyridin-3-yl]-N-methyl-isobutyramide, 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide, 2-(3,5-bis-trifluoromethyl-phenyl)-N-[6-(4,4-dioxo-1-oxa-4λ⁶-thia-8-aza-spiro[4.5]dec-8-yl)-4-(4-fluoro-2-methyl-phenyl)-pyridin-3-yl]-N-methyl-isobutyramide, 2-(3,5-bis-trifluoromethyl-phenyl)-N-[4-(4-fluoro-2-methyl-phenyl)-6-(1-oxa-5-thia-9-aza-spiro[5.5]undec-9-yl)-pyridin-3-yl]-N-methyl-isobutyramide, 2-(3,5-bis-trifluoromethyl-phenyl)-N-[6-(5,5-dioxo-1-oxa-5λ⁶-thia-9-aza-spiro[5.5]undec-9-yl)-4-(4-fluoro-2-methyl-phenyl)-pyridin-3-yl]-N-methyl-isobutyramide, 2-(3,5-bis-trifluoromethyl-phenyl)-N-[4-(4-fluoro-2-methyl-phenyl)-6-(1,1,4,4-tetraoxo-λ⁶,4λ⁶-dithia-8-aza-spiro[4.5]dec-8-yl)-pyridin-3-yl]-N-methyl-isobutyramide, 2-(3,5-bis-trifluoromethyl-phenyl)-N-[4-(4-fluoro-2-methyl-phenyl)-6-(1,1,5,5-tetraoxo-1λ⁶,5λ⁶-dithia-9-aza-spiro[5.5]undec-9-yl)-pyridin-3-yl]-N-methyl-isobutyramide, 2-(3,5-bis-trifluoromethyl-phenyl)-N-[4-(4-fluoro-2-methyl-phenyl)-6-(1-oxa-8-aza-spiro[4.5]dec-8-yl)-pyridin-3-yl]-N-methyl-isobutyramide, 2-(3,5-bis-trifluoromethyl-phenyl)-N-[(1S,5R)-4-(4-fluoro-2-methyl-phenyl)-6-8-oxa-3-aza-bicyclo[3.2.1]oct-3-yl-pyridin-3-yl]-N-methyl-isobutyramide, (1S,5R)-2-(3,5-bis-trifluoromethyl-phenyl)-N-[6-(8,8-dioxo-8λ⁶-thia-3-aza-bicyclo[3.2.1]oct-3-yl)-4-(4-fluoro-2-methyl-phenyl)-pyridin-3-yl]-N-methyl-isobutyramide, (1S,4S)-2-(3,5-bis-trifluoromethyl-phenyl)-N-[4-(4-fluoro-2-methyl-phenyl)-6-((1S,4S)-5-methanesulfonyl-2,5-diaza-bicyclo[2.2.1]hept-2-yl)-pyridin-3-yl]-N-methyl-isobutyramide and (1R,5S)-2-(3,5-bis-trifluoromethyl-phenyl)-N-[4-(4-fluoro-2-methyl-phenyl)-6-(8-methanesulfonyl-3,8-diaza-bicyclo[3.2.1]oct-3-yl)-pyridin-3-yl]-N-methyl-isobutyramide.

The present compounds of formula I and their pharmaceutically acceptable salts can be prepared by methods known in the art, described in schemes 1 to 14 and in specific examples 1 to 421 and, for example, by a process described below, which process comprises a) reacting a compound of formula

II with a compound of formula

NHR$^4$R$^5$     III to produce a compound of formula

I wherein R$^1$, R$^2$, R$^3$, R$^4$ and R$^5$ have the significances given above,
or
b) reacting a compound of formula

IV with a compound of formula

R$^1$—B(OH)$_2$ or

R$^1$—B(pinacol) or

R$^1$—ZnCl to produce a compound of formula

I wherein R$^1$, R$^2$, R$^3$, R$^4$ and R$^5$ have the significances given above, and
if desired, modifying one or more substituents R$^1$-R$^5$ within the definitions given above, and
if desired, converting the compound obtained into a pharmaceutically acceptable acid addition salt.

In general, the compounds of formula I may be prepared as follows:

a) To a solution of a compound of formula II, for example N-[6-chloro-4-(2-chloro-phenyl)-pyridin-3-yl]-2-(3,5-dichloro-phenyl)-N-methyl-isobutyramide and an amine of formula III, for example L-prolinol in dimethyl sulfoxide, Na$_2$CO$_3$ or K$_2$CO$_3$ is added, and the solution is stirred at 120-150° C. for about 22 h. After cooling to ambient temperature, the solution is worked up in conventional manner or b) A mixture of a compound of formula IV, 2-chlorophenyl-boronic acid, palladium(II) acetate, triphenylphosphine, sodium carbonate and dimethoxyethane is heated at about 80° C. for 90 min. Then the reaction mixture is cooled to room temperature, worked up and purified.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1-14 describe the processes for preparation of compounds of formula I in more detail. The starting materials are known compounds, described in EP 1035115, WO 02/08232 or WO 02/16324, or they may be prepared according to methods known in the art. Furthermore, the preparation of intermediates 1, 2, 3A-3L, 4A-4L and 5A-5I are described in more detail in the experimental part.

In the schemes the following abbreviations have been used:
DMF N,N-dimethylformamide
TFA trifluoroacetic acid
DME ethylene glycol dimethyl ether
KHMDS potassium hexamethyldisilazide
DMSO di-methyl sulfoxide
TBDMS tert-butyldimethylsilyl-protecting group
THF tetrahydrofuran
Oxone potassium peroxymonosulfate
DEAD diethyl azodicarboxylate
DIAD diisopropyl azodicarboxylate
DMAP 4-(N,N-dimethylamine)pyridine
RT room temperature
DBU 1,8-diazabicyclo[5.4.0]undec-7-ene
MW microwave
MCPBA 3-chloroperbenzoic acid Scheme 1
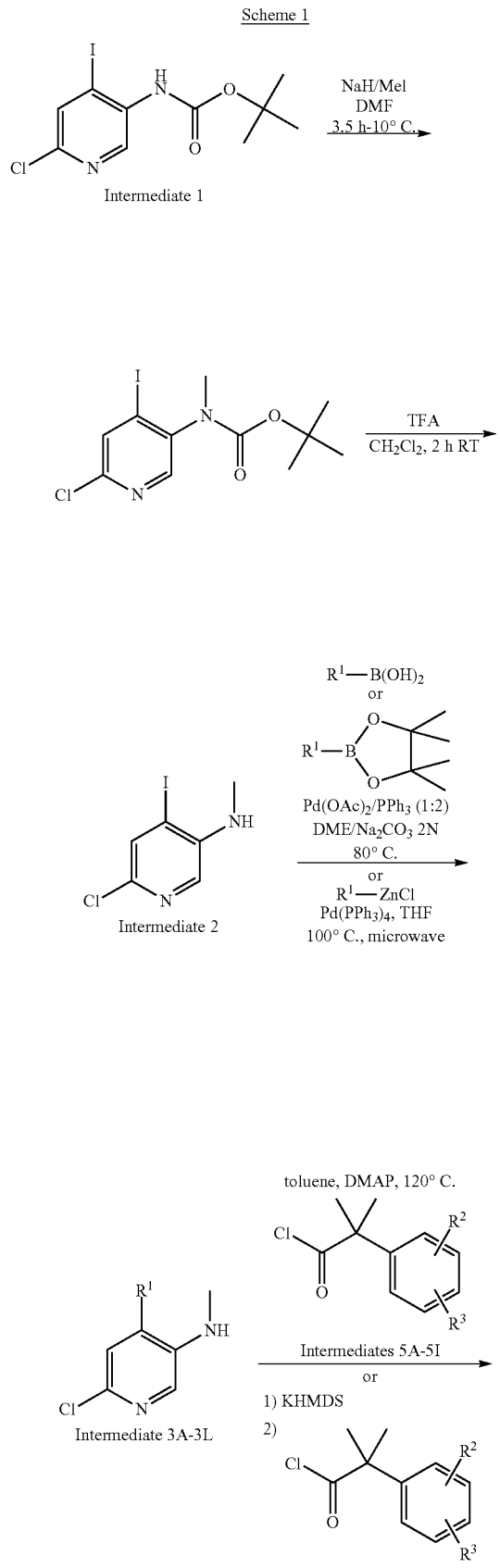
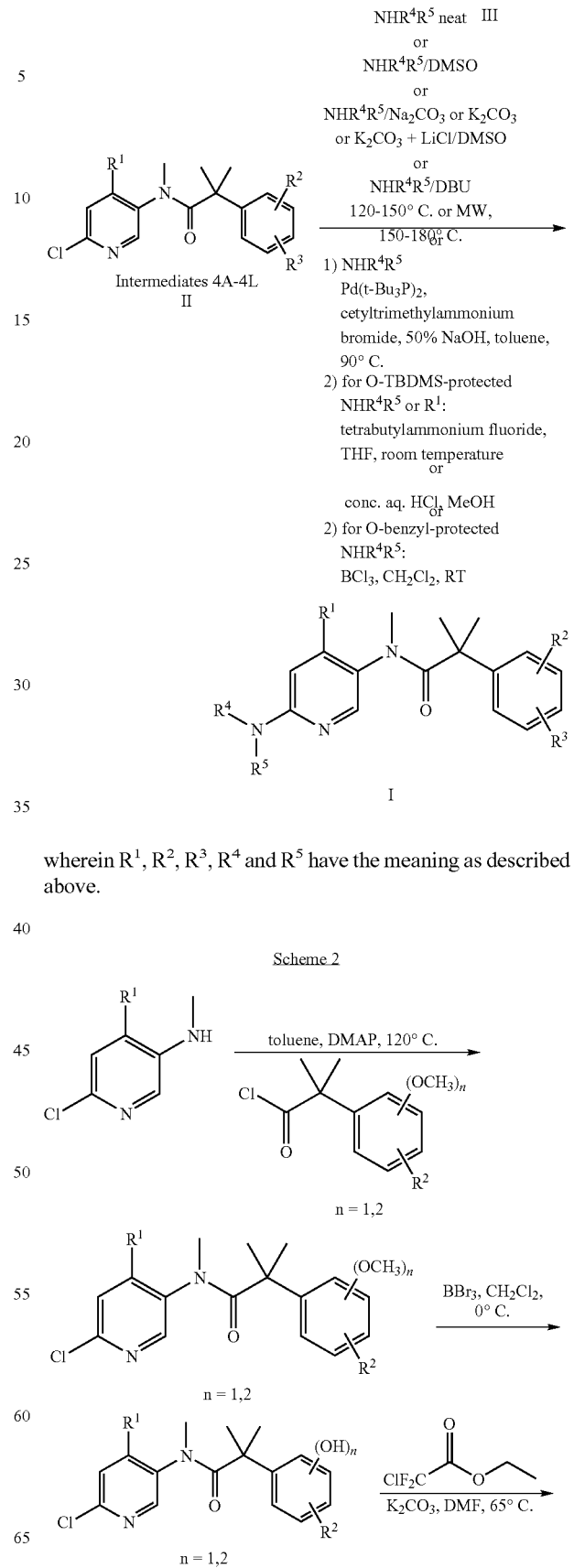
wherein $R^1$, $R^2$, $R^3$, $R^4$ and $R^5$ have the meaning as described above.

-continued
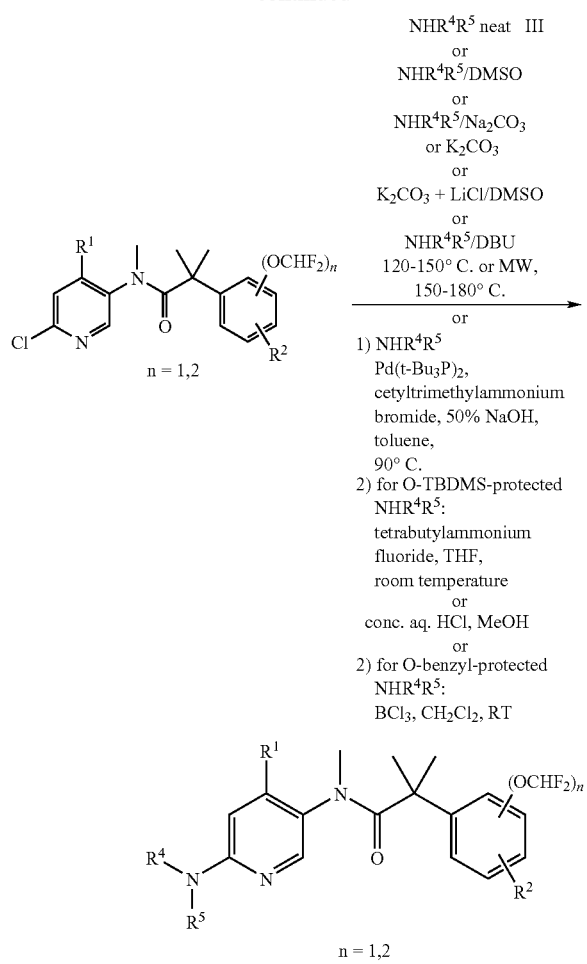
wherein $R^1$, $R^2$, $R^4$ and $R^5$ have the meaning as described above.
Scheme 3
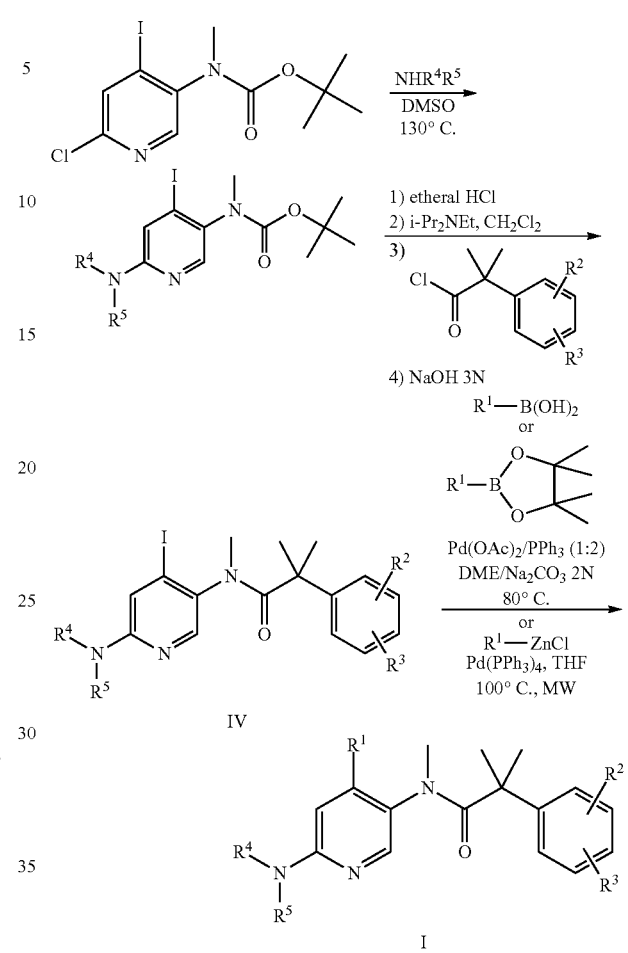
wherein $R^1$, $R^2$, $R^3$, $R^4$ and $R^5$ have the meaning as described above.
Scheme 4
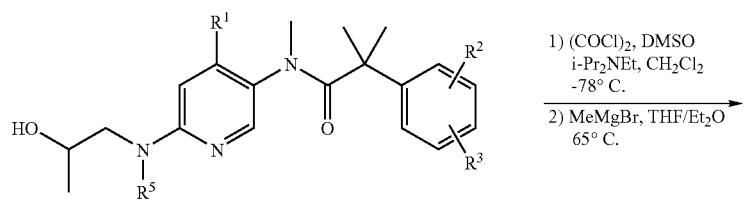
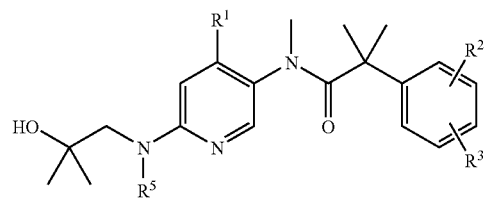
wherein $R^1$, $R^2$, $R^3$ and $R^5$ have the meaning as described above.

Scheme 5

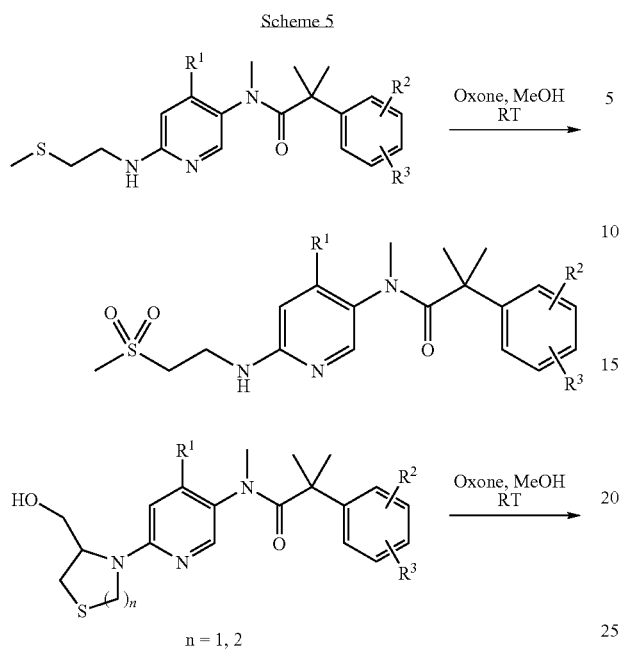

Scheme 6

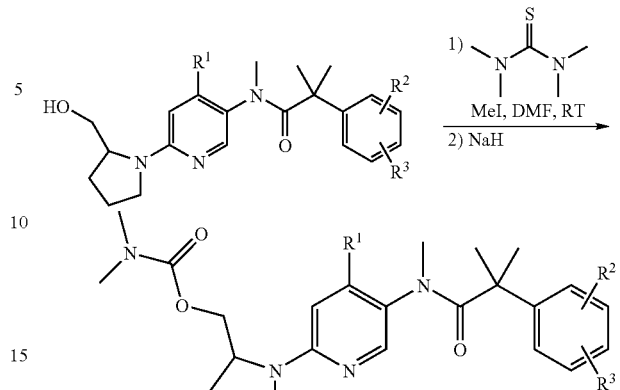

wherein $R^1$, $R^2$ and $R^3$ have the meaning as described above.

Method 7

The present compounds of formula I and their pharmaceutically acceptable salts can be prepared by
reacting a compound of formula

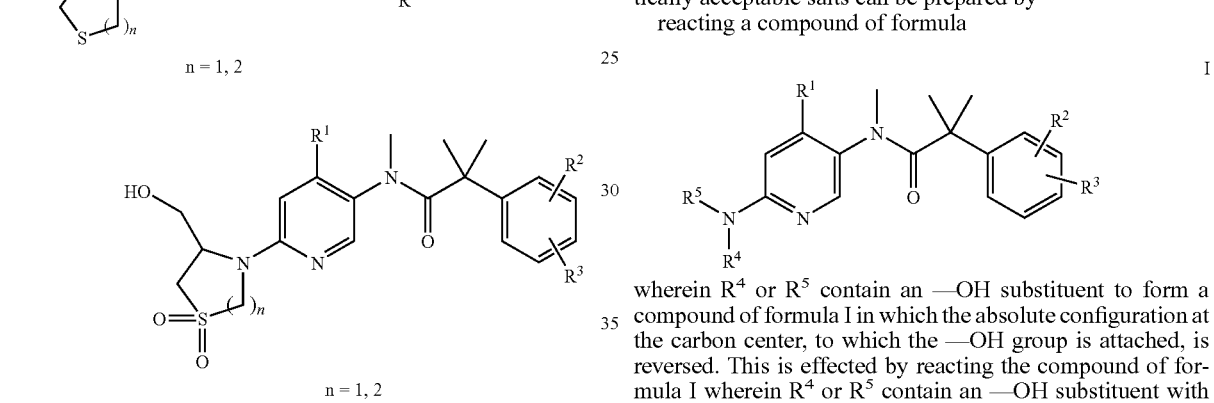

wherein $R^4$ or $R^5$ contain an —OH substituent to form a compound of formula I in which the absolute configuration at the carbon center, to which the —OH group is attached, is reversed. This is effected by reacting the compound of formula I wherein $R^4$ or $R^5$ contain an —OH substituent with triphenylphosphine, diethyl or diisopropyl azodicarboxylate and benzoic acid in THF followed by treatment with sodium methylate or sodium hydroxide in methanol.

wherein $R^1$, $R^2$ and $R^3$, have the meaning as described above.

Scheme 8

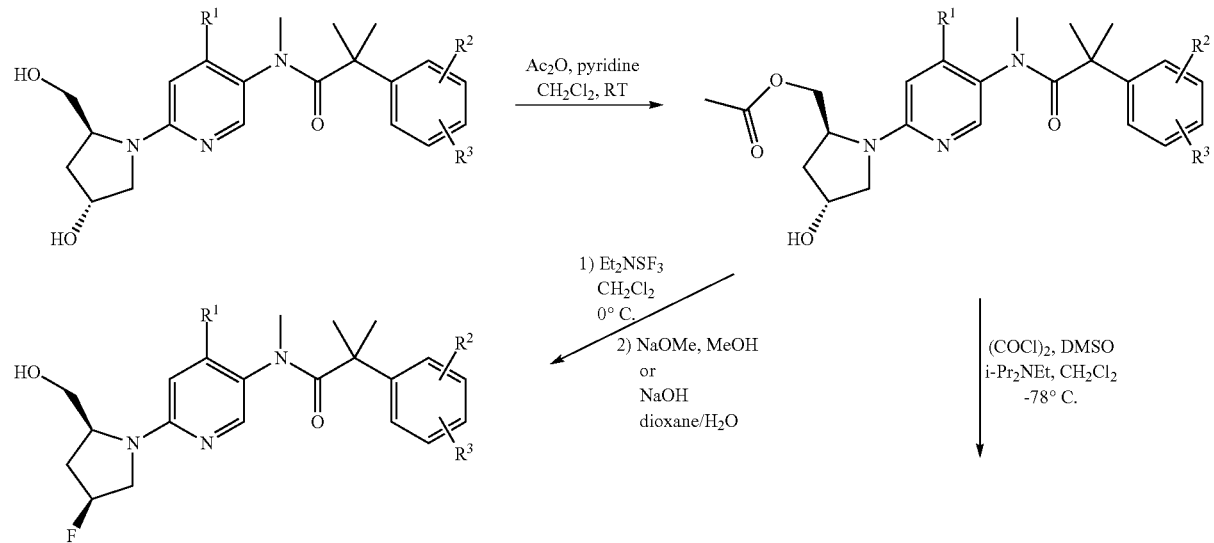

75
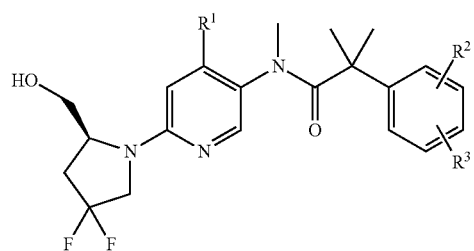
76
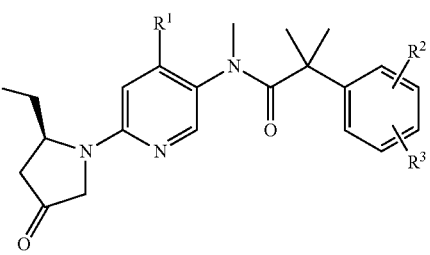
1) Et₂NSF₃
CH₂Cl₂, RT
2) NaOMe, MeOH
or
NaOH
dioxane/H₂O
-continued
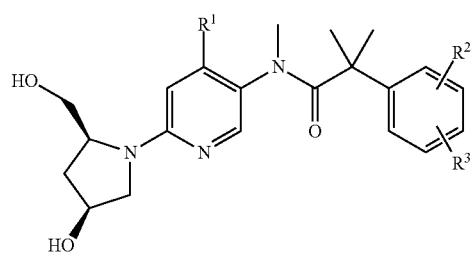
Ac₂O, pyridine
CH₂Cl₂, RT
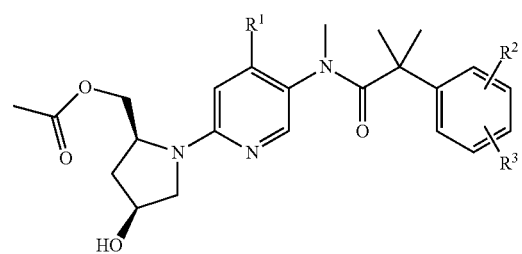
1) Et₂NSF₃, CH₂Cl₂
0° C.
2) NaOMe, MeOH
or
NaOH, dioxane/H₂O
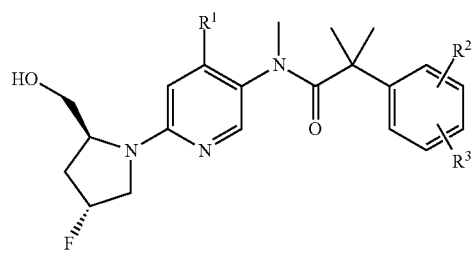
wherein R¹, R² and R³, have the meaning as described above.
Scheme 9
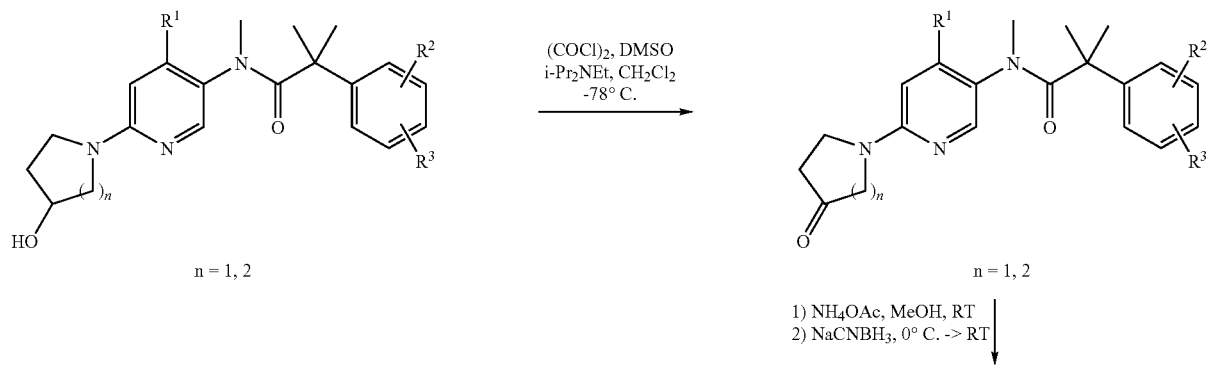
(COCl)₂, DMSO
i-Pr₂NEt, CH₂Cl₂
-78° C.
1) NH₄OAc, MeOH, RT
2) NaCNBH₃, 0° C. -> RT

77
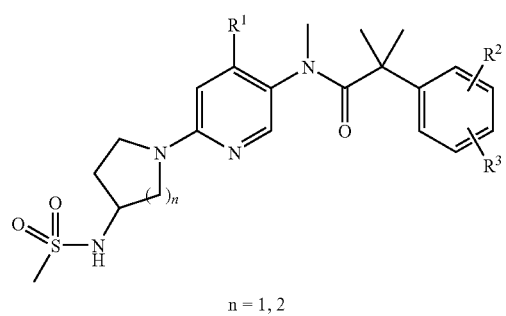
n = 1, 2
KHMDS, R'―I
THF, RT
or
NaH, R'―I
DMF, RT ↓
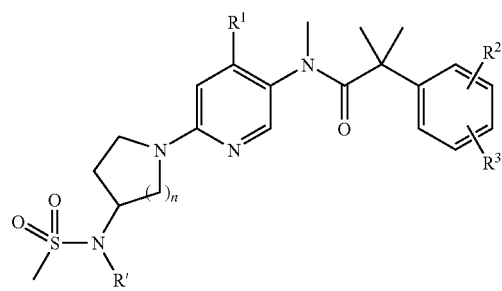
n = 1, 2
-continued
78
CH₃CO₂Cl
i-Pr₂NEt, DMAP
CH₂Cl₂, RT →
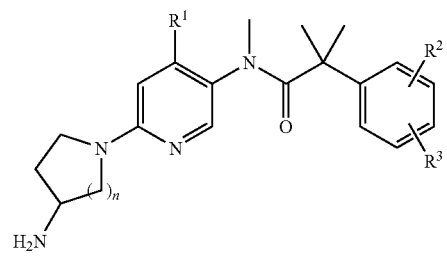
n = 1, 2
CH₃COCl
i-Pr₂NEt
CH₂Cl₂, RT ↓
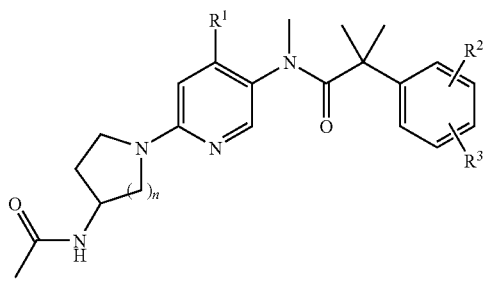
n = 1, 2
KHMDS, R'―I
THF, RT
or
NaH, R'―I
DMF, RT ↓
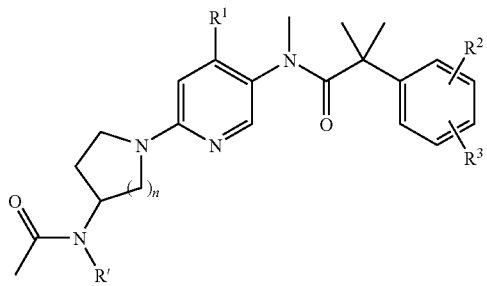
n = 1, 2
wherein n, R¹, R² and R³ have the meaning as described above.
Scheme 10
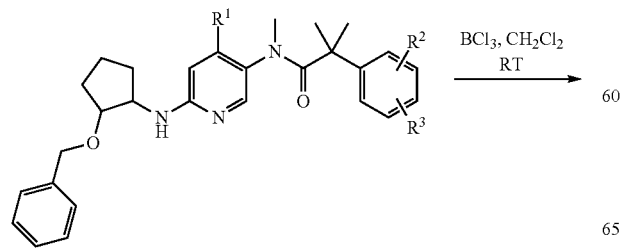
BCl₃, CH₂Cl₂
RT →
-continued
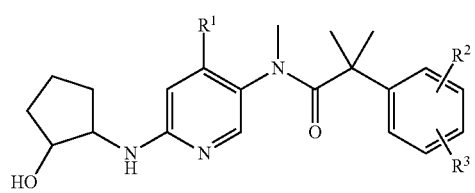
wherein R¹, R² and R³ have the meaning as described above.

-continued
Scheme 11
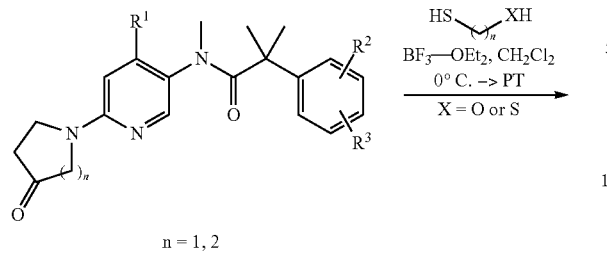
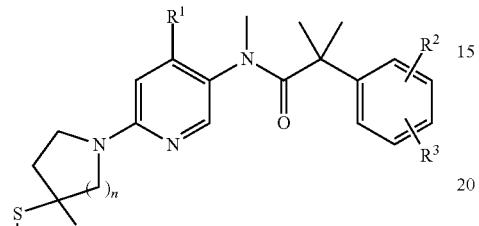
↓ MCPBA
CH₂Cl₂
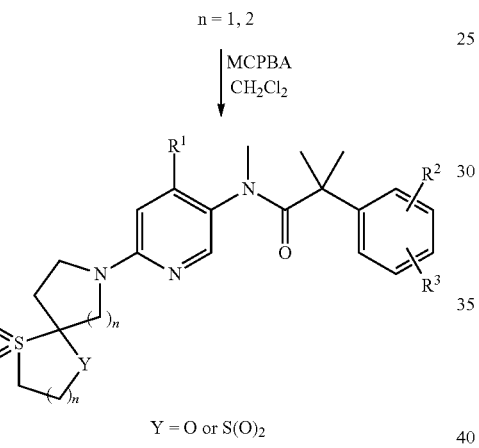
Y = O or S(O)₂
Scheme 12
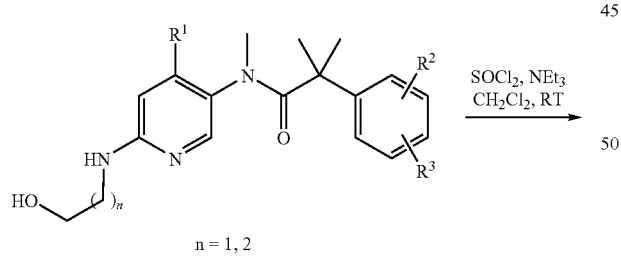
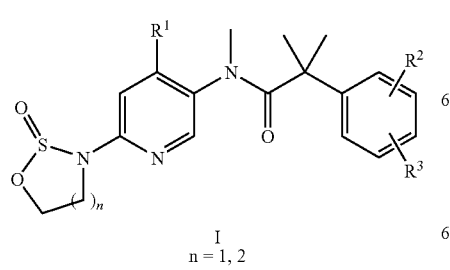
n = 1, 2
-continued
Scheme 13
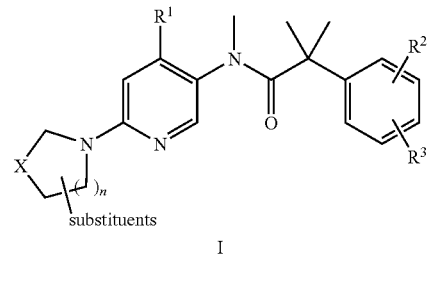
n = 1, 2
X = O, S, S(O)₂N-alkyl, NH, NC(O)-alkyl, NS(O)₂-alkyl
Scheme 14
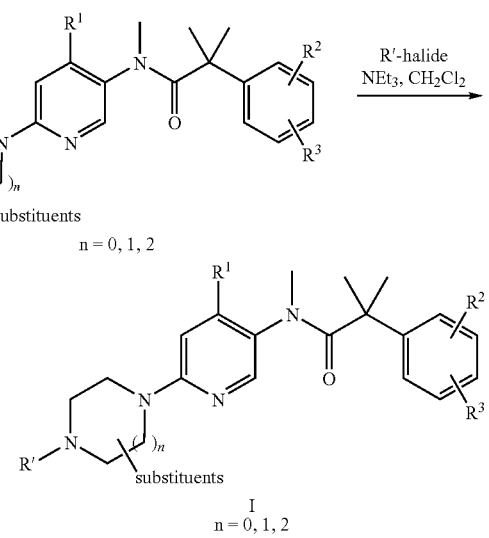
Method 15
The present compounds of formula I and their pharmaceutically acceptable salts can be prepared by reacting a compound of formula
I
wherein R⁴ or R⁵ contain an —OH substituent to form a compound of formula I in which the —OH group has been transformed into an —S-alkyl, —S(O)-alkyl or S(O)₂-alkyl group under inversion of the absolute configuration at the carbon center to which the —OH group has been attached using the following procedure:

The —OH group is first transformed into a —OS(O)₂CH₃ group by reaction with methanesulfonyl chloride and triethylamine in dichloromethane. By treatment with the salt of a thioalkane such as sodium methanethiolate in methanol or DMF the —OS(O)₂CH₃ group is further transformed into the —S-alkyl group. The —S-alkyl group can be oxidized to an —S(O)-alkyl group by treatment with Oxone in methanol or MCPBA in dichloromethane. The compounds of formula I containing an —S(O)-alkyl group can be isolated or oxidized further without isolation to compounds containing an —S(O)₂-alkyl group by treatment with Oxone in methanol or MCPBA in dichloromethane (Examples 331 and 388).

Method 16

The present compounds of formula I and their pharmaceutically acceptable salts can be prepared by
reacting a compound of formula

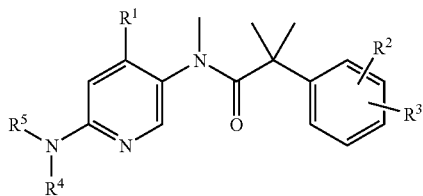
I wherein R⁴ or R⁵ contain an —OH substituent to form a compound of formula I in which the —OH group has been transformed into an —S(O)₂—NR'R" group under inversion of the absolute configuration at the carbon center to which the —OH group has been attached using the following procedure:

The —OH group is transformed into a —SC(O)CH₃ group by reaction with triphenylphosphine, diethyl azodicarboxylate and thioacetic acid in THF. The —SC(O)CH₃ group is oxidized to an —SO₃H group by reaction with an aqueous solution of hydrogen peroxide in acetic acid. Compounds containing the —SO₃H are treated consecutively with oxalyl chloride and a catalytic amount of DMF in dichloromethane and an amine to form compounds of formula I wherein R⁴ or R⁵ contain an —S(O)₂—NR'R" group.

As mentioned earlier, the compounds of formula I and their pharmaceutically usable addition salts possess valuable pharmacological properties. It has been found that the compounds of the present invention are dual antagonists of the Neurokinin 1 and 3 receptors.

The compounds were investigated in accordance with the tests given hereinafter.

NK₁

The affinity of test compounds for the NK₁ receptor was evaluated at human NK₁ receptors in CHO cells infected with the human NK₁ receptor (using the Semliki virus expression system) and radiolabelled with [³H]substance P (final concentration 0.6 nM). Binding assays were performed in HEPES buffer (50 mM, pH 7.4) containing BSA (0.04%) leupeptin (16.8 μg/ml), MnCl₂ (3 mM) and phosphoramidon (2 μM). Binding assays consisted of 250 μl of membrane suspension (approximately 1.5 μg/well in a 96 well plate), 0.125 μl of buffer of displacing agent and 125 μl of [³H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 3×1 ml washes of HEPES buffer (50 mM, pH 7.4). The radioactivity retained on the filters was measured by scintillation counting. All assays were performed in duplicate in at least 2 separate experiments.

NK₃

Recombinant human NK₃ (hNK₃) receptor affinity was determined in a 96 well plate assay, using [³H]SR142801 (final concentration 0.3 nM) to radiolabel the hNK₃ receptor in the presence of 10 concentrations of competing compound or buffer. Non specific binding was determined using 10 μM SB222200. Assay buffer consisted of Tris-HCl (50 mM, pH 7.4), BSA (0.1%), MnCl₂ (4 mM) and phosphoramidon (1 μM). Membrane preparations of hNK3 receptors (approximately 2.5 μg/well in a 96 well plate) were used to initiate the incubation for 90 min at room temperature. This assay was terminated by rapid filtration under vacuum through GF/C filters, presoaked for 90 min with PEI (0.3%), with 3×0.5 ml washes of ice-cold Tris buffer (50 mM, pH 7.4) containing 0.1% BSA. The radioactivity retained on the filters was measured by scintillation counting. All assays were performed in duplicate in at least two separate experiments.

The activity of the present compounds is described in the table below:

| Subst. on R¹ | R²/R³ | R⁴ | R⁵ | R¹ | pKi NK1/NK3 | Expl. |
|---|---|---|---|---|---|---|
| 2-Cl | 3,5-di Cl | —(CH₂)₂OH | H | phenyl | 8.56/8.05 | 1 |
| 2-Cl | 3,5-di Cl | are together with the N-atom 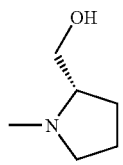 | | phenyl | 8.47/9.05 | 2 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di Cl | are together with the N-atom | (pyrrolidine with CH₂OH and OH substituents) | phenyl | 8.85/9.06 | 3 |
| 2-Cl | 3-F/5-CF₃ | are together with the N atom | (pyrrolidine with CH₂OH substituent) | phenyl | 8.35/8.81 | 4 |
| 2-Cl | 3-F/5-CF₃ | are together with the N-atom | (pyrrolidine with OH and CH₂OH substituents) | phenyl | 8.81/8.76 | 5 |
| 2-Cl | 3,5-di-F | are together with the N atom | (pyrrolidine with OH and CH₂OH substituents) | phenyl | 8.14/8.31 | 6 |
| 2-Cl | 3-OCH₃/5-Cl | are together with the N-atom | (pyrrolidine with CH₂OH substituent) | phenyl | 8.32/8.75 | 7 |
| 2-Cl | 3-OCH₃/5-Cl | are together with the N atom | (pyrrolidine with OH and CH₂OH substituents) | phenyl | 8.77/8.90 | 8 |
| 2-Cl | 3,5-di-CH₃ | are together with the N-atom | (pyrrolidine with CH₂OH substituent) | phenyl | 8.19/8.44 | 9 |
| 2-Cl | 3,5-di-CH₃ | are together with the N atom | (pyrrolidine with OH and CH₂OH substituents) | phenyl | 8.67/8.44 | 10 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-Cl | are together with the N atom | (pyrrolidine with CH₂OH at 2-position, N-methyl) | phenyl | 8.75/8.96 | 11 |
| 2-CH₃ | 3,5-di-Cl | are together with the N-atom | (pyrrolidine with CH₂OH at 2-position and OH at 4-position, N-methyl) | phenyl | 8.95/8.86 | 12 |
| 2-CH₃ | 3-CF₃/5-F | are together with the N-atom | (pyrrolidine with CH₂OH at 2-position, N-methyl) | phenyl | 8.66/8.81 | 13 |
| 2-CH₃ | 3-F/5-CF₃ | are together with the N atom | (pyrrolidine with CH₂OH at 2-position and OH at 4-position, N-methyl) | phenyl | 8.89/8.52 | 14 |
| 2-CH₃ | 3,5-di-F | are together with the N atom | (pyrrolidine with CH₂OH at 2-position, N-methyl) | phenyl | 8.20/8.35 | 15 |
| 2-CH₃ | 3,5-di-F | are together with the N-atom | (pyrrolidine with CH₂OH at 2-position and OH at 4-position, N-methyl) | phenyl | 8.58/8.39 | 16 |
| 2-CH₃ | 3-OCH₃/5-Cl | are together with the N-atom | (pyrrolidine with CH₂OH at 2-position, N-methyl) | phenyl | 8.41/8.50 | 17 |
| 2-CH₃ | 3-OCH₃/5-Cl | are together with the N-atom | (pyrrolidine with CH₂OH at 2-position and OH at 4-position, N-methyl) | phenyl | 8.93/8.60 | 18 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-CH₃ | are together with the N-atom (pyrrolidine-CH₂OH) | | phenyl | 8.53/8.29 | 19 |
| 2-CH₃ | 3,5-di-CH₃ | are together with the N-atom (hydroxypyrrolidine-CH₂OH) | | phenyl | 8.94/8.21 | 20 |
| 2-CH₃/4-F | 3,5-di-Cl | —(CH₂)₂OH | H | phenyl | 8.89/8.06 | 21 |
| 2-CH₃/4-F | 3,5-di-Cl | are together with the N-atom (pyrrolidine-CH₂OH) | | phenyl | 8.29/8.93 | 22 |
| 2-CH₃/4-F | 3,5-di-Cl | are together with the N-atom (hydroxypyrrolidine-CH₂OH) | | phenyl | 9.05/8.80 | 23 |
| 2-CH₃/4-F | 3-CF₃/5-F | are together with the N-atom (pyrrolidine-CH₂OH) | | phenyl | 8.88/9.05 | 24 |
| 2-CH₃/4-F | 3-CF₃/5-F | are together with the N-atom (hydroxypyrrolidine-CH₂OH) | | phenyl | 9.03/8.76 | 25 |
| 2-CH₃/4-F | H/5-CF₃ | are together with the N atom (pyrrolidine-CH₂OH) | | phenyl | 8.52/8.24 | 26 |

-continued

| Subst. on R¹ | R²/R³ | R⁴ | R⁵ | R¹ | pKi NK1/NK3 | Expl. |
|---|---|---|---|---|---|---|
| 2-CH₃/4-F | H/5-CF₃ | are together with the N-atom | (2,4-dihydroxypyrrolidinyl) | phenyl | 8.82/7.97 | 27 |
| 2-CH₃/4-F | 3,5-di-F | are together with the N atom | (2-hydroxymethylpyrrolidinyl) | phenyl | 8.55/8.40 | 28 |
| 2-CH₃/4-F | 3,5-di-F | are together with the N atom | (2,4-dihydroxypyrrolidinyl) | phenyl | 8.81/8.45 | 29 |
| 2-CH₃/4-F | 3-OCH₃/5-Cl | are together with the N-atom | (2-hydroxymethylpyrrolidinyl) | phenyl | 8.43/8.45 | 30 |
| 2-CH₃/4-F | 3-OCH₃/5-Cl | are together with the N atom | (2,4-dihydroxypyrrolidinyl) | phenyl | 9.01/8.78 | 31 |
| 2-CH₃/4-F | 3,5-di-CH₃ | are together with the N atom | (2-hydroxymethylpyrrolidinyl) | phenyl | 8.51/8.52 | 32 |
| 2-CH₃/4-F | 3,5-di-CH₃ | are together with the N-atom | (2,4-dihydroxypyrrolidinyl) | phenyl | 8.93/8.52 | 33 |
| 2-Cl | 3-OCHF₂/5-Cl | are together with the N atom | (2-hydroxymethylpyrrolidinyl) | phenyl | 8.41/9.08 | 34 |

-continued

| Subst. on R¹ | R²/R³ | R⁴ | R⁵ | R¹ | pKi NK1/NK3 | Expl. |
|---|---|---|---|---|---|---|
| 2-Cl | 3-OCHF₂/5-Cl | are together with the N atom | (pyrrolidine with OH and CH₂OH) | phenyl | 8.71/9.26 | 35 |
| 2-CH₃ | 3-OCHF₂/5-Cl | are together with the N atom | (pyrrolidine with CH₂OH) | phenyl | 8.37/9.15 | 36 |
| 2-CH₃ | 3-OCHF₂/5-Cl | are together with the N-atom | (pyrrolidine with OH and CH₂OH) | phenyl | 8.92/9.21 | 37 |
| 2-CH₃/4-F | 3-OCHF₂/5-Cl | are together with the N atom | (pyrrolidine with CH₂OH) | phenyl | 8.45/8.65 | 38 |
| 2-CH₃/4-F | 3-OCHF₂/5-Cl | are together with the N atom | (pyrrolidine with OH and CH₂OH) | phenyl | 8.98/8.89 | 39 |
| 2-Cl | 3,5-di-CF₃ | are together with the N atom | (pyrrolidine with NHC(O)CH₃ and CH₂OH) | phenyl | 9.19/8.99 | 40 |
| 2-Cl | 3,5-di-CF₃ | are together with the N-atom | (pyrrolidine with CH₂OH) | phenyl | 8.97/8.12 | 41 |
| 2-Cl | 3,5-di-CF₃ | are together with the N atom | (pyrrolidine with CH₂OH) | phenyl | 8.78/9.08 | 42 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di-CF₃ | are together with the N atom | *N-methylpyrrolidin-3-yl with NHC(O)CH₃ (one stereoisomer)* | phenyl | 8.62/7.45 | 43 |
| 2-Cl | 3,5-di-CF₃ | are together with the N-atom | *N-methylpyrrolidin-3-yl with NHC(O)CH₃ (other stereoisomer)* | phenyl | 9.20/7.81 | 44 |
| 2-Cl | 3,5-di-CF₃ | are together with the N-atom | *N-methylpyrrolidin-3-yl with N(Et)C(O)CH₃* | phenyl | 8.64/8.70 | 45 |
| 2-Cl | 3,5-di-CF₃ | are together with the N-atom | *N-methyl-3-hydroxypyrrolidin-3-yl* | phenyl | 9.22/8.06 | 46 |
| 2-Cl | 3,5-di-CF₃ | are together with the N-atom | *N-methyl-3-hydroxypyrrolidin-3-yl* | phenyl | 8.71/8.20 | 47 |
| 2-Cl | 3,5-di-CF₃ | are together with the N-atom | *N-methyl-3,4-dihydroxypyrrolidinyl (cis)* | phenyl | 9.27/8.06 | 48 |
| 2-Cl | 3,5-di-CF₃ | are together with the N-atom | *N-methyl-3,4-dihydroxypyrrolidinyl (trans)* | phenyl | 9.32/7.83 | 49 |
| 2-Cl | 3,5-di-CF₃ | are together with the N-atom | *N-methyl-3-hydroxypiperidinyl* | phenyl | 8.85/7.84 | 50 |
| 2-Cl | 3,5-di-CF₃ | are together with the N atom | *N-methyl-4-hydroxypiperidinyl* | phenyl | 9.19/7.54 | 51 |
| 2-Cl | 3,5-di-CF₃ | are together with the N atom | *N-methyl-4-(hydroxymethyl)piperidinyl* | phenyl | 8.96/8.10 | 52 |

-continued

| Subst. on R$^1$ | R$^2$/R$^3$ | R$^4$ | R$^5$ | R$^1$ | pKi NK1/NK3 | Expl. |
|---|---|---|---|---|---|---|
| 2-Cl | 3,5-di-CF$_3$ | are together with the N atom 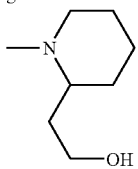 | | phenyl | 8.60/7.61 | 53 |
| 2-Cl | 3,5-di-CF$_3$ | —(CH$_2$)$_2$OH | —CH$_3$ | phenyl | 9.00/8.57 | 54 |
| 2-Cl | 3,5-di-CF$_3$ | —(CH$_2$)$_2$OH | —CH$_2$CH$_3$ | phenyl | 8.48/7.95 | 55 |
| 2-Cl | 3,5-di-CF$_3$ | —(CH$_2$)$_2$OH | —(CH$_2$)$_2$CH$_3$ | phenyl | 8.34/8.28 | 56 |
| 2-Cl | 3,5-di-CF$_3$ | —(CH$_2$)$_2$OH | —(CH$_2$)$_3$CH$_3$ | phenyl | 8.00/7.56 | 57 |
| 2-Cl | 3,5-di-CF$_3$ | —CH$_2$CH(OH)CH$_2$OH | CH$_3$ | phenyl | 8.62/8.24 | 58 |
| 2-Cl | 3,5-di-CF$_3$ | CH(CH$_2$OH)CH$_2$CH(CH$_3$)$_2$ | H | phenyl | 8.49/8.31 | 59 |
| 2-Cl | 3,5-di-CF$_3$ | 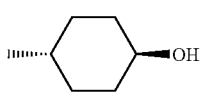 | H | phenyl | 8.90/8.10 | 60 |
| 2-Cl | 3,5-di-CF$_3$ | are together with the N-atom 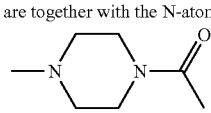 | | phenyl | 9.38/7.85 | 61 |
| 2-Cl | 3,5-di-CF$_3$ | are together with the N-atom 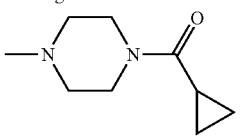 | | phenyl | 8.99/8.18 | 62 |
| 2-Cl | 3,5-di-CF$_3$ | are together with the N-atom 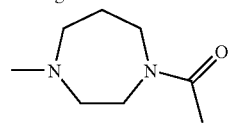 | | phenyl | 8.74/8.93 | 63 |
| 2-Cl | 3,5-di-CF$_3$ | are together with the N-atom 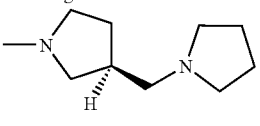 | | phenyl | 9.00/8.54 | 64 |
| 2-Cl | 3,5-di-CF$_3$ | are together with the N-atom 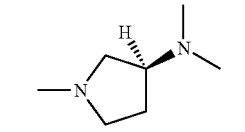 | | phenyl | 8.94/8.56 | 65 |
| 2-Cl | 3,5-di-CF$_3$ | are together with the N-atom 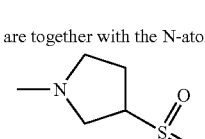 | | phenyl | 8.83/8.89 | 66 |
| 2-Cl | 3,5-di-CF$_3$ | —(CH$_2$)$_2$OH | H | phenyl | 9.14/7.94 | 67 |
| 2-CH$_3$/4-F | 3,5-di-CF$_3$ | —(CH$_2$)$_2$OH | H | phenyl | 8.84/8.49 | 68 |
| 2-Cl/4-F | 3,5-di-CF$_3$ | —(CH$_2$)$_2$OH | H | phenyl | 8.95/7.84 | 69 |
| 2-Cl/4-Cl | 3,5-di-CF$_3$ | —(CH$_2$)$_2$OH | H | phenyl | 8.70/8.39 | 70 |

-continued

| Subst. on R¹ | R²/R³ | R⁴ | R⁵ | R¹ | pKi NK1/NK3 | Expl. |
|---|---|---|---|---|---|---|
| 2-Cl/4-Cl | 3,5-di-CF₃ | (S)-CH(CH₃)CH₂CH₃ with OH (butan-2-ol, wedge) | H | phenyl | 8.69/8.04 | 71 |
| 2-Cl | 3,5-di-CF₃ | (S)-butan-2-ol | H | phenyl | 9.14/7.58 | 72 |
| 2-Cl | 3,5-di-CF₃ | (R)-butan-2-ol | H | phenyl | 9.06/8.13 | 73 |
| 2-Cl | 3,5-di-CF₃ | butan-2-ol | H | phenyl | 9.06/8.24 | 74 |
| 2-Cl | 3,5-di-CF₃ | 2-methylbutan-2-ol | H | phenyl | 8.77/7.91 | 75 |
| 2-Cl | 3,5-di-CF₃ | pentan-3-ol | H | phenyl | 8.80/7.97 | 76 |
| 2-CH₃/4-F | 3,5-di-CF₃ | (S)-butan-2-ol | H | phenyl | 9.19/8.32 | 77 |
| 2-Cl | 3,5-di-CF₃ | butane-1,3-diol | H | phenyl | 8.55/8.21 | 78 |
| 2-Cl | 3,5-di-CF₃ | (S)-2-methylpropan-1-ol | H | phenyl | 8.87/7.98 | 79 |
| 2-Cl | 3,5-di-CF₃ | (R)-2-methylpropan-1-ol | H | phenyl | 8.90/8.05 | 80 |
| 2-Cl | 3,5-di-CF₃ | 2-methylpropane-1,3-diol | H | phenyl | 8.68/8.25 | 81 |
| 2-Cl | 3,5-di-CF₃ | CH₂CH₂CH₂OH | CH₂CH₂CH₂OH | phenyl | 9.03/9.09 | 82 |
| 2-CH₃ | 3,5-di-CF₃ | CH₂CH₂CH₂OH | CH₂CH₂CH₂OH | phenyl | 8.93/8.96 | 83 |
| 2-CH₃/4-F | 3,5-di-CF₃ | CH₂CH₂CH₂OH | CH₂CH₂CH₂OH | phenyl | 8.47/8.76 | 84 |
| 2-CH₃/4-F | 3,5-di-CF₃ | CH₂CH₂CH₂CH₂OH | CH₂CH₂CH₂OH | phenyl | 8.63/8.64 | 85 |
| 2-Cl/4-Cl | 3,5-di-CF₃ | CH₂CH₂CH₂OH | CH₂CH₂CH₂OH | phenyl | 8.78/8.45 | 86 |
| 3-Cl/4-Cl | 3,5-di-CF₃ | CH₂CH₂CH₂OH | CH₂CH₂CH₂OH | phenyl | 8.80/8.02 | 87 |
| 4-F | 3,5-di-CF₃ | CH₂CH₂CH₂OH | CH₂CH₂CH₂OH | phenyl | 8.87/8.03 | 88 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di-CF₃ | propyl methyl sulfone | H | phenyl | 9.31/8.49 | 89 |
| 2-Cl | 3,5-di-CF₃ | N-propyl acetamide | H | phenyl | 8.75/8.22 | 90 |
| 2-Cl/4-Cl | 3,5-di-CF₃ | trans-4-hydroxycyclohexyl | H | phenyl | 8.61/8.25 | 91 |
| 2-CH₃/4-F | 3,5-di-CF₃ | trans-4-hydroxycyclohexyl | H | phenyl | 8.99/7.67 | 92 |
| 2-CH₃/4-F | 3,5-di-CF₃ | are together with the N-atom (1-methyl-2-(hydroxymethyl)pyrrolidine) | | phenyl | 8.95/8.13 | 93 |
| 2-Cl/4-Cl | 3,5-di-CF₃ | are together with the N-atom (1-methyl-2-(hydroxymethyl)pyrrolidine) | | phenyl | 8.37/7.83 | 94 |
| 3-Cl/4-Cl | 3,5-di-CF₃ | are together with the N-atom (1-methyl-2-(hydroxymethyl)pyrrolidine) | | phenyl | 8.42/8.03 | 95 |
| 2-Cl | 3,5-di-CF₃ | are together with the N-atom (1-methyl-2-(hydroxymethyl)-4-hydroxypyrrolidine) | | phenyl | 8.16/7.84 | 96 |
| 2-Cl | 3,5-di-CF₃ | are together with the N-atom (1-methyl-2-(hydroxymethyl)-4-hydroxypyrrolidine) | | phenyl | 9.13/8.89 | 97 |
| 2-Cl | 3,5-di-CF₃ | are together with the N-atom (1-methyl-3-hydroxyazetidine) | | phenyl | 9.16/8.46 | 98 |

-continued

| Subst. on R¹ | R²/R³ | R⁴ R⁵ | R¹ | pKi NK1/NK3 | Expl. |
|---|---|---|---|---|---|
| 2-CH₃/4-F | 3,5-di-CF₃ | are together with the N-atom 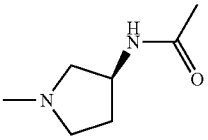 | phenyl | 9.09/7.26 | 99 |
| 2-CH₃/4-F | 3,5-di-CF₃ | are together with the N-atom 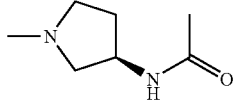 | phenyl | 8.74/7.70 | 100 |
| 2-CH₃/4-F | 3,5-di-CF₃ | are together with the N-atom 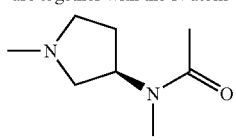 | phenyl | 8.77/8.03 | 101 |
| 2-CH₃/4-F | 3,5-di-CF₃ | are together with the N-atom 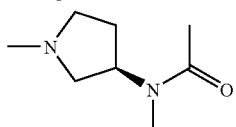 | phenyl | 8.71/7.88 | 102 |
| 2-CH₃/4-F | 3,5-di-CF₃ | are together with the N-atom 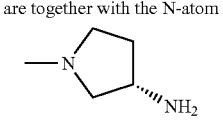 | phenyl | 8.78/7.80 | 103 |
| 2-CH₃/4-F | 3,5-di-CF₃ | are together with the N atom 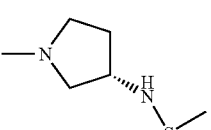 | phenyl | 8.79/8.17 | 104 |
| 2-CH₃/4-F | 3,5-di-CF₃ | are together with the N-atom 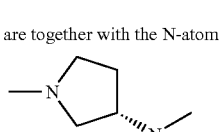 | phenyl | 8.99/8.28 | 105 |
| 2-CH₃/4-F | 3,5-di-CF₃ | are together with the N-atom 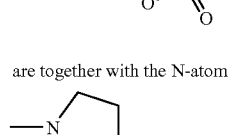 | phenyl | 9.23/8.33 | 106 |

-continued

| Subst. on R¹ | R²/R³ | R⁴ | R⁵ | R¹ | pKi NK1/NK3 | Expl. |
|---|---|---|---|---|---|---|
| 2-CH₃/4-F | 3,5-di-CF₃ | are together with the N-atom (N-methyl pyrrolidinyl with N(CH₃)C(O)CH₃) | | phenyl | 8.63/7.93 | 107 |
| 2-CH₃/4-F | 3,5-di-CF₃ | are together with the N atom (N-methyl pyrrolidinyl with N(Et)C(O)CH₃) | | phenyl | 8.61/8.05 | 108 |
| 2-CH₃/4-F | 3,5-di-CF₃ | are together with the N atom (N-methyl-3-hydroxypyrrolidinyl, stereo) | | phenyl | 8.69/7.87 | 109 |
| 2-CH₃/4-F | 3,5-di-CF₃ | are together with the N-atom (N-methyl-3-hydroxypyrrolidinyl) | | phenyl | 8.58/7.86 | 110 |
| 2-CH₃/4-F | 3,5-di-CF₃ | are together with the N-atom (N-methyl-3-oxopyrrolidinyl) | | phenyl | 8.68/8.39 | 111 |
| 2-Cl | 3,5-di-CF₃ | are together with the N-atom (N-methyl-4-aminopiperidinyl) | | phenyl | 9.25/8.26 | 112 |
| 2-Cl | 3,5-di-CF₃ | are together with the N-atom (N-methyl-4-(methylsulfonamido)piperidinyl) | | phenyl | 8.24/8.46 | 113 |
| 2-CH₃/4-F | 3,5-di-CF₃ | are together with the N-atom (N-methyl-4-acetamidopiperidinyl) | | phenyl | 9.22/7.79 | 114 |
| 4-F | 3,5-di-CF₃ | —(CH₂)₂OH | CH₃ | phenyl | 8.73/7.52 | 115 |
| 4-F | 3,5-di-CF₃ | —(CH₂)₂OH | CH₂CH₃ | phenyl | 8.41/7.49 | 116 |
| 2-CH₃ | 3,5-di-CF₃ | —(CH₂)₂OH | CH₃ | phenyl | 8.68/8.51 | 117 |
| 2-CH₃ | 3,5-di-CF₃ | —(CH₂)₂OH | CH₂CH₃ | phenyl | 8.44/8.34 | 118 |
| 2-CH₃ | 3,5-di-CF₃ | —(CH₂)₂OH | CH₂CH₂CH₃ | phenyl | 8.40/8.64 | 119 |
| 2-CH₃ | 3,5-di-CF₃ | CH(CH₃)CH(OH)CH₃ (stereo) | H | phenyl | 8.86/8.00 | 120 |
| 2-CH₃ | 3,5-di-CF₃ | CH(OH)CH(CH₃)— (sec-butanol) | CH(CH₃)CH₂OH (sec-butanol) | phenyl | 8.54/7.96 | 121 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-CF₃ | 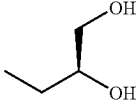 | H | phenyl | 8.72/7.71 | 122 |
| 2-CH₃ | 3,5-di-CF₃ | 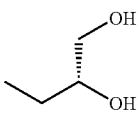 | H | phenyl | 8.60/7.90 | 123 |
| 2-Cl | 3,5-di-CF₃ | 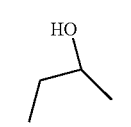 | 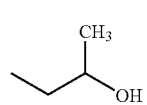 | phenyl | 8.58/7.86 | 124 |
| 2-Cl | 3,5-di-CF₃ | 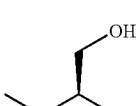 | H | phenyl | 8.55/7.86 | 125 |
| 2-Cl | 3,5-di-CF₃ | 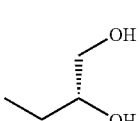 | H | phenyl | 8.60/8.11 | 126 |
| 2-CH₃/3-F | 3,5-di-CF₃ | 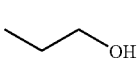 | 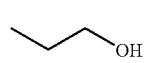 | phenyl | 8.66/8.82 | 127 |
| 2-CH₃/5-F | 3,5-di-CF₃ | 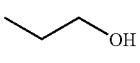 | 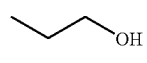 | phenyl | 8.58/8.25 | 128 |
| 2-Br | 3,5-di-CF₃ | are together with the N-atom 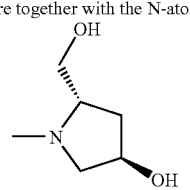 | | phenyl | 9.07/8.58 | 129 |
| 2-Br | 3,5-di-CF₃ | are together with the N-atom 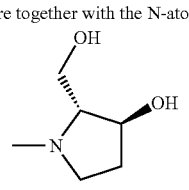 | | phenyl | 8.78/8.64 | 130 |
| 2-Br | 3,5-di-CF₃ | 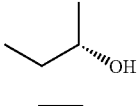 | H | phenyl | 8.97/8.37 | 131 |
| 2-Br | 3,5-di-CF₃ | 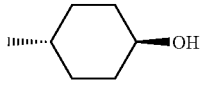 | H | phenyl | 8.88/8.14 | 132 |
| 2-Br | 3,5-di-CF₃ | are together with the N-atom 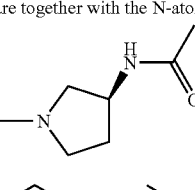 | | phenyl | 9.10/8.70 | 133 |
| 2-Br | 3,5-di-CF₃ |  |  | phenyl | 8.65/8.66 | 134 |

-continued

| Subst. on R¹ | R²/R³ | R⁴ | R⁵ | R¹ | pKi NK1/NK3 | Expl. |
|---|---|---|---|---|---|---|
| 3,4-di-Cl | 3,5-di-CF₃ | are together with the N-atom (pyrrolidine with CH₂OH and OH substituents) | | phenyl | 8.37/7.50 | 135 |
| 2,4-di-Cl | 3,5-di-CF₃ | are together with the N-atom (pyrrolidine with CH₂OH and OH substituents) | | phenyl | 8.79/8.84 | 136 |
| 2,4-di-Cl | 3,5-di-CF₃ | are together with the N-atom (pyrrolidine with CH₂OH and OH substituents) | | phenyl | 8.55/8.87 | 137 |
| 2-Cl | 3,5-di-CF₃ | are together with the N-atom (pyrrolidine with CH₂OH and OH substituents) | | phenyl | 8.78/9.00 | 138 |
| 2-Cl | 3,5-di-CF₃ | are together with the N atom (pyrrolidine with OH and CH₂OH substituents) | | phenyl | 9.17/7.90 | 139 |
| 2-Cl | 3,5-di-CF₃ | are together with the N-atom (pyrrolidine with OH and CH₂OH substituents) | | phenyl | 9.11/8.83 | 140 |
| 2-Cl | 3,5-di-CF₃ | are together with the N-atom (piperidine with CH₂OH substituent) | | phenyl | 8.19/7.73 | 141 |
| 2-CH₃/4-F | 3,5-di-CF₃ | CH₂C(CH₃)(CH₂OH)OH (2-methyl-1,3-propanediol) | H | phenyl | 8.89/8.59 | 142 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-CF₃ | 2-methyl-1,3-propanediol | H | phenyl | 8.52/8.44 | 143 |
| 2-Cl | 3,5-di-CF₃ | (2R,3S)-3-methylbutane-2,3-diol-like | H | phenyl | 8.44/8.92 | 144 |
| 2-Cl | 3,5-di-CF₃ | 3-methylbutane-diol | H | phenyl | 9.08/8.10 | 145 |
| 2-Cl | 3,5-di-CF₃ | 3-methylbutane-diol | H | phenyl | 9.05/7.93 | 146 |
| 2-Cl | 3,5-di-CF₃ | 3-methylbutane-diol | H | phenyl | 9.14/7.98 | 147 |
| 2-Cl | 3,5-di-CF₃ | (CH₂)₂OH | (CH₂)₅CH₃ | phenyl | 8.68/7.92 | 148 |
| 2-Cl | 3,5-di-CF₃ | (CH₂)₂OH | (CH₂)₄CH₃ | phenyl | 8.89/8.21 | 149 |
| 2-Cl | 3,5-di-CF₃ | (CH₂)₃OH | (CH₂)₂OH | phenyl | 8.88/9.01 | 150 |
| 2-Cl | 3,5-di-CF₃ | 2-methylcyclohexanol | H | phenyl | 8.94/7.56 | 151 |
| 2-Cl | 3,5-di-CF₃ | 2-methylcyclopentanol | H | phenyl | 9.12/8.11 | 152 |
| 2-Cl | 3,5-di-CF₃ | 2-methylcyclopentanol | H | phenyl | 9.31/8.39 | 153 |
| 2-CH₃/4-F | 3,5-di-CF₃ | 2-methylcyclopentanol | H | phenyl | 8.50/8.24 | 154 |

-continued

| Subst. on R¹ | R²/R³ | R⁴ R⁵ | R¹ | pKi NK1/NK3 | Expl. |
|---|---|---|---|---|---|
| 2-CH₃/4-F | 3,5-di-CF₃ | are together with the N-atom (pyrrolidine with CH₂OH and OH substituents) | phenyl | 8.76/9.06 | 155 |
| 2-CH₃/4-F | 3,5-di-CF₃ | are together with the N-atom (pyrrolidine with OH and CH₂OH substituents) | phenyl | 8.76/8.80 | 156 |
| 2-CH₃/4-F | 3,5-di-CF₃ | are together with the N-atom (dihydropyrrole with CH₂OH substituent) | phenyl | 8.60/8.80 | 157 |
| 2-CH₃/4-F | 3,5-di-CF₃ | are together with the N-atom (pyrrolidine with CH₂OH and OH substituents) | phenyl | 8.78/9.02 | 158 |
| 2-CH₃/4-F | 3,5-di-CF₃ | are together with the N-atom (pyrrolidine with C(CH₃)₂OH substituent) | phenyl | 8.75/8.02 | 159 |
| 2-Cl | 3,5-di-CF₃ | are together with the N-atom (piperidine with CH₂OH substituent) | phenyl | 8.69/7.52 | 160 |
| 2-Cl | 3,5-di-CF₃ | are together with the N-atom (piperidine with CH₂OH substituent) | phenyl | 7.94/8.17 | 161 |
| 2-CH₃/4-F | 3,5-di-CF₃ | are together with the N-atom (azetidine with OH substituent) | phenyl | 8.68/7.73 | 162 |

-continued

| Subst. on R¹ | R²/R³ | R⁴ R⁵ | R¹ | pKi NK1/NK3 | Expl. |
|---|---|---|---|---|---|
| 2-CH₃ | 3,5-di-CF₃ | are together with the N-atom<br>(azetidine with OH) | phenyl | 8.74/7.55 | 163 |
| 2-CH₃/4-F | 3,5-di-CF₃ | are together with the N-atom<br>(N-methyl diazepanone) | phenyl | 8.79/7.80 | 164 |
| 2-CH₃/4-F | 3,5-di-CF₃ | are together with the N-atom<br>(N-methyl pyrrolidine with CH₂OH, stereochem) | phenyl | 8.68/8.96 | 165 |
| 2-CH₃/5-F | 3,5-di-CF₃ | are together with the N-atom<br>(N-methyl pyrrolidine with CH₂OH, stereochem) | phenyl | 8.42/8.92 | 166 |
| 2-CH₃/3-F | 3,5-di-CF₃ | are together with the N-atom<br>(N-methyl pyrrolidine with CH₂OH, stereochem) | phenyl | 8.35/9.01 | 167 |
| 2-CH₃ | 3,5-di-CF₃ | are together with the N-atom<br>(N-methyl pyrrolidine with CH₂OH) | phenyl | 8.68/8.00 | 168 |
| 2-CH₃/4-F | 3,5-di-CF₃ | are together with the N-atom<br>(N-methyl pyrrolidine with CH₂-pyrrolidine) | phenyl | 8.85/7.67 | 169 |
| 2-CH₃/4-F | 3,5-di-CF₃ | are together with the N-atom<br>(N-methyl pyrrolidine with SO₂CH₃) | phenyl | 8.71/8.04 | 170 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di-CF₃ | are together with the N-atom 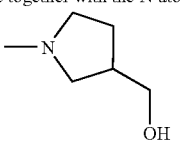 | | phenyl | 8.43/7.61 | 171 |
| 2-CH₃ | 3,5-di-CF₃ | are together with the N-atom 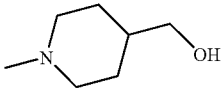 | | phenyl | 8.15/7.89 | 172 |
| 2-CH₃ | 3,5-di-CF₃ |  | H | phenyl | 8.72/8.73 | 173 |
| 2-CH₃/4-F | 3,5-di-CF₃ | are together with the N-atom 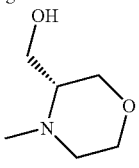 | | phenyl | 8.78/8.59 | 174 |
| 2-CH₃ | 3,5-di-CF₃ | are together with the N-atom 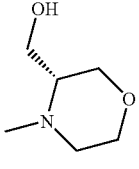 | | phenyl | 8.79/8.67 | 175 |
| 2-CH₃ | 3,5-di-CF₃ | are together with the N-atom 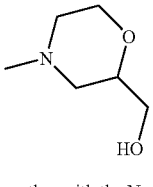 | | phenyl | 8.68/7.58 | 176 |
| 2-CH₃/4-F | 3,5-di-CF₃ | are together with the N-atom 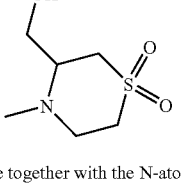 | | phenyl | 8.92/8.58 | 177 |
| 2-CH₃ | 3,5-di-CF₃ | are together with the N-atom 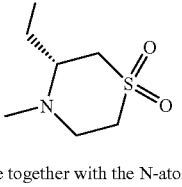 | | phenyl | 9.03/8.46 | 178 |
| 2-CH₃ | 3,5-di-CF₃ | are together with the N-atom 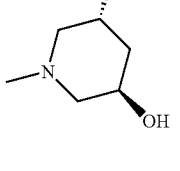 | | phenyl | 8.82/8.39 | 179 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di-CF₃ | are together with the N-atom (N-methylpiperidine-3,5-diol) | | phenyl | 8.79/8.49 | 180 |
| 2-Cl | 3,5-di-CF₃ | are together with the N-atom (N-methylpiperidine-3,5-diol) | | phenyl | 8.70/8.47 | 181 |
| 2-Cl | 3,5-di-CF₃ | are together with the N-atom (N-methylpyrrolidine-3,4-diol) | | phenyl | 9.03/7.49 | 182 |
| 2-CH₃ | 3,5-di-CF₃ | are together with the N-atom (N-methylpyrrolidine-3,4-diol) | | phenyl | 8.96/7.57 | 183 |
| 2-CH₃ | 3,5-di-CF₃ | are together with the N-atom (N-methylpyrrolidine-3,4-diol) | | phenyl | 8.91/7.70 | 184 |
| 2-CH₃ | 3,5-di-CF₃ | are together with the N-atom (N-methylpiperidine-3,4-diol) | | phenyl | 8.81/7.49 | 185 |
| 2-CH₃ | 3,5-di-CF₃ | are together with the N-atom (N-methylpiperidine-3,4-diol) | | phenyl | 8.85/7.91 | 186 |
| 2-Cl | 3,5-di-CF₃ | are together with the N-atom (N-methylpiperidine-3,4-diol) | | phenyl | 8.78/7.59 | 187 |
| 2-Cl | 3,5-di-CF₃ | are together with the N-atom (N-methylpiperidine-3,4-diol) | | phenyl | 8.88/7.81 | 188 |

-continued

| Subst. on R¹ | R²/R³ | R⁴ | R⁵ | R¹ | pKi NK1/NK3 | Expl. |
|---|---|---|---|---|---|---|
| 2-Cl | 3,5-di-CF₃ | are together with the N-atom (piperidine with CH₂OH and OH) | | phenyl | 8.82/8.40 | 189 |
| 2-CH₃ | 3,5-di-CF₃ | are together with the N-atom (piperidine with CH₂OH and OH) | | phenyl | 8.80/8.39 | 190 |
| 2-CH₃ | 3,5-di-CF₃ | are together with the N-atom (piperidine with CH₂OH and OH) | | phenyl | 8.69/7.61 | 191 |
| 2-CH₃ | 3,5-di-CF₃ | are together with the N-atom (piperidine with CH₂OH and OH) | | phenyl | 8.52/7.46 | 192 |
| 2-Cl | 3,5-di-CF₃ | are together with the N-atom (piperidine with OH and CH₂OH) | | phenyl | 8.84/7.92 | 193 |
| 2-Cl | 3,5-di-CF₃ | are together with the N-atom (piperidine with OH and CH₂OH) | | phenyl | 8.78/7.76 | 194 |
| 2-Cl | 3,5-di-CF₃ | are together with the N-atom (piperidine with CH₂OH and OH) | | phenyl | 8.74/7.54 | 195 |
| 2-CH₃/4-F | 3,5-di-CF₃ | HO-CH₂-CH(CH₃)-CH₂-OH | CH₃ | phenyl | 8.76/8.34 | 196 |

-continued

| Subst. on R¹ | R²/R³ | R⁴ | R⁵ | R¹ | pKi NK1/NK3 | Expl. |
|---|---|---|---|---|---|---|
| 2-CH₃/4-F | 3,5-di-CF₃ | are together with the N-atom (pyrrolidine with two CH₂OH groups) | | phenyl | 8.54/8.41 | 197 |
| 2-CH₃/4-F | 3,5-di-CF₃ | are together with the N-atom (pyrrolidine with two CH₂OH groups, stereochem) | | phenyl | 8.75/8.96 | 198 |
| 2-CH₃/4-F | 3,5-di-CF₃ | are together with the N-atom (pyrrolidine with two CH₂OH groups, stereochem) | | phenyl | 8.60/7.81 | 199 |
| 4-CH₃ | 3,5-di-CF₃ | are together with the N-atom (pyrrolidine with OH and CH₂OH) | | phenyl | 8.63/7.74 | 200 |
| — | 3,5-di-CF₃ | are together with the N atom (pyrrolidine with OH and CH₂OH) | | phenyl | 8.83/8.06 | 201 |
| 4-F | 3,5-di-CF₃ | are together with the N-atom (pyrrolidine with OH and CH₂OH) | | phenyl | 8.92/8.13 | 202 |
| 4-Cl | 3,5-di-CF₃ | are together with the N-atom (pyrrolidine with OH and CH₂OH) | | phenyl | 8.69/7.98 | 203 |

-continued

| Subst. on R¹ | R²/R³ | R⁴ | R⁵ | R¹ | pKi NK1/NK3 | Expl. |
|---|---|---|---|---|---|---|
| 4-N(CH₃)₂ | 3,5-di-CF₃ | are together with the N atom (pyrrolidine with OH and CH₂OH) | | phenyl | 7.82/7.83 | 204 |
| 3-Br | 3,5-di-CF₃ | are together with the N-atom (pyrrolidine with OH and CH₂OH) | | phenyl | 8.71/8.07 | 205 |
| 3-Cl | 3,5-di-CF₃ | are together with the N-atom (pyrrolidine with OH and CH₂OH) | | phenyl | 8.73/7.80 | 206 |
| 3-F | 3,5-di-CF₃ | are together with the N-atom (pyrrolidine with OH and CH₂OH) | | phenyl | 8.86/8.33 | 207 |
| 3,5-di-F | 3,5-di-CF₃ | are together with the N-atom (pyrrolidine with OH and CH₂OH) | | phenyl | 8.87/8.21 | 208 |
| 3,4-di-F | 3,5-di-CF₃ | are together with the N-atom (pyrrolidine with OH and CH₂OH) | | phenyl | 8.87/8.46 | 209 |
| 3-F/4-CH₃ | 3,5-di-CF₃ | are together with the N-atom (pyrrolidine with OH and CH₂OH) | | phenyl | 8.64/7.86 | 210 |

-continued

| Subst. on R¹ | R²/R³ | R⁴ | R⁵ | R¹ | pKi NK1/NK3 | Expl. |
|---|---|---|---|---|---|---|
| 3-CH₃/4-F | 3,5-di-CF₃ | are together with the N-atom forming N-pyrrolidine with OH and CH₂OH substituents | | phenyl | 8.78/7.81 | 211 |
| 3-Cl/4-F | 3,5-di-CF₃ | are together with the N-atom forming N-pyrrolidine with OH and CH₂OH substituents | | phenyl | 9.09/8.60 | 212 |
| 2-NH₂ | 3,5-di-CF₃ | are together with the N-atom forming N-pyrrolidine with OH and CH₂OH substituents | | phenyl | 9.18/8.49 | 213 |
| 2-OCH₃ | 3,5-di-CF₃ | are together with the N-atom forming N-pyrrolidine with OH and CH₂OH substituents | | phenyl | 8.99/8.56 | 214 |
| 2-OH | 3,5-di-CF₃ | are together with the N atom forming N-pyrrolidine with OH and CH₂OH substituents | | phenyl | 8.99/8.35 | 215 |
| 2-CH₃ | 3,5-di-CF₃ | are together with the N-atom forming N-pyrrolidine with OH and CH₂OH substituents | | phenyl | 8.87/9.10 | 216 |
| 2-SCH₃ | 3,5-di-CF₃ | are together with the N-atom forming N-pyrrolidine with OH and CH₂OH substituents | | phenyl | 8.98/8.62 | 217 |

-continued

| Subst. on R¹ | R²/R³ | R⁴ | R⁵ | R¹ | pKi NK1/NK3 | Expl. |
|---|---|---|---|---|---|---|
| 2-SO₂CH₃ | 3,5-di-CF₃ | are together with the N-atom [pyrrolidine with OH and CH₂OH] | | phenyl | 8.58/8.14 | 218 |
| 2-CONH₂ | 3,5-di-CF₃ | are together with the N-atom [pyrrolidine with OH and CH₂OH] | | phenyl | 8.84/7.69 | 219 |
| 2,4-di-F | 3,5-di-CF₃ | are together with the N-atom [pyrrolidine with OH and CH₂OH] | | phenyl | 8.82/8.18 | 220 |
| 2-Cl/4-F | 3,5-di-CF₃ | are together with the N-atom [pyrrolidine with OH and CH₂OH] | | phenyl | 9.03/8.28 | 221 |
| 2-CHO/4-F | 3,5-di-CF₃ | are together with the N-atom [pyrrolidine with OH and CH₂OH] | | phenyl | 8.98/8.99 | 222 |
| 2-CH₂OH/4-F | 3,5-di-CF₃ | are together with the N-atom [pyrrolidine with OH and CH₂OH] | | phenyl | 9.15/8.51 | 223 |
| 2-CHO | 3,5-di-CF₃ | are together with the N-atom [pyrrolidine with OH and CH₂OH] | | phenyl | 8.95/8.82 | 224 |

-continued

| Subst. on R¹ | R²/R³ | R⁴ | R⁵ | R¹ | pKi NK1/NK3 | Expl. |
|---|---|---|---|---|---|---|
| 2-CH₂OH | 3,5-di-CF₃ | are together with the N-atom | ![pyrrolidine-N-CH2OH with OH] | phenyl | 8.78/8.59 | 225 |
| 2,5-di-Cl | 3,5-di-CF₃ | are together with the N-atom | ![pyrrolidine-N-CH2OH with OH] | phenyl | 8.11/7.78 | 226 |
| 2-CH₃/5-F | 3,5-di-CF₃ | are together with the N-atom | ![pyrrolidine-N-CH2OH with OH] | phenyl | 8.96/8.86 | 227 |
| 2-CH₃/3-F | 3,5-di-CF₃ | are together with the N atom | ![pyrrolidine-N-CH2OH with OH] | phenyl | 8.93/8.85 | 228 |
| 2,3-di-Cl | 3,5-di-CF₃ | are together with the N-atom | ![pyrrolidine-N-CH2OH with OH] | phenyl | 8.53/8.73 | 229 |
| 3,5-di-CH₃ | 3,5-di-CF₃ | are together with the N-atom | ![pyrrolidine-N-CH2OH with OH] | Isoxazol-4-yl | 9.13/8.57 | 230 |
| 2,4-di-OCH₃ | 3,5-di-CF₃ | are together with the N-atom | ![pyrrolidine-N-CH2OH with OH] | Pyridin-3-yl | 8.61/7.85 | 231 |

-continued

| Subst. on R¹ | R²/R³ | R⁴ R⁵ | R¹ | pKi NK1/NK3 | Expl. |
|---|---|---|---|---|---|
| 2-Cl | 3,5-di-CF₃ | are together with the N-atom (pyrrolidine with CH₂OH and OH) | Pyridin-3-yl | 9.24/8.87 | 232 |
| 2-CH₃ | 3,5-di-CF₃ | are together with the N-atom (pyrrolidine with CH₂OH and OH) | Pyridin-3-yl | 9.37/8.41 | 233 |
| 3-Cl | 3,5-di-CF₃ | are together with the N-atom (pyrrolidine with CH₂OH and OH) | Pyridin-2-yl | 8.66/7.96 | 234 |
| 2-Cl/4-F | 3,5-di-CF₃ | are together with the N-atom (pyrrolidine with CH₂OH and OH) | phenyl | 8.78/8.90 | 235 |
| 2,4-di-Cl | 3,5-di-CF₃ | are together with the N-atom (pyrrolidine with OH and CH₂OH) | phenyl | 8.75/8.75 | 236 |
| 2,4-di-F | 3,5-di-CF₃ | are together with the N-atom (pyrrolidine with OH and CH₂OH) | phenyl | 8.99/8.11 | 237 |
| 2-CH₃/4-F | 3,5-di-CF₃ | are together with the N-atom (pyrrolidine with CH₂OH and OH) | phenyl | 8.91/8.99 | 238 |

-continued

| Subst. on R¹ | R²/R³ | R⁴ R⁵ | R¹ | pKi NK1/NK3 | Expl. |
|---|---|---|---|---|---|
| 2-CHO/4-F | 3,5-di-CF₃ | are together with the N-atom 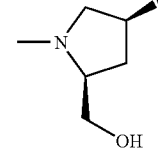 | phenyl | 8.79/8.83 | 239 |
| 2-CH₂OH/4-F | 3,5-di-CF₃ | are together with the N-atom 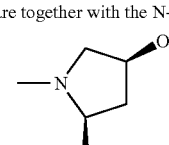 | phenyl | 9.10/8.52 | 240 |
| 2-CH₃ | 3,5-di-CF₃ | are together with the N-atom 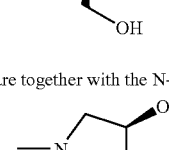 | phenyl | 8.84/8.79 | 241 |
| 2-F | 3,5-di-CF₃ | are together with the N-atom 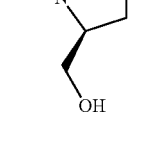 | phenyl | 8.88/8.16 | 242 |
| 2-CF₃ | 3,5-di-CF₃ | are together with the N atom 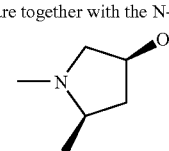 | phenyl | 8.41/8.33 | 243 |
| 2-OCH₃ | 3,5-di-CF₃ | are together with the N-atom 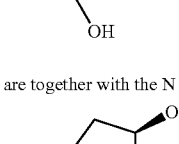 | phenyl | 9.00/8.15 | 244 |
| 2-CN | 3,5-di-CF₃ | are together with the N atom 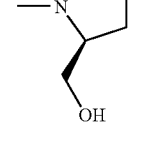 | phenyl | 8.92/8.96 | 245 |

-continued

| Subst. on R¹ | R²/R³ | R⁴ R⁵ | R¹ | pKi NK1/NK3 | Expl. |
|---|---|---|---|---|---|
| 2-Br | 3,5-di-CF₃ | are together with the N-atom, pyrrolidine with OH and CH₂OH | phenyl | 8.72/8.83 | 246 |
| — | 3,5-di-CF₃ | are together with the N-atom, pyrrolidine with OH and CH₂OH | phenyl | 8.82/7.80 | 247 |
| 3-CH₃/4-F | 3,5-di-CF₃ | are together with the N atom, pyrrolidine with OH and CH₂OH | phenyl | 8.66/7.56 | 248 |
| 2-CH₃/3-F | 3,5-di-CF₃ | are together with the N-atom, pyrrolidine with OH and CH₂OH | phenyl | 8.70/8.99 | 249 |
| 2-CH₃/5-F | 3,5-di-CF₃ | are together with the N-atom, pyrrolidine with OH and CH₂OH | phenyl | 8.71/8.70 | 250 |
| 3-F | 3,5-di-CF₃ | are together with the N-atom, pyrrolidine with OH and CH₂OH | phenyl | 8.88/8.05 | 251 |
| 3,4-di-Cl | 3,5-di-CF₃ | are together with the N atom, pyrrolidine with OH and CH₂OH | phenyl | 8.78/8.21 | 252 |

-continued

| Subst. on R¹ | R²/R³ | R⁴ | R⁵ | R¹ | pKi NK1/NK3 | Expl. |
|---|---|---|---|---|---|---|
| 2,3-di-Cl | 3,5-di-CF₃ | are together with the N-atom | 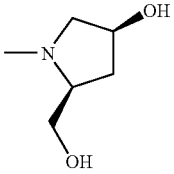 | phenyl | 8.54/8.50 | 253 |
| 2-Cl | 3,5-di-CF₃ | are together with the N-atom | 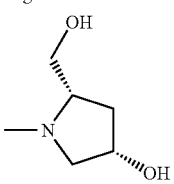 | Pyridin-3-yl | 9.01/8.51 | 254 |
| 2-CH₃ | 3,5-di-CF₃ | are together with the N-atom | 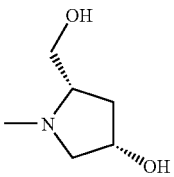 | Pyridin-3-yl | 9.02/7.97 | 255 |
| 6-Cl | 3,5-di-CF₃ | are together with the N-atom | 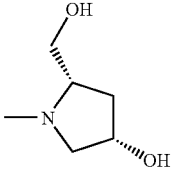 | Pyridin-2-yl | 8.62/7.70 | 256 |
| 2CH₃ | 3,5-di-CF₃ | are together with the N-atom | 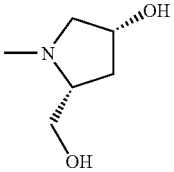 | phenyl |  | 257 |
| 2-CH₃/4-F | 3,5-di-CF₃ | are together with the N-atom | 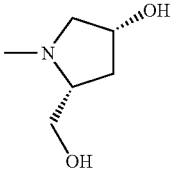 | phenyl | 8.70/8.00 | 258 |
| 2-CH₃/4-F | 3,5-di-CF₃ | are together with the N-atom | 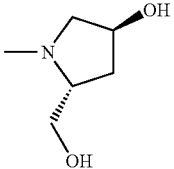 | phenyl | 8.78/7.82 | 259 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-CF₃ | are together with the N-atom | pyrrolidine with OH (wedge up) and CH₂OH | phenyl | 8.85/7.75 | 260 |
| 2-CH₃ | 3,5-di-CF₃ | are together with the N-atom | pyrrolidine with OH and CH₂OH | phenyl | 8.89/9.04 | 261 |
| 2-CF₃ | 3,5-di-CF₃ | are together with the N-atom | pyrrolidine with OH and CH₂OH | phenyl | 8.10/8.01 | 262 |
| 2-OCH₃ | 3,5-di-CF₃ | are together with the N-atom | pyrrolidine with OH and CH₂OH | phenyl | 8.99/8.87 | 263 |
| 2-F | 3,5-di-CF₃ | are together with the N-atom | pyrrolidine with OH and CH₂OH | phenyl | 8.83/8.67 | 264 |
| — | 3,5-di-CF₃ | are together with the N-atom | pyrrolidine with OH and CH₂OH | phenyl | 8.84/8.31 | 265 |
| 4-F | 3,5-di-CF₃ | are together with the N-atom | pyrrolidine with OH and CH₂OH | phenyl | 8.92/8.42 | 266 |
| 4-CH₃ | 3,5-di-CF₃ | are together with the N-atom | pyrrolidine with OH and CH₂OH | phenyl | 8.44/7.54 | 267 |

-continued

| Subst. on R¹ | R²/R³ | R⁴ | R⁵ | R¹ | pKi NK1/NK3 | Expl. |
|---|---|---|---|---|---|---|
| 3,4-di-Cl | 3,5-di-CF₃ | are together with the N-atom | (pyrrolidine with CH₂OH and OH) | phenyl | 8.64/8.62 | 268 |
| 3-Cl | 3,5-di-CF₃ | are together with the N-atom | (pyrrolidine with OH and CH₂OH) | phenyl | 8.73/8.45 | 269 |
| 2,5-di-Cl | 3,5-di-CF₃ | are together with the N-atom | (pyrrolidine with OH and CH₂OH) | phenyl | 8.58/8.66 | 270 |
| 2,3-di-Cl | 3,5-di-CF₃ | are together with the N atom | (pyrrolidine with OH and CH₂OH) | phenyl | 8.52/8.86 | 271 |
| 2-Cl/4-F | 3,5-di-CF₃ | are together with the N-atom | (pyrrolidine with CH₂OH and OH) | phenyl | 8.70/8.96 | 272 |
| 2-CHO/4-F | 3,5-di-CF₃ | are together with the N-atom | (pyrrolidine with OH and CH₂OH) | phenyl | 8.84/8.81 | 273 |
| 2-CH₂OH/4-F | 3,5-di-CF₃ | are together with the N-atom | (pyrrolidine with OH and CH₂OH) | phenyl | 8.89/8.82 | 274 |
| 2-CH₃/3-F | 3,5-di-CF₃ | are together with the N-atom | (pyrrolidine with OH and CH₂OH) | phenyl | 8.83/9.24 | 275 |

-continued

| Subst. on R¹ | R²/R³ | R⁴ | R⁵ | R¹ | pKi NK1/NK3 | Expl. |
|---|---|---|---|---|---|---|
| 2-CH₃/5-F | 3,5-di-CF₃ | are together with the N-atom | 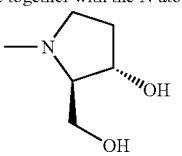 | phenyl | 8.84/8.86 | 276 |
| 2,5-di-F | 3,5-di-CF₃ | are together with the N-atom | 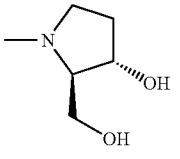 | phenyl | 8.83/8.61 | 277 |
| 2-CH₃ | 3,5-di-CF₃ | are together with the N-atom | 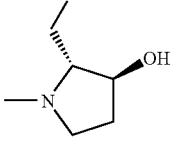 | Pyridin-3-yl | 9.09/8.57 | 278 |
| 2-CH₃ | 3,5-di-CF₃ | are together with the N-atom | 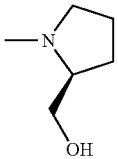 | phenyl | 8.55/8.93 | 279 |
| 2-OCH₃ | 3,5-di-CF₃ | are together with the N-atom | 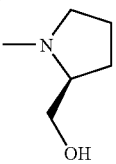 | phenyl | 8.74/8.73 | 280 |
| 2-Br | 3,5-di-CF₃ | are together with the N-atom | 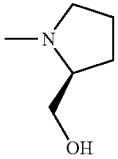 | phenyl | 8.46/8.74 | 281 |
| 2-F | 3,5-di-CF₃ | are together with the N-atom | 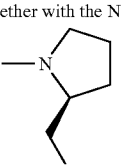 | phenyl | 8.51/8.65 | 282 |
| 2,4-di-Cl | 3,5-di-CF₃ | are together with the N-atom | 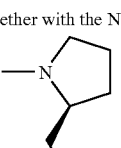 | phenyl | 8.55/8.83 | 283 |

-continued

| Subst. on R¹ | R²/R³ | R⁴ | R⁵ | R¹ | pKi NK1/NK3 | Expl. |
|---|---|---|---|---|---|---|
| 2,5-di-Cl | 3,5-di-CF₃ | are together with the N-atom (pyrrolidin-2-yl-methanol) | | phenyl | 8.83/8.84 | 284 |
| 2,3-di-Cl | 3,5-di-CF₃ | are together with the N-atom (pyrrolidin-2-yl-methanol) | | phenyl | 8.80/8.73 | 285 |
| 3,4-di-Cl | 3,5-di-CF₃ | are together with the N-atom (pyrrolidin-2-yl-methanol) | | phenyl | 8.87/8.43 | 286 |
| 4-Cl | 3,5-di-CF₃ | are together with the N-atom (pyrrolidin-2-yl-methanol) | | phenyl | 8.20/8.13 | 287 |
| 4-F | 3,5-di-CF₃ | are together with the N-atom (pyrrolidin-2-yl-methanol) | | phenyl | 8.58/8.60 | 288 |
| — | 3,5-di-CF₃ | are together with the N-atom (pyrrolidin-2-yl-methanol) | | phenyl | 8.52/8.30 | 289 |
| 2-CH₃ | 3,5-di-CF₃ | are together with the N-atom (pyrrolidin-2-yl-methanol, stereo) | | Pyridin-3-yl | 8.84/8.75 | 290 |
| 2-CH₃ | 3,5-di-CF₃ | propan-1-ol | propan-1-ol | Pyridin-3-yl | 8.48/8.11 | 291 |

-continued

| Subst. on R¹ | R²/R³ | R⁴ | R⁵ | R¹ | pKi NK1/NK3 | Expl. |
|---|---|---|---|---|---|---|
| 6-CH₃ | 3,5-di-CF₃ | are together with the N-atom 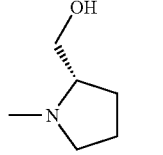 | | Pyridin-3-yl | 8.44/9.11 | 292 |
| 6-CH₃ | 3,5-di-CF₃ | 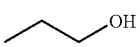 | 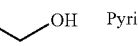 | Pyridin-3-yl | 8.42/8.79 | 293 |
| 6-CH₃ | 3,5-di-CF₃ | 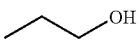 | CH₃ | Pyridin-3-yl | 8.29/8.37 | 294 |
| 2-CH₃ | 3,5-di-CF₃ | are together with the N-atom 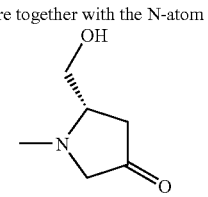 | | phenyl | 8.81/8.78 | 295 |
| 2-CH₃/4-F | 3,5-di-CF₃ | are together with the N-atom 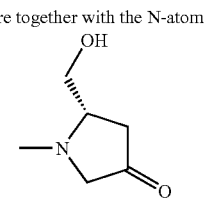 | | phenyl | 8.60/8.76 | 296 |
| 2-CH₃ | 3,5-di-CF₃ | are together with the N-atom 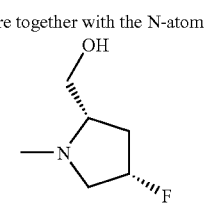 | | phenyl | 8.54/8.88 | 297 |
| 2-CH₃/4-F | 3,5-di-CF₃ | are together with the N-atom 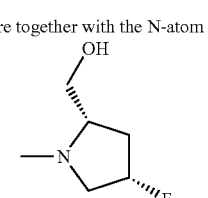 | | phenyl | 8.81/915 | 298 |
| 2-CH₃ | 3,5-di-CF₃ | are together with the N-atom 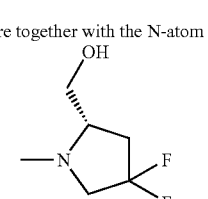 | | phenyl | 8.59/8.97 | 299 |
| 2-CH₃/4-F | 3,5-di-CF₃ | are together with the N-atom 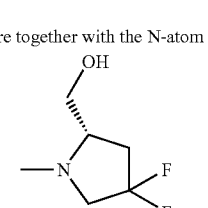 | | phenyl | 9.02/9.31 | 300 |

-continued

| Subst. on R¹ | R²/R³ | R⁴ | R⁵ | R¹ | pKi NK1/NK3 | Expl. |
|---|---|---|---|---|---|---|
| 2-CH₃ | 3,5-di-CF₃ | are together with the N-atom | 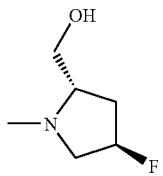 | phenyl | 8.67/8.64 | 301 |
| 2-CH₃/4-F | 3,5-di-CF₃ | are together with the N-atom | 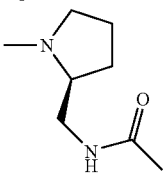 | phenyl | 8.60/7.69 | 302 |
| 2-CH3/4-F | 3,5-di-CF3 | are together with the N-atom | 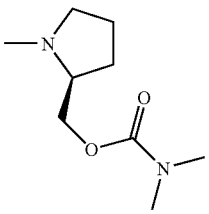 | phenyl | 8.88/7.82 | 303 |
| —CH3/4-F | ,5-di-CF3 | are together with the N-atom | 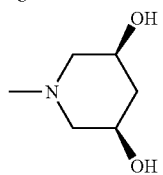 | henyl | .77/8.73 | 04 |
| —Cl/H | ,5-di-CF₃ | are together with the N-atom | 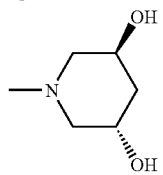 | henyl | .65/8.18 | 05 |
| —CH₃/H | ,5-di-CF₃ | are together with the N-atom | 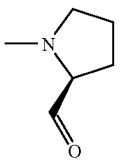 | henyl | .76/7.92 | 06 |
| —CH₃/4-F | ,5-di-CF₃ | are together with the N-atom | 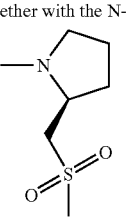 | henyl | .06/7.66 | 07 |

-continued

| Subst. on R¹ | R²/R³ | R⁴ | R⁵ | R¹ | pKi NK1/NK3 | Expl. |
|---|---|---|---|---|---|---|
| —CH₃/4-F | ,5-di-CF₃ | are together with the N-atom | 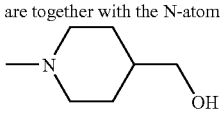 | henyl | .65/8.25 | 08 |
| —CH₃/4-F | ,5-di-CF₃ | are together with the N-atom | 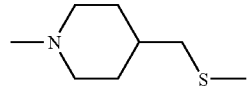 | henyl | .67/7.88 | 09 |
| —CH₃/4-F | ,5-di-CF₃ | are together with the N-atom | 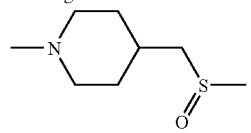 | henyl | .83/7.70 | 10 |
| —CH₃/4-F | ,5-di-CF₃ | are together with the N-atom | 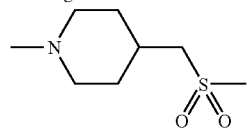 | henyl | .93/7.94 | 11 |
| —CH₃/4-F | ,5-di-CF₃ | are together with the N-atom | 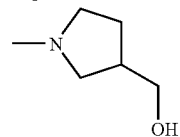 | henyl | .65/8.18 | 12 |
| —CH₃/4-F | ,5-di-CF₃ | are together with the N-atom | 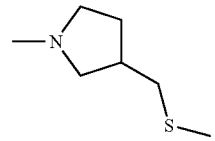 | henyl | .93/8.32 | 13 |
| —CH₃/4-F | ,5-di-CF₃ | are together with the N-atom | 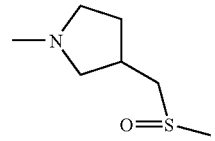 | henyl | .90/8.14 | 14 |
| —CH₃/4-F | ,5-di-CF₃ | are together with the N-atom | 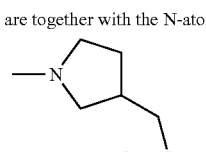 | henyl | .99/8.51 | 15 |
| —CH₃/4-F | ,5-di-CF₃ | are together with the N-atom | 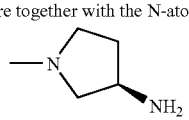 | henyl | .88/7.76 | 16 |

-continued

| Subst. on R¹ | R²/R³ | R⁴ | R⁵ | R¹ | pKi NK1/NK3 | Expl. |
|---|---|---|---|---|---|---|
| —CH₃/4-F | ,5-di-CF₃ | are together with the N-atom | 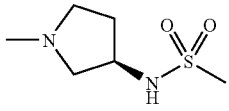 | henyl | .97/8.40 | 17 |
| —CH₃/4-F | ,5-di-CF₃ | are together with the N-atom | 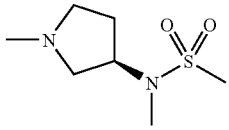 | henyl | .11/8.50 | 18 |
| —CH₃/4-F | ,5-di-CF₃ | are together with the N-atom | 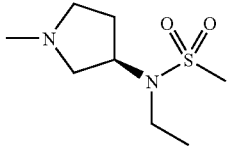 | henyl | .12/8.34 | 19 |
| —CH₃/4-F | ,5-di-CF₃ | are together with the N-atom | 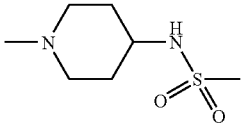 | henyl | .90/7.80 | 20 |
| —CH₃/4-F | ,5-di-CF₃ | are together with the N-atom | 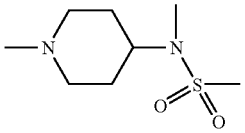 | henyl | .81/7.98 | 21 |
| —CH₃/4-F | ,5-di-CF₃ | are together with the N-atom | 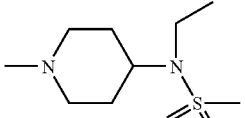 | henyl | .75/7.61 | 22 |
| —CH₃/4-F | ,5-di-CF₃ | are together with the N-atom | 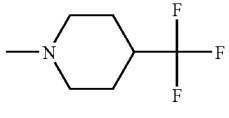 | henyl | .15/8.07 | 23 |
| —CH₃/4-F | ,5-di-CF₃ | are together with the N-atom | 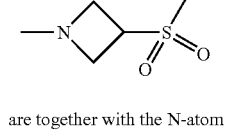 | henyl | .67/7.93 | 24 |
| —CH₃/4-F | ,5-di-CF₃ | are together with the N-atom | 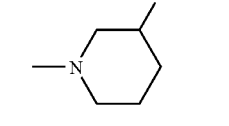 | henyl | .05/8.05 | 25 |

-continued

| Subst. on $R^1$ | $R^2/R^3$ | $R^4$ | $R^5$ | $R^1$ | pKi NK1/NK3 | Expl. |
|---|---|---|---|---|---|---|
| —CH₃/4-F | ,5-di-CF₃ | are together with the N-atom 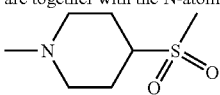 | | henyl | .87/8.58 | 26 |
| —CH₃/4-F | ,5-di-CF₃ | are together with the N-atom 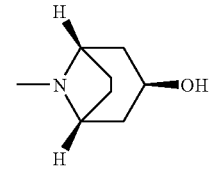 | | henyl | .91/7.89 | 27 |
| —CH₃/4-F | ,5-di-CF₃ | are together with the N-atom 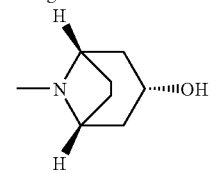 | | henyl | .70/8.34 | 28 |
| —CH₃/4-F | ,5-di-CF₃ | are together with the N-atom 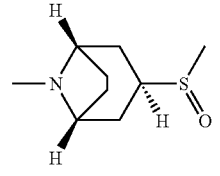 | | henyl | .63/7.70 | 29 |
| —CH₃/4-F | ,5-di-CF₃ | are together with the N-atom 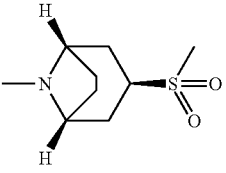 | | henyl | .92/7.83 | 30 |
| —CH₃/4-F | ,5-di-CF₃ | are together with the N-atom 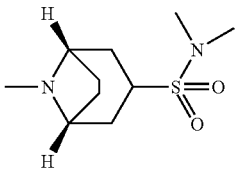 | | henyl | .02/8.60 | 31 |
| —Cl/H | ,5-di-CF₃ | are together with the N-atom 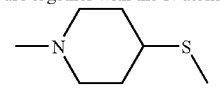 | | henyl | .70/8.04 | 32 |
| —Cl/H | ,5-di-CF₃ | are together with the N-atom 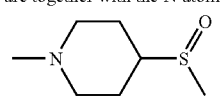 | | henyl | .82/8.06 | 33 |
| —Cl/H | ,5-di-CF₃ | are together with the N-atom 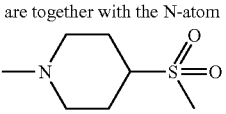 | | henyl | .01/8.56 | 34 |

-continued

| Subst. on R¹ | R²/R³ | R⁴ R⁵ | R¹ | pKi NK1/NK3 | Expl. |
|---|---|---|---|---|---|
| —CH₃/4-F | ,5-di-CF₃ | are together with the N-atom | henyl | .59/8.25 | 35 |
| —CH₃/4-F | ,5-di-CF₃ | are together with the N-atom | henyl | .00/8.67 | 36 |
| —CH₃/4-F | ,5-di-CF₃ | are together with the N-atom | henyl | .79/7.99 | 37 |
| —CH₃/4-F | ,5-di-CF₃ | are together with the N-atom | henyl | .05/8.74 | 38 |
| —CH₃/4-F | ,5-di-CF₃ | are together with the N-atom | henyl | .97/7.98 | 39 |
| —CH₃/4-F | ,5-di-CF₃ | are together with the N-atom | henyl | .88/7.81 | 40 |
| —CH₃/4-F | ,5-di-CF₃ | are together with the N-atom | henyl | .92/8.18 | 41 |
| —CH₃/4-F | ,5-di-CF₃ | are together with are together with the N-atom | henyl | .65/8.93 | 42 |
| —CH₃/4-F | ,5-di-CF₃ | are together with the N-atom | henyl | .78/7.70 | 43 |

-continued

| Subst. on R[1] | R[2]/R[3] | R[4] | R[5] | R[1] | pKi NK1/NK3 | Expl. |
|---|---|---|---|---|---|---|
| —CH$_3$/4-F | ,5-di-CF$_3$ | are together with the N-atom (bicyclic N-oxa structure) | | henyl | .99/7.69 | 44 |
| —CH$_3$/4-F | ,5-di-CF$_3$ | (CH$_2$)$_2$SCH$_3$— | | henyl | .00/7.95 | 45 |
| —CH$_3$/4-F | ,5-di-CF$_3$ | (CH$_2$)$_2$S(O)$_2$CH3— | | henyl | .81/8.08 | 46 |
| —CH$_3$/4-F | ,5-di-CF$_3$ | are together with the N-atom (thiazolidine) | | henyl | .93/7.93 | 47 |
| —CH$_3$/4-F | ,5-di-CF$_3$ | are together with the N-atom (hydroxymethyl thiazolidine S-oxide) | | henyl | .97/8.55 | 48 |
| —CH$_3$/4-F | ,5-di-CF$_3$ | are together with the N-atom (hydroxymethyl thiazolidine S-oxide) | | henyl | .85/.65 | 49 |
| —CH$_3$/4-F | ,5-di-CF$_3$ | are together with the N-atom (hydroxymethyl thiazolidine S,S-dioxide) | | henyl | .80/8.31 | 50 |
| —CH$_3$/4-F | ,5-di-CF$_3$ | are together with the N-atom (bicyclic thia-S,S-dioxide) | | henyl | .39/8.27 | 51 |
| —CH$_3$/H | ,5-di-CF$_3$ | are together with the N-atom (hydroxymethyl thiomorpholine S,S-dioxide) | | henyl | .07/8.33 | 52 |

-continued

| Subst. on R¹ | R²/R³ | R⁴ | R⁵ | R¹ | pKi NK1/NK3 | Expl. |
|---|---|---|---|---|---|---|
| —CH₃/H | ,5-di-CF₃ | are together with the N-atom (thiomorpholine-S,S-dioxide with CH₂OH) | | henyl | .08/8.81 | 53 |
| —CH₃/4-F | ,5-di-CF₃ | are together with the N-atom (7-membered ring with S=O) | | henyl | .65/7.70 | 54 |
| —CH₃/4-F | ,5-di-CF₃ | are together with the N-atom (7-membered ring with SO₂) | | henyl | .63/7.72 | 55 |
| —CH₃/4-F | ,5-di-CF₃ | are together with the N-atom (thiomorpholine-S,S-dioxide) | | henyl | .95/7.92 | 56 |
| —CH₃/4-F | ,5-di-CF₃ | (CH₂)₂NH₂⁻ | | henyl | .74/7.65 | 57 |
| —CH₃/4-F | ,5-di-CF₃ | (CH₂)₂NHS(O)₂CH₃⁻ | | henyl | .47/7.77 | 58 |
| —CH₃/4-F | ,5-di-CF₃ | are together with the N-atom (imidazolidine-N-SO₂CH₃) | | henyl | .90/8.00 | 59 |
| —CH₃/4-F | ,5-di-CF₃ | (CH₂)₂NHC(O)CH₃⁻ | | henyl | .78/7.84 | 60 |
| —CH₃/4-F | ,5-di-CF₃ | are together with the N-atom (imidazolidine-N-C(O)CH₃) | | henyl | .42/7.89 | 61 |
| —CH₃/H | ,5-di-CF₃ | are together with the N-atom (piperazine-N-SO₂CH₃) | | henyl | .03/8.32 | 62 |
| —Cl/H | ,5-di-CF₃ | are together with are together with the N-atom (piperazine-N-SO₂CH₃) | | henyl | .13/8.57 | 63 |
| —CH₃/3-Cl | ,5-di-CF₃ | are together with the N-atom (piperazine-N-SO₂CH₃) | | henyl | .15/7.78 | 64 |

-continued

| Subst. on R¹ | R²/R³ | R⁴ R⁵ are together with the N-atom | R¹ | pKi NK1/NK3 | Expl. |
|---|---|---|---|---|---|
| —CH₃/3-F | ,5-di-CF₃ | piperazine-N-SO₂-CH(CH₃)₂ style (N-S(=O)₂-isopropyl) | henyl | .03/8.42 | 65 |
| —CH₃/4-F | ,5-di-CF₃ | piperazine-N-SO₂-isopropyl | henyl | .22/8.67 | 66 |
| —CH₃/4-F | ,5-di-CF₃ | piperazine-N-SO₂-ethyl | henyl | .11/8.44 | 67 |
| —CH₃/4-F | ,5-di-CF₃ | piperazine-N-SO₂-CH₂Cl | henyl | .98/8.39 | 68 |
| —CH₃/4-F | ,5-di-CF₃ | piperazine-N-SO₂-N(CH₃)₂ | henyl | .16/8.67 | 69 |
| —CH₃/4-F | ,5-di-CF₃ | (3-methyl)piperazine-N-SO₂-CH₃ | henyl | .03/8.55 | 70 |
| —CH₃/4-F | ,5-di-CF₃ | (methyl)piperazine-N-SO₂-CH₃ | henyl | .03/8.91 | 71 |
| —Cl/H | ,5-di-CF₃ | (methyl)piperazine-N-SO₂-CH₃ | henyl | .05/8.68 | 72 |
| —CH₃/H | ,5-di-CF₃ | (methyl)piperazine-N-SO₂-CH₃ | henyl | .16/8.80 | 73 |
| —CH₃/4-F | ,5-di-CF₃ | (methyl)piperazine-N-SO₂-CH₃ | henyl | .21/9.22 | 74 |

-continued

| Subst. on R¹ | R²/R³ | R⁴ R⁵ | R¹ | pKi NK1/NK3 | Expl. |
|---|---|---|---|---|---|
| —Cl/H | ,5-di-CF₃ | are together with the N-atom (piperazine, S(=O)₂, stereo) | henyl | .09/8.95 | 75 |
| —CH₃/H | ,5-di-CF₃ | are together with the N-atom (piperazine, S(=O)₂, stereo) | henyl | .14/9.06 | 76 |
| —CH₃/4-F | ,5-di-CF₃ | are together with the N-atom (piperazine, S(=O)₂, stereo) | henyl | .93/8.44 | 77 |
| —CH₃/4-F | ,5-di-CF₃ | are together with the N-atom (piperazine, S(=O)₂, stereo) | henyl | .24/8.76 | 78 |
| —CH₃/4-F | ,5-di-CF₃ | are together with the N-atom (piperazine, S(=O)₂, stereo) | henyl | .79/8.32 | 79 |
| —CH₃/4-F | ,5-di-CF₃ | are together with the N-atom (piperazine, S(=O)₂, stereo) | henyl | .06/8.67 | 80 |
| —CH₃/4-F | ,5-di-CF₃ | are together with the N-atom (bicyclic, S(=O)₂, stereo) | henyl | .01/7.90 | 81 |
| —CH₃/4-F | ,5-di-CF₃ | are together with the N-atom (bicyclic, S(=O)₂, stereo) | henyl | .07/7.96 | 82 |

-continued

| Subst. on R¹ | R²/R³ | R⁴ | R⁵ | R¹ | pKi NK1/NK3 | Expl. |
|---|---|---|---|---|---|---|
| —CH₃/4-F | ,5-di-CF₃ | are together with the N-atom 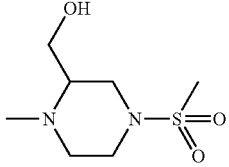 | | henyl | .89/9.31 | 83 |
| —CH₃/4-F | ,5-di-CF₃ | are together with the N-atom 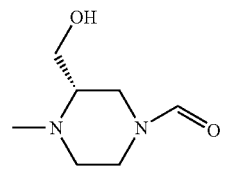 | | henyl | .74/8.99 | 84 |
| —CH₃/4-F | ,5-di-CF₃ | are together with the N-atom 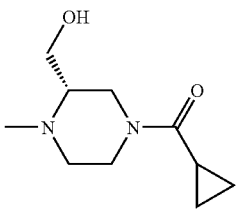 | | henyl | .84/9.19 | 85 |
| —CH₃/4-F | ,5-di-CF₃ | are together with the N-atom 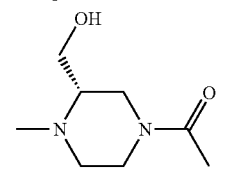 | | henyl | .77/9.18 | 86 |
| —CH₃/4-F | ,5-di-CF₃ | are together with the N-atom 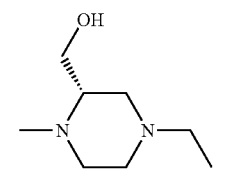 | | henyl | .58/8.67 | 87 |
| —Cl/H | ,5-di-CF₃ | (CH₂)₂S(O)₂NHCH₃— | | henyl | .65/8.04 | 88 |
| —Cl/H | ,5-di-CF₃ | are together with the N-atom 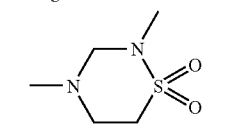 | | henyl | .03/8.13 | 89 |
| —Cl/H | ,5-di-CF₃ | are together with the N-atom 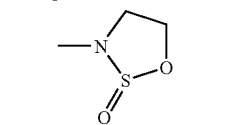 | | henyl | .09/8.22 | 90 |

-continued

| Subst. on R¹ | R²/R³ | R⁴ | R⁵ | R¹ | pKi NK1/NK3 | Expl. |
|---|---|---|---|---|---|---|
| —CH₃/4-F | ,5-di-CF₃ | are together with the N-atom | (piperazine with CH₂OH, N-SO₂Me) | henyl | .85/8.26 | 91 |
| —CH₃/H | ,5-di-CF₃ | are together with the N-atom | (piperazine with CH₂OH, N-SO₂Me) | henyl | .72/8.77 | 92 |
| —CH₃/4-F | ,5-di-CF₃ | are together with the N-atom | (piperazine with CH₂OH, N-SO₂Me) | henyl | .79/8.90 | 93 |
| —CH₃/4-F | ,5-di-CF₃ | are together with the N-atom | (gem-dimethyl piperazine, N-SO₂Me) | henyl | .22/8.64 | 94 |
| —CH₃/H | ,5-di-CF₃ | are together with the N-atom | (gem-dimethyl piperazine, N-SO₂Me) | henyl | .12/8.31 | 95 |
| —CH₂OH/H | ,5-di-CF₃ | are together with the N-atom | (methyl piperazine, N-SO₂Me) | henyl | .85/8.04 | 96 |
| —CH₃/4-F | ,5-di-CF₃ | are together with the N-atom | (gem-dimethyl piperazine, N-SO₂Me) | henyl | .26/8.24 | 97 |
| —CH₃/H | ,5-di-CF₃ | are together with the N-atom | (gem-dimethyl piperazine, N-SO₂Me) | henyl | .85/7.73 | 98 |
| —CH₃/H | ,5-di-OCH₃ | are together with the N-atom | (pyrrolidine with CH₂OH) | henyl | .05/8.15 | 99 |

-continued

| Subst. on R¹ | R²/R³ | R⁴ | R⁵ | R¹ | pKi NK1/NK3 | Expl. |
|---|---|---|---|---|---|---|
| —CH₃/H | ,5-di-OCH₃ | are together with the N-atom (pyrrolidine with OH at 4-position and CH₂OH at 2-position) | | henyl | .48/8.22 | 00 |
| —CH₃/4-F | ,5-di-OCH₃ | (CH₂)₂OH⁻ | | henyl | .59/7.70 | 01 |
| —CH₃/4-F | ,5-di-OCH₃ | are together with the N-atom (pyrrolidine with CH₂OH at 2-position) | | henyl | .44/8.33 | 02 |
| —CH₃/4-F | ,5-di-OCH₃ | are together with the N-atom (pyrrolidine with OH at 4-position and CH₂OH at 2-position) | | henyl | .82/8.24 | 03 |
| —Cl/H | ,5-di-OCH₃ | are together with the N-atom (pyrrolidine with OH at 4-position and CH₂OH at 2-position) | | henyl | .40/8.28 | 04 |
| —CH₃/H | ,5-di-OCHF₂ | (CH₂)₂OH⁻ | | henyl | .72/8.30 | 05 |
| —CH₃/H | ,5-di-OCHF₂ | are together with the N-atom (pyrrolidine with OH at 4-position and CH₂OH at 2-position) | | henyl | .98/9.04 | 06 |
| —CH₃/H | ,5-di-OCHF₂ | are together with the N-atom (pyrrolidine with CH₂OH at 2-position) | | henyl | .53/9.06 | 07 |
| —CH₃/4-F | ,5-di-OCHF₂ | (CH₂)₂OH⁻ | H | henyl | .71/8.25 | 08 |
| —CH₃/4-F | ,5-di-OCHF₂ | are together with the N-atom (pyrrolidine with CH₂OH at 2-position) | | henyl | .51/8.99 | 09 |

-continued

| Subst. on R¹ | R²/R³ | R⁴ | R⁵ | R¹ | pKi NK1/NK3 | Expl. |
|---|---|---|---|---|---|---|
| —Cl/H | ,5-di-OCHF₂ | are together with the N-atom (pyrrolidine with ⸠OH and CH₂OH) | | henyl | .86/9.14 | 10 |
| —Cl/H | ,5-di-OCHF₂ | are together with the N-atom (pyrrolidine with CH₂OH) | | henyl | .46/9.17 | 11 |
| —Cl/H | ,5-di-OCHF₂ | (CH₂)₂OH⁻ | | henyl | .59/8.41 | 12 |
| —CH₃/4-F | ,5-di-OCHF₂ | are together with the N-atom (pyrrolidine with ⸠OH and CH₂OH) | | henyl | .05/9.05 | 13 |
| —CH₃/H | —OCF₃ | are together with the N-atom (pyrrolidine with ⸠OH and CH₂OH) | | henyl | .10/8.23 | 14 |
| —CH₃/4-F | —OCF₃ | are together with the N-atom (pyrrolidine with ⸠OH and CH₂OH) | | henyl | .39/8.24 | 15 |
| —Cl/H | ,5-di-OCHF₂ | are together with the N-atom (piperazine NH) | | henyl | .83/7.64 | 16 |
| —CH₃/4-F | ,5-di-OCHF₂ | are together with the N-atom (piperazine NH) | | henyl | .13/7.63 | 17 |
| —Cl/H | ,5-di-OCHF₂ | are together with the N-atom (piperazine N-SO₂CH₃) | | henyl | .01/8.45 | 18 |
| —CH₃/4-F | ,5-di-OCHf₂ | are together with the N-atom (piperazine N-SO₂CH₃) | | henyl | .18/8.42 | 19 |

-continued

| Subst. on R¹ | R²/R³ | R⁴ | R⁵ | R¹ | pKi NK1/NK3 | Expl. |
|---|---|---|---|---|---|---|
| —CH₃/H | ,5-di-OCHf₂ | are together with the N-atom —N⟨  ⟩NH | | henyl | .13/8.49 | 20 |
| —CH₃/H | ,5-di-OCHF₂ | are together with the N-atom —N⟨  ⟩N—S(=O)(=O)—  | | henyl | .10/7.61 | 21 |

The present invention also provides pharmaceutical compositions containing compounds of formula I or pharmaceutically usable acid addition salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of formula I or a pharmaceutically usable acid addition salt thereof, contain a pharmaceutically acceptable excipient. Suitable pharmaceutically inert excipients include pharmaceutically inert, inorganic or organic excipients for the production of tablets, coated tablets, dragées and hard gelatine capsules. Lactose, corn starch or derivatives thereof, talc, stearic acid or its salts etc. can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions of the invention can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the present invention are dual NK-1/NK-3 antagonists. Therefore, the present invention also provides a method for the treatment of schizophrenia. Such method includes administering a therapeutically effective amount of a compound of formula I, or a pharmaceutically acceptable addition salt thereof, to an individual. In particular, such method includes administering a therapeutically effective amount of a compound of formula I-1, or a pharmaceutically acceptable acid addition salt thereof, to an individual.

In individual embodiments, the present invention provides methods for the treatment of schizophrenia which comprise administering to an individual an effective amount of a compound of formula IA, IB, IC, ID, IE, IF, IG, IH, IJ, or a pharmaceutically acceptable acid addition salt of any one or more of these compounds.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions or suspensions. The pharmaceutical compositions also can be administered rectally, for example, in the form of suppositories or parenterally, for example, in the form of injectable solutions.

The dosage at which the compound of the invention is administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

Intermediate 1

(6-Chloro-4-iodo-pyridin-3-yl)-methyl-carbamic acid tert-butyl Ester

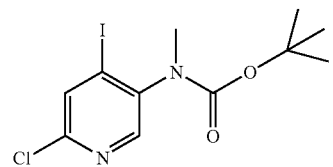

To a solution of 1.00 g (2.82 mmol) (6-chloro-4-iodo-pyridin-3-yl)-carbamic acid tert-butyl ester in 10 ml DMF were added 0.12 g (3.1 mmol) sodium hydride (60% in mineral oil) at −10° C. (The preparation of (6-chloro-4-iodo-pyridin-3-yl)-carbamic acid tert-butyl ester has been described in US 2002/0022624 A1.) The reaction mixture was allowed to warm to room temperature. After 1 h, the mixture was cooled back to −10° C., and 0.44 ml (7.1 mmol) iodomethane were added during 5 min. The reaction mixture was allowed to warm to room temperature. After 2.5 h at room temperature, the reaction was quenched by addition of 10 ml of a saturated aqueous solution of NaHCO₃ and the mixture was extracted with ethyl acetate. The combined organic layers were washed with brine, dried over Na₂SO₄ and concentrated in vacuo. The crude product was purified by column chromatography (silica gel, hexanes/ethyl acetate=4:1) to give 1.06 g (100%) of the title compound as a colorless oil.

MS m/e (%): 368 (M⁺, 1)

Intermediate 2

(6-Chloro-4-iodo-pyridin-3-yl)-methyl-amine

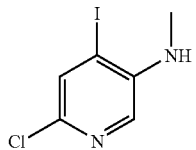

To a solution of 8.65 g (19.6 mmol) (6-chloro-4-iodo-pyridin-3-yl)-methyl-carbamic acid tert-butyl ester in 20 ml dichloromethane were added 20.0 ml (261 mmol) trifluoroacetic acid at 0° C. After stirring for 2 h at room temperature the reaction mixture was concentrated in vacuo. The residue was treated with 50 ml saturated sodium carbonate solution and extracted three times with 75 ml ethyl acetate. The combined organic layers were washed with 50 ml brine, dried over sodium sulfate and concentrated in vacuo to give 6.1 g (87%) of the title compound as a light brown solid.

MS m/e (%): 268 (M+, 1)

Intermediate 3A

[6-Chloro-4-(2-chloro-phenyl)-pyridin-3-yl]-methyl-amine

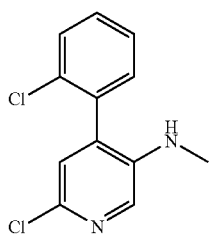

A mixture of 6.05 g (19.3 mmol) (6-chloro-4-iodo-pyridin-3-yl)-methyl-amine, 23.6 g (23.6 mmol) 2-chlorophenylboronic acid, 441 mg (1.96 mmol) palladium(II) acetate, 1.03 g (3.93 mmol) triphenylphosphine, 47.1 ml 2 N sodium carbonate solution and 50 ml 1,2-dimethoxyethane was heated at 80° C. for 90 min. The reaction mixture was cooled to room temperature and diluted with 100 ml ethyl acetate. The aqueous layer was separated and extracted with 100 ml ethyl acetate. The combined organic layers were dried over sodium sulfate, concentrated in vacuo and purified by flash chromatography to give 4.1 g (83%) of the title compound as a light brown solid.

MS m/e (%): 253 (M+H+, 100)

Intermediate 3B

[4-(2-Bromo-phenyl)-6-chloro-pyridin-3-yl]-methyl-amine

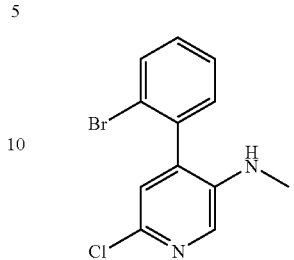

The title compound was obtained as a brown solid in 86% yield after flash chromatography according to the procedure described above for the preparation of [6-chloro-4-(2-chloro-phenyl)-pyridin-3-yl]-methyl-amine using 2-bromophenylboronic acid instead of 2-chlorophenylboronic acid.

MS m/e (%): 297 (M+H+, 85)

Intermediate 3C

[6-Chloro-4-(2-chloro-4-fluoro-phenyl)-pyridin-3-yl]-methyl-amine

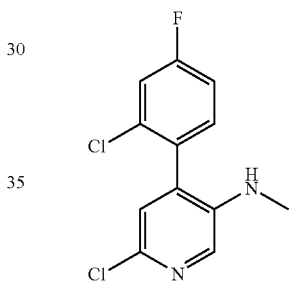

The title compound was obtained as a light brown solid in 69% yield after flash chromatography according to the procedure described above for the preparation of [6-chloro-4-(2-chloro-phenyl)-pyridin-3-yl]-methyl-amine using 2-chloro-4-fluorophenylboronic acid instead of 2-chlorophenylboronic acid.

MS m/e (%): 271 (M+H+, 100)

Intermediate 3D

[6-Chloro-4-(4-fluoro-2-methyl-phenyl)-pyridin-3-yl]-methyl-amine

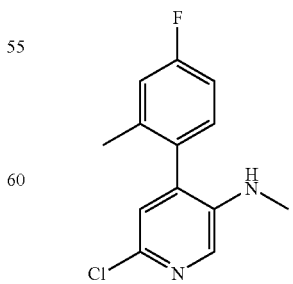

The title compound was obtained as a orange solid in 80% yield after flash chromatography according to the procedure described above for the preparation of [6-chloro-4-(2-chlorophenyl)-pyridin-3-yl]-methyl-amine using 4-fluoro-2-methyl-phenylboronic acid instead of 2-chlorophenylboronic acid.

MS m/e (%): 251 (M+H$^+$, 100)

Intermediate 3E

[6-Chloro-4-(3-fluoro-2-methyl-phenyl)-pyridin-3-yl]-methyl-amine

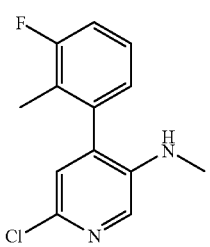

The title compound was obtained as an off-white solid in comparable yield after flash chromatography according to the procedure described above for the preparation of [6-chloro-4-(2-chloro-phenyl)-pyridin-3-yl]-methyl-amine using 3-fluoro-2-methyl-phenylboronic acid instead of 2-chlorophenylboronic acid.

MS m/e (%): 251 (M+H$^+$, 100)

Intermediate 3F

[6-Chloro-4-(5-fluoro-2-methyl-phenyl)-pyridin-3-yl]-methyl-amine

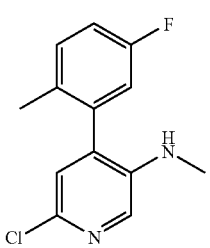

The title compound was obtained as an off-white solid in comparable yield after flash chromatography according to the procedure described above for the preparation of [6-chloro-4-(2-chloro-phenyl)-pyridin-3-yl]-methyl-amine using 5-fluoro-2-methyl-phenylboronic acid instead of 2-chlorophenylboronic acid.

MS m/e (%): 251 (M+H$^+$, 100)

Intermediate 3G (6-Chloro-4-o-tolyl-pyridin-3-yl)-methyl-amine

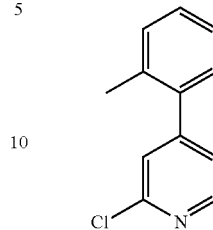

The title compound was obtained as a light brown solid in 92% yield after flash chromatography according to the procedure described above for the preparation of [6-chloro-4-(2-chloro-phenyl)-pyridin-3-yl]-methyl-amine using o-tolylboronic acid instead of 2-chlorophenylboronic acid.

MS m/e (%): 233 (M+H$^+$, 100)

Intermediate 3H

[6-Chloro-4-(2,4-dichloro-phenyl)-pyridin-3-yl]-methyl-amine

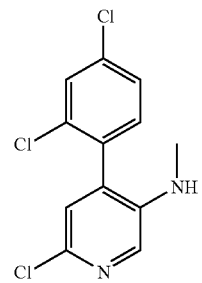

The title compound was obtained as a light brown solid in 70% yield after flash chromatography according to the procedure described above for the preparation of [6-chloro-4-(2-chloro-phenyl)-pyridin-3-yl]-methyl-amine using 2,4-dichlorophenylboronic acid instead of 2-chlorophenylboronic acid.

MS m/e (%): 287 (M+H$^+$, 100)

Intermediate 3I

[6-Chloro-4-(3,4-dichloro-phenyl)-pyridin-3-yl]-methyl-amine

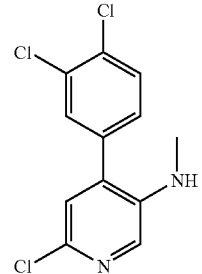

The title compound was obtained as a light brown solid in 68% yield after flash chromatography according to the procedure described above for the preparation of [6-chloro-4-(2- chloro-phenyl)-pyridin-3-yl]-methyl-amine using 3,4-dichlorophenylboronic acid instead of 2-chlorophenylboronic acid.

MS m/e (%): 287 (M+H$^+$, 100)

Intermediate 3J

[6-Chloro-4-(4-fluoro-phenyl)-pyridin-3-yl]-methyl-amine

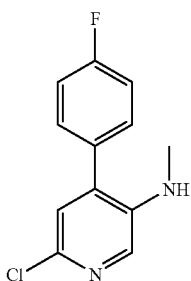

The title compound was obtained as an off-white solid in comparable yield according to the procedure described above for the preparation of [6-chloro-4-(2-chloro-phenyl)-pyridin-3-yl]-methyl-amine using 4-fluorophenylboronic acid instead of 2-chlorophenylboronic acid.

MS m/e (%): 237 (M+H$^+$, 100)

Intermediate 3K

[6-Chloro-4-(3-chloro-2-methyl-phenyl)-pyridin-3-yl]-methyl-amine a) 3-Chloro-2-methyl-phenylboronic acid

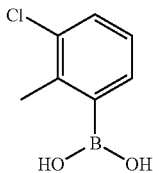

To a solution of 10.0 g (48.7 mmol) 2-bromo-6-chlorotoluene and 11.3 ml (48.7 mmol) triisopropyl borate in 90 ml dry THF were added dropwise 30 ml (49 mmol) of a 1.6 M solution on n-butyllithium in hexanes at −78° C. under argon. After 45 min the reaction mixture was allowed to warm to room temperature. The reaction was quenched by addition of 5 ml water and the solvent was evaporated in vacuo. Addition of 1 M aqueous hydrochloric acid solution was followed by extraction with four portions of dichloromethane. The combined organic extracts were dried over sodium sulfate and concentrated in vacuo. Crystallisation from heptane gave 5.08 g (61%) of the title compound as a white solid.

b) [6-Chloro-4-(3-chloro-2-methyl-phenyl)-pyridin-3-yl]-methyl-amine

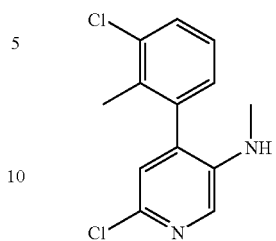

The title compound was obtained as an off-white solid in comparable yield after flash chromatography according to the procedure described above for the preparation of [6-chloro-4-(2-chloro-phenyl)-pyridin-3-yl]-methyl-amine (Intermediate 3A) using 3-chloro-2-methyl-phenylboronic acid instead of 2-chlorophenylboronic acid.

Intermediate 3L

{4-[2-(tert-Butyl-dimethyl-silanyloxymethyl)-phenyl]-6-chloro-pyridin-3-yl}-methyl-amine a) [2-(2-Chloro-5-methylamino-pyridin-4-yl)-phenyl]-methanol

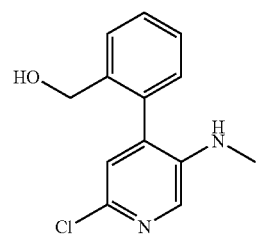

The title compound was obtained as a yellow oil in comparable yield according to the procedure described above for the preparation of [6-chloro-4-(2-chloro-phenyl)-pyridin-3-yl]-methyl-amine using 2-(hydroxymethyl)benzeneboronic acid instead of 2-chlorophenylboronic acid.

MS m/e (%): 249 (M+H$^+$, 100)

b) {4-[2-(tert-Butyl-dimethyl-silanyloxymethyl)-phenyl]-6-chloro-pyridin-3-yl}-methyl-amine

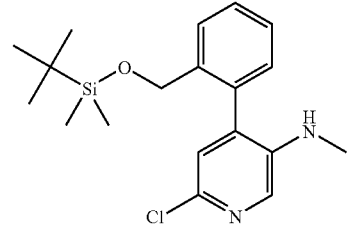

The crude title compound was obtained as a yellow oil in quantitative yield after extraction according to the procedure described above for the preparation of (S)-4-benzyl-3-(tert-butyl-dimethyl-silanyloxymethyl)-morpholine (Example 174a)) using [2-(2-chloro-5-methylamino-pyridin-4-yl)-phenyl]-methanol instead of (R)-(4-benzyl-morpholin-3-yl)-methanol.

MS m/e (%): 363 (M+H$^+$, 100)

Intermediate 4A 2-(3,5-Bis-trifluoromethyl-phenyl)-N-[6-chloro-4-(2-chloro-phenyl)-pyridin-3-yl]-N-methyl-isobutyramide

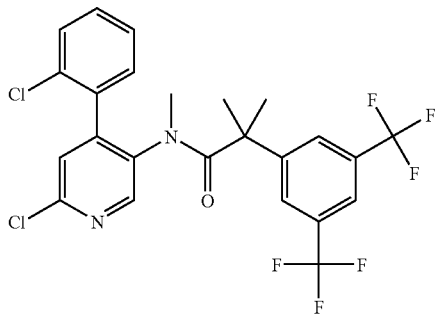

To a solution of 20 g (79 mmol) [6-chloro-4-(2-chlorophenyl)-pyridin-3-yl]-methyl-amine in 200 ml tetrahydrofuran were added dropwise at 0° C. 113 ml (94.8 mmol) of a 0.91 M solution of potassium bis(trimethylsilyl)amide in tetrahydrofuran. The reaction mixture was stirred at room temperature for 30 min. After cooling to 0° C. 27.7 g (86.9 mmol) 2-(3,5-bis-trifluoromethyl-phenyl)-2-methyl-propionyl chloride were added dropwise. The reaction mixture was allowed to warm to room temperature and stirred at room temperature for 1 h. The reaction mixture was treated with 220 ml 1 N sodium hydrogencarbonate solution and extracted with three 200-ml portions of ethyl acetate. The combined organic layers were dried over sodium sulfate and triturated with 150 ml diethylether to give 34.6 g (82%) of the title compound as a white solid.

MS m/e (%): 535 (M+H$^+$, 100)

Intermediate 4B 2-(3,5-Bis-trifluoromethyl-phenyl)-N-[4-(2-bromo-phenyl)-6-chloro-pyridin-3-yl]-N-methyl-isobutyramide

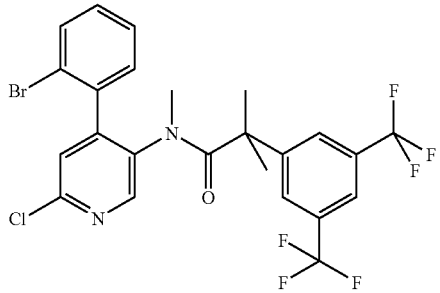

The title compound was obtained as a light yellow solid in 68% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [4-(2-bromophenyl)-6-chloro-pyridin-3-yl]-methyl-amine instead of [6-chloro-4-(2-chloro-phenyl)-pyridin-3-yl]-methyl-amine.

MS m/e (%): 579 (M+H$^+$, 98)

Intermediate 4C 2-(3,5-Bis-trifluoromethyl-phenyl)-N-[6-chloro-4-(2-chloro-4-fluoro-phenyl)-pyridin-3-yl]-N-methyl-isobutyramide

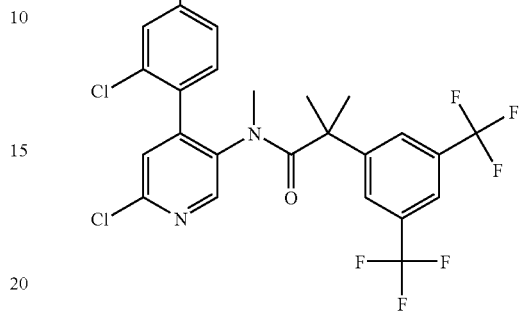

The title compound was obtained as a white foam in 52% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(2-chloro-4-fluoro-phenyl)-pyridin-3-yl]-methyl-amine instead of [6-chloro-4-(2-chloro-phenyl)-pyridin-3-yl]-methyl-amine.

MS m/e (%): 553 (M+H$^+$, 100)

Intermediate 4D 2-(3,5-Bis-trifluoromethyl-phenyl)-N-[6-chloro-4-(4-fluoro-2-methyl-phenyl)-pyridin-3-yl]-N-methyl-isobutyramide

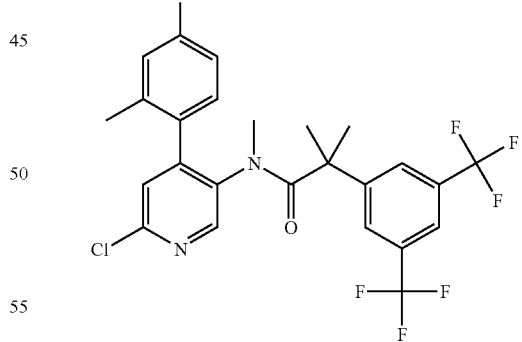

The title compound was obtained as a light yellow foam in 87% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(4-fluoro-2-methyl-phenyl)-pyridin-3-yl]-methyl-amine instead of [6-chloro-4-(2-chloro-phenyl)-pyridin-3-yl]-methyl-amine.

MS m/e (%): 533 (M+H$^+$, 100)

Intermediate 4E 2-(3,5-Bis-trifluoromethyl-phenyl)-N-[6-chloro-4-(3-fluoro-2-methyl-phenyl)-pyridin-3-yl]-N-methyl-isobutyramide

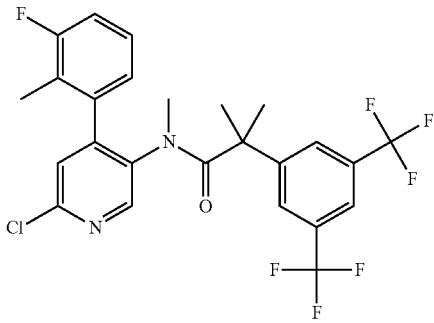

The title compound was obtained as a light brown solid in 78% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(3-fluoro-2-methyl-phenyl)-pyridin-3-yl]-methyl-amine instead of [6-chloro-4-(2-chloro-phenyl)-pyridin-3-yl]-methyl-amine.

MS m/e (%): 533 (M+H$^+$, 100)

Intermediate 4F 2-(3,5-Bis-trifluoromethyl-phenyl)-N-[6-chloro-4-(5-fluoro-2-methyl-phenyl)-pyridin-3-yl]-N-methyl-isobutyramide

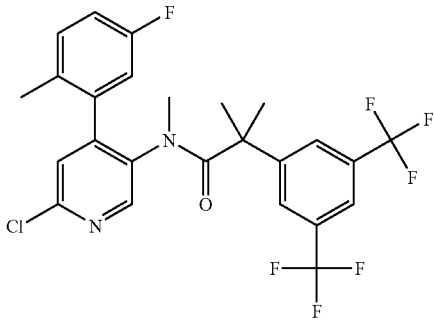

The title compound was obtained as a light yellow solid in comparable yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(3-fluoro-2-methyl-phenyl)-pyridin-3-yl]-methyl-amine instead of [6-chloro-4-(2-chloro-phenyl)-pyridin-3-yl]-methyl-amine.

MS m/e (%): 533 (M+H$^+$, 100)

Intermediate 4G 2-(3,5-Bis-trifluoromethyl-phenyl)-N-(6-chloro-4-o-tolyl-pyridin-3-yl)-N-methyl-isobutyramide

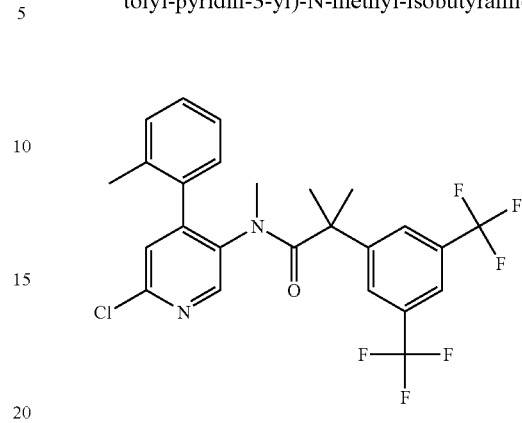

The title compound was obtained as a white solid in 78% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using (6-chloro-4-o-tolyl-pyridin-3-yl)-methyl-amine instead of [6-chloro-4-(2-chloro-phenyl)-pyridin-3-yl]-methyl-amine.

MS m/e (%): 514 (M$^+$, 5)

Intermediate 4H 2-(3,5-Bis-trifluoromethyl-phenyl)-N-[6-chloro-4-(2,4-dichloro-phenyl)-pyridin-3-yl]-N-methyl-isobutyramide

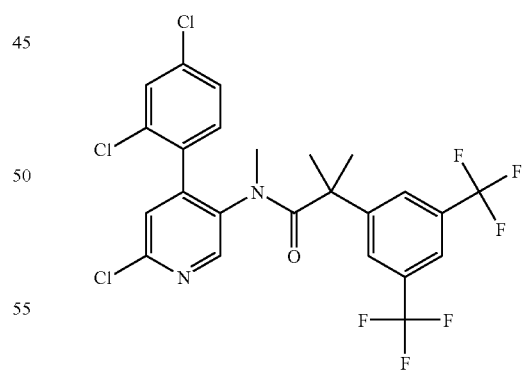

The title compound was obtained as a light yellow foam in 57% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(2,4-dichloro-phenyl)-pyridin-3-yl]-methyl-amine instead of [6-chloro-4-(2-chloro-phenyl)-pyridin-3-yl]-methyl-amine.

MS m/e (%): 569 (M+H$^+$, 100)

Intermediate 4I 2-(3,5-Bis-trifluoromethyl-phenyl)-N-[6-chloro-4-(3,4-dichloro-phenyl)-pyridin-3-yl]-N-methyl-isobutyramide

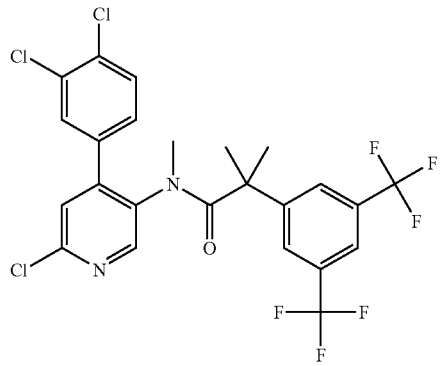

The title compound was obtained as a light yellow foam in 45% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(3,4-dichloro-phenyl)-pyridin-3-yl]-methyl-amine instead of [6-chloro-4-(2-chloro-phenyl)-pyridin-3-yl]-methyl-amine.

MS m/e (%): 569 (M+H$^+$, 100)

Intermediate 4J 2-(3,5-Bis-trifluoromethyl-phenyl)-N-[6-chloro-4-(4-fluoro-phenyl)-pyridin-3-yl]-N-methyl-isobutyramide

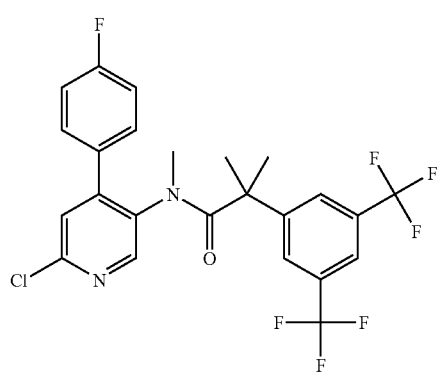

The title compound was obtained as a light brown solid in 92% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using [6-chloro-4-(3,4-dichloro-phenyl)-pyridin-3-yl]-methyl-amine instead of [6-chloro-4-(2-chloro-phenyl)-pyridin-3-yl]-methyl-amine.

MS m/e (%): 519 (M+H$^+$, 100)

Intermediate 4K 2-(3,5-Bis-trifluoromethyl-phenyl)-N-[6-chloro-4-(3-chloro-2-methyl-phenyl)-pyridin-3-yl]-N-methyl-isobutyramide

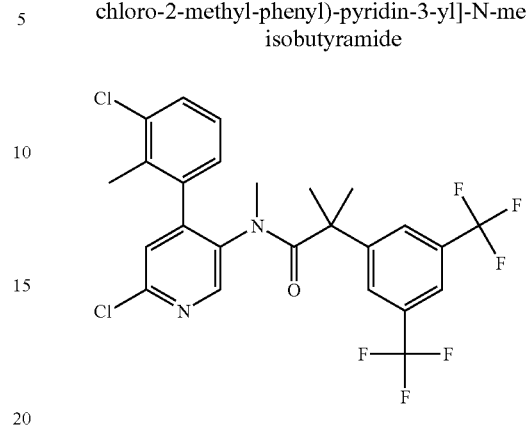

The title compound was obtained as a white solid in 49% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide (Intermediate 4A) using [6-chloro-4-(3-chloro-2-methyl-phenyl)-pyridin-3-yl]-methyl-amine instead of [6-chloro-4-(2-chloro-phenyl)-pyridin-3-yl]-methyl-amine.

MS m/e (%): 549 (M+H$^+$, 100)

Intermediate 4L 2-(3,5-Bis-trifluoromethyl-phenyl)-N-{4-[2-(tert-butyl-dimethyl-silanyloxymethyl)-phenyl]-6-chloro-pyridin-3-yl}-N-methyl-isobutyramide

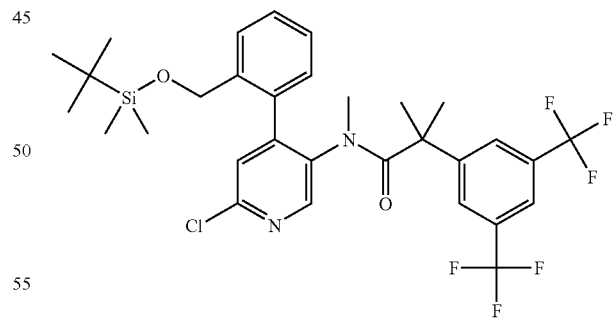

The title compound was obtained as a light yellow oil in 76% yield after flash chromatography according to the procedure described above for the preparation of 2-(3,5-bis-trifluoromethyl-phenyl)-N-[6-chloro-4-(2-chloro-phenyl)-pyridin-3-yl]-N-methyl-isobutyramide using {4-[2-(tert-butyl-dimethyl-silanyloxymethyl)-phenyl]-6-chloro-pyridin-3-yl}-methyl-amine instead of [6-chloro-4-(2-chloro-phenyl)-pyridin-3-yl]-methyl-amine.

MS m/e (%): 645 (M+H$^+$, 100)

Intermediate 5A

2-(3,5-Dichloro-phenyl)-2-methyl-propionyl Chloride a) 2-(3,5-Dichloro-phenyl)-2-methyl-propionic Acid Methyl Ester

A solution of 18.2 g (82.8 mmol) (3,5-dichloro-phenyl)-acetic acid methyl ester in 15 ml THF was added to a solution of lithium diisopropylamide in THF (obtained by adding 49.7 ml (99.4 mmol) of a 2 M solution of lithium diisopropylamide in THF/heptane/ethylbenzene to 125 ml THF at −20° C. After stirring for 45 min. 6.3 ml (99.4 mmol) methyl iodide in 12 ml THF was added at the same temperature over a period of 30 min. To this solution another 49.7 ml (99.4 mmol) lithium diisopropylamide solution (2 M) in THF/heptane/ethylbenzene was added at −20° C. followed by 6.3 ml (99.4 mmol) methyl iodide in 12 ml THF. After stirring for 2 h at ambient temperature the solution was poured into 500 ml 2 N hydrochloric acid solution and extracted three times with 300 ml $CH_2Cl_2$. The combined organic layers were dried ($Na_2SO_4$), filtered and evaporated. The residue was purified by flash-chromatography ($SiO_2$, $CH_2Cl_2$/hexanes 1:2) to yield 17.0 g (83%) 2-(3,5-dichloro-phenyl)-2-methyl-propionic acid methyl ester as a light yellow oil.

MS m/e (%): 246 ($M^+$, 38), 187 (100).

b) 2-(3,5-Dichloro-phenyl)-2-methyl-propionic Acid

To a solution of 9.0 g (36 mmol) 2-(3,5-dichloro-phenyl)-2-methyl-propionic acid methyl ester in 40 ml ethanol 40 ml 2 N sodium hydroxide solution was added. After stirring for 4 hrs at RT 150 ml water was added and the solution washed twice with 200 ml $Et_2O$. The aqueous phase was acidified with 25% hydrochloric acid solution and three times extracted with 150 ml $CH_2Cl_2$. The combined organic layers were dried ($Na_2SO_4$), filtered and evaporated to yield 8.3 g (97%) 2-(3,5-dichloro-phenyl)-2-methyl-propionic acid as a off-white solid.

MS m/e (%): 232 ($M^+$, 28), 187 (100).

c) 2-(3,5-Dichloro-phenyl)-2-methyl-propionyl Chloride

To a solution of 8.3 g (35.6 mmol) 2-(3,5-dichloro-phenyl)-2-methyl-propionic acid in 80 ml $CH_2Cl_2$ and 4 drops DMF 6.1 ml (71.2 mmol) oxalyl chloride was added at 0° C. and the resulting mixture stirred for 12 h After evaporation of the solvent 8.3 g (93%) 2-(3,5-dichloro-phenyl)-2-methyl-propionyl chloride was obtained as a light yellow oil, which was used without further purification.

Intermediate 5B

2-(3-Fluoro-5-trifluoromethyl-phenyl)-2-methyl-propionyl Chloride

The title compound was obtained as a yellow oil in an analogous manner to that described for 2-(3,5-dichloro-phenyl)-2-methyl-propionyl chloride using (3-fluoro-5-trifluoromethyl-phenyl)-acetic acid methyl ester in step a).

Intermediate 5C

2-Methyl-2-(3-trifluoromethyl-phenyl)-propionyl Chloride

The title compound was obtained as a yellow oil in an analogous manner to that described for 2-(3,5-dichloro-phenyl)-2-methyl-propionyl chloride using (3-trifluoromethyl-phenyl)-acetic acid methyl ester in step a).

Intermediate 5D

2-(3,5-Difluoro-phenyl)-2-methyl-propionyl Chloride

The title compound was obtained as a yellow oil in analogous manner to that described for 2-(3,5-dichloro-phenyl)-2-methyl-propionyl chloride using (3,5-difluoro-phenyl)-acetic acid methyl ester in step a).

Intermediate 5E

2-(3-Chloro-5-methoxy-phenyl)-2-methyl-propionyl Chloride

The title compound was obtained as a yellow oil in an analogous manner to that described for 2-(3,5-dichloro-phenyl)-2-methyl-propionyl chloride using (3-chloro-5-methoxy-phenyl)-acetic acid methyl ester in step a).

Intermediate 5F

2-(3,5-Dimethyl-phenyl)-2-methyl-propionyl Chloride

The title compound was obtained as a yellow oil in an analogous manner to that described for 2-(3,5-dichloro-phenyl)-2-methyl-propionyl chloride using (3,5-dimethyl-phenyl)-acetic acid methyl ester in step a).

Intermediate 5G

2-(3,5-Bis-trifluoromethyl-phenyl)-2-methyl-propionyl Chloride

The title compound is obtained according to the procedure described in WO 0279134 A1.

Intermediate 5H

2-(3,5-Dimethoxy-phenyl)-2-methyl-propionyl Chloride

The title compound was obtained as a light red oil in an analogous manner to that described for 2-(3,5-dichloro-phenyl)-2-methyl-propionyl chloride using (3,5-dimethoxy-phenyl)-acetic acid ethyl ester in step a).

Intermediate 5I

2-Methyl-2-(3-trifluoromethoxy-phenyl)-propionyl Chloride

The title compound was obtained as a light yellow oil in an analogous manner to that described for 2-(3,5-dichloro-phenyl)-2-methyl-propionyl chloride using (3-trifluoromethoxy-phenyl)-acetic acid ethyl ester in step a).

EXAMPLE 1

N-[4-(2-Chloro-phenyl)-6-(2-hydroxy-ethylamino)-pyridin-3-yl]-2-(3,5-dichloro-phenyl)-N-methyl-isobutyramide a) N-[6-Chloro-4-(2-chloro-phenyl)-pyridin-3-yl]-2-(3,5-dichloro-phenyl)-N-methyl-isobutyramide To a solution of 1.20 g (4.74 mmol) [6-chloro-4-(2-chloro-phenyl)-pyridin-3-yl]-methyl-amine and 1.43 g (5.68 mmol) 2-(3,5-dichloro-phenyl)-2-methyl-propionyl chloride in 20 ml toluene 1.27 g (10.42 mmol) 4-dimethylaminopyridine was added and the resulting solution stirred at 120° for 48 h. After cooling to ambient temperature, the solution was poured into 100 ml 0.5 N NaHCO$_3$-solution and extracted three times with 50 ml CH$_2$Cl$_2$. The combined organic layers were dried (Na$_2$SO$_4$), filtered and evaporated. The residue was purified by flash-chromatography (SiO$_2$, hexanes/ethyl acetate 4:1) to give 1.90 g (85%) of the title compound as a white solid.
MS m/e (%): 469.1 (M+H$^+$, 100).

b) N-[4-(2-Chloro-phenyl)-6-(2-hydroxy-ethylamino)-pyridin-3-yl]-2-(3,5-dichloro-phenyl)-N-methyl-isobutyramide A solution of 0.14 g (0.29 mmol) N-[6-chloro-4-(2-chloro-phenyl)-pyridin-3-yl]-2-(3,5-dichloro-phenyl)-N-methyl-isobutyramide and 4 ml ethanolamine was stirred at 130° for 9 h. After cooling to ambient temperature, the solution was poured into 20 ml 0.5N NaHCO$_3$-solution and extracted three times with 30 ml CH$_2$Cl$_2$. The combined organic layers were dried (Na$_2$SO$_4$), filtered and evaporated. The residue was purified by flash-chromatography (SiO$_2$, CH$_2$Cl$_2$/ethyl acetate 1:3) to give 0.08 g (54%) of the title compound as a white foam.
MS m/e (%): 492.2 (M+H$^+$, 100).

EXAMPLE 2

(S)-N-[4-(2-Chloro-phenyl)-6-(2-hydroxymethyl-pyrrolidin-1-yl)-pyridin-3-yl]-2-(3,5-dichloro-phenyl)-N-methyl-isobutyramide To a solution of 0.15 g (0.32 mmol) N-[6-chloro-4-(2-chloro-phenyl)-pyridin-3-yl]-2-(3,5-dichloro-phenyl)-N-methyl-isobutyramide and 0.25 g (2.47 mmol) L-prolinol in 2 ml dimethyl sulfoxide 0.2 g (1.55 mmol) Na$_2$CO$_3$ was added and the solution was stirred at 13° C. for 22 h. After cooling to ambient temperature, the solution was poured into 20 ml 0.5 N NaHCO$_3$-solution and extracted three times with 30 ml CH$_2$Cl$_2$. The combined organic layers were dried (Na$_2$SO$_4$), filtered and evaporated. The residue was purified by flash-chromatography (SiO$_2$, CH$_2$Cl$_2$/ethyl acetate 1:2) to give 0.15 g (87%) of the title compound as a white foam.
MS m/e (%): 532.2 (M+H$^+$, 100).

EXAMPLE 3

(2S,4R)-N-[4-(2-Chloro-phenyl)-6-(4-hydroxy-2-hydroxymethyl-pyrrolidin-1-yl)-pyridin-3-yl]-2-(3,5-dichloro-phenyl)-N-methyl-isobutyramide To a solution of 0.15 g (0.32 mmol) N-[6-chloro-4-(2-chloro-phenyl)-pyridin-3-yl]-2-(3,5-dichloro-phenyl)-N-methyl-isobutyramide and 0.25 g (2.13 mmol) (2S,4R)-4-hydroxy-2-hydroxymethyl-pyrrolidine in 2 ml dimethyl sulfoxide 0.2 g (1.55 mmol) Na$_2$CO$_3$ was added and the solution was stirred at 13° C. for 9 h After cooling to ambient temperature, the solution was poured into 20 ml 0.5 N NaHCO$_3$-solution and extracted three times with 30 ml CH$_2$Cl$_2$. The combined organic layers were dried (Na$_2$SO$_4$), filtered and evaporated. The residue was purified by flash-chromatography (SiO$_2$, CH$_2$Cl$_2$/ethyl acetate 1:2) to give 0.05 g (31%) of the title compound as a white foam.
MS m/e (%): 548.3 (M+H$^+$, 100).

EXAMPLE 4

(S)-N-[4-(2-Chloro-phenyl)-6-(2-hydroxymethyl-pyrrolidin-1-yl)-pyridin-3-yl]-2-(3-fluoro-5-trifluoromethyl-phenyl)-N-methyl-isobutyramide a) N-[6-Chloro-4-(2-chloro-phenyl)-pyridin-3-yl]-2-(3-fluoro-5-trifluoromethyl-phenyl)-N-methyl-isobutyramide The title compound was obtained in an analogous manner to that described in example 1a) from [6-chloro-4-(2-chloro-phenyl)-pyridin-3-yl]-methyl-amine and 2-(3-fluoro-5-trifluoromethyl-phenyl)-2-methyl-propionyl chloride as a white solid.
MS m/e (%): 485.3 (M+H$^+$, 100).

b) (S)-N-[4-(2-Chloro-phenyl)-6-(2-hydroxymethyl-pyrrolidin-1-yl)-pyridin-3-yl]-2-(3-fluoro-5-trifluoromethyl-phenyl)-N-methyl-isobutyramide The title compound was obtained in an analogous manner to that described in example 2) from N-[6-chloro-4-(2-chloro-phenyl)-pyridin-3-yl]-2-(3-fluoro-5-trifluoromethyl-phenyl)-N-methyl-isobutyramide and L-prolinol as a white foam.
MS m/e (%): 550.3 (M+H$^+$, 100).

EXAMPLE 5

(2S,4R)-N-[4-(2-Chloro-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide The title compound was obtained in an analogous manner to that described in example 3) from N-[6-chloro-4-(2-chloro-phenyl)-pyridin-3-yl]-2-(3-fluoro-5-trifluoromethyl-phenyl)-N-methyl-isobutyramide and (2S,4R)-4-hydroxy-2-hydroxymethyl-pyrrolidine as a light yellow foam.
MS m/e (%): 566.3 (M+H$^+$, 100).

EXAMPLE 6

(2S,4R)-N-[4-(2-Chloro-phenyl)-6-(4-hydroxy-2-hydroxymethyl-pyrrolidin-1-yl)-pyridin-3-yl]-2-(3,5-difluoro-phenyl)-N-methyl-isobutyramide a) N-[6-Chloro-4-(2-chloro-phenyl)-pyridin-3-yl]-2-(3,5-difluoro-phenyl)-N-methyl-isobutyramide The title compound was obtained in an analogous manner to that described in example 1a) from [6-chloro-4-(2-chloro-phenyl)-pyridin-3-yl]-methyl-amine and 2-(3,5-difluoro-phenyl)-2-methyl-propionyl chloride as a light yellow solid.
MS m/e (%): 435.2 (M+H$^+$, 100).

b) (2S,4R)-N-[4-(2-Chloro-phenyl)-6-(4-hydroxy-2-hydroxymethyl-pyrrolidin-1-yl)-pyridin-3-yl]-2-(3,5-difluoro-phenyl)-N-methyl-isobutyramide The title compound was obtained in an analogous manner to that described in example 3) from N-[6-chloro-4-(2-chloro-phenyl)-pyridin-3-yl]-2-(3,5-difluoro-phenyl)-N-methyl-isobutyramide and (2S,4R)-4-hydroxy-2-hydroxymethyl-pyrrolidine as a light yellow foam.
MS m/e (%): 516.3 (M+H$^+$, 100).

EXAMPLE 7

(S)-2-(3-Chloro-5-methoxy-phenyl)-N-[4-(2-chloro-phenyl)-6-(2-hydroxymethyl-pyrrolidin-1-yl)-pyridin-3-yl]-N-methyl-isobutyramide a) N-[6-Chloro-4-(2-chloro-phenyl)-pyridin-3-yl]-2-(3-chloro-5-methoxy-phenyl)-N-methyl-isobutyramide The title compound was obtained in an analogous manner to that described in example 1a) from [6-chloro-4-(2-chloro-phenyl)-pyridin-3-yl]-methyl-amine and 2-(3-chloro-5-methoxy-phenyl)-2-methyl-propionyl chloride as a light yellow solid.
MS m/e (%): 463.2 (M+H$^+$, 100).

b) (S)-2-(3-Chloro-5-methoxy-phenyl)-N-[4-(2-chloro-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(2-chloro-phenyl)-pyridin-3-yl]-2-(3-chloro-5-methoxy-phenyl)-N-methyl-isobutyramide and L-prolinol as a white foam.
MS m/e (%): 528.2 (M+H$^+$, 100).

EXAMPLE 8

(2S,4R)-2-(3-Chloro-5-methoxy-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(2-chloro-phenyl)-pyridin-3-yl]-2-(3-chloro-5-methoxy-phenyl)-N-methyl-isobutyramide and (2S,4R)-4-hydroxy-2-hydroxymethyl-pyrrolidine as a light yellow foam.
MS m/e (%): 544.3 (M+H$^+$, 100).

EXAMPLE 9

(S)-N-[4-(2-Chloro-phenyl)-6-(2-hydroxymethyl-pyrrolidin-1-yl)-pyridin-3-yl]-2-(3,5-dimethyl-phenyl)-N-methyl-isobutyramide a) N-[6-Chloro-4-(2-chloro-phenyl)-pyridin-3-yl]-2-(3,5-dimethyl-phenyl)-N-methyl-isobutyramide The title compound was obtained in an analogous manner to that described in example 1a) from [6-chloro-4-(2-chloro-phenyl)-pyridin-3-yl]-methyl-amine and 2-(3,5-dimethyl-phenyl)-2-methyl-propionyl chloride as a white solid.
MS m/e (%): 427.1 (M+H$^+$, 100).

b) (S)-N-[4-(2-Chloro-phenyl)-6-(2-hydroxymethyl-pyrrolidin-1-yl)-pyridin-3-yl]-2-(3,5-dimethyl-phenyl)-N-methyl-isobutyramide The title compound was obtained in an analogous manner to that described in example 2) from N-[6-chloro-4-(2-chloro-phenyl)-pyridin-3-yl]-2-(3,5-dimethyl-phenyl)-N-methyl-isobutyramide and L-prolinol as a white foam.
MS m/e (%): 492.3 (M+H$^+$, 100).

EXAMPLE 10

(2S,4R)-N-[4-(2-Chloro-phenyl)-6-(4-hydroxy-2-hydroxymethyl-pyrrolidin-1-yl)-pyridin-3-yl]-2-(3,5-dimethyl-phenyl)-N-methyl-isobutyramide The title compound was obtained in an analogous manner to that described in example 3) from N-[6-chloro-4-(2-chloro-phenyl)-pyridin-3-yl]-2-(3,5-dimethyl-phenyl)-N-methyl-isobutyramide and (2S,4R)-4-hydroxy-2-hydroxymethyl-pyrrolidine as a light yellow foam.
MS m/e (%): 508.3 (M+H$^+$, 100).

EXAMPLE 11

(S)-2-(3,5-Dichloro-phenyl)-N-[6-(2-hydroxymethyl-pyrrolidin-1-yl)-4-o-tolyl-pyridin-3-yl]-N-methyl-isobutyramide a) N-(6-Chloro-4-o-tolyl-pyridin-3-yl)-2-(3,5-dichloro-phenyl)-N-methyl-isobutyramide The title compound was obtained in an analogous manner to that described in example 1a) from (6-chloro-4-o-tolyl-pyridin-3-yl)-methyl-amine and 2-(3,5-dichloro-phenyl)-2-methyl-propionyl chloride as a white solid. MS m/e (%): 449.2 (M+H$^+$, 100).

b) (S)-2-(3,5-Dichloro-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from N-(6-chloro-4-o-tolyl-pyridin-3-yl)-2-(3,5-dichloro-phenyl)-N-methyl-isobutyramide and L-prolinol as a white foam.
MS m/e (%): 512.4 (M+H$^+$, 100).

EXAMPLE 12

(2S,4R)-2-(3,5-Dichloro-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from N-(6-chloro-4-o-tolyl-pyridin-3-yl)-2-(3,5-dichloro-phenyl)-N-methyl-isobutyramide and (2S,4R)-4-hydroxy-2-hydroxymethyl-pyrrolidine as a white foam.
MS m/e (%): 528.3 (M+H$^+$, 100).

EXAMPLE 13

(S)-2-(3-Fluoro-5-trifluoromethyl-phenyl)-N-[6-(2-hydroxymethyl-pyrrolidin-1-yl)-4-o-tolyl-pyridin-3-yl]-N-methyl-isobutyramide a) N-(6-Chloro-4-o-tolyl-pyridin-3-yl)-2-(3-fluoro-5-trifluoromethyl-phenyl)-N-methyl-isobutyramide The title compound was obtained in an analogous manner to that described in Example 1a) from (6-chloro-4-o-tolyl-pyridin-3-yl)-methyl-amine and 2-(3-fluoro-5-trifluoromethyl-phenyl)-2-methyl-propionyl chloride as a white foam.
MS m/e (%): 465.2 (M+H$^+$, 100).

b) (S)-2-(3-Fluoro-5-trifluoromethyl-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from N-(6-chloro-4-o-tolyl-pyridin-3-yl)-2-(3-fluoro-5-trifluoromethyl-phenyl)-N-methyl-isobutyramide and L-prolinol as a white foam.
MS m/e (%): 530.2 (M+H$^+$, 100).

EXAMPLE 14

(2R,4S)-2-(3-Fluoro-5-trifluoromethyl-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from N-(6-chloro-4-o-tolyl-pyridin-3-yl)-2-(3-fluoro-5-trifluoromethyl-phenyl)-N-methyl-isobutyramide and (2S,4R)-4-hydroxy-2-hydroxymethyl-pyrrolidine as a orange foam.
MS m/e (%): 546.3 (M+H$^+$, 100).

EXAMPLE 15

(S)-2-(3,5-Difluoro-phenyl)-N-[6-(2-hydroxymethyl-pyrrolidin-1-yl)-4-o-tolyl-pyridin-3-yl]-N-methyl-isobutyramide a) N-(6-Chloro-4-o-tolyl-pyridin-3-yl)-2-(3,5-difluoro-phenyl)-N-methyl-isobutyramide The title compound was obtained in an analogous manner to that described in example 1a) from (6-chloro-4-o-tolyl-pyridin-3-yl)-methyl-amine and 2-(3,5-difluoro-phenyl)-2-methyl-propionyl chloride as a light yellow solid.
MS m/e (%): 415.2 (M+H$^+$, 100).

b) (S)-2-(3,5-Difluoro-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from N-(6-Chloro-4-o-tolyl-pyridin-3-yl)-2-(3,5-difluoro-phenyl)-N-methyl-isobutyramide and L-prolinol as a light yellow foam.
MS m/e (%): 480.2 (M+H$^+$, 100).

EXAMPLE 16

(2S,4R)-2-(3,5-Difluoro-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from N-(6-chloro-4-o-tolyl-pyridin-3-yl)-2-(3,5-difluoro-phenyl)-N-methyl-isobutyramide and (2S,4R)-4-hydroxy-2-hydroxymethyl-pyrrolidine as a orange foam.
MS m/e (%): 496.4 (M+H$^+$, 100).

EXAMPLE 17

(S)-2-(3-Chloro-5-methoxy-phenyl)-N-[6-(2-hydroxymethyl-pyrrolidin-1-yl)-4-o-tolyl-pyridin-3-yl]-N-methyl-isobutyramide a) 2-(3-Chloro-5-methoxy-phenyl)-N-(6-chloro-4-o-tolyl-pyridin-3-yl)-N-methyl-isobutyramide The title compound was obtained in an analogous manner to that described in example 1a) from (6-chloro-4-o-tolyl-pyridin-3-yl)-methyl-amine and 2-(3-chloro-5-methoxy-phenyl)-2-methyl-propionyl chloride as a light yellow solid.
MS m/e (%): 443.1 (M+H$^+$, 100).

b) (S)-2-(3-Chloro-5-methoxy-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from 2-(3-chloro-5-methoxy-phenyl)-N-(6-chloro-4-o-tolyl-pyridin-3-yl)-N-methyl-isobutyramide and L-prolinol as a white foam.
MS m/e (%): 508.2 (M+H$^+$, 100).

EXAMPLE 18

(2S,4R)-2-(3-Chloro-5-methoxy-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from 2-(3-chloro-5-methoxy-phenyl)-N-(6-chloro-4-o-tolyl-pyridin-3-yl)-N-methyl-isobutyramide and (2S,4R)-4-hydroxy-2-hydroxymethyl-pyrrolidine as a white foam.
MS m/e (%): 524.3 (M+H$^+$, 100).

EXAMPLE 19

(S)-2-(3,5-Dimethyl-phenyl)-N-[6-(2-hydroxymethyl-pyrrolidin-1-yl)-4-o-tolyl-pyridin-3-yl]-N-methyl-isobutyramide a) N-(6-Chloro-4-o-tolyl-pyridin-3-yl)-2-(3,5-dimethyl-phenyl)-N-methyl-isobutyramide The title compound was obtained to that described in example 1a) from (6-Chloro-4-o-tolyl-pyridin-3-yl)-methyl-amine and 2-(3,5-dimethyl-phenyl)-2-methyl-propionyl chloride as a light yellow foam.
MS m/e (%): 407.1 (M+H$^+$, 100).

b) (S)-2-(3,5-Dimethyl-phenyl)-N-[6-(2-hydroxymethyl-pyrrolidin-1-yl)-4-O-tolyl-pyridin-3-yl]-N-methyl-isobutyramide The title compound was obtained in an analogous manner to that described in example 2) from N-(6-chloro-4-o-tolyl-pyridin-3-yl)-2-(3,5-dimethyl-phenyl)-N-methyl-isobutyramide and L-prolinol as a white foam.

MS m/e (%): 472.3 (M+H$^+$, 100).

EXAMPLE 20

(2S,4R)-2-(3,5-Dimethyl-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from N-(6-chloro-4-o-tolyl-pyridin-3-yl)-2-(3,5-dimethyl-phenyl)-N-methyl-isobutyramide and (2S,4R)-4-hydroxy-2-hydroxymethyl-pyrrolidine as a light yellow foam.

MS m/e (%): 488.3 (M+H$^+$, 100)

EXAMPLE 21

2-(3,5-Dichloro-phenyl)-N-[4-(4-fluoro-2-methyl-phenyl)-6-(2-hydroxy-ethylamino)-pyridin-3-yl]-N-methyl-isobutyramide a) N-[6-Chloro-4-(4-fluoro-2-methyl-phenyl)-pyridin-3-yl]-2-(3,5-dichloro-phenyl)-N-methyl-isobutyramide The title compound was obtained to that described in example 1a) from [6-chloro-4-(4-fluoro-2-methyl-phenyl)-pyridin-3-yl]-methyl-amine and 2-(3,5-dichloro-phenyl)-2-methyl-propionyl chloride as a white foam.

MS m/e (%): 464.1 (M$^+$, 5).

b) 2-(3,5-Dichloro-phenyl)-N-[4-(4-fluoro-2-methyl-phenyl)-6-(2-hydroxy-ethylamino)-pyridin-3-yl]-N-methyl-isobutyramide The title compound was obtained in an analogous manner to that described in example 1b) from N-[6-chloro-4-(4-fluoro-2-methyl-phenyl)-pyridin-3-yl]-2-(3,5-dichloro-phenyl)-N-methyl-isobutyramide and ethanolamine as a white foam.

MS m/e (%): 490.2 (M+H$^+$, 100).

EXAMPLE 22

(S)-2-(3,5-Dichloro-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(4-fluoro-2-methyl-phenyl)-pyridin-3-yl]-2-(3,5-dichloro-phenyl)-N-methyl-isobutyramide and L-prolinol as a white foam.

MS m/e (%): 530.2 (M+H$^+$, 100).

EXAMPLE 23

(2S,4R)-2-(3,5-Dichloro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(4-fluoro-2-methyl-phenyl)-pyridin-3-yl]-2-(3,5-dichloro-phenyl)-N-methyl-isobutyramide and (2S,4R)-4-hydroxy-2-hydroxymethyl-pyrrolidine as a white foam.

MS m/e (%): 546.2 (M+H$^+$, 100).

EXAMPLE 24

(S)-N-[4-(4-Fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide a) N-[6-Chloro-4-(4-fluoro-2-methyl-phenyl)-pyridin-3-yl]-2-(3-fluoro-5-trifluoromethyl-phenyl)-N-methyl-isobutyramide The title compound was obtained in an analogous manner to that described in example 1a) from [6-chloro-4-(4-fluoro-2-methyl-phenyl)-pyridin-3-yl]-methyl-amine and 2-(3-fluoro-5-trifluoromethyl-phenyl)-2-methyl-propionyl chloride as a white foam.

MS m/e (%): 483.2 (M+H$^+$, 100).

b) (S)-N-[4-(4-Fluoro-2-methyl-phenyl)-6-(2-hydroxymethyl-pyrrolidin-1-yl)-pyridin-3-yl]-2-(3-fluoro-5-trifluoromethyl-phenyl)-N-methyl-isobutyramide The title compound was obtained in an analogous manner to that described in example 2) from N-[6-chloro-4-(4-fluoro-2-methyl-phenyl)-pyridin-3-yl]-2-(3-fluoro-5-trifluoromethyl-phenyl)-N-methyl-isobutyramide and L-prolinol as a white foam.

MS m/e (%): 548.4 (M+H$^+$, 100).

EXAMPLE 25

(2S,4R)-N-[4-(4-Fluoro-2-methyl-phenyl)-6-(4-hydroxy-2-hydroxymethyl-pyrrolidin-1-yl)-pyridin-3-yl]-2-(3-fluoro-5-trifluoromethyl-phenyl)-N-methyl-isobutyramide The title compound was obtained in an analogous manner to that described in example 3) from N-[6-chloro-4-(4-fluoro-2-methyl-phenyl)-pyridin-3-yl]-2-(3-fluoro-5-trifluoromethyl-phenyl)-N-methyl-isobutyramide and (2S,4R)-4-hydroxy-2-hydroxymethyl-pyrrolidine as a white foam.

MS m/e (%): 564.4 (M+H$^+$, 100).

EXAMPLE 26

(S)-N-[4-(4-Fluoro-2-methyl-phenyl)-6-(2-hydroxymethyl-pyrrolidin-1-yl)-pyridin-3-yl]-N-methyl-2-(3-trifluoromethyl-phenyl)-isobutyramide a) N-[6-Chloro-4-(4-fluoro-2-methyl-phenyl)-pyridin-3-yl]-N-methyl-2-(3-trifluoromethyl-phenyl)-isobutyramide The title compound was obtained in an analogous manner to that described in example 1a) from [6-chloro-4-(4-fluoro-2-methyl-phenyl)-pyridin-3-yl]-methyl-amine and 2-methyl-2-(3-trifluoromethyl-phenyl)-propionyl chloride as a white solid.
MS m/e (%): 465.4 (M+H$^+$, 100).

b) (S)-N-[4-(4-Fluoro-2-methyl-phenyl)-6-(2-hydroxymethyl-pyrrolidin-1-yl)-pyridin-3-yl]-N-methyl-2-(3-trifluoromethyl-phenyl)-isobutyramide The title compound was obtained in an analogous manner to that described in example 2) from N-[6-chloro-4-(4-fluoro-2-methyl-phenyl)-pyridin-3-yl]-N-methyl-2-(3-trifluoromethyl-phenyl)-isobutyramide and L-prolinol as a white foam.
MS m/e (%): 530.3 (M+H$^+$, 100).

EXAMPLE 27

(2S,4R)-N-[4-(4-Fluoro-2-methyl-phenyl)-6-(4-hydroxy-2-hydroxymethyl-pyrrolidin-1-yl)-pyridin-3-yl]-N-methyl-2-(3-trifluoromethyl-phenyl)-isobutyramide The title compound was obtained in an analogous manner to that described in example 3) from N-[6-chloro-4-(4-fluoro-2-methyl-phenyl)-pyridin-3-yl]-N-methyl-2-(3-trifluoromethyl-phenyl)-isobutyramide and (2S,4R)-4-hydroxy-2-hydroxymethyl-pyrrolidine as a white foam.
MS m/e (%): 546.3 (M+H$^+$, 100).

EXAMPLE 28

(S)-2-(3,5-Difluoro-phenyl)-N-[4-(4-fluoro-2-methyl-phenyl)-6-(2-hydroxymethyl-pyrrolidin-1-yl)-pyridin-3-yl]-N-methyl-isobutyramide a) N-[6-Chloro-4-(4-fluoro-2-methyl-phenyl)-pyridin-3-yl]-2-(3,5-difluoro-phenyl)-N-methyl-isobutyramide The title compound was obtained in an analogous manner to that described in example 1a) from [6-chloro-4-(4-fluoro-2-methyl-phenyl)-pyridin-3-yl]-methyl-amine and 2-(3,5-difluoro-phenyl)-2-methyl-propionyl chloride as a white solid.
MS m/e (%): 433.3 (M+H$^+$, 100).

b) (S)-2-(3,5-Difluoro-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(4-fluoro-2-methyl-phenyl)-pyridin-3-yl]-2-(3,5-difluoro-phenyl)-N-methyl-isobutyramide and L-prolinol as a light yellow foam.
MS m/e (%): 498.3 (M+H$^+$, 100).

EXAMPLE 29

(2S,4R)-2-(3,5-Difluoro-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(4-fluoro-2-methyl-phenyl)-pyridin-3-yl]-2-(3,5-difluoro-phenyl)-N-methyl-isobutyramide and (2S,4R)-4-hydroxy-2-hydroxymethyl-pyrrolidine as a light yellow foam.
MS m/e (%): 513.2 (M$^+$), 482.2 (100).

EXAMPLE 30

(S)-2-(3-Chloro-5-methoxy-phenyl)-N-[4-(4-fluoro-2-methyl-phenyl)-6-(2-hydroxymethyl-pyrrolidin-1-yl)-pyridin-3-yl]-N-methyl-isobutyramide a) N-[6-Chloro-4-(4-fluoro-2-methyl-phenyl)-pyridin-3-yl]-2-(3-chloro-5-methoxy-phenyl)-N-methyl-isobutyramide The title compound was obtained in an analogous manner to that described in example 1a) from [6-chloro-4-(4-fluoro-2-methyl-phenyl)-pyridin-3-yl]-methyl-amine and 2-(3-chloro-5-methoxy-phenyl)-2-methyl-propionyl chloride as a waxy solid.
MS m/e (%): 461.1 (M+H$^+$, 100).

b) (S)-2-(3-Chloro-5-methoxy-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(4-fluoro-2-methyl-phenyl)-pyridin-3-yl]-2-(3-chloro-5-methoxy-phenyl)-N-methyl-isobutyramide and L-prolinol as a white foam.
MS m/e (%): 526.2 (M+H$^+$, 100).

EXAMPLE 31

(2S,4R)-2-(3-Chloro-5-methoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(4-fluoro-2-methyl-phenyl)-pyridin-3-yl]-2-(3-chloro-5-methoxy-phenyl)-N-methyl-isobutyramide and (2S,4R)-4-hydroxy-2-hydroxymethyl-pyrrolidine as a light yellow foam.
MS m/e (%): 542.2 (M+H$^+$, 100).

EXAMPLE 32

(S)-(3,5-Dimethyl-phenyl)-N-[4-(4-fluoro-2-methyl-phenyl)-6-(2-hydroxymethyl-pyrrolidin-1-yl)-pyridin-3-yl]-N-methyl-isobutyramide a) N-[6-Chloro-4-(4-fluoro-2-methyl-phenyl)-pyridin-3-yl]-2-(3,5-dimethyl-phenyl)-N-methyl-isobutyramide The title compound was obtained in an analogous manner to that described in example 1a) from [6-chloro-4-(4-fluoro- 2-methyl-phenyl)-pyridin-3-yl]-methyl-amine and 2-(3,5-dimethyl-phenyl)-2-methyl-propionyl chloride as a white foam.
MS m/e (%): 425.2 (M+H$^+$, 100).

b) (S)-(3,5-Dimethyl-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(4-fluoro-2-methyl-phenyl)-pyridin-3-yl]-2-(3,5-dimethyl-phenyl)-N-methyl-isobutyramide and L-prolinol as a white foam.
MS m/e (%): 490.4 (M+H$^+$, 100).

EXAMPLE 33

(2S,4R)-2-(3,5-Dimethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(4-fluoro-2-methyl-phenyl)-pyridin-3-yl]-2-(3,5-dimethyl-phenyl)-N-methyl-isobutyramide and (2S,4R)-4-hydroxy-2-hydroxymethyl-pyrrolidine as a light yellow foam.
MS m/e (%): 506.3 (M+H$^+$, 100).

EXAMPLE 34

(S)-2-(3-Chloro-5-difluoromethoxy-phenyl)-N-[4-(2-chloro-phenyl)-6-(2-hydroxymethyl-pyrrolidin-1-yl)-pyridin-3-yl]-N-methyl-isobutyramide a) N-[6-Chloro-4-(2-chloro-phenyl)-pyridin-3-yl]-2-(3-chloro-5-hydroxy-phenyl)-N-methyl-isobutyramide To a solution of 1.10 g (2.37 mmol) N-[6-chloro-4-(2-chloro-phenyl)-pyridin-3-yl]-2-(3-chloro-5-methoxy-phenyl)-N-methyl-isobutyramide in 20 ml CH$_2$Cl$_2$ 4.74 ml (4.74 mmol) BBr$_3$ (1 M in CH$_2$Cl$_2$) was added at 0° C. The reaction mixture was allowed to reach ambient temperature and stirred for 6 h After addition of 50 ml water the mixture was extracted three times with 60 ml CH$_2$Cl$_2$. The combined organic solvents were dried (Na$_2$SO$_4$), filtered and evaporated. The residue was purified by flash-chromatography (SiO$_2$, CH$_2$Cl$_2$/ethyl acetate 4:1) to give 0.70 g (65%) of the title compound as a white foam.
MS m/e (%): 449.1 (M+H$^+$, 100).

b) N-[6-Chloro-4-(2-chloro-phenyl)-pyridin-3-yl]-2-(3-chloro-5-difluoromethoxy-phenyl)-N-methyl-isobutyramide To a solution of 0.700 g (1.56 mmol) N-[6-chloro-4-(2-chloro-phenyl)-pyridin-3-yl]-2-(3-chloro-5-hydroxy-phenyl)-N-methyl-isobutyramide in 10 ml N,N-Dimethylformamide 0.215 g (1.56 mmol) K$_2$CO$_3$ and 0.2 ml (1.56 mmol) ethyl chlordifluoroacetate was added and the resulting suspension heated at 65° C. for 15 h. After cooling to ambient temperature, the reaction mixture was poured into 75 ml water and extracted three times with 80 ml CH$_2$Cl$_2$. The combined organic solvents were dried (Na$_2$SO$_4$), filtered and evaporated. The residue was purified by flash-chromatography (SiO$_2$, CH$_2$Cl$_2$/ethyl acetate 4:1) to give 0.38 g (49%) of the title compound as a white solid.
MS m/e (%): 499.1 (M+H$^+$, 100).

c) (S)-2-(3-Chloro-5-difluoromethoxy-phenyl)-N-[4-(2-chloro-phenyl)-6-(2-hydroxymethyl-pyrrolidin-1-yl)-pyridin-3-yl]-N-methyl-isobutyramide The title compound was obtained in an analogous manner to that described in example 2 from N-[6-chloro-4-(2-chloro-phenyl)-pyridin-3-yl]-2-(3-chloro-5-difluoromethoxy-phenyl)-N-methyl-isobutyramide and L-prolinol as a white foam.
MS m/e (%): 564.2 (M+H$^+$, 100).

EXAMPLE 35

(2S,4R)-2-(3-Chloro-5-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(2-chloro-phenyl)-pyridin-3-yl]-2-(3-chloro-5-difluoromethoxy-phenyl)-N-methyl-isobutyramide and (2S,4R)-4-hydroxy-2-hydroxymethyl-pyrrolidine as a white foam.
MS m/e (%): 580.5 (M+H$^+$, 100).

EXAMPLE 36

(S)-2-(3-Chloro-5-difluoromethoxy-phenyl)-N-[6-(2-hydroxymethyl-pyrrolidin-1-yl)-4-o-tolyl-pyridin-3-yl]-N-methyl-isobutyramide a) 2-(3-Chloro-5-difluoromethoxy-phenyl)-N-(6-chloro-4-o-tolyl-pyridin-3-yl)-N-methyl-isobutyramide The title compound was obtained in an analogous manner to that described in example 34a), b) from 2-(3-chloro-5-methoxy-phenyl)-N-(6-chloro-4-o-tolyl-pyridin-3-yl)-N-methyl-isobutyramide as a white foam.
MS m/e (%): 479.1 (M+H$^+$, 100).

b) (S)-2-(3-Chloro-5-difluoromethoxy-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from 2-(3-chloro-5-difluoromethoxy-phenyl)-N-(6-chloro-4-o-tolyl-pyridin-3-yl)-N-methyl-isobutyramide and L-prolinol as a white foam.
MS m/e (%): 544.3 (M+H$^+$, 100).

EXAMPLE 37

(2S,4R)-2-(3-Chloro-5-difluoromethoxy-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from 2-(3-chloro-5-difluoromethoxy-phenyl)-N-(6-chloro-4-o-tolyl-pyridin-3-yl)-N-methyl-isobutyramide and (2S,4R)-4-hydroxy-2-hydroxymethyl-pyrrolidine as a light yellow foam.
MS m/e (%): 560.3 (M+H$^+$, 100).

EXAMPLE 38

(S)-2-(3-Chloro-5-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide a) 2-(3-Chloro-5-difluoromethoxy-phenyl)-N-[6-chloro-4-(4-fluoro-2-methyl-phenyl)-pyridin-3-yl]-N-methyl-isobutyramide The title compound was obtained in an analogous manner to that described in example 34a), b) from N-[6-chloro-4-(4-fluoro-2-methyl-phenyl)-pyridin-3-yl]-2-(3-chloro-5-methoxy-phenyl)-N-methyl-isobutyramide as a white foam.
MS m/e (%): 497.1 (M+H$^+$, 100).

b) (S)-2-(3-Chloro-5-difluoromethoxy-phenyl)-N-[4-(4-fluoro-2-methyl-phenyl)-6-(2S-hydroxymethyl-pyrrolidin-1-yl)-pyridin-3-yl]-N-methyl-isobutyramide The title compound was obtained in an analogous manner to that described in example 2) from 2-(3-chloro-5-difluoromethoxy-phenyl)-N-[6-chloro-4-(4-fluoro-2-methyl-phenyl)-pyridin-3-yl]-N-methyl-isobutyramide and L-prolinol as a white foam.
MS m/e (%): 562.2 (M+H$^+$, 100).

EXAMPLE 39

(2S,4R)-2-(3-Chloro-5-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from 2-(3-chloro-5-difluoromethoxy-phenyl)-N-[6-chloro-4-(4-fluoro-2-methyl-phenyl)-pyridin-3-yl]-N-methyl-isobutyramide and (2S,4R)-4-hydroxy-2-hydroxymethyl-pyrrolidine as a light brown foam.
MS m/e (%): 578.3 (M+H$^+$, 100).

EXAMPLE 40

(2S,4S)-N-[6-(4-Acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide A mixture of 30 mg (0.056 mmol) 2-(3,5-bis-trifluoromethyl-phenyl)-N-[6-chloro-4-(2-chloro-phenyl)-pyridin-3-yl]-N-methyl-isobutyramide, 200 mg (1.27 mmol) (2S,4S)-4-acetylamino-2-hydroxymethyl-pyrrolidine and 0.2 ml dimethyl sulfoxide was heated at 130° C. for 24 h. After cooling to room temperature, 22 mg (59%) of the title compound were isolated as a white solid by automated, preparative HPLC (YMC CombiPrep C18 column 50×20 mm, solvent gradient 5-95% CH$_3$CN in 0.1% TFA(aq) over 6.0 min, λ=230 nm, flow rate 40 ml/min). (2S,4S)-4-Acetylamino-2-hydroxymethyl-pyrrolidine can be obtained by the method described by Terry Rosen, Daniel T. W. Chu, Isabella M. Lico, Isabella M. Lico, Prabhavathi B. Fernandes, Kennan Marsh, Linus Shen, Valerie G. Cepa, André G. Pernet, *J. Med. Chem.* 1988, 31, 1598.
MS m/e (%): 657 (M+H$^+$)

EXAMPLE 41

(R)-2-(3,5-Bis-trifluoromethyl-phenyl)-N-[4-(2-chloro-phenyl)-6-(2-hydroxymethyl-pyrrolidin-1-yl)-pyridin-3-yl]-N-methyl-isobutyramide The title compound was obtained from D-prolinol as a light grey solid in 8% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 600 (M+H$^+$)

EXAMPLE 42

(S)-2-(3,5-Bis-trifluoromethyl-phenyl)-N-[4-(2-chloro-phenyl)-6-(2-hydroxymethyl-pyrrolidin-1-yl)-pyridin-3-yl]-N-methyl-isobutyramide The title compound was obtained from L-prolinol as a white solid in 49% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 600 (M+H$^+$)

EXAMPLE 43

(S)-N-[6-(3-Acetylamino-pyrrolidin-1-yl)-4-(2-chloro-phenyl)-pyridin-3-yl]-2-(3,5-bis-trifluoromethyl-phenyl)-N-methyl-isobutyramide The title compound was obtained from (S)-3-acetamidopyrrolidine as a white solid in 42% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 627 (M+H$^+$)

EXAMPLE 44

(R)-N-[6-(3-Acetylamino-pyrrolidin-1-yl)-4-(2-chloro-phenyl)-pyridin-3-yl]-2-(3,5-bis-trifluoromethyl-phenyl)-N-methyl-isobutyramide The title compound was obtained from (R)-3-acetamidopyrrolidine as a white solid in 56% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 627 (M+H$^+$)

EXAMPLE 45

(RS)-N-[6-[3-(Acetyl-ethyl-amino)-pyrrolidin-1-yl]-4-(2-chloro-phenyl)-pyridin-3-yl]-2-(3,5-bis-trifluoromethyl-phenyl)-N-methyl-isobutyramide The title compound was obtained from (RS)-3-(N-acetyl-N-ethylamino)pyrrolidine as a white solid in 54% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 655 (M+H⁺)

EXAMPLE 46

(S)-2-(3,5-Bis-trifluoromethyl-phenyl)-N-[4-(2-chloro-phenyl)-6-(3-hydroxy-pyrrolidin-1-yl)-pyridin-3-yl]-N-methyl-isobutyramide The title compound was obtained from (S)-3-pyrrolidinol as a light grey solid in 7% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 586 (M+H⁺)

EXAMPLE 47

(R)-2-(3,5-Bis-trifluoromethyl-phenyl)-N-[4-(2-chloro-phenyl)-6-(3-hydroxy-pyrrolidin-1-yl)-pyridin-3-yl]-N-methyl-isobutyramide The title compound was obtained from (R)-3-pyrrolidinol as an off-white solid in 30% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 586 (M+H⁺)

EXAMPLE 48

(3R,4S)-2-(3,5-Bis-trifluoromethyl-phenyl)-N-[4-(2-chloro-phenyl)-6-(3,4-dihydroxy-pyrrolidin-1-yl)-pyridin-3-yl]-N-methyl-isobutyramide The title compound was obtained from (3R,4S)-pyrrolidin-3,4-diol as a white solid in 47% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide. (3R,4S)-Pyrrolidine-3,4-diol can be obtained by the method described by Albert Defoin, Joaquim Pires, Jaques Streith, *Helv. Chim. Acta* 1991, 74, 1653.
MS m/e (%): 602 (M+H⁺)

EXAMPLE 49

(3R,4R)-2-(3,5-Bis-trifluoromethyl-phenyl)-N-[4-(2-chloro-phenyl)-6-(3,4-dihydroxy-pyrrolidin-1-yl)-pyridin-3-yl]-N-methyl-isobutyramide The title compound was obtained from (3R,4R)-pyrrolidin-3,4-diol as a white solid in 61% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 602 (M+H⁺)

EXAMPLE 50

(RS)-2-(3,5-Bis-trifluoromethyl-phenyl)-N-[4'-(2-chloro-phenyl)-3-hydroxy-3,4,5,6-tetrahydro-2H-[1,2']bipyridinyl-5'-yl]-N-methyl-isobutyramide The title compound was obtained from (RS)-3-piperidinol as a white solid in 55% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 600 (M+H⁺)

EXAMPLE 51

2-(3,5-Bis-trifluoromethyl-phenyl)-N-[4'-(2-chloro-phenyl)-4-hydroxy-3,4,5,6-tetrahydro-2H-[1,2']bipyridinyl-5'-yl]-N-methyl-isobutyramide The title compound was obtained from 4-hydroxypiperidine as a white solid in 47% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 600 (M+H⁺)

EXAMPLE 52

2-(3,5-Bis-trifluoromethyl-phenyl)-N-[4'-(2-chloro-phenyl)-4-hydroxymethyl-3,4,5,6-tetrahydro-2H-[1,2']bipyridinyl-5'-yl]-N-methyl-isobutyramide The title compound was obtained from 4-(hydroxymethyl)-piperidine as a white foam in 43% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 614 (M+H⁺)

EXAMPLE 53

(RS)-2-(3,5-Bis-trifluoromethyl-phenyl)-N-[4'-(2-chloro-phenyl)-2-(2-hydroxy-ethyl)-3,4,5,6-tetrahydro-2H-[1,2']bipyridinyl-5'-yl]-N-methyl-isobutyramide The title compound was obtained from (RS)-2-piperidin-2-yl-ethanol as a light yellow solid in 5% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.
MS m/e (%): 628 (M+H⁺)

EXAMPLE 54

2-(3,5-Bis-trifluoromethyl-phenyl)-N-{4-(2-chloro-phenyl)-6-[(2-hydroxy-ethyl)-methyl-amino]-pyridin-3-yl}-N-methyl-isobutyramide The title compound was obtained from N-methylethanolamine as a white solid in 54% yield according to the procedure described above for the preparation of (2S,4S)—N-[6-(4- acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 574 (M+H$^+$)

EXAMPLE 55

2-(3,5-Bis-trifluoromethyl-phenyl)-N-{4-(2-chloro-phenyl)-6-[ethyl-(2-hydroxy-ethyl)-amino]-pyridin-3-yl}-N-methyl-isobutyramide The title compound was obtained from 2-ethylamino-ethanol as a white solid in 50% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 588 (M+H$^+$)

EXAMPLE 56

2-(3,5-Bis-trifluoromethyl-phenyl)-N-{4-(2-chloro-phenyl)-6-[(2-hydroxy-ethyl)-propyl-amino]-pyridin-3-yl}-N-methyl-isobutyramide The title compound was obtained from N-propylethanolamine as a white solid in 34% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 602 (M+H$^+$)

EXAMPLE 57

2-(3,5-Bis-trifluoromethyl-phenyl)-N-[6-[butyl-(2-hydroxy-ethyl)-amino]-4-(2-chloro-phenyl)-pyridin-3-yl]-N-methyl-isobutyramide The title compound was obtained from N-butylethanolamine as a colorless waxy solid in 37% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 616 (M+H$^+$)

EXAMPLE 58

(RS)-2-(3,5-Bis-trifluoromethyl-phenyl)-N-{4-(2-chloro-phenyl)-6-[(2,3-dihydroxy-propyl)-methyl-amino]-pyridin-3-yl}-N-methyl-isobutyramide The title compound was obtained from (RS)-2,3-dihydroxy-N-methylpropylamine as a white solid in 48% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 604 (M+H$^+$)

EXAMPLE 59

(S)-2-(3,5-Bis-trifluoromethyl-phenyl)-N-[4-(2-chloro-phenyl)-6-(1-hydroxymethyl-3-methyl-butylamino)-pyridin-3-yl]-N-methyl-isobutyramide The title compound was obtained from L-leucinol as a white solid in 42% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 616 (M+H$^+$)

EXAMPLE 60 trans-2-(3,5-Bis-trifluoromethyl-phenyl)-N-[4-(2-chloro-phenyl)-6-(4-hydroxy-cyclohexylamino)-pyridin-3-yl]-N-methyl-isobutyramide The title compound was obtained from trans-4-aminocyclohexanol as a white solid in 42% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 614 (M+H$^+$)

EXAMPLE 61

N-[6-(4-Acetyl-piperazin-1-yl)-4-(2-chloro-phenyl)-pyridin-3-yl]-2-(3,5-bis-trifluoromethyl-phenyl)-N-methyl-isobutyramide The title compound was obtained from 1-acetylpiperazine as a white solid in 52% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 627 (M+H$^+$)

EXAMPLE 62

2-(3,5-Bis-trifluoromethyl-phenyl)-N-[4-(2-chloro-phenyl)-6-(4-cyclopropanecarbonyl-piperazin-1-yl)-pyridin-3-yl]-N-methyl-isobutyramide The title compound was obtained from 1-cyclopropylcarbonylpiperazine as a white solid in 32% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 653 (M+H$^+$)

EXAMPLE 63

N-[6-(4-Acetyl-[1,4]diazepan-1-yl)-4-(2-chloro-phenyl)-pyridin-3-yl]-2-(3,5-bis-trifluoromethyl-phenyl)-N-methyl-isobutyramide The title compound was obtained from 1-acetylhomopiperazine as a white solid in 50% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 641 (M+H$^+$)

EXAMPLE 64

(S)-2-(3,5-Bis-trifluoromethyl-phenyl)-N-[4-(2-chloro-phenyl)-6-(–2-pyrrolidin-1-ylmethyl-pyrrolidin-1-yl)-pyridin-3-yl]-N-methyl-isobutyramide The title compound was obtained from (S)-(+)-1-(2-pyrrolidinyl-methyl)pyrrolidine as a white solid in 54% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 653 (M+H$^+$)

EXAMPLE 65

(S)-2-(3,5-Bis-trifluoromethyl-phenyl)-N-[4-(2-chloro-phenyl)-6-(3-dimethylamino-pyrrolidin-1-yl)-pyridin-3-yl]-N-methyl-isobutyramide The title compound was obtained from (S)-(−)-3-(dimethylamino)pyrrolidine as a white solid in 56% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 613 (M+H$^+$)

EXAMPLE 66

(RS)-2-(3,5-Bis-trifluoromethyl-phenyl)-N-[4-(2-chloro-phenyl)-6-(3-methanesulfonyl-pyrrolidin-1-yl)-pyridin-3-yl]-N-methyl-isobutyramide The title compound was obtained from (RS)-3-methylsulfonylpyrrolidine as a white solid in 57% yield according to the procedure described above for the preparation of (2S,4S)-N-[6-(4-acetylamino-2-hydroxymethyl-pyrrolidin-1-yl)-4-(2-chloro-phenyl)-pyridin-3-yl]-2-(3,5-bis-trifluoromethyl-phenyl)-N-methyl-isobutyramide.

MS m/e (%): 648 (M+H$^+$)

EXAMPLE 67

2-(3,5-Bis-trifluoromethyl-phenyl)-N-[4-(2-chloro-phenyl)-6-(2-hydroxy-ethylamino)-pyridin-3-yl]-N-methyl-isobutyramide A mixture of 28.6 g (56 mmol) 2-(3,5-bis-trifluoromethyl-phenyl)-N-[6-chloro-4-(2-chloro-phenyl)-pyridin-3-yl]-N-methyl-isobutyramide, 50 ml dimethyl sulfoxide and 50 ml (830 mmol) ethanolamine was stirred at 140° C. for 24 h. The reaction mixture was cooled to room temperature, diluted with 200 ml ethyl acetate and washed with 200 ml 1 N sodium carbonate solution and 100 ml water. The aqueous layers were extracted with two 200-ml portions of ethyl acetate. The combined organic layers were dried over sodium sulfate and concentrated in vacuo. The residue was crystallized from a mixture of 150 ml diisopropyl ether and 150 ml heptane to give 29.1 g (93%) of the title compound as white crystals. M.p. 117-118° C.

MS m/e (%): 560 (M+H$^+$, 100)

EXAMPLE 68

2-(3,5-Bis-trifluoromethyl-phenyl)-N-[4-(4-fluoro-2-methyl-phenyl)-6-(2-hydroxy-ethylamino)-pyridin-3-yl]-N-methyl-isobutyramide The title compound was obtained as a white foam in 28% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 558 (M+H$^+$, 100)

EXAMPLE 69

2-(3,5-Bis-trifluoromethyl-phenyl)-N-[4-(2-chloro-4-fluoro-phenyl)-6-(2-hydroxy-ethylamino)-pyridin-3-yl]-N-methyl-isobutyramide The title compound was obtained as a white foam in 48% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2-chloro-4-fluoro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 578 (M+H$^+$, 100)

EXAMPLE 70

2-(3,5-Bis-trifluoromethyl-phenyl)-N-[4-(2,4-dichloro-phenyl)-6-(2-hydroxy-ethylamino)-pyridin-3-yl]-N-methyl-isobutyramide The title compound was obtained as a light yellow foam in 91% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 594 (M+H$^+$, 100)

EXAMPLE 71

(S)-2-(3,5-Bis-trifluoromethyl-phenyl)-N-[4-(2,4-dichloro-phenyl)-6-(2-hydroxy-propylamino)-pyridin-3-yl]-N-methyl-isobutyramide The title compound was obtained as a light yellow foam in 78% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and (S)-1-amino-2-propanol instead of ethanolamine.

MS m/e (%): 608 (M+H$^+$, 100)

EXAMPLE 72

(S)-2-(3,5-Bis-trifluoromethyl-phenyl)-N-[4-(2-chloro-phenyl)-6-(2-hydroxy-propylamino)-pyridin-3-yl]-N-methyl-isobutyramide The title compound was obtained as an off-white foam in 65% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (S)-1-amino-2-propanol instead of ethanolamine.
MS m/e (%): 574 (M+H+, 100)

EXAMPLE 73

(R)-2-(3,5-Bis-trifluoromethyl-phenyl)-N-[4-(2-chloro-phenyl)-6-(2-hydroxy-propylamino)-pyridin-3-yl]-N-methyl-isobutyramide The title compound was obtained as a white foam in 84% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (R)-1-amino-2-propanol instead of ethanolamine.
MS m/e (%): 574 (M+H+, 100)

EXAMPLE 74

(RS)-2-(3,5-Bis-trifluoromethyl-phenyl)-N-[4-(2-chloro-phenyl)-6-(2-hydroxy-propylamino)-pyridin-3-yl]-N-methyl-isobutyramide The title compound was obtained as a light brown foam in 79% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (RS)-1-amino-2-propanol instead of ethanolamine.
MS m/e (%): 574 (M+H+, 100)

EXAMPLE 75

2-(3,5-Bis-trifluoromethyl-phenyl)-N-[4-(2-chloro-phenyl)-6-(2-hydroxy-2-methyl-propylamino)-pyridin-3-yl]-N-methyl-isobutyramide a) 2-(3,5-Bis-trifluoromethyl-phenyl)-N-[4-(2-chloro-phenyl)-6-(2-oxo-propylamino)-pyridin-3-yl]-N-methyl-isobutyramide To a solution of 457 mg (3.60 mmol) oxalyl chloride in 17 ml dichloromethane was added dropwise during 5 minutes at −75° C. a solution of 562 mg (7.20 mmol) dimethyl sulfoxide in 5 ml dichloromethane. After stirring for 5 minutes a solution of 1.72 g (3.00 mmol) (RS)-2-(3,5-bis-trifluoromethyl-phenyl)-N-[4-(2-chloro-phenyl)-6-(2-hydroxy-propylamino)-pyridin-3-yl]-N-methyl-isobutyramide in 5 ml dichloromethane was added dropwise at −65° C. Stirring was continued at −70° C. for 1 h, followed by addition of 2.6 ml (15 mmol) ethyldiisopropylamine. After stirring at room temperature for 3 h the reaction mixture was diluted with 20 ml dichloromethane and washed with 20 ml water, 20 ml 1 N hydrochloric acid solution and 20 ml saturated sodium carbonate solution. The combined organic layers were dried over sodium sulfate, concentrated in vacuo and purified by flash chromatography to give 1.45 g (85%) of the title compound as a white foam.
MS m/e (%): 572 (M+H+, 100)

b) 2-(3,5-Bis-trifluoromethyl-phenyl)-N-[4-(2-chloro-phenyl)-6-(2-hydroxy-2-methyl-propylamino)-pyridin-3-yl]-N-methyl-isobutyramide To a solution of 100 mg (0.175 mmol) 2-(3,5-bis-trifluoromethyl-phenyl)-N-[4-(2-chloro-phenyl)-6-(2-oxo-propylamino)-pyridin-3-yl]-N-methyl-isobutyramide in 1 ml tetrahydrofuran was added a 3 N solution of methylmagnesium bromide in diethyl ether at room temperature. The reaction mixture was stirred at room temperature for 1 h and at 65° C. for 3 h. After cooling to room temperature few drops of a 1 N aqueous solution of hydrochloric acid were added to the reaction mixture, followed by extraction with dichloromethane and washing with saturated sodium carbonate solution. The combined organic layers were dried over sodium sulfate, concentrated in vacuo and purified by flash chromatography to give 51 mg (50%) of the title compound as a white foam.
MS m/e (%): 588 (M+H+, 100)

EXAMPLE 76

2-(3,5-Bis-trifluoromethyl-phenyl)-N-[4-(2-chloro-phenyl)-6-(2-hydroxy-butylamino)-pyridin-3-yl]-N-methyl-isobutyramide The title compound was obtained as a yellow foam in 55% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 1-amino-2-butanol instead of ethanolamine.
MS m/e (%): 588 (M+H+, 100)

EXAMPLE 77

(S)-2-(3,5-Bis-trifluoromethyl-phenyl)-N-[4-(4-fluoro-2-methyl-phenyl)-6-(2-hydroxy-propylamino)-pyridin-3-yl]-N-methyl-isobutyramide The title compound was obtained as a white foam in 59% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (S)-1-amino-2-propanol instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide
MS m/e (%): 572 (M+H+, 100)

EXAMPLE 78

(RS)-2-(3,5-Bis-trifluoromethyl-phenyl)-N-[4-(2-chloro-phenyl)-6-(2,3-dihydroxy-propylamino)-pyridin-3-yl]-N-methyl-isobutyramide The title compound was obtained as a white solid in 100% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (RS)-3-amino-1,2-propandiol instead of ethanolamine.
MS m/e (%): 590 (M+H+, 100)

EXAMPLE 79

(S)-2-(3,5-Bis-trifluoromethyl-phenyl)-N-[4-(2-chloro-phenyl)-6-(2-hydroxy-1-methyl-ethylamino)-pyridin-3-yl]-N-methyl-isobutyramide The title compound was obtained as a light yellow solid in 14% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using L-alaninol instead of ethanolamine.
MS m/e (%): 574 (M+H$^+$, 100)

EXAMPLE 80

(R)-2-(3,5-Bis-trifluoromethyl-phenyl)-N-[4-(2-chloro-phenyl)-6-(2-hydroxy-1-methyl-ethylamino)-pyridin-3-yl]-N-methyl-isobutyramide The title compound was obtained as a white foam in 24% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (R)-2-amino-1-propanol instead of ethanolamine.
MS m/e (%): 574 (M+H$^+$, 100)

EXAMPLE 81

2-(3,5-Bis-trifluoromethyl-phenyl)-N-[4-(2-chloro-phenyl)-6-(2-hydroxy-1-hydroxymethyl-ethylamino)-pyridin-3-yl]-N-methyl-isobutyramide The title compound was obtained as a white foam in 34% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-amino-1,3-propandiol instead of ethanolamine.
MS m/e (%): 590 (M+H$^+$, 100)

EXAMPLE 82

N-[6-[Bis-(2-hydroxy-ethyl)-amino]-4-(2-chloro-phenyl)-pyridin-3-yl]-2-(3,5-bis-trifluoromethyl-phenyl)-N-methyl-isobutyramide The title compound was obtained as a white solid in 41% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine.
MS m/e (%): 604 (M+H$^+$, 100)

EXAMPLE 83

N-{6-[Bis-(2-hydroxy-ethyl)-amino]-4-o-tolyl-pyridin-3-yl}-2-(3,5-bis-trifluoromethyl-phenyl)-N-methyl-isobutyramide The title compound was obtained as a white solid in 55% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.
MS m/e (%): 584 (M+H$^+$, 100)

EXAMPLE 84

N-[6-[Bis-(2-hydroxy-ethyl)-amino]-4-(4-fluoro-2-methyl-phenyl)-pyridin-3-yl]-2-(3,5-bis-trifluoromethyl-phenyl)-N-methyl-isobutyramide The title compound was obtained as a white solid in 52% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.
MS m/e (%): 602 (M+H$^+$, 100)

EXAMPLE 85

2-(3,5-Bis-trifluoromethyl-phenyl)-N-{4-(4-fluoro-2-methyl-phenyl)-6-[(2-hydroxy-ethyl)-(3-hydroxy-propyl)-amino]-pyridin-3-yl}-N-methyl-isobutyramide The title compound was obtained as a light brown solid in 15% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 3-(2-hydroxyethylamino)-1-propanol instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.
MS m/e (%): 616 (M+H$^+$, 100)

EXAMPLE 86

N-[6-[Bis-(2-hydroxy-ethyl)-amino]-4-(2,4-dichloro-phenyl)-pyridin-3-yl]-2-(3,5-bis-trifluoromethyl-phenyl)-N-methyl-isobutyramide The title compound was obtained as a light yellow foam in 48% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide. and diethanolamine instead of ethanolamine.
MS m/e (%): 638 (M+H$^+$, 100)

EXAMPLE 87

N-[6-[Bis-(2-hydroxy-ethyl)-amino]-4-(3,4-dichloro-phenyl)-pyridin-3-yl]-2-(3,5-bis-trifluoromethyl-phenyl)-N-methyl-isobutyramide The title compound was obtained as a yellow foam in 65% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3, 5-bis-trifluoromethyl-phenyl)-N-[6-chloro-4-(3,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and diethanolamine instead of ethanolamine.

MS m/e (%): 638 (M+H$^+$, 100)

EXAMPLE 88

N-[6-[Bis-(2-hydroxy-ethyl)-amino]-4-(4-fluoro-phenyl)-pyridin-3-yl]-2-(3,5-bis-trifluoromethyl-phenyl)-N-methyl-isobutyramide The title compound was obtained as a white solid in 68% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine and 2-(3,5-bis-trifluoromethyl-phenyl)-N-[6-chloro-4-(4-fluoro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 588 (M+H$^+$, 100)

EXAMPLE 89

2-(3,5-Bis-trifluoromethyl-phenyl)-N-[4-(2-chloro-phenyl)-6-(2-methanesulfonyl-ethylamino)-pyridin-3-yl]-N-methyl-isobutyramide a) 2-(3,5-Bis-trifluoromethyl-phenyl)-N-[4-(2-chloro-phenyl)-6-(2-methylsulfanyl-ethylamino)-pyridin-3-yl]-N-methyl-isobutyramide The title compound was obtained as a white foam in 30% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(methylthio)ethylamine instead of ethanolamine.

MS m/e (%): 590 (M+H$^+$, 100)

b) 2-(3,5-Bis-trifluoromethyl-phenyl)-N-[4-(2-chloro-phenyl)-6-(2-methanesulfonyl-ethylamino)-pyridin-3-yl]-N-methyl-isobutyramide A mixture of 50 mg (0.087 mmol) 2-(3,5-bis-trifluoromethyl-phenyl)-N-[4-(2-chloro-phenyl)-6-(2-methylsulfanyl-ethylamino)-pyridin-3-yl]-N-methyl-isobutyramide and 130 mg (0.212 mmol) potassium monopersulfate triple salt in 1 ml methanol was stirred at room temperature for 3 days. The reaction was quenched with 1 ml sodium hydrogen sulfite solution 38%. The mixture was treated with 3 ml saturated sodium carbonate solution and extracted with three 5-ml portions of ethyl acetate. The combined organic layers were dried over sodium sulfate, concentrated in vacuo and purified by flash chromatography to give 29 mg (55%) of the title compound as a white foam.

MS m/e (%): 622 (M+H$^+$, 100)

EXAMPLE 90

N-[6-(2-Acetylamino-ethylamino)-4-(2-chloro-phenyl)-pyridin-3-yl]-2-(3,5-bis-trifluoromethyl-phenyl)-N-methyl-isobutyramide The title compound was obtained as a white foam in 65% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using N-acetylethylenediamine instead of ethanolamine.

MS m/e (%): 601 (M+H$^+$, 100)

EXAMPLE 91 trans-2-(3,5-Bis-trifluoromethyl-phenyl)-N-[4-(2,4-dichloro-phenyl)-6-(4-hydroxy-cyclohexylamino)-pyridin-3-yl]-N-methyl-isobutyramide The title compound was obtained as a light yellow foam in 42% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and trans-4-aminocyclohexanol instead of ethanolamine.

MS m/e (%): 648 (M+H$^+$, 100)

EXAMPLE 92 trans-2-(3,5-Bis-trifluoromethyl-phenyl)-N-[4-(4-fluoro-2-methyl-phenyl)-6-(4-hydroxy-cyclohexylamino)-pyridin-3-yl]-N-methyl-isobutyramide The title compound was obtained as a light brown foam in 23% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using trans-4-aminocyclohexanol instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide MS m/e (%): 612 (M+H$^+$, 100)

EXAMPLE 93

(R)-2-(3,5-Bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained as a white foam in 58% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using D-prolinol instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide MS m/e (%): 598 (M+H$^+$, 100)

EXAMPLE 94

(R)-2-(3,5-Bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide The title compound was obtained as a light yellow foam in 96% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide. and D-prolinol instead of ethanolamine.

MS m/e (%): 634 (M+H$^+$, 100)

EXAMPLE 95

(R)-2-(3,5-Bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide The title compound was obtained as a yellow foam in 97% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(3,4-dichloro-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and D-prolinol instead of ethanolamine.

MS m/e (%): 634 (M+H$^+$, 100)

EXAMPLE 96

(2R,4R)-2-(3,5-Bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained as a white foam in 76% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (2R,4R)-2-(hydroxymethyl)-4-hydroxypyrrolidine instead of ethanolamine.

MS m/e (%): 616 (M+H$^+$, 100)

EXAMPLE 97

(2S,4R)-2-(3,5-Bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained as an off-white foam in 62% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (2S,4R)-2-(hydroxymethyl)-4-hydroxypyrrolidine instead of ethanolamine.

MS m/e (%): 616 (M+H$^+$, 100)

EXAMPLE 98

2-(3,5-Bis-trifluoromethyl-phenyl)-N-[4-(2-chloro-phenyl)-6-(3-hydroxy-azetidin-1-yl)-pyridin-3-yl]-N-methyl-isobutyramide The title compound was obtained as a light yellow foam in 23% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using azetidin-3-ol instead of ethanolamine.

MS m/e (%): 572 (M+H$^+$, 100)

EXAMPLE 99

(S)—N-[6-(3-Acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide The title compound was obtained as a white foam in 58% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (S)-3-acetamidopyrrolidine instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 625 (M+H$^+$, 100)

EXAMPLE 100

(R)—N-[6-(3-Acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide The title compound was obtained as an off-white foam in 75% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (R)-3-acetamidopyrrolidine instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 625 (M+H$^+$, 100)

EXAMPLE 101

(R)—N-[6-[3-(Acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide To a solution of 146 mg (0.234 mmol) (R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide in 5 ml tetrahydrofuran were added dropwise at room temperature 0.31 ml (0.28 mmol) of a 0.91 N potassium bis(trimethylsilyl)amide solution in tetrahydrofuran. After stirring at room temperature for 30 min. 43 mg (30 mmol) iodomethane were added. The reaction mixture was stirred at room temperature for 18 h, followed by dilution with 10 ml ethyl acetate and washing with 10 ml saturated sodium carbonate solution. The combined organic layers were dried over sodium sulfate, concentrated in vacuo and purified by flash chromatography to give 130 mg (87%) of the title compound as a white foam.

MS m/e (%): 639 (M+H$^+$, 100)

EXAMPLE 102

(R)—N-[6-[3-(Acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide The title compound was obtained as a white foam in 41% yield after flash chromatography according to the procedure described above for the preparation of (R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide using iodoethane instead of iodomethane.

MS m/e (%): 653 (M+H$^+$, 100)

EXAMPLE 103

(S)—N-[6-(3-Amino-pyrrolidin-1-yl)-4-(4-fluoro-2-methyl-phenyl)-pyridin-3-yl]-2-(3,5-bis-trifluoromethyl-phenyl)-N-methyl-isobutyramide A mixture of 975 mg (1.83 mmol) 2-(3,5-bis-trifluoromethyl-phenyl)-N-[6-chloro-4-(4-fluoro-2-methyl-phenyl)-pyridin-3-yl]-N-methyl-isobutyramide, 1.26 g (9.15 mmol) potassium carbonate and 800 mg (3.66 mmol) (S)-3-(trifluoro-acetamido)pyrrolidine hydrochloride in 10 ml dimethyl sulfoxide was stirred at 130° C. for 52 h. After cooling to room temperature the reaction mixture was diluted with 30 ml tert-butyl methyl ether and washed with 20 ml of water and 10 ml of a saturated aqueous solution of sodium carbonate. The combined organic layers were dried over sodium sulfate and concentrated. The residue was dissolved in 25 ml of a 2 N solution of ammonia in ethanol. The solution was stirred at room temperature for 18 h. The reaction mixture was concentrated and purified by flash chromatography to give 640 mg (60%) of the title compound as a light brown foam.

MS m/e (%): 583 (M+H$^+$, 100)

EXAMPLE 104

(S)-2-(3,5-Bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide To a solution of 600 mg (1.03 mmol) (S)—N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide in 6 ml dichloromethane were added 6 mg (0.05 mmol) 4-(N,N-dimethylamino)pyridine, 266 mg (2.06 mmol) N,N-diisopropylethylamine and 153 mg (1.34 mmol) methanesulfonyl chloride. After stirring at room temperature for 18 h the reaction mixture was diluted with 20 ml dichloromethane and washed with 20 ml of a saturated aqueous solution of sodium carbonate. The combined organic layers were dried over sodium sulfate, concentrated and purified by flash chromatography to give 553 mg (81%) of the title compound as an off-white foam.

MS m/e (%): 659 ([M−H$^+$]$^−$, 100)

EXAMPLE 105

(S)-2-(3,5-Bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide The title compound was obtained as an off-white foam in 48% yield after flash chromatography according to the procedure described above for the preparation of (R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide using (S)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide instead of (R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide.

MS m/e (%): 675 (M+H$^+$, 100)

EXAMPLE 106

(S)-(2-(3,5-Bis-trifluoromethyl-phenyl)-N-[6-[3-(ethyl-methanesulfonyl-amino)-pyrrolidin-1-yl]-4-(4-fluoro-2-methyl-phenyl)-pyridin-3-yl]-N-methyl-isobutyramide To a solution of 150 mg (0.227 mmol) (S)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide in 1 ml dimethylformamide were added 14 mg (0.35 mmol) sodium hydride (60% dispersion in mineral oil). After stirring at room temperature for 30 min. 22 mg (0.27 mmol) iodoethane were added. The reaction mixture was stirred at room temperature for 18 h, followed by dilution with 10 ml tert-butyl methyl ether and washing with 20 ml water and with 10 ml of a saturated aqueous solution of sodium carbonate. The combined organic layers were dried over sodium sulfate, concentrated and purified by flash chromatography to give 86 mg (55%) of the title compound as an off-white foam.

MS m/e (%): 689 (M+H$^+$, 100)

EXAMPLE 107

(S)—N-[6-[3-(Acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide The title compound was obtained as a white foam in 62% yield after flash chromatography according to the procedure described above for the preparation of (R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide using (S)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide instead of (R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide.

MS m/e (%): 639 (M+H$^+$, 100)

EXAMPLE 108

(S)—N-[6-[3-(Acetyl-ethyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide The title compound was obtained as a white foam in 59% yield after flash chromatography according to the procedure described above for the preparation of (R)—N-[6-[3-(acetyl-methyl-amino)-pyrrolidin-1-yl]-4-(4-fluoro-2-methyl-phenyl)-pyridin-3-yl]-2-(3,5-bis-trifluoromethyl-phenyl)-N-methyl-isobutyramide using (S)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide instead of (R)—N-[6-(3-acetylamino-pyrrolidin-1-yl)-4-(4-fluoro-2-methyl-phenyl)-pyridin-3-yl]-2-(3,5-bis-trifluoromethyl-phenyl)-N-methyl-isobutyramide and iodoethane instead of iodomethane.

MS m/e (%): 639 (M+H$^+$, 100)

EXAMPLE 109

(S)-2-(3,5-Bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide The title compound was obtained as a white foam in 62% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (S)-3-hydroxypyrrolidine instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide MS m/e (%): 584 (M+H$^+$, 100)

EXAMPLE 110

(RS)-2-(3,5-Bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide The title compound was obtained as an off-white foam in 73% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using (RS)-3-pyrrolidinol instead of ethanolamine and 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide MS m/e (%): 584 (M+H$^+$, 100)

EXAMPLE 111

2-(3,5-Bis-trifluoromethyl-phenyl)-N-[4-(4-fluoro-2-methyl-phenyl)-6-(3-oxo-pyrrolidin-1-yl)-pyridin-3-yl]-N-methyl-isobutyramide The title compound was obtained as a off-white foam in 73% yield after flash chromatography according to the procedure described above for the preparation of 2-(3,5-bis-trifluoromethyl-phenyl)-N-[4-(2-chloro-phenyl)-6-(2-oxo-propylamino)-pyridin-3-yl]-N-methyl-isobutyramide using (RS)-2-(3,5-bis-trifluoromethyl-phenyl)-N-[4-(4-fluoro-2-methyl-phenyl)-6-(3-hydroxy-pyrrolidin-1-yl)-pyridin-3-yl]-N-methyl-isobutyramide instead of (RS)-2-(3,5-bis-trifluoromethyl-phenyl)-N-[4-(2-chloro-phenyl)-6-(2-hydroxy-propylamino)-pyridin-3-yl]-N-methyl-isobutyramide.

MS m/e (%): 582 (M+H$^+$, 100)

EXAMPLE 112

N-[4-Amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide a) 2-(3,5-Bis-trifluoromethyl-phenyl)-N-[4'-(2-chloro-phenyl)-4-oxo-3,4,5,6-tetrahydro-2H-[1,2']bipyridinyl-5'-yl]-N-methyl-isobutyramide The title compound was obtained as a white foam in 72% yield after flash chromatography according to the procedure described above for the preparation of 2-(3,5-bis-trifluoromethyl-phenyl)-N-[4-(2-chloro-phenyl)-6-(2-oxo-propylamino)-pyridin-3-yl]-N-methyl-isobutyramide using 2-(3,5-bis-trifluoromethyl-phenyl)-N-[4'-(2-chloro-phenyl)-4-hydroxy-3,4,5,6-tetrahydro-2H-[1,2']bipyridinyl-5'-yl]-N-methyl-isobutyramide instead of (RS)-2-(3,5-bis-trifluoromethyl-phenyl)-N-[4-(2-chloro-phenyl)-6-(2-hydroxy-propylamino)-pyridin-3-yl]-N-methyl-isobutyramide.

MS m/e (%): 598 (M+H$^+$, 100)

b) N-[4-Amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide To a solution of 752 mg (1.26 mmol) 2-(3,5-bis-trifluoromethyl-phenyl)-N-[4'-(2-chloro-phenyl)-4-oxo-3,4,5,6-tetrahydro-2H-[1,2']bipyridinyl-5'-yl]-N-methyl-isobutyramide in 7 ml methanol 970 mg (12.6 mmol) ammonium acetate were added at room temperature. The mixture was stirred 5 minutes at this temperature, cooled to 0° C. and treated with 119 mg (1.89 mmol) sodium cyanoborohydride. The reaction mixture was allowed to slowly warm to room temperature during 5 h, followed by dilution with 20 ml ethyl acetate, washing with 10 ml brine and extraction with 20 ml ethyl acetate. The combined organic layers were dried over sodium sulfate, concentrated in vacuo and purified by flash chromatography to give 480 mg (64%) of the title compound as a white foam.

MS m/e (%): 600 (M+H$^+$, 100)

EXAMPLE 113

2-(3,5-Bis-trifluoromethyl-phenyl)-N-[4'-(2-chloro-phenyl)-4-methanesulfonylamino-3,4,5,6-tetrahydro-2H-[1,2']bipyridinyl-5'-yl]-N-methyl-isobutyramide The title compound was obtained as a white foam in 16% yield after flash chromatography according to the procedure described above for the preparation of (S)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide using N-[4-amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide instead of (S)—N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide.

MS m/e (%): 677 (M+H$^+$, 100)

EXAMPLE 114

N-[4-Acetylamino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide a) 2-(3,5-Bis-trifluoromethyl-phenyl)-N-[4'-(4-fluoro-2-methyl-phenyl)-4-hydroxy-3,4,5,6-tetrahydro-2H-[1,2']bipyridinyl-5'-yl]-N-methyl-isobutyramide The title compound was obtained as a light yellow foam in 93% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and 4-hydroxy-piperidine instead of ethanolamine.

MS m/e (%): 598 (M+H$^+$, 100)

b) 2-(3,5-Bis-trifluoromethyl-phenyl)-N-[4'-(4-fluoro-2-methyl-phenyl)-4-oxo-3,4,5,6-tetrahydro-2H-[1,2']bipyridinyl-5'-yl]-N-methyl-isobutyramide The title compound was obtained as a white foam in 96% yield after flash chromatography according to the procedure described above for the preparation of 2-(3,5-bis-trifluoromethyl-phenyl)-N-[4-(2-chloro-phenyl)-6-(2-oxo-propylamino)-pyridin-3-yl]-N-methyl-isobutyramide using 2-(3,5-bis-trifluoromethyl-phenyl)-N-[4'-(4-fluoro-2-methyl-phenyl)-4-hydroxy-3,4,5,6-tetrahydro-2H-[1,2']bipyridinyl-5'-yl]-N-methyl-isobutyramide instead of (RS)-2-(3,5-bis-trifluoromethyl-phenyl)-N-[4-(2-chloro-phenyl)-6-(2-hydroxy-propylamino)-pyridin-3-yl]-N-methyl-isobutyramide MS m/e (%): 596 (M+H$^+$, 100)

c) N-[4-Amino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide The title compound was obtained as a white foam in 45% yield after flash chromatography according to the procedure described above for the preparation of N-[4-amino-4'-(2-chloro-phenyl)-3,4,5,6-tetrahydro-2H-[1,2']bipyridinyl-5'-yl]-2-(3,5-bis-trifluoromethyl-phenyl)-N-methyl-isobutyramide using 2-(3,5-bis-trifluoromethyl-phenyl)-N-[4'-(4-fluoro-2-methyl-phenyl)-4-oxo-3,4,5,6-tetrahydro-2H-[1,2']bipyridinyl-5'-yl]-N-methyl-isobutyramide instead of 2-(3,5-bis-trifluoromethyl-phenyl)-N-[4'-(2-chloro-phenyl)-4-oxo-3,4,5,6-tetrahydro-2H-[1,2']bipyridinyl-5'-yl]-N-methyl-isobutyramide.

MS m/e (%): 597 (M+H$^+$, 100)

d) N-[4-Acetylamino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide To a solution of 80 mg (0.13 mmol) N-[4-amino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide and 26 mg (0.20 mmol) N,N-diisopropylethylamine in 3 ml dichloromethane were added 12 mg (0.15 mmol) acetyl chloride at 0° C. The reaction mixture was stirred at room temperature for 18 h. The mixture was diluted with 10 ml dichloromethane and washed with 10 ml of a saturated aqueous solution of sodium carbonate. The combined organic layers were dried over sodium sulfate, concentrated and purified by flash chromatography to give 82 mg (95%) of the title compound as a white foam.

MS m/e (%): 639 (M+H$^+$, 100)

EXAMPLE 115

2-(3,5-Bis-trifluoromethyl-phenyl)-N-{4-(4-fluoro-phenyl)-6-[(2-hydroxy-ethyl)-methyl-amino]-pyridin-3-yl}-N-methyl-isobutyramide A mixture of 0.10 g (0.20 mmol) 2-(3,5-bis-trifluoromethyl-phenyl)-N-[6-chloro-4-(4-fluoro-phenyl)-pyridin-3-yl]-N-methyl-isobutyramide and 0.45 g (6.0 mmol) 2-(methylamino)ethanol was stirred 6 h at 140° C. After cooling to room temperature the reaction mixture was partitioned between water and tert-butyl methyl ether and extracted with three portions of tert-butyl methyl ether. The combined organic extracts were washed with a saturated aqueous solution of ammonium chloride and water, dried over sodium sulfate and concentrated in vacuo. Flash column chromatography gave 87 mg (78%) of the title compound as a light yellow solid.

MS m/e (%): 558 (M+H$^+$, 100)

EXAMPLE 116

2-(3,5-Bis-trifluoromethyl-phenyl)-N-[6-[ethyl-(2-hydroxy-ethyl)-amino]-4-(4-fluoro-phenyl)-pyridin-3-yl]-N-methyl-isobutyramide The title compound was obtained as a white solid in 23% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(ethylamino)ethanol instead of 2-(methylamino)ethanol.

MS m/e (%): 572 (M+H$^+$, 100)

EXAMPLE 117

2-(3,5-Bis-trifluoromethyl-phenyl)-N-{6-[(2-hydroxy-ethyl)-methyl-amino]-4-o-tolyl-pyridin-3-yl}-N-methyl-isobutyramide The title compound was obtained as a white solid in 87% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide.

MS m/e (%): 554 (M+H$^+$, 100)

EXAMPLE 118

2-(3,5-Bis-trifluoromethyl-phenyl)-N-{6-[ethyl-(2-hydroxy-ethyl)-amino]-4-o-tolyl-pyridin-3-yl}-N-methyl-isobutyramide The title compound was obtained as a white solid in 91% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and 2-(ethylamino)ethanol instead of 2-(methylamino)ethanol.

MS m/e (%): 568 (M+H$^+$, 100)

EXAMPLE 119

2-(3,5-Bis-trifluoromethyl-phenyl)-N-{6-[(2-hydroxy-ethyl)-propyl-amino]-4-o-tolyl-pyridin-3-yl}-N-methyl-isobutyramide The title compound was obtained as a white solid in 72% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and 2-(propylamino)ethanol instead of 2-(methylamino)ethanol.

MS m/e (%): 568 (M+H$^+$, 100)

EXAMPLE 120

(S)-2-(3,5-Bis-trifluoromethyl-phenyl)-N-[6-(2-hydroxy-propylamino)-4-o-tolyl-pyridin-3-yl]-N-methyl-isobutyramide The title compound was obtained as a light yellow solid in 55% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and (S)-1-amino-2-propanol instead of 2-(methylamino)ethanol.

MS m/e (%): 554 (M+H$^+$, 100)

EXAMPLE 121

N-{6-[Bis-(2-hydroxy-propyl)-amino]-4-o-tolyl-pyridin-3-yl}-2-(3,5-bis-trifluoromethyl-phenyl)-N-methyl-isobutyramide The title compound was obtained as a white solid in 51% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and bis-(2-hydroxypropyl)amine instead of 2-(methylamino)ethanol.

MS m/e (%): 612 (M+H$^+$, 100)

EXAMPLE 122

(S)-2-(3,5-Bis-trifluoromethyl-phenyl)-N-[6-(2,3-dihydroxy-propylamino)-4-o-tolyl-pyridin-3-yl]-N-methyl-isobutyramide The title compound was obtained as a white solid in 76% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and (S)-3-amino-1,2-propandiol instead of 2-(methylamino)ethanol.

MS m/e (%): 570 (M+H$^+$, 100)

EXAMPLE 123

(R)-2-(3,5-Bis-trifluoromethyl-phenyl)-N-[6-(2,3-dihydroxy-propylamino)-4-o-tolyl-pyridin-3-yl]-N-methyl-isobutyramide The title compound was obtained as a white solid in 74% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and (R)-3-amino-1,2-propandiol instead of 2-(methylamino)ethanol.

MS m/e (%): 570 (M+H$^+$, 100)

EXAMPLE 124

N-[6-[Bis-(2-hydroxy-propyl)-amino]-4-(2-chloro-phenyl)-pyridin-3-yl]-2-(3,5-bis-trifluoromethyl-phenyl)-N-methyl-isobutyramide The title compound was obtained as a white solid in 71% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and bis-(2-hydroxypropyl)amine instead of 2-(methylamino) ethanol.

MS m/e (%): 632 (M+H$^+$, 100)

EXAMPLE 125

(S)-2-(3,5-Bis-trifluoromethyl-phenyl)-N-[4-(2-chloro-phenyl)-6-(2,3-dihydroxy-propylamino)-pyridin-3-yl]-N-methyl-isobutyramide The title compound was obtained as a white solid in 73% yield after flash chromatography according to the procedure described above for the preparation of 2-(3,5-bis-trifluoromethyl-phenyl)-N{4-(4-fluoro-phenyl)-6-[(2-hydroxy-ethyl)- methyl-amino]-pyridin-3-yl}-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and (S)-3-amino-1,2-propandiol instead of 2-(methylamino)ethanol.

MS m/e (%): 590 (M+H$^+$, 100)

EXAMPLE 126

(R)-2-(3,5-Bis-trifluoromethyl-phenyl)-N-[4-(2-chloro-phenyl)-6-(2,3-dihydroxy-propylamino)-pyridin-3-yl]-N-methyl-isobutyramide The title compound was obtained as a white solid in 65% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and (R)-3-amino-1,2-propandiol instead of 2-(methylamino)ethanol.

MS m/e (%): 590 (M+H$^+$, 100)

EXAMPLE 127

N-[6-[Bis-(2-hydroxy-ethyl)-amino]-4-(3-fluoro-2-methyl-phenyl)-pyridin-3-yl]-2-(3,5-bis-trifluoromethyl-phenyl)-N-methyl-isobutyramide The title compound was obtained as a light yellow solid in 34% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-[6-chloro-4-(3-fluoro-2-methyl-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and 2-(2-hydroxy-ethylamino)-ethanol instead of 2-(methylamino)ethanol.

MS m/e (%): 602 (M+H$^+$, 100)

EXAMPLE 128

N-[6-[Bis-(2-hydroxy-ethyl)-amino]-4-(5-fluoro-2-methyl-phenyl)-pyridin-3-yl]-2-(3,5-bis-trifluoromethyl-phenyl)-N-methyl-isobutyramide The title compound was obtained as a light yellow solid in 9% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide using 2-(3,5-bis-trifluoromethyl-phenyl)-N-[6-chloro-4-(5-fluoro-2-methyl-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and 2-(2-hydroxy-ethylamino)-ethanol instead of 2-(methylamino)ethanol.

MS m/e (%): 602 (M+H$^+$, 100)

EXAMPLE 129

(2S,4R)-2-(3,5-Bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide A mixture of 800 mg (1.38 mmol) 2-(3,5-bis-trifluoromethyl-phenyl)-N-[4-(2-bromo-phenyl)-6-chloro-pyridin-3-yl]-N-methyl-isobutyramide, 4 ml dimethyl sulfoxide and 1.15 g (6.9 mmol) (2S,4R)-2-(hydroxymethyl)-4-hydroxypyrrolidine was stirred at 130° C. for 24 h. The reaction mixture was cooled to room temperature, diluted with 100 ml ethyl acetate and washed with 200 ml 1 N sodium carbonate solution and 100 ml water. The combined aqueous layers were extracted twice with 100 ml ethyl acetate. The combined organic layers were dried over sodium sulfate and evaporated. Purification by flash chromatography gave 434 mg (48%) of the title compound as a yellow foam.

MS m/e (%): 660 (M+H$^+$, 100)

EXAMPLE 130

(2R,3S)-2-(3,5-Bis-trifluoromethyl-phenyl)-N-[4-(2-bromo-phenyl)-6-(3-hydroxy-2-hydroxymethyl-pyrrolidin-1-yl)-pyridin-3-yl]-N-methyl-isobutyramide The title compound was obtained as a yellow foam in 27% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using (2R,3S)-2-(hydroxymethyl)-3-hydroxypyrrolidine instead of (2S,4R)-2-(hydroxymethyl)-4-hydroxypyrrolidine.

MS m/e (%): 660 (M+H$^+$, 100)

EXAMPLE 131

(S)-2-(3,5-Bis-trifluoromethyl-phenyl)-N-[4-(2-bromo-phenyl)-6-(2-hydroxy-propylamino)-pyridin-3-yl]-N-methyl-isobutyramide The title compound was obtained as a white foam in 52% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using (S)-1-amino-2-propanol instead of (2S,4R)-2-(hydroxymethyl)-4-hydroxypyrrolidine.

MS m/e (%): 618 (M+H$^+$, 89)

EXAMPLE 132 trans-2-(3,5-Bis-trifluoromethyl-phenyl)-N-[4-(2-bromo-phenyl)-6-(4-hydroxy-cyclohexylamino)-pyridin-3-yl]-N-methyl-isobutyramide The title compound was obtained as a white foam in 39% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using trans-4-aminocyclohexanol instead of (2S,4R)-2-(hydroxymethyl)-4-hydroxypyrrolidine.

MS m/e (%): 658 (M+H$^+$, 83)

EXAMPLE 133

(S)—N-[6-(3-Acetylamino-pyrrolidin-1-yl)-4-(2-bromo-phenyl)-pyridin-3-yl]-2-(3,5-bis-trifluoromethyl-phenyl)-N-methyl-isobutyramide The title compound was obtained as a white foam in 67% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using (S)-acetamidopyrrolidine instead of (2S,4R)-2-(hydroxymethyl)-4-hydroxypyrrolidine.

MS m/e (%): 671 (M+H$^+$, 100)

EXAMPLE 134

N-[6-[Bis-(2-hydroxy-ethyl)-amino]-4-(2-bromo-phenyl)-pyridin-3-yl]-2-(3,5-bis-trifluoromethyl-phenyl)-N-methyl-isobutyramide The title compound was obtained as a light yellow foam in 23% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using diethanolamine instead of (2S,4R)-2-(hydroxymethyl)-4-hydroxypyrrolidine.

MS m/e (%): 648 (M+H$^+$, 100)

EXAMPLE 135

(2S,4R)-2-(3,5-Bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide The title compound was obtained as a yellow foam in 61% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(3,4-dichloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide.

MS m/e (%): 650 (M+H$^+$, 100)

EXAMPLE 136

(2S,4R)-2-(3,5-Bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide The title compound was obtained as a yellow foam in 50% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide.

MS m/e (%): 650 (M+H$^+$, 100)

EXAMPLE 137

(2R,3S)-2-(3,5-Bis-trifluoromethyl-phenyl)-N-[4-(2,4-dichloro-phenyl)-6-(3-hydroxy-2-hydroxymethyl-pyrrolidin-1-yl)-pyridin-3-yl]-N-methyl-isobutyramide The title compound was obtained as a yellow foam in 45% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2,4-dichloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and (2R,3S)-2-hydroxymethyl-pyrrolidin-3-ol instead of (2S,4R)-2-(hydroxymethyl)-4-hydroxypyrrolidine.

MS m/e (%): 650 (M+H$^+$, 100)

EXAMPLE 138

(2R,3S)-2-(3,5-Bis-trifluoromethyl-phenyl)-N-[4-(2-chloro-phenyl)-6-(3-hydroxy-2-hydroxymethyl-pyrrolidin-1-yl)-pyridin-3-yl]-N-methyl-isobutyramide The title compound was obtained as an off-white foam in 26% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and (2R,3S)-2-(hydroxymethyl)-3-hydroxypyrrolidine instead of (2S,4R)-2-(hydroxymethyl)-4-hydroxypyrrolidine.

MS m/e (%): 616 (M+H$^+$, 100)

EXAMPLE 139

(2R,4S)-2-(3,5-Bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained as an off-white foam in 67% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and (2R,4S)-2-(hydroxymethyl)-4-hydroxypyrrolidine instead of (2S,4R)-2-(hydroxymethyl)-4-hydroxypyrrolidine.

MS m/e (%): 616 (M+H$^+$, 100)

EXAMPLE 140

(2S,4S)-2-(3,5-Bis-trifluoromethyl-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained as a white foam in 50% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and (2S,4S)-2-(hydroxymethyl)-4-hydroxypyrrolidine instead of (2S,4R)-2-(hydroxymethyl)-4-hydroxypyrrolidine.

MS m/e (%): 616 (M+H$^+$, 100)

EXAMPLE 141

(RS)-2-(3,5-Bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide The title compound was obtained as a white foam in 45% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and (RS)-2-piperidinemethanol instead of (2S,4R)-2-(hydroxymethyl)-4-hydroxypyrrolidine.

MS m/e (%): 614 (M+H$^+$, 100)

EXAMPLE 142

2-(3,5-Bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide The title compound was obtained as a light yellow solid in 23% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino)pyridine and 2-amino-1,3-propandiol instead of (2S,4R)-2-(hydroxymethyl)-4-hydroxypyrrolidine.

MS m/e (%): 588 (M+H$^+$, 100)

EXAMPLE 143

2-(3,5-Bis-trifluoromethyl-phenyl)-N-[6-(2-hydroxy-1-hydroxymethyl-ethylamino)-4-o-tolyl-pyridin-3-yl]-N-methyl-isobutyramide The title compound was obtained as an off-white solid in 55% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 2-amino-1,3-propandiol instead of (2S,4R)-2-(hydroxymethyl)-4-hydroxypyrrolidine.

MS m/e (%): 570 (M+H$^+$, 100)

EXAMPLE 144

(1R,2R)-2-(3,5-Bis-trifluoromethyl-phenyl)-N-[4-(2-chloro-phenyl)-6-(2-hydroxy-1-hydroxymethyl-propylamino)-pyridin-3-yl]-N-methyl-isobutyramide The title compound was obtained as an off-white solid in 32% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino)pyridine and L-threoninol instead of (2S,4R)-2-(hydroxymethyl)-4-hydroxypyrrolidine.

MS m/e (%): 604 (M+H$^+$, 100)

EXAMPLE 145

(1R,2S)-2-(3,5-Bis-trifluoromethyl-phenyl)-N-[4-(2-chloro-phenyl)-6-(2-hydroxy-1-hydroxymethyl-propylamino)-pyridin-3-yl]-N-methyl-isobutyramide The title compound was obtained as an off-white solid in 23% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino)pyridine and L-allo-threoninol instead of (2S,4R)-2-(hydroxymethyl)-4-hydroxypyrrolidine.

MS m/e (%): 604 (M+H$^+$, 100)

EXAMPLE 146

(1S,2R)-2-(3,5-Bis-trifluoromethyl-phenyl)-N-[4-(2-chloro-phenyl)-6-(2-hydroxy-1-hydroxymethyl-propylamino)-pyridin-3-yl]-N-methyl-isobutyramide The title compound was obtained as an off-white solid in 18% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino)

pyridine and D-allo-threoninol instead of (2S,4R)-2-(hydroxymethyl)-4-hydroxypyrrolidine.
MS m/e (%): 604 (M+H+, 100)

EXAMPLE 147

(1S,2S)-2-(3,5-Bis-trifluoromethyl-phenyl)-N-[4-(2-chloro-phenyl)-6-(2-hydroxy-1-hydroxymethyl-propylamino)-pyridin-3-yl]-N-methyl-isobutyramide The title compound was obtained as an off-white solid in 4% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino) pyridine and D-threoninol instead of (2S,4R)-2-(hydroxymethyl)-4-hydroxypyrrolidine.
MS m/e (%): 604 (M+H+, 100)

EXAMPLE 148

2-(3,5-Bis-trifluoromethyl-phenyl)-N-{4-(2-chloro-phenyl)-6-[hexyl-(2-hydroxy-ethyl)-amino]-pyridin-3-yl}-N-methyl-isobutyramide The title compound was obtained as a light yellow solid in 39% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 2-(hexylamino)ethanol instead of (2S,4R)-2-(hydroxymethyl)-4-hydroxypyrrolidine.
MS m/e (%): 644 (M+H+, 100)

EXAMPLE 149

2-(3,5-Bis-trifluoromethyl-phenyl)-N-{4-(2-chloro-phenyl)-6-[(2-hydroxy-ethyl)-pentyl-amino]-pyridin-3-yl}-N-methyl-isobutyramide The title compound was obtained as a light yellow solid in 38% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 2-(N-amylamino) ethanol instead of (2S,4R)-2-(hydroxymethyl)-4-hydroxypyrrolidine.
MS m/e (%): 630 (M+H+, 100)

EXAMPLE 150

2-(3,5-Bis-trifluoromethyl-phenyl)-N-{4-(2-chloro-phenyl)-6-[(2-hydroxy-ethyl)-(3-hydroxy-propyl)-amino]-pyridin-3-yl}-N-methyl-isobutyramide The title compound was obtained as an off-white solid in 26% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 3-(hydroxyethylamino)-1-propanol instead of (2S,4R)-2-(hydroxymethyl)-4-hydroxypyrrolidine.
MS m/e (%): 618 (M+H+, 100)

EXAMPLE 151

(1RS,2RS)-2-(3,5-Bis-trifluoromethyl-phenyl)-N-[4-(2-chloro-phenyl)-6-(2-hydroxy-cyclohexylamino)-pyridin-3-yl]-N-methyl-isobutyramide The title compound was obtained as a light brown solid in 46% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino) pyridine and (1RS,2RS)-2-aminocyclohexanol instead of (2S,4R)-2-(hydroxymethyl)-4-hydroxypyrrolidine.
MS m/e (%): 614 (M+H+, 100)

EXAMPLE 152

(1R,2R)-2-(3,5-Bis-trifluoromethyl-phenyl)-N-[4-(2-chloro-phenyl)-6-(2-hydroxy-cyclopentylamino)-pyridin-3-yl]-N-methyl-isobutyramide a) (1R,2R)—N-[6-(2-Benzyloxy-cyclopentylamino)-4-(2-chloro-phenyl)-pyridin-3-yl]-2-(3,5-bis-trifluoromethyl-phenyl)-N-methyl-isobutyramide The title compound was obtained as a brown solid in 58% yield after flash chromatography according to the procedure described above for the preparation of (2S,4R)-2-(3,5-bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[4-(2-bromo-phenyl)-6-chloro-pyridin-3-yl]-N-methyl-isobutyramide and 5 mol-% 4-(N,N-dimethylamino) pyridine and (1R,2R)-2-benzyloxy-cyclopentylamine instead of (2S,4R)-2-(hydroxymethyl)-4-hydroxypyrrolidine.

b) (1R,2R)-2-(3,5-Bis-trifluoromethyl-phenyl)-N-[4-(2-chloro-phenyl)-6-(2-hydroxy-cyclopentylamino)-pyridin-3-yl]-N-methyl-isobutyramide To a solution of 0.15 g (0.22 mmol) (1R,2R)—N-[6-(2-benzyloxy-cyclopentylamino)-4-(2-chloro-phenyl)-pyridin-3-yl]-2-(3,5-bis-trifluoromethyl-phenyl)-N-methyl-isobutyramide in 2 ml dichloromethane were added 0.87 ml (0.87 mmol) of a 1 M boron trichloride solution in dichloromethane at room temperature. After 2 h the reaction was quenched by addition of 2 ml of a 1 M aqueous hydrochloric acid solution.

EXAMPLE 153

(1S,2S)-2-(3,5-Bis-trifluoromethyl-phenyl)-N-[4-(2-chloro-phenyl)-6-(2-hydroxy-cyclopentylamino)-pyridin-3-yl]-N-methyl-isobutyramide The title compound was obtained as an off-white solid in 8% yield over two steps according to the procedures described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide using (1S,2S)-2-benzyloxy-cyclopentylamine instead of (1R,2R)-2-benzyloxy-cyclopentylamine in step a).

MS m/e (%): 600 (M+H$^+$, 100)

EXAMPLE 154

(1S,2S)-2-(3,5-Bis-trifluoromethyl-phenyl)-N-[4-(4-fluoro-2-methyl-phenyl)-6-(2-hydroxy-cyclopentylamino)-pyridin-3-yl]-N-methyl-isobutyramide The title compound was obtained as a light brown solid in 15% yield over two steps according to the procedures described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide and (1S,2S)-2-benzyloxy-cyclopentylamine instead of (1R,2R)-2-benzyloxy-cyclopentylamine in step a).

MS m/e (%): 598 (M+H$^+$, 100)

EXAMPLE 155

(2R,3S)-2-(3,5-Bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide A mixture of 11.0 g (20.6 mmol) 2-(3,5-bis-trifluoromethyl-phenyl)-N-[6-chloro-4-(4-fluoro-2-methyl-phenyl)-pyridin-3-yl]-N-methyl-isobutyramide, 14.3 g (103 mmol) potassium carbonate and 12.2 g (75.7 mmol) (2R,3S)-2-(hydroxymethyl)-3-hydroxypyrrolidine in 110 ml dimethyl sulfoxide was stirred at 130° C. for 68 h. The reaction mixture was diluted with 800 ml ethyl acetate and washed with 800 ml saturated sodium carbonate solution, 500 ml water and 750 ml brine. The combined aqueous layers were extracted with two 800-ml portions of ethyl acetate. The combined organic layers were dried over sodium sulfate and concentrated in vacuo. Purification by flash chromatography gave 8.48 g (67%) of the title compound as a light yellow foam.

MS m/e (%): 614 (M+H$^+$, 100)

EXAMPLE 156

(2R,3R)-2-(3,5-Bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide and

EXAMPLE 157

(S)-2-(3,5-Bis-trifluoromethyl-phenyl)-N-[4-(4-fluoro-2-methyl-phenyl)-6-(2-hydroxymethyl-2,5-dihydro-pyrrol-1-yl)-pyridin-3-yl]-N-methyl-isobutyramide To a solution of 400 mg (0.65 mmol) (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide in 6.5 ml tetrahydrofuran were added at 0° C. 0.67 ml (3.26 mmol) diisopropyl azodicarboxylate and 398 mg (3.26 mmol) benzoic acid. The reaction mixture was cooled to −78° C., followed by addition of 855 mg (3.26 mmol) triphenylphosphine. The reaction mixture was allowed to slowly warm to room temperature over night. Addition of 75 ml of a saturated sodium carbonate solution was followed by extraction with two 75-ml portions of tert-butyl methyl ether. The organic layers were washed with 75 ml brine, dried over sodium sulfate, concentrated in vacuo and purified by flash chromatography. The residue was dissolved in 20 ml methanol and treated with 0.1 ml of a 5.5 M sodium methylate solution in methanol. After stirring 3 h at room temperature the reaction mixture was concentrated in vacuo. The residue was dissolved in 75 ml dichloromethane and washed with 60 ml water, dried over sodium sulfate and purified by flash chromatography to give 117 mg (29%) of (2R,3R)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide as a white foam and 155 mg (40%) of (S)-2-(3,5-bis-trifluoromethyl-phenyl)-N-[4-(4-fluoro-2-methyl-phenyl)-6-(2-hydroxymethyl-2,5-dihydro-pyrrol-1-yl)-pyridin-3-yl]-N-methyl-isobutyramide as a white foam.

(2R,3R)-2-(3,5-Bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide: MS m/e (%): 614 (M+H$^+$, 100)

(S)-2-(3,5-Bis-trifluoromethyl-phenyl)-N-[4-(4-fluoro-2-methyl-phenyl)-6-(2-hydroxymethyl-2,5-dihydro-pyrrol-1-yl)-pyridin-3-yl]-N-methyl-isobutyramide: MS m/e (%): 596 (M+H$^+$, 100)

EXAMPLE 158

(2S,4R)-2-(3,5-Bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained as an off-white foam in 66% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using (2S,4R)-2-(hydroxymethyl)-4-hydroxypyrrolidine instead of (2R,3S)-2-(hydroxymethyl)-3-hydroxypyrrolidine.

MS m/e (%): 614 (M+H$^+$, 100)

---

Neutralisation with 1 M aqueous NaOH solution was followed by extraction with 3 portions of tert-butyl methyl ether. The combined organic layers were dried over sodium sulfate and concentrated in vacuo. Flash column chromatography gave 60 mg (46%) of the title compound as an off-white solid.

MS m/e (%): 600 (M+H$^+$, 100)

EXAMPLE 159

(S)-2-(3,5-Bis-trifluoromethyl-phenyl)-N-{4-(4-fluoro-2-methyl-phenyl)-6-[2-(1-hydroxy-1-methyl-ethyl)-pyrrolidin-1-yl]-pyridin-3-yl}-N-methyl-isobutyramide The title compound was obtained as a light brown amorphous material in 36% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using (S)-2-pyrrolidin-2-yl-propan-2-ol instead of (2R,3S)-2-(hydroxymethyl)-3-hydroxypyrrolidine.

MS m/e (%): 626 (M+H$^+$, 100)

EXAMPLE 160

(R)-2-(3,5-Bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide The title compound was obtained as a light brown gum in 14% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide and (R)-piperidine-2-ylmethanol instead of (2R,3S)-2-(hydroxymethyl)-3-hydroxypyrrolidine.

MS m/e (%): 614 (M+H$^+$, 100)

EXAMPLE 161

(S)-2-(3,5-Bis-trifluoromethyl-phenyl)-N-[4'-(2-chloro-phenyl)-2-hydroxymethyl-3,4,5,6-tetrahydro-2H-[1,2']bipyridinyl-5'-yl]-N-methyl-isobutyramide The title compound was obtained as a light brown oil in 15% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using (S)-piperidine-2-yl-methanol instead of (2R,3S)-2-(hydroxymethyl)-3-hydroxypyrrolidine and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 614 (M+H$^+$, 100)

EXAMPLE 162

2-(3,5-Bis-trifluoromethyl-phenyl)-N-[4-(4-fluoro-2-methyl-phenyl)-6-(3-hydroxy-azetidin-1-yl)-pyridin-3-yl]-N-methyl-isobutyramide The title compound was obtained as a light yellow foam in 65% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using azetidin-3-ol instead of (2R,3S)-2-(hydroxymethyl)-3-hydroxypyrrolidine.

MS m/e (%): 570 (M+H$^+$, 100)

EXAMPLE 163

2-(3,5-Bis-trifluoromethyl-phenyl)-N-[6-(3-hydroxy-azetidin-1-yl)-4-o-tolyl-pyridin-3-yl]-N-methyl-isobutyramide The title compound was obtained as a light yellow foam in 62% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using azetidin-3-ol instead of (2R,3S)-2-(hydroxymethyl)-3-hydroxypyrrolidine and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 552 (M+H$^+$, 100)

EXAMPLE 164

2-(3,5-Bis-trifluoromethyl-phenyl)-N-[4-(4-fluoro-2-methyl-phenyl)-6-(5-oxo-[1,4]diazepan-1-yl)-pyridin-3-yl]-N-methyl-isobutyramide The title compound was obtained as a light yellow solid in 36% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide using 2,3,6,7-tetrahydro-(1H)-1,4-diazepin-5-(4H)-one instead of (2R,3S)-2-(hydroxymethyl)-3-hydroxypyrrolidine.

MS m/e (%): 611 (M+H$^+$, 100)

EXAMPLE 165

(S)-2-(3,5-Bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide A mixture of 0.20 g (0.38 mmol) 2-(3,5-bis-trifluoromethyl-phenyl)-N-[6-chloro-4-(4-fluoro-2-methyl-phenyl)-pyridin-3-yl]-N-methyl-isobutyramide, 0.23 g (2.3 mmol) L-prolinol and 0.15 g (1.1 mmol) potassium carbonate in 0.5 ml dimethyl sulfoxide was heated at 180° C. under microwave irradiation for 30 min. in a sealed tube. After cooling to room temperature the reaction mixture was diluted with water and extracted with three portions of tert-butyl methyl ether. The combined organic extracts were washed with water and brine, dried over sodium sulfate and concentrated in vacuo. Flash column chromatography gave 0.18 g (78%) of the title compound as an off-white solid.

MS m/e (%): 598 (M+H$^+$, 100)

EXAMPLE 166

(S)-2-(3,5-Bis-trifluoromethyl-phenyl)-N-[4-(5-fluoro-2-methyl-phenyl)-6-(2-hydroxymethyl-pyrrolidin-1-yl)-pyridin-3-yl]-N-methyl-isobutyramide The title compound was obtained as a white solid in 47% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-[6-chloro-4-(5-fluoro-2-methyl-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 598 (M+H$^+$, 100)

EXAMPLE 167

(S)-2-(3,5-Bis-trifluoromethyl-phenyl)-N-[4-(3-fluoro-2-methyl-phenyl)-6-(2-hydroxymethyl-pyrrolidin-1-yl)-pyridin-3-yl]-N-methyl-isobutyramide The title compound was obtained as a white solid in 40% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-[6-chloro-4-(3-fluoro-2-methyl-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 598 (M+H$^+$, 100)

EXAMPLE 168

(R)-2-(3,5-Bis-trifluoromethyl-phenyl)-N-[6-(2-hydroxymethyl-pyrrolidin-1-yl)-4-o-tolyl-pyridin-3-yl]-N-methyl-isobutyramide The title compound was obtained as a white solid in 45% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide and D-prolinol instead of L-prolinol.

MS m/e (%): 580 (M+H$^+$, 100)

EXAMPLE 169

(S)-2-(3,5-Bis-trifluoromethyl-phenyl)-N-[4-(4-fluoro-2-methyl-phenyl)-6-(2-pyrrolidin-1-ylmethyl-pyrrolidin-1-yl)-pyridin-3-yl]-N-methyl-isobutyramide The title compound was obtained as an off-white solid in 57% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using (S)-(+)-1-(2-pyrrolidinylmethyl)pyrrolidine instead of L-prolinol.

MS m/e (%): 651 (M+H$^+$, 100)

EXAMPLE 170

(RS)-2-(3,5-Bis-trifluoromethyl-phenyl)-N-[4-(4-fluoro-2-methyl-phenyl)-6-(3-methanesulfonyl-pyrrolidin-1-yl)-pyridin-3-yl]-N-methyl-isobutyramide The title compound was obtained as a light yellow solid in 48% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 3-(methylsulfonyl)pyrrolidine instead of L-prolinol.

MS m/e (%): 646 (M+H$^+$, 100)

EXAMPLE 171

(RS)-2-(3,5-Bis-trifluoromethyl-phenyl)-N-[4-(2-chloro-phenyl)-6-(3-hydroxymethyl-pyrrolidin-1-yl)-pyridin-3-yl]-N-methyl-isobutyramide The title compound was obtained as an off-white solid in 84% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide and (RS)-pyrrolidin-3-yl-methanol instead of L-prolinol.

MS m/e (%): 600 (M+H$^+$, 100)

EXAMPLE 172

2-(3,5-Bis-trifluoromethyl-phenyl)-N-(4-hydroxymethyl-4'-o-tolyl-3,4,5,6-tetrahydro-2H-[1,2']bipyridinyl-5'-yl)-N-methyl-isobutyramide The title compound was obtained as a light yellow solid in 54% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide and 4-(hydroxymethyl)piperidine instead of L-prolinol.

MS m/e (%): 594 (M+H$^+$, 100)

EXAMPLE 173

(R)-2-(3,5-Bis-trifluoromethyl-phenyl)-N-[6-(2-hydroxy-propylamino)-4-o-tolyl-pyridin-3-yl]-N-methyl-isobutyramide The title compound was obtained as an off-white solid in 30% yield after flash chromatography according to the procedure described above for the preparation of (S)-2-(3,5-bis-trifluoromethyl-phenyl)-N-[4-(4-fluoro-2-methyl-phenyl)-

6-(2-hydroxymethyl-pyrrolidin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide and (R)-1-amino-2-propanol instead of L-prolinol.

MS m/e (%): 554 (M+H$^+$, 100)

EXAMPLE 174

(R)-2-(3,5-Bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide a) (S)-4-Benzyl-3-(tert-butyl-dimethyl-silanyloxymethyl)-morpholine A solution of 1.00 g (4.82 mmol) (R)-(4-benzyl-morpholin-3-yl)-methanol, 0.80 g (5.3 mmol) tert-butyl-chloro-dimethyl-silane and 0.72 g (0.11 mmol) imidazole in 10 ml N,N-dimethylformamide was stirred at room temperature for 90 min. Consecutive addition of water and 1 M aqueous sodium hydroxide solution was followed by extraction with three portions of tert-butyl methyl ether. The combined organic layers were washed with 1 M aqueous sodium hydroxide solution, dried over sodium sulphate and concentrated in vacuo to give 1.54 g (99.3%) of the crude title compound as a colorless oil.

MS m/e (%): 322 (M+H$^+$, 100)

b) (S)-3-(tert-Butyl-dimethyl-silanyloxymethyl)-morpholine

A solution of 1.54 g (4.79 mmol) (S)-4-benzyl-3-(tert-butyl-dimethyl-silanyloxymethyl)-morpholine in 24 ml ethanol was deoxygenated by three cycles of evacuation and flushing with argon. After addition of 0.5 g palladium on charcoal (10%) the reaction vessel was evacuated and filled with hydrogen gas. The reaction mixture was stirred at room temperature under an atmosphere of hydrogen over night. Filtration over decalite and evaporation of the solvent in vacuo gave 1.08 g (97.4%) of the crude title compound as a colorless oil.

MS m/e (%): 232 (M+H$^+$, 100)

c) (R)-2-(3,5-Bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide A mixture of 0.30 g (0.56 mmol) 2-(3,5-bis-trifluoromethyl-phenyl)-N-[6-chloro-4-(4-fluoro-2-methyl-phenyl)-pyridin-3-yl]-N-methyl-isobutyramide, 0.17 g (0.73 mmol) (S)-3-(tert-butyl-dimethyl-silanyloxymethyl)-morpholine, 0.01 g (0.03 mmol) cetyltrimethylammonium bromide, 0.029 g (0.056 mmol) bis(tri-t-butylphosphine)palladium(0), 0.07 ml NaOH 50% and 3 ml toluene was degassed by two freeze-thaw cycles. The reaction mixture was heated under argon at 90° C. for 3 h. After cooling to room temperature the mixture was diluted with water and extracted with three portions of toluene. The combined organic layers were dried over sodium sulphate and concentrated in vacuo. The residue was dissolved in a mixture of 10 ml methanol and 0.5 ml concentrated aqueous hydrochloric acid solution. After stirring at room temperature for 90 min. the reaction mixture was neutralized with 0.5 M aqueous sodium hydroxide solution and extracted with three portions of tert-butyl methyl ether. The combined organic layers were dried over sodium sulfate and concentrated in vacuo. Flash column chromatography gave 0.10 g (30%) of the title compound as an off-white solid.

MS m/e (%): 614 (M+H$^+$, 100)

EXAMPLE 175

(R)-(2-(3,5-Bis-trifluoromethyl-phenyl)-N-[6-(3-hydroxymethyl-morpholin-4-yl)-4-o-tolyl-pyridin-3-yl]-N-methyl-isobutyramide The title compound was obtained as a white solid in 61% yield after flash chromatography according to the procedure described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 596 (M+H$^+$, 100)

EXAMPLE 176

(RS)-2-(3,5-Bis-trifluoromethyl-phenyl)-N-[6-(2-hydroxymethyl-morpholin-4-yl)-4-o-tolyl-pyridin-3-yl]-N-methyl-isobutyramide The title compound was obtained as a light brown solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (RS)-(4-benzyl-morpholin-2-yl)-methanol instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 596 (M+H$^+$, 100)

EXAMPLE 177

(RS)-2-(3,5-Bis-trifluoromethyl-phenyl)-N-[4-(4-fluoro-2-methyl-phenyl)-6-(3-hydroxymethyl-1,1-dioxo-1λ$^6$-thiomorpholin-4-yl)-pyridin-3-yl]-N-methyl-isobutyramide a) (RS)-3-(tert-Butyl-dimethyl-silanyloxymethyl)-thiomorpholine The crude title compound was obtained as an orange oil in 92% yield according to the procedure described above for the preparation of (S)-4-benzyl-3-(tert-butyl-dimethyl-silanyloxymethyl)-morpholine using (RS)-thiomorpholin-3-yl-methanol instead of (R)-(4-benzyl-morpholin-3-yl)-methanol.

MS m/e (%): 248 (M+H$^+$, 100)

b) (RS)-2-(3,5-Bis-trifluoromethyl-phenyl)-N-[4-(4-fluoro-2-methyl-phenyl)-6-(3-hydroxymethyl-thiomorpholin-4-yl)-pyridin-3-yl]-N-methyl-isobutyramide The title compound was obtained as an off-white solid in 55% yield after flash chromatography according to step c) of the procedure described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (RS)-3-(tert-butyl-dimethyl-silanyloxymethyl)-thiomorpholine instead of (S)-3-(tert-butyl-dimethyl-silanyloxymethyl)-morpholine.

MS m/e (%): 630 (M+H$^+$, 100)

c) (RS)-2-(3,5-Bis-trifluoromethyl-phenyl)-N-[4-(4-fluoro-2-methyl-phenyl)-6-(3-hydroxymethyl-1,1-dioxo-1$\lambda^6$-thiomorpholin-4-yl)-pyridin-3-yl]-N-methyl-isobutyramide The title compound was obtained as a white solid in 80% yield after flash chromatography according to the procedure described above for the preparation of 2-(3,5-bis-trifluoromethyl-phenyl)-N-[4-(2-chloro-phenyl)-6-(2-methanesulfonyl-ethylamino)-pyridin-3-yl]-N-methyl-isobutyramide using (RS)-2-(3,5-bis-trifluoromethyl-phenyl)-N-[4-(4-fluoro-2-methyl-phenyl)-6-(3-hydroxymethyl-thiomorpholin-4-yl)-pyridin-3-yl]-N-methyl-isobutyramide instead of 2-(3,5-bis-trifluoromethyl-phenyl)-N-[4-(2-chloro-phenyl)-6-(2-methylsulfanyl-ethylamino)-pyridin-3-yl]-N-methyl-isobutyramide.

MS m/e (%): 662 (M+H$^+$, 100)

EXAMPLE 178

(RS)-2-(3,5-Bis-trifluoromethyl-phenyl)-N-[6-(3-hydroxymethyl-1,1-dioxo-1$\lambda^6$-thiomorpholin-4-yl)-4-o-tolyl-pyridin-3-yl]-N-methyl-isobutyramide The title compound was obtained as a white solid in comparable yields after flash chromatography according to the procedures described above for the preparation of (RS)-2-(3,5-bis-trifluoromethyl-phenyl)-N-[4-(4-fluoro-2-methyl-phenyl)-6-(3-hydroxymethyl-1,1-dioxo-1$\lambda^6$-thiomorpholin-4-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 644 (M+H$^+$, 100)

EXAMPLE 179

(3R,5R)-2-(3,5-Bis-trifluoromethyl-phenyl)-N-(3,5-dihydroxy-4'-o-tolyl-3,4,5,6-tetrahydro-2H-[1,2']bipyridinyl-5'-yl)-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3R,5R)-1-benzyl-piperidine-3,5-diol instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 596 (M+H$^+$, 100)

EXAMPLE 180

(3R,5R)-2-(3,5-Bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3R,5R)-1-benzyl-piperidine-3,5-diol instead of (R)-(4-benzyl-morpholin-3-yl)-methanol in step a) and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 616 (M+H$^+$, 100)

EXAMPLE 181

(3S,5R)-5-Bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide a) (3R,5R)-1-Benzyl-5-(tert-butyl-dimethyl-silanyloxy)-piperidin-3-ol The title compound was obtained as a light brown oil in 38% yield after flash chromatography according to the procedure described above for the preparation of (S)-4-benzyl-3-(tert-butyl-dimethyl-silanyloxymethyl)-morpholine using (3R,5R)-1-benzyl-piperidine-3,5-diol instead of (R)-(4-benzyl-morpholin-3-yl)-methanol.

MS m/e (%): 322 (M+H$^+$, 100)

b) (3S,5R)-1-Benzyl-5-(tert-butyl-dimethyl-silanyloxy)-piperidin-3-ol

To a solution of 1.8 g (5.6 mmol) (3R,5R)-1-benzyl-5-(tert-butyl-dimethyl-silanyloxy)-piperidin-3-ol in 50 ml tetrahydrofuran were added at 0° C. 0.97 ml (6.2 mmol) diethyl azodicarboxylate and 0.75 g (6.2 mmol) benzoic acid. The reaction mixture was cooled to 0° C., followed by addition of 1.6 g (6.2 mmol) triphenylphosphine. The reaction mixture was stirred at 0° C. for 6 h. Addition of a saturated sodium carbonate solution was followed by extraction with three portions of tert-butyl methyl ether. The combined organic layers were washed with saturated sodium carbonate solution and brine, dried over sodium sulfate, concentrated in vacuo and purified by flash chromatography. The residue was dissolved in a mixture of 50 ml dioxane and 18 ml 1 N aqueous sodium hydroxide solution. After stirring at 70° C. for 5 h the reaction mixture was diluted with tert-butyl methyl ether. The layers were separated and the organic layer was washed with a saturation aqueous sodium carbonate solution. The combined aqueous layers were extracted with two portions of tert-butyl methyl ether. The combined organic layers were washed with brine, dried over sodium sulfate and concentrated in vacuo. Flash chromatography gave 0.1 g (6%) of the title compound as a light brown oil.

MS m/e (%): 322 (M+H$^+$, 100)

c) (3S,5R)-3,5-Bis-(tert-butyl-dimethyl-silanyloxy)-piperidine

The title compound was obtained as a white solid in comparable yields according to the procedures described above for the preparation of (S)-3-(tert-butyl-dimethyl-silanyloxymethyl)-morpholine using (3S,5R)-1-benzyl-5-(tert-butyl-dimethyl-silanyloxy)-piperidin-3-ol instead of (R)-(4-benzyl-morpholin-3-yl)-methanol in step a).

MS m/e (%): 346 (M+H+, 100)

d) (3S,5R)-5-Bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide The title compound was obtained as a white solid in comparable yield after flash chromatography according to the procedure described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3S,5R)-3,5-bis-(tert-butyl-dimethyl-silanyloxy)-piperidine instead of (S)-3-(tert-butyl-dimethyl-silanyloxymethyl)-morpholine and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 616 (M+H+, 100)

EXAMPLE 182

(3S,4S)-2-(3,5-Bis-trifluoromethyl-phenyl)-N-[4-(2-chloro-phenyl)-6-(3,4-dihydroxy-pyrrolidin-1-yl)-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3S,4S)-1-benzyl-pyrrolidine-3,4-diol instead of (R)-(4-benzyl-morpholin-3-yl)-methanol in step a) and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 602 (M+H+, 100)

EXAMPLE 183

(3S,4S)-2-(3,5-Bis-trifluoromethyl-phenyl)-N-[6-(3,4-dihydroxy-pyrrolidin-1-yl)-4-o-tolyl-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3S,4S)-1-benzyl-pyrrolidine-3,4-diol instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 582 (M+H+, 100)

EXAMPLE 184

(3R,4S)-2-(3,5-Bis-trifluoromethyl-phenyl)-N-[6-(3,4-dihydroxy-pyrrolidin-1-yl)-4-o-tolyl-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3R,4S)-3,4-dihydroxy-pyrrolidine-1-carboxylic acid benzyl ester instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 582 (M+H+, 100)

EXAMPLE 185

(3RS,4SR)-2-(3,5-Bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide The title compound was obtained as an off-white solid in comparable yields after flash chromatography according to the procedures described above for the preparation of (R)-2-(3,5-bis-trifluoromethyl-phenyl)-N-[4-(4-fluoro-2-methyl-phenyl)-6-(3 hydroxymethyl-morpholin-4-yl)-pyridin-3-yl]-N-methyl-isobutyramide using (3RS,4SR)-3,4-dihydroxy-piperidine-1-carboxylic acid benzyl ester instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 596 (M+H+, 100)

EXAMPLE 186

(3RS,4RS)-2-(3,5-Bis-trifluoromethyl-phenyl)-N-(3,4-dihydroxy-4'-o-tolyl-3,4,5,6-tetrahydro-2H-[1,2']bipyridinyl-5'-yl)-N-methyl-isobutyramide The title compound was obtained as an off-white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3RS,4SR)-3,4-dihydroxy-piperidine-1-carboxylic acid benzyl ester instead of (R)-(4-benzyl-morpholin-3-yl)-methanol in step a) and 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 596 (M+H+, 100)

EXAMPLE 187

(3RS,4SR)-2-(3,5-Bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3, 5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3RS,4SR)-3,4-dihydroxy-piperidine-1-carboxylic acid benzyl ester instead of (R)-(4-benzyl-morpholin-3-yl)-methanol in step a) and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 616 (M+H$^+$, 100)

EXAMPLE 188

(3RS,4RS)-2-(3,5-Bis-trifluoromethyl-phenyl)-N-[4'-(2-chloro-phenyl)-3,4-dihydroxy-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3, 5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3RS,4SR)-3,4-dihydroxy-piperidine-1-carboxylic acid benzyl ester instead of (R)-(4-benzyl-morpholin-3-yl)-methanol in step a) and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 616 (M+H$^+$, 100)

EXAMPLE 189

(2RS,4SR)-2-(3,5-Bis-trifluoromethyl-phenyl)-N-[4'-(2-chloro-phenyl)-4-hydroxy-2-hydroxymethyl-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3, 5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and (2RS,4SR)-1-benzyl-2-hydroxymethyl-piperidin-4-ol instead of (R)-(4-benzyl-morpholin-3-yl)-methanol in step a). (2RS,4SR)-1-Benzyl-2-hydroxymethyl-piperidin-4-ol is obtained by reduction of (1RS,5SR)-2-benzyl-6-oxa-2-azabicyclo[3.2.1]octan-7-one with lithium aluminum hydride in tetrahydrofuran at room temperature for 1 h.

MS m/e (%): 630 (M+H$^+$, 100)

EXAMPLE 190

(2RS,4SR)-2-(3,5-Bis-trifluoromethyl-phenyl)-N-(4-hydroxy-2-hydroxymethyl-4'-o-tolyl-3,4,5,6-tetrahydro-2H-[1,2']bipyridinyl-5'-yl)-N-methyl-isobutyramide The title compound was obtained as a white solid in comparable yields after flash chromatography according to the procedures described above for the preparation of (R)-2-(3, 5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and (2RS,4SR)-1-benzyl-2-hydroxymethyl-piperidin-4-ol instead of (R)-(4-benzyl-morpholin-3-yl)-methanol in step a).

MS m/e (%): 610 (M+H$^+$, 100)

EXAMPLE 191

(3RS,4SR)-2-(3,5-Bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide The title compound was obtained as a light yellow solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and 1-benzyl-3-hydroxymethyl-piperidin-4-ol as a mixture of racemic diastereomers (Gueller, Rolf; Binggeli, Alfred; Breu, Volker; Bur, Daniel; Fischli, Walter; et al.; Bioorg. Med. Chem. Lett. 1999, 9, 1403-1408.) instead of (R)-(4-benzyl-morpholin-3-yl)-methanol in step a). (3RS,4SR)-1-Benzyl-4-(tert-butyl-dimethyl-silanyloxy)-3-(tert-butyl-dimethyl-silanyloxymethyl)-piperidine was separated from (3RS,4RS)-1-benzyl-4-(tert-butyl-dimethyl-silanyloxy)-3-(tert-butyl-dimethyl-silanyloxymethyl)-piperidine by flash column chromatography and used in step b).

MS m/e (%): 610 (M+H$^+$, 100)

EXAMPLE 192

(3RS,4RS)-2-(3,5-Bis-trifluoromethyl-phenyl)-N-(4-hydroxy-3-hydroxymethyl-4'-o-tolyl-3,4,5,6-tetrahydro-2H-[1,2']bipyridinyl-5'-yl)-N-methyl-isobutyramide The title compound was obtained as a white solid in comparable yields after flash chromatography according to the procedures described above for the preparation of (R)-2-(3, 5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and 1-benzyl-3-hydroxymethyl-piperidin-4-ol as a mixture of racemic diastereomers (Gueller, Rolf; Binggeli, Alfred; Breu, Volker; Bur, Daniel; Fischli, Walter; et al.; Bioorg. Med. Chem. Lett. 1999, 9, 1403-1408.) instead of (R)-(4-benzyl-morpholin-3-yl)-methanol in step a). (3RS,4RS)-1-Benzyl-4-(tert-butyl-dimethyl-silanyloxy)-3-(tert-butyl-dimethyl-silanyloxymethyl)-piperidine was separated from (3RS,4SR)-1-benzyl-4-(tert-butyl-dimethyl-silanyloxy)-3-(tert-butyl-

EXAMPLE 193

(3RS,4SR)-2-(3,5-Bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and 1-benzyl-3-hydroxymethyl-piperidin-4-ol as a mixture of racemic diastereomers (Gueller, Rolf; Binggeli, Alfred; Breu, Volker; Bur, Daniel; Fischli, Walter; et al.; Bioorg. Med. Chem. Lett. 1999, 9, 1403-1408.) instead of (R)-(4-benzyl-morpholin-3-yl)-methanol in step a). (3RS,4SR)-1-Benzyl-4-(tert-butyl-dimethyl-silanyloxy)-3-(tert-butyl-dimethyl-silanyloxymethyl)-piperidine was separated from (3RS,4RS)-1-benzyl-4-(tert-butyl-dimethyl-silanyloxy)-3-(tert-butyl-dimethyl-silanyloxymethyl)-piperidine by flash column chromatography and used in step b).

MS m/e (%): 630 (M+H⁺, 100)

EXAMPLE 194

(3RS,4RS)-2-(3,5-Bis-trifluoromethyl-phenyl)-N-[4'-(2-chloro-phenyl)-4-hydroxy-3-hydroxymethyl-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and 1-benzyl-3-hydroxymethyl-piperidin-4-ol as a mixture of racemic diastereomers (Gueller, Rolf; Binggeli, Alfred; Breu, Volker; Bur, Daniel; Fischli, Walter; et al.; Bioorg. Med. Chem. Lett. 1999, 9, 1403-1408.) instead of (R)-(4-benzyl-morpholin-3-yl)-methanol in step a). (3RS,4RS)-1-Benzyl-4-(tert-butyl-dimethyl-silanyloxy)-3-(tert-butyl-dimethyl-silanyloxymethyl)-piperidine was separated from (3RS,4SR)-1-benzyl-4-(tert-butyl-dimethyl-silanyloxy)-3-(tert-butyl-dimethyl-silanyloxymethyl)-piperidine by flash column chromatography and used in step b).

MS m/e (%): 630 (M+H⁺, 100)

EXAMPLE 195

(2RS,3RS)-2-(3,5-Bis-trifluoromethyl-phenyl)-N-[4'-(2-chloro-phenyl)-3-hydroxy-2-hydroxymethyl-3,4,5,6-tetrahydro-2H-[1,2']bipyridinyl-5'-yl]-N-methyl-isobutyramide a) (2RS,3RS)-3-Hydroxy-2-hydroxymethyl-piperidine-1-carboxylic Acid Benzyl Ester A mixture of 20.0 g (105 mmol) 3-hydroxy-2-(hydroxymethyl)-pyridine hydrochloride, 4.0 g (18 mmol) platinum(IV) oxide, 4 g charcoal (Norit SX1) and 300 ml acetic acid was stirred at room temperature for 20 h under a hydrogen pressure of 10 bar in an autoclave. The catalyst was filtered off and washed with acetic acid. The filtrate was concentrated in vacuo, redissolved in isopropanol and treated with 29.0 g (210 mmol) potassium carbonate. After stirring for 30 min. the mixture was filtered, and the solvent was evaporated in vacuo to give 15.7 g of crude (2RS,3RS)-2-hydroxymethyl-piperidin-3-ol. A portion of 2.0 g of the crude intermediate was dissolved in 50 ml dichloromethane and treated with 5.2 ml (30 mmol) N,N-diisopropylethylamine and 2.4 ml (16 mmol) benzyl chloroformate at 0° C. After 45 min. water and saturated ammonium chloride solution were added. The mixture was extracted with four portions of dichloromethane. The combined organic layers were dried over sodium sulfate and concentrated in vacuo. Flash chromatography gave 0.82 g (23% based on 3-hydroxy-2-(hydroxymethyl)-pyridine hydrochloride) of the title compound as an off-white oil.

MS m/e (%): 266 (M+H⁺, 92)

b) (2RS,3RS)-2-(3,5-Bis-trifluoromethyl-phenyl)-N-[4'-(2-chloro-phenyl)-3-hydroxy-2-hydroxymethyl-3,4,5,6-tetrahydro-2H-[1,2']bipyridinyl-5'-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c) and (2RS,3RS)-3-hydroxy-2-hydroxymethyl-piperidine-1-carboxylic acid benzyl ester instead of (R)-(4-benzyl-morpholin-3-yl)-methanol in step a).

MS m/e (%): 630 (M+H⁺, 100)

EXAMPLE 196

2-(3,5-Bis-trifluoromethyl-phenyl)-N-{4-(4-fluoro-2-methyl-phenyl)-6-[(2-hydroxy-1-hydroxymethyl-ethyl)-methyl-amino]-pyridin-3-yl}-N-methyl-isobutyramide a) [2-(tert-Butyl-dimethyl-silanyloxy)-1-(tert-butyl-dimethyl-silanyloxymethyl)-ethyl]-methyl-amine To 26 ml (0.21 mmol) of a 8 M solution of methylamine in ethanol were added dropwise at 0° C. 31 ml (0.11 mmol) titanium(IV) isopropoxide. The mixture was allowed to warm to room temperature over a period of 15 min. A solution of 17 g (0.52 mmol) 1,3-bis-(tert-butyl-dimethyl-silanyloxy)-propan-2-one in 10 ml ethanol was added. The reaction mixture was stirred at room temperature over night, followed by addition of 6.6 g (0.11 mmol) sodium cyanoborohydride. After stirring for 24 h the reaction was quenched by the addition of silica gel. The mixture was concentrated in vacuo, and the residue was transferred to a silica gel chromatography column. Flash chromatography and Kugelrohr distillation (120° C./2 mbar) gave 5.2 g (30%) of the title compound as a light yellow viscous oil.

MS m/e (%): 334 (M+H$^+$, 100)

b) 2-(3,5-Bis-trifluoromethyl-phenyl)-N-{4-(4-fluoro-2-methyl-phenyl)-6-F (2-hydroxy-1-hydroxymethyl-ethyl)-methyl-amino 1-pyridin-3-yl}-N-methyl-isobutyramide The title compound was obtained as a light yellow solid in comparable yield after flash chromatography according to the procedure described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using [2-(tert-butyl-dimethyl-silanyloxy)-1-(tert-butyl-dimethyl-silanyloxymethyl)-ethyl]-methyl-amine instead of (S)-3-(tert-butyl-dimethyl-silanyloxymethyl)-morpholine in step c).

MS m/e (%): 602 (M+H$^+$, 100)

EXAMPLE 197

(2R,5S)—N-[6-(2,5-Bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide and

EXAMPLE 198

(2S,5S)—N-[6-(2,5-Bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide A mixture of 0.30 g (0.56 mmol) 2-(3,5-bis-trifluoromethyl-phenyl)-N-[6-chloro-4-(4-fluoro-2-methyl-phenyl)-pyridin-3-yl]-N-methyl-isobutyramide, 0.11 g (0.68 mmol) (2S,5S)-(−)-2,5-bis(methoxymethyl)pyrrolidine, 5 mg (0.01 mmol) cetyltrimethylammonium bromide, 0.014 g (0.027 mmol) bis(tri-t-butylphosphine)palladium(0), 0.07 ml NaOH 50% and 2 ml toluene was degassed by two freeze-thaw cycles. The reaction mixture was heated under argon at 90° C. over night. After cooling to room temperature the mixture was diluted with water and extracted with three portions of tert-butyl methyl ether. The combined organic layers were dried over sodium sulphate and concentrated in vacuo. Flash column chromatography gave 0.09 g of the crude coupling product. This material was dissolved in 2 ml dichloromethane and treated with 1.1 ml (1.1 mmol) of a 1 M solution of boron tribromide in dichloromethane at 0° C. After 15 min. the reaction was quenched by the addition of water, followed by extraction with three portions of dichloromethane. The combined organic layers were dried over sodium sulphate and concentrated in vacuo. Flash column chromatography gave 7 mg (2%) of (2R,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide as a light brown solid and 6 mg (2%) of (2S,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide as a light brown solid.

(2R,5S)—N-[6-(2,5-Bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide MS m/e (%): 628 (M+H$^+$, 100)

(2S,5S)—N-[6-(2,5-Bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide MS m/e (%): 628 (M+H$^+$, 100)

EXAMPLE 199

(2R,5R)—N-[6-(2,5-Bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide The title compound was obtained as a light brown solid in comparable yield after flash chromatography according to the procedure described above for the preparation of (2S,5S)—N-[6-(2,5-bis-hydroxymethyl-pyrrolidin-1-yl)-4-(4-fluoro-2-methyl-phenyl)-pyridin-3-yl]-2-(3,5-bis-trifluoromethyl-phenyl)-N-methyl-isobutyramide using (2R,5R)-(+)-2,5-bis(methoxymethyl)pyrrolidine instead of (2S,5S)-(−)-2,5-bis(methoxymethyl)pyrrolidine.

MS m/e (%): 628 (M+H$^+$, 100)

EXAMPLE 200

(2S,4R)-2-(3,5-Bis-trifluoromethyl-phenyl)-N-[6-(4-hydroxy-2-hydroxymethyl-pyrrolidin-1-yl)-4-p-tolyl-pyridin-3-yl]-N-methyl-isobutyramide a) (2S,4R)-[6-(4-Hydroxy-2-hydroxymethyl-pyrrolidin-1-yl)-4-iodo-pyridin-3-yl]-methyl-carbamic Acid tert-butyl Ester A mixture of 26.5 g (71.8 mmol) (6-chloro-4-iodo-pyridin-3-yl)-methyl-carbamic acid tert-butyl ester and 25.4 g (144 mmol) (2S,4R)-2-(hydroxymethyl)-4-hydroxypyrrolidine in 260 ml dimethyl sulfoxide was stirred at 130° C. for 32 h. The reaction mixture was concentrated in vacuo, treated with 200 ml 2 N sodium carbonate solution and extracted with three 200-ml portions of ethyl acetate. The organic layers were washed with 200 ml 2 N sodium carbonate solution and 200 ml brine and dried over sodium sulfate. Flash chromatography gave 15.5 g (48%) of the title compound as a white foam.

MS m/e (%): 450 (M+H$^+$, 100)

b) (2S,4R)-2-(3,5-Bis-trifluoromethyl-phenyl)-N-[6-(4-hydroxy-2-hydroxymethyl-pyrrolidin-1-yl)-4-iodo-pyridin-3-yl]-N-methyl-isobutyramide To a solution of 8.94 g (19.9 mmol) (2S,4R)-[6-(4-hydroxy-2-hydroxymethyl-pyrrolidin-1-yl)-4-iodo-pyridin-3-yl]-methyl-carbamic acid tert-butyl ester in 85 ml dichloromethane were added 50 ml of a 2 M solution of hydrogen chloride in diethylether at 0° C. The reaction mixture was stirred at room temperature for 22 h and concentrated in vacuo. The residue was re-dissolved in 85 ml dichloromethane and treated with 17 ml (99.4 mmol) N-ethyldiisopropylamine. At 0° C. 19.0 g (59.7 mmol) 2-(3,5-bis-trifluoromethyl-phenyl)-2-methyl-propionyl chloride were added dropwise. The reaction mixture was stirred at room temperature for 4 h and concentrated in vacuo. After addition of 250 ml methanol and 70 ml 3 N potassium hydroxide solution the mixture was stirred at room temperature for 2 h. The mixture was concentrated to remove methanol and extracted with four 750 ml-portions of dichloromethane. The combined organic layers were washed with 500 ml 1 N sodium hydroxide solution and 500 ml brine, dried over sodium sulfate and evaporated. Flash-chromatography gave 11 g (87%) of the title compound as a light yellow foam.

MS m/e (%): 632 (M+H$^+$, 100)

c) (2S,4R)-2-(3,5-Bis-trifluoromethyl-phenyl)-N-[6-(4-hydroxy-2-hydroxymethyl-pyrrolidin-1-yl)-4-p-tolyl-pyridin-3-yl]-N-methyl-isobutyramide A mixture of 150 mg (0.238 mmol) (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide, 38.7 mg (0.284 mmol) 4-tolylboronic acid, 0.75 ml 2 N sodium carbonate solution, 5.3 mg (0.024 mmol) palladium acetate and 12 mg (0.048 mmol) triphenylphosphine in 1.5 ml 1,2-dimethoxyethane was stirred at 80° C. for 2 h. The reaction mixture was treated with 10 ml 2 N sodium carbonate solution and extracted with two 15-ml portions of ethyl acetate. The combined organic layers were dried over sodium sulfate and evaporated. Flash chromatography gave 112 mg (79%) of the title compound as a yellow foam.

MS m/e (%): 596 (M+H$^+$, 100)

EXAMPLE 201

(2S,4R)-2-(3,5-Bis-trifluoromethyl-phenyl)-N-[6-(4-hydroxy-2-hydroxymethyl-pyrrolidin-1-yl)-4-phenyl-pyridin-3-yl]-N-methyl-isobutyramide The title compound was obtained as a white foam in 72% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using phenylboronic acid instead of 4-tolylboronic acid in step c).

MS m/e (%): 596 (M+H$^+$, 100)

EXAMPLE 202

(2S,4R)-2-(3,5-Bis-trifluoromethyl-phenyl)-N-[4-(4-fluoro-phenyl)-6-(4-hydroxy-2-hydroxymethyl-pyrrolidin-1-yl)-pyridin-3-yl]-N-methyl-isobutyramide The title compound was obtained as a brown foam in 62% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-fluorophenylboronic acid instead of 4-tolylboronic acid in step c).

MS m/e (%): 600 (M+H$^+$, 100)

EXAMPLE 203

(2S,4R)-2-(3,5-Bis-trifluoromethyl-phenyl)-N-[4-(4-chloro-phenyl)-6-(4-hydroxy-2-hydroxymethyl-pyrrolidin-1-yl)-pyridin-3-yl]-N-methyl-isobutyramide The title compound was obtained as a white foam in 41% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-chlorophenylboronic acid instead of 4-tolylboronic acid in step c).

MS m/e (%): 616 (M+H$^+$, 100)

EXAMPLE 204

(2S,4R)-2-(3,5-Bis-trifluoromethyl-phenyl)-N-[4-(4-dimethylamino-phenyl)-6-(4-hydroxy-2-hydroxymethyl-pyrrolidin-1-yl)-pyridin-3-yl]-N-methyl-isobutyramide The title compound was obtained as a brown foam in 76% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-dimethylaminophenylboronic acid instead of 4-tolylboronic acid in step c).

MS m/e (%): 625 (M+H$^+$, 73)

EXAMPLE 205

(2S,4R)-2-(3,5-Bis-trifluoromethyl-phenyl)-N-[4-(3-bromo-phenyl)-6-(4-hydroxy-2-hydroxymethyl-pyrrolidin-1-yl)-pyridin-3-yl]-N-methyl-isobutyramide The title compound was obtained as a brown foam in 59% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-bromophenylboronic acid instead of 4-tolylboronic acid in step c).

MS m/e (%): 660 (M+H$^+$, 45)

EXAMPLE 206

(2S,4R)-2-(3,5-Bis-trifluoromethyl-phenyl)-N-[4-(3-chloro-phenyl)-6-(4-hydroxy-2-hydroxymethyl-pyrrolidin-1-yl)-pyridin-3-yl]-N-methyl-isobutyramide The title compound was obtained as a brown foam in 68% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-chlorophenylboronic acid instead of 4-tolylboronic acid in step c).

MS m/e (%): 616 (M+H$^+$, 100)

EXAMPLE 207

(2S,4R)-2-(3,5-Bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide The title compound was obtained as a light brown foam in 97% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-fluorophenylboronic acid instead of 4-tolylboronic acid in step c).

MS m/e (%): 600 (M+H$^+$, 100)

EXAMPLE 208

(2S,4R)-2-(3,5-Bis-trifluoromethyl-phenyl)-N-[4-(3,5-difluoro-phenyl)-6-(4-hydroxy-2-hydroxymethyl-pyrrolidin-1-yl)-pyridin-3-yl]-N-methyl-isobutyramide The title compound was obtained as a white foam in 74% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3,5-difluorophenylboronic acid instead of 4-tolylboronic acid in step c).

MS m/e (%): 618 (M+H$^+$, 100)

EXAMPLE 209

(2S,4R)-2-(3,5-Bis-trifluoromethyl-phenyl)-N-[4-(3,4-difluoro-phenyl)-6-(4-hydroxy-2-hydroxymethyl-pyrrolidin-1-yl)-pyridin-3-yl]-N-methyl-isobutyramide The title compound was obtained as a solid in 85% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3,4-difluorophenylboronic acid instead of 4-tolylboronic acid in step c).

MS m/e (%): 618 (M+H$^+$, 100)

EXAMPLE 210

(2S,4R)-2-(3,5-Bis-trifluoromethyl-phenyl)-N-[4-(3-fluoro-4-methyl-phenyl)-6-(4-hydroxy-2-hydroxymethyl-pyrrolidin-1-yl)-pyridin-3-yl]-N-methyl-isobutyramide The title compound was obtained as a yellow foam in 60% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-fluoro-4-methylphenylboronic acid instead of 4-tolylboronic acid in step c).

MS m/e (%): 614 (M+H$^+$, 100)

EXAMPLE 211

(2S,4R)-2-(3,5-Bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide The title compound was obtained as a brown foam in 60% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-fluoro-3-methylphenylboronic acid instead of 4-tolylboronic acid in step c).

MS m/e (%): 614 (M+H$^+$, 100)

EXAMPLE 212

(2S,4R)-2-(3,5-Bis-trifluoromethyl-phenyl)-N-[4-(3-chloro-4-fluoro-phenyl)-6-(4-hydroxy-2-hydroxymethyl-pyrrolidin-1-yl)-pyridin-3-yl]-N-methyl-isobutyramide The title compound was obtained as a light brown foam in 97% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-chloro-4-fluorophenylboronic acid instead of 4-tolylboronic acid in step c).

MS m/e (%): 634 (M+H$^+$, 100)

EXAMPLE 213

(2S,4R)—N-[4-(2-Amino-phenyl)-6-(4-hydroxy-2-hydroxymethyl-pyrrolidin-1-yl)-pyridin-3-yl]-2-(3,5-bis-trifluoromethyl-phenyl)-N-methyl-isobutyramide The title compound was obtained as a brown foam in 82% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-(4,4,5,5-tetramethyl-1,3,2-dioxaborolan-2-yl)aniline instead of 4-tolylboronic acid in step c).

MS m/e (%): 597 (M+H$^+$, 100)

EXAMPLE 214

(2S,4R)-2-(3,5-Bis-trifluoromethyl-phenyl)-N-[6-(4-hydroxy-2-hydroxymethyl-pyrrolidin-1-yl)-4-(2-methoxy-phenyl)-pyridin-3-yl]-N-methyl-isobutyramide The title compound was obtained as a brown foam in 88% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-methoxyphenylboronic acid instead of 4-tolylboronic acid in step c).

MS m/e (%): 612 (M+H$^+$, 100)

EXAMPLE 215

(2S,4R)-2-(3,5-Bis-trifluoromethyl-phenyl)-N-[6-(4-hydroxy-2-hydroxymethyl-pyrrolidin-1-yl)-4-(2-hydroxy-phenyl)-pyridin-3-yl]-N-methyl-isobutyramide The title compound was obtained as a brown foam in 61% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-(4,4,5,5-tetramethyl-1,3,2-dioxaborolan-2-yl)phenol instead of 4-tolylboronic acid in step c).

MS m/e (%): 598 (M+H$^+$, 100)

EXAMPLE 216

(2S,4R)-2-(3,5-Bis-trifluoromethyl-phenyl)-N-[6-(4-hydroxy-2-hydroxymethyl-pyrrolidin-1-yl)-4-o-tolyl-pyridin-3-yl]-N-methyl-isobutyramide The title compound was obtained as a brown foam in 79% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-tolylboronic acid instead of 4-tolylboronic acid in step c).
MS m/e (%): 596 (M+H$^+$, 100)

EXAMPLE 217

(2S,4R)-2-(3,5-Bis-trifluoromethyl-phenyl)-N-[6-(4-hydroxy-2-hydroxymethyl-pyrrolidin-1-yl)-4-(2-methylsulfanyl-phenyl)-pyridin-3-yl]-N-methyl-isobutyramide The title compound was obtained as a brown foam in 86% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using (2-methylthio)phenylboronic acid instead of 4-tolylboronic acid in step c).
MS m/e (%): 628 (M+H$^+$, 100)

EXAMPLE 218

(2S,4R)-2-(3,5-Bis-trifluoromethyl-phenyl)-N-[6-(4-hydroxy-2-hydroxymethyl-pyrrolidin-1-yl)-4-(2-methanesulfonyl-phenyl)-pyridin-3-yl]-N-methyl-isobutyramide To a solution of 150 mg (0.239 mmol) (2S,4R)-2-(3,5-bis-trifluoromethyl-phenyl)-N-[6-(4-hydroxy-2-hydroxymethyl-pyrrolidin-1-yl)-4-(2-methylsulfanyl-phenyl)-pyridin-3-yl]-N-methyl-isobutyramide in 1.5 ml methanol were added 250 mg (0.406 mmol) potassium monopersulfate triple salt. The reaction mixture was stirred at room temperature for 24 h. The reaction mixture was treated with 0.5 ml sodium hydrogen sulfite solution (38%) and stirred for 30 minutes. Addition of 5 ml 2 N sodium carbonate solution was followed by extraction with two 10-ml portions of dichloromethane. The combined organic layers were dried over sodium sulfate and purified by flash chromatography to give 131 mg (83%) of the title compound as a white foam.
MS m/e (%): 660 (M+H$^+$, 100)

EXAMPLE 219

(2S,4R)-2-[5-{[2-(3,5-Bis-trifluoromethyl-phenyl)-2-methyl-propionyl]-methyl-amino}-2-(4-hydroxy-2-hydroxymethyl-pyrrolidin-1-yl)-pyridin-4-yl]-benzamide The title compound was obtained as a light brown foam in 33% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using (2-aminocarbonyl)phenylboronic acid instead of 4-tolylboronic acid in step c).
MS m/e (%): 625 (M+H$^+$, 100)

EXAMPLE 220

(2S,4R)-2-(3,5-Bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide The title compound was obtained as a brown foam in 78% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2,4-difluorophenylboronic acid instead of 4-tolylboronic acid in step c).
MS m/e (%): 618 (M+H$^+$, 100)

EXAMPLE 221

(2S,4R)-2-(3,5-Bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide The title compound was obtained as a light brown foam in 76% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-chloro-4-fluorophenylboronic acid instead of 4-tolylboronic acid in step c).
MS m/e (%): 634 (M+H$^+$, 100)

EXAMPLE 222

(2S,4R)-2-(3,5-Bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide a) 2-(2-Bromo-5-fluoro-phenyl)-1,3 dioxolane To a solution of 2.0 g (9.9 mmol) 2-bromo-5-fluorobenzaldehyde in 20 ml toluene were added 0.722 ml (13.0 mmol) ethane-1,2-diol and 5 mg (0.03 mmol) toluene-4-sulfonic acid monohydrate. The reaction mixture was heated in a rotary evaporator at 60° C. and 200 mbar during 4 h. After evaporation of the solvent and flash chromatography 2.32 g (95%) of the title compound were obtained as a colorless liquid.
MS m/e (%): 246 (M$^+$, 13)

b) 4-Fluoro-2-formylphenylboronic Acid

To a solution of 2.30 g (9.31 mmol) 2-(2-bromo-5-fluoro-phenyl)-[1,3]dioxolane in 15 ml tetrahydrofuran was added dropwise at −70° C. 6.11 ml (9.77 mmol) of a 1.6 M solution of n-butyllithium in hexane. The reaction mixture was stirred at −74° C. for 1 h. After dropwise addition of 2.65 ml (11.2 mmol) triisopropyl borate at −70° C. the reaction mixture was allowed to warm to 15° C. during a period of 2 h. Water (7 ml) was added, and the mixture was acidified to pH 1 by addition of 37% hydrochloric acid solution. After heating at 60° C. for 1 h, the mixture was cooled to room temperature and extracted with three 50-ml portions of diethyl ether. The combined organic layers were washed with 50 ml brine, dried over sodium sulfate and concentrated. Flash chromatography gave 1.2 g (77%) of the title compound as a light yellow liquid.

MS m/e (%): 167 (M$^+$, 1)

c) (2S,4R)-2-(3,5-Bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide The title compound was obtained as a light brown foam in 80% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-fluoro-2-formylphenylboronic acid instead of 4-tolylboronic acid in step c).

MS m/e (%): 628 (M+H$^+$, 100)

EXAMPLE 223

(2S,4R)-2-(3,5-Bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide To a solution of 24 mg (0.637 mmol) sodium borohydride in 1 ml methanol were added 100 mg (0.159 mmol) (2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide at room temperature. After stirring for 1 h the reaction mixture was concentrated in vacuo and partitioned between ethyl acetate and saturated sodium carbonate solution. The layers were separated and the aqueous layer was extracted with ethyl acetate. The combined organic layers were dried over sodium sulfate, concentrated in vacuo and purified by flash chromatography to give 78 mg (78%) of the title compound as a white foam.

MS m/e (%): 630 (M+H$^+$, 100)

EXAMPLE 224

(2S,4R)-2-(3,5-Bis-trifluoromethyl-phenyl)-N-[4-(2-formyl-phenyl)-6-(4-hydroxy-2-hydroxymethyl-pyrrolidin-1-yl)-pyridin-3-yl]-N-methyl-isobutyramide The title compound was obtained as a white foam in 68% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-formylphenylboronic acid instead of 4-tolylboronic acid in step c).

MS m/e (%): 610 (M+H$^+$, 100)

EXAMPLE 225

(2S,4R)-2-(3,5-Bis-trifluoromethyl-phenyl)-N-[6-(4-hydroxy-2-hydroxymethyl-pyrrolidin-1-yl)-4-(2-hydroxymethyl-phenyl)-pyridin-3-yl]-N-methyl-isobutyramide The title compound was obtained as a white foam in 52% yield after flash chromatography according to the procedure described above for the preparation of (2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide using (2S,4R)-2-(3,5-bis-trifluoromethyl-phenyl)-N-[4-(2-formyl-phenyl)-6-(4-hydroxy-2-hydroxymethyl-pyrrolidin-1-yl)-pyridin-3-yl]-N-methyl-isobutyramide instead of (2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide.

MS m/e (%): 612 (M+H$^+$, 100)

EXAMPLE 226

(2S,4R)-2-(3,5-Bis-trifluoromethyl-phenyl)-N-[4-(2,5-dichloro-phenyl)-6-(4-hydroxy-2-hydroxymethyl-pyrrolidin-1-yl)-pyridin-3-yl]-N-methyl-isobutyramide The title compound was obtained as a light brown foam in 60% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2,5-dichlorophenylboronic acid instead of 4-tolylboronic acid in step c).

MS m/e (%): 650 (M+H$^+$, 49)

EXAMPLE 227

(2S,4R)-2-(3,5-Bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide The title compound was obtained as a brown foam in 67% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 5-fluoro-2-methylphenylboronic acid instead of 4-tolylboronic acid in step c).

MS m/e (%): 614 (M+H$^+$, 100)

EXAMPLE 228

(2S,4R)-2-(3,5-Bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide The title compound was obtained as a brown foam in 100% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3-fluoro-2-methylphenylboronic acid instead of 4-tolylboronic acid in step c).

MS m/e (%): 614 (M+H$^+$, 100)

EXAMPLE 229

(2S,4R)-2-(3,5-Bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide The title compound was obtained as a white foam in 20% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2,3-dichlorophenylboronic acid instead of 4-tolylboronic acid in step c).

MS m/e (%): 650 (M+H$^+$, 100)

EXAMPLE 230

(2S,4R)-2-(3,5-Bis-trifluoromethyl-phenyl)-N-[4-(3,5-dimethyl-isoxazol-4-yl)-6-(4-hydroxy-2-hydroxymethyl-pyrrolidin-1-yl)-pyridin-3-yl]-N-methyl-isobutyramide The title compound was obtained as a light brown foam in 80% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 3,5-dimethylisoxazole-4-boronic acid instead of 4-tolylboronic acid in step c).

MS m/e (%): 601 (M+H$^+$, 100)

EXAMPLE 231

(2S,4R)-2-(3,5-Bis-trifluoromethyl-phenyl)-N-[6'-(4-hydroxy-2-hydroxymethyl-pyrrolidin-1-yl)-2,6-dimethoxy-[3,4']bipyridinyl-3'-yl]-N-methyl-isobutyramide The title compound was obtained as a brown foam in 67% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2,6-dimethoxy-3-(4,4,5,5-tetramethyl-1,3,2-dioxaborolan-2-yl)pyridine instead of 4-tolylboronic acid in step c).

MS m/e (%): 643 (M+H$^+$, 100)

EXAMPLE 232

(2S,4R)-2-(3,5-Bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide The title compound was obtained as a light brown solid in 49% yield after flash chromatography according to the procedures described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using (2-chloro-3-pyridyl)boronic acid instead of 4-tolylboronic acid in step c).

MS m/e (%): 617 (M+H$^+$, 100)

EXAMPLE 233

(2S,4R)-2-(3,5-Bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide A mixture of 0.12 g (0.48 mmol) trifluoro-methanesulfonic acid 2-methyl-pyridin-3-yl ester, 0.13 g (0.52 mmol) bis(pinacolato)diboron, 0.14 g (1.4 mmol) potassium acetate and 0.02 g (0.02 mmol) dichloro[1,1'-bis(diphenylphosphino)ferrocene]palladium(II) dichloromethane adduct in 2.5 ml N,N-dimethylformamide was heated at 80° C. over night under argon. After cooling to room temperature 0.10 g (0.16 mmol) (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide and 1.3 ml of a deoxygenated 2 M aqueous solution of sodium carbonate were added. The reaction mixture was heated at 80° C. for 6 h. After cooling to room temperature the mixture was diluted with water and extracted with three portions of tert-butyl methyl ether. The combined organic layers were dried over sodium sulfate and concentrated in vacuo. Flash column chromatography gave 37 mg (39%) of the title compound as an off-white solid.

MS m/e (%): 597 (M+H$^+$, 100)

EXAMPLE 234

(2S,4R)-2-(3,5-Bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide To a solution of 0.500 g (2.09 mmol) 3-chloro-2-iodo-pyridine in 6 ml tetrahydrofuran 1.04 ml (2.09 mmol) of a 2 M solution of isopropylmagnesium chloride in tetrahydrofuran was added dropwise at −40° C. under an atmosphere of argon. After 30 min. 2.3 ml (4.2 mmol) of an anhydrous 1.8 M solution of zinc chloride in tetrahydrofuran was added slowly. The cooling bath was removed after completed addition, and the reaction mixture was stirred at room temperature for 90 min. A portion of 1.6 ml of this solution was added to a solution of 0.15 g (0.24 mmol) (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide and 14 mg (0.012 mmol) tetrakis(triphenylphosphine)palladium(0) in 1 ml tetrahydrofuran. The mixture was heated at 100° C. under microwave irradiation for 30 min. After cooling to room temperature a 0.5 M solution of sodium hydroxide was added, and the mixture was extracted with three portions of dichloromethane. The combined organic layers were dried over sodium sulfate and concentrated in vacuo. Flash column chromatography gave 58 mg (40%) of the title compound as a light yellow solid.

MS m/e (%): 617 (M+H$^+$, 100)

EXAMPLE 235

(2S,4S)-2-(3,5-Bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide a) (2S,4S)-[6-(4-Hydroxy-2-hydroxymethyl-pyrrolidin-1-yl)-4-iodo-pyridin-3-yl]-methyl-carbamic Acid tert-butyl Ester The title compound was obtained as a light yellow foam in 60% yield after flash chromatography according to the procedure described above for the preparation of (2S,4R)-[6-(4-hydroxy-2-hydroxymethyl-pyrrolidin-1-yl)-4-iodo-pyridin-3-yl]-methyl-carbamic acid tert-butyl ester using (2S,4S)-2-(hydroxymethyl)-4-hydroxypyrrolidine instead of (2S,4R)-2-(hydroxymethyl)-4-hydroxypyrrolidine.

MS m/e (%): 450 (M+H$^+$, 100)

b) (2S,4S)-2-(3,5-Bis-trifluoromethyl-phenyl)-N-[6-(4-hydroxy-2-hydroxymethyl-pyrrolidin-1-yl)-4-iodo-pyridin-3-yl]-N-methyl-isobutyramide The title compound was obtained as a light yellow foam in 87% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide using (2S,4S)-[6-(4-hydroxy-2-hydroxymethyl-pyrrolidin-1-yl)-4-iodo-pyridin-3-yl]-methyl-carbamic acid tert-butyl ester instead of (2S,4R)-[6-(4-hydroxy-2-hydroxymethyl-pyrrolidin-1-yl)-4-iodo-pyridin-3-yl]-methyl-carbamic acid tert-butyl ester.

MS m/e (%): 632 (M+H$^+$, 100)

c) (2S,4S)-2-(3,5-Bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide The title compound was obtained as a brown foam in 58% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-chloro-4-fluorophenylboronic acid instead of 4-tolylboronic acid and (2S,4S)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.

MS m/e (%): 634 (M+H$^+$, 100)

EXAMPLE 236

(2S,4S)-2-(3,5-Bis-trifluoromethyl-phenyl)-N-[4-(2,4-dichloro-phenyl)-6-(4-hydroxy-2-hydroxymethyl-pyrrolidin-1-yl)-pyridin-3-yl]-N-methyl-isobutyramide The title compound was obtained as a light yellow foam in 56% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2,4-dichlorophenylboronic acid instead of 2-chloro-4-fluorophenylboronic acid in step c).

MS m/e (%): 650 (M+H$^+$, 100)

EXAMPLE 237

(2S,4S)-2-(3,5-Bis-trifluoromethyl-phenyl)-N-[4-(2,4-difluoro-phenyl)-6-(4-hydroxy-2-hydroxymethyl-pyrrolidin-1-yl)-pyridin-3-yl]-N-methyl-isobutyramide The title compound was obtained as a light yellow foam in 78% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2,4-difluorophenylboronic acid instead of 2-chloro-4-fluorophenylboronic acid in step c).

MS m/e (%): 618 (M+H$^+$, 100)

EXAMPLE 238

(2S,4S)-2-(3,5-Bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained as a brown foam in 84% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 4-fluoro-2-methylphenylboronic acid instead of 2-chloro-4-fluorophenylboronic acid in step c).

MS m/e (%): 614 (M+H$^+$, 100)

EXAMPLE 239

(2S,4S)-2-(3,5-Bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide The title compound was obtained as a light yellow foam in 71% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 4-fluoro-2-formylphenylboronic acid instead of 2-chloro-4-fluorophenylboronic acid in step c).

MS m/e (%): 628 (M+H$^+$, 100)

EXAMPLE 240

(2S,4S)-2-(3,5-Bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide The title compound was obtained as a white foam in 47% yield after flash chromatography according to the procedure described above for the preparation of (2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide using (2S,4S)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide instead of (2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide.

MS m/e (%): 630 (M+H$^+$, 100)

EXAMPLE 241

(2S,4S)-2-(3,5-Bis-trifluoromethyl-phenyl)-N-[6-(4-hydroxy-2-hydroxymethyl-pyrrolidin-1-yl)-4-o-tolyl-pyridin-3-yl]-N-methyl-isobutyramide The title compound was obtained as a light yellow foam in 90% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-tolylboronic acid instead of 2-chloro-4-fluorophenylboronic acid in step c).

MS m/e (%): 596 (M+H$^+$, 100)

EXAMPLE 242

(2S,4S)-2-(3,5-Bis-trifluoromethyl-phenyl)-N-[4-(2-fluoro-phenyl)-6-(4-hydroxy-2-hydroxymethyl-pyrrolidin-1-yl)-pyridin-3-yl]-N-methyl-isobutyramide The title compound was obtained as a light yellow foam in 47% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-fluorophenylboronic acid instead of 2-chloro-4-fluorophenylboronic acid in step c).

MS m/e (%): 600 (M+H$^+$, 100)

EXAMPLE 243

(2S,4S)-2-(3,5-Bis-trifluoromethyl-phenyl)-N-[6-(4-hydroxy-2-hydroxymethyl-pyrrolidin-1-yl)-4-(2-trifluoromethyl-phenyl)-pyridin-3-yl]-N-methyl-isobutyramide The title compound was obtained as a light yellow foam in 79% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-trifluoromethylphenylboronic acid instead of 2-chloro-4-fluorophenylboronic acid in step c).

MS m/e (%): 650 (M+H$^+$, 100)

EXAMPLE 244

(2S,4S)-2-(3,5-Bis-trifluoromethyl-phenyl)-N-[6-(4-hydroxy-2-hydroxymethyl-pyrrolidin-1-yl)-4-(2-methoxy-phenyl)-pyridin-3-yl]-N-methyl-isobutyramide The title compound was obtained as a light yellow foam in 84% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-methoxyphenylboronic acid instead of 2-chloro-4-fluorophenylboronic acid in step c).

MS m/e (%): 612 (M+H$^+$, 100)

EXAMPLE 245

(2S,4S)-2-(3,5-Bis-trifluoromethyl-phenyl)-N-[4-(2-cyano-phenyl)-6-(4-hydroxy-2-hydroxymethyl-pyrrolidin-1-yl)-pyridin-3-yl]-N-methyl-isobutyramide The title compound was obtained as a light yellow foam in 10% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-(4,4,5,5-tetramethyl-1,3,2-dioxaborolan-2-yl)benzonitrile instead of 2-chloro-4-fluorophenylboronic acid in step c).

MS m/e (%): 607 (M+H$^+$, 100)

EXAMPLE 246

(2S,4S)-2-(3,5-Bis-trifluoromethyl-phenyl)-N-[4-(2-bromo-phenyl)-6-(4-hydroxy-2-hydroxymethyl-pyrrolidin-1-yl)-pyridin-3-yl]-N-methyl-isobutyramide The title compound was obtained as a light yellow foam in 68% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2-bromophenylboronic acid instead of 2-chloro-4-fluorophenylboronic acid in step c).

MS m/e (%): 660 (M+H$^+$, 100)

EXAMPLE 247

(2S,4S)-2-(3,5-Bis-trifluoromethyl-phenyl)-N-[6-(4-hydroxy-2-hydroxymethyl-pyrrolidin-1-yl)-4-phenyl-pyridin-3-yl]-N-methyl-isobutyramide The title compound was obtained as a light yellow foam in 80% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using phenylboronic acid instead of 2-chloro-4-fluorophenylboronic acid in step c).

MS m/e (%): 582 (M+H$^+$, 100)

EXAMPLE 248

(2S,4S)-2-(3,5-Bis-trifluoromethyl-phenyl)-N-[4-(4-fluoro-3-methyl-phenyl)-6-(4-hydroxy-2-hydroxymethyl-pyrrolidin-1-yl)-pyridin-3-yl]-N-methyl-isobutyramide The title compound was obtained as a light yellow foam in 92% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 4-fluoro-3-methylphenylboronic acid instead of 2-chloro-4-fluorophenylboronic acid in step c).

MS m/e (%): 614 (M+H$^+$, 100)

EXAMPLE 249

(2S,4S)-2-(3,5-Bis-trifluoromethyl-phenyl)-N-[4-(3-fluoro-2-methyl-phenyl)-6-(4-hydroxy-2-hydroxymethyl-pyrrolidin-1-yl)-pyridin-3-yl]-N-methyl-isobutyramide The title compound was obtained as a light brown foam in 87% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 3-fluoro-2- methylphenylboronic acid instead of 2-chloro-4-fluorophenylboronic acid in step c).
MS m/e (%): 614 (M+H$^+$, 100)

EXAMPLE 250

(2S,4S)-2-(3,5-Bis-trifluoromethyl-phenyl)-N-[4-(5-fluoro-2-methyl-phenyl)-6-(4-hydroxy-2-hydroxymethyl-pyrrolidin-1-yl)-pyridin-3-yl]-N-methyl-isobutyramide The title compound was obtained as a light brown foam in 48% yield after flash chromatography according to the procedure described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 5-fluoro-2-methylphenylboronic acid instead of 2-chloro-4-fluorophenylboronic acid in step c).
MS m/e (%): 614 (M+H$^+$, 100)

EXAMPLE 251

(2S,4S)-2-(3,5-Bis-trifluoromethyl-phenyl)-N-[4-(3-fluoro-phenyl)-6-(4-hydroxy-2-hydroxymethyl-pyrrolidin-1-yl)-pyridin-3-yl]-N-methyl-isobutyramide The title compound was obtained as a light yellow foam in 87% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 3-fluorophenylboronic acid instead of 2-chloro-4-fluorophenylboronic acid in step c).
MS m/e (%): 600 (M+H$^+$, 100)

EXAMPLE 252

(2S,4S)-2-(3,5-Bis-trifluoromethyl-phenyl)-N-[4-(3,4-dichloro-phenyl)-6-(4-hydroxy-2-hydroxymethyl-pyrrolidin-1-yl)-pyridin-3-yl]-N-methyl-isobutyramide The title compound was obtained as a light yellow foam in 64% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 3,4-dichlorophenylboronic acid instead of 2-chloro-4-fluorophenylboronic acid in step c).
MS m/e (%): 650 (M+H$^+$, 100)

EXAMPLE 253

(2S,4S)-2-(3,5-Bis-trifluoromethyl-phenyl)-N-[4-(2,3-dichloro-phenyl)-6-(4-hydroxy-2-hydroxymethyl-pyrrolidin-1-yl)-pyridin-3-yl]-N-methyl-isobutyramide The title compound was obtained as a light yellow foam in 77% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using 2,3-dichlorophenylboronic acid instead of 2-chloro-4-fluorophenylboronic acid in step c).
MS m/e (%): 650 (M+H$^+$, 100)

EXAMPLE 254

(2S,4S)-2-(3,5-Bis-trifluoromethyl-phenyl)-N-[2-chloro-6'-(4-hydroxy-2-hydroxymethyl-pyrrolidin-1-yl)-[3,4']bipyridinyl-3'-yl]-N-methyl-isobutyramide The title compound was obtained as a light brown solid in 48% yield after flash chromatography according to the procedures described above for the preparation of (2S,4S)-2-(3,5-bis-trifluoromethyl-phenyl)-N-[4-(2-chloro-4-fluoro-phenyl)-6-(4-hydroxy-2-hydroxymethyl-pyrrolidin-1-yl)-pyridin-3-yl]-N-methyl-isobutyramide using (2-chloro-3-pyridyl)boronic acid instead of 2-chloro-4-fluorophenylboronic acid in step c).
MS m/e (%): 617 (M+H$^+$, 100)

EXAMPLE 255

(2S,4S)-2-(3,5-Bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide The title compound was obtained as a light brown solid in 48% yield after flash chromatography according to the procedure described above for the preparation of (2S,4R)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide using (2S,4S)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.
MS m/e (%): 597 (M+H$^+$, 100)

EXAMPLE 256

(2S,4S)-2-(3,5-Bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide The title compound was obtained as a light yellow solid in 24% yield after flash chromatography according to the procedure described above for the preparation of (2S,4R)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide using (2S,4S)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.
MS m/e (%): 617 (M+H$^+$, 100)

EXAMPLE 257

(2R,4R)-2-(3,5-Bis-trifluoromethyl-phenyl)-N-[6-(4-hydroxy-2-hydroxymethyl-pyrrolidin-1-yl)-4-o-tolyl-pyridin-3-yl]-N-methyl-isobutyramide a) (2R,4R)-[6-(4-Hydroxy-2-hydroxymethyl-pyrrolidin-1-yl)-4-iodo-pyridin-3-yl]-methyl-carbamic Acid tert-butyl Ester The title compound was obtained as a light brown foam in 28% yield after flash chromatography according to the procedure described above for the preparation of (2S,4R)-[6-(4-hydroxy-2-hydroxymethyl-pyrrolidin-1-yl)-4-iodo-pyridin-3-yl]-methyl-carbamic acid tert-butyl ester using (2R,4R)-2-(hydroxymethyl)-4-hydroxypyrrolidine instead of (2S,4R)-2-(hydroxymethyl)-4-hydroxypyrrolidine.

MS m/e (%): 450 (M+H$^+$, 100)

b) (2R,4R)-2-(3,5-Bis-trifluoromethyl-phenyl)-N-[6-(4-hydroxy-2-hydroxymethyl-pyrrolidin-1-yl)-4-iodo-pyridin-3-yl]-N-methyl-isobutyramide The title compound was obtained as a light brown foam in 82% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide using (2R,4R)-[6-(4-hydroxy-2-hydroxymethyl-pyrrolidin-1-yl)-4-iodo-pyridin-3-yl]-methyl-carbamic acid tert-butyl ester instead of (2S,4R)-[6-(4-hydroxy-2-hydroxymethyl-pyrrolidin-1-yl)-4-iodo-pyridin-3-yl]-methyl-carbamic acid tert-butyl ester.

MS m/e (%): 632 (M+H$^+$, 100)

c) (2R,4R)-2-(3,5-Bis-trifluoromethyl-phenyl)-N-[6-(4-hydroxy-2-hydroxymethyl-pyrrolidin-1-yl)-4-o-tolyl-pyridin-3-yl]-N-methyl-isobutyramide The title compound was obtained as a light yellow foam in 78% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-tolylboronic acid instead of 4-tolylboronic acid and (2R,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.

MS m/e (%): 596 (M+H$^+$, 100)

EXAMPLE 258

(2R,4R)-2-(3,5-Bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained as a light yellow foam in 85% yield after flash chromatography according to the procedures described above for the preparation of (2R,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide using 4-fluoro-2-methylphenylboronic acid instead of 2-tolylboronic acid in step c).

MS m/e (%): 614 (M+H$^+$, 100)

EXAMPLE 259

(2R,4S)-2-(3,5-Bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide a) (2R,4S)-[6-(4-Hydroxy-2-hydroxymethyl-pyrrolidin-1-yl)-4-iodo-pyridin-3-yl]-methyl-carbamic Acid tert-butyl Ester The title compound was obtained as a light brown foam in 14% yield after flash chromatography according to the procedure described above for the preparation of (2S,4R)-[6-(4-hydroxy-2-hydroxymethyl-pyrrolidin-1-yl)-4-iodo-pyridin-3-yl]-methyl-carbamic acid tert-butyl ester using (2R,4S)-2-(hydroxymethyl)-4-hydroxypyrrolidine instead of (2S,4R)-2-(hydroxymethyl)-4-hydroxypyrrolidine.

MS m/e (%): 450 (M+H$^+$, 100)

b) (2R,4S)-2-(3,5-Bis-trifluoromethyl-phenyl)-N-[6-(4-hydroxy-2-hydroxymethyl-pyrrolidin-1-yl)-4-iodo-pyridin-3-yl]-N-methyl-isobutyramide The title compound was obtained as a light yellow foam in 71% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide using (2R,4S)-[6-(4-hydroxy-2-hydroxymethyl-pyrrolidin-1-yl)-4-iodo-pyridin-3-yl]-methyl-carbamic acid tert-butyl ester instead of (2S,4R)-[6-(4-hydroxy-2-hydroxymethyl-pyrrolidin-1-yl)-4-iodo-pyridin-3-yl]-methyl-carbamic acid tert-butyl ester.

MS m/e (%): 632 (M+H$^+$, 100)

c) (2R,4S)-2-(3,5-Bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained as a light yellow foam in 78% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 4-fluoro-2-methylphenylboronic acid instead of 4-tolylboronic acid and (2R,4S)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.

MS m/e (%): 614 (M+H$^+$, 100)

EXAMPLE 260

(2R,4S)-2-(3,5-Bis-trifluoromethyl-phenyl)-N-[6-(4-hydroxy-2-hydroxymethyl-pyrrolidin-1-yl)-4-o-tolyl-pyridin-3-yl]-N-methyl-isobutyramide The title compound was obtained as a light yellow foam in 94% yield after flash chromatography according to the procedures described above for the preparation of (2R,4S)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide using 2-tolylboronic acid instead of 4-fluoro-2-methylphenylboronic acid in step c).

MS m/e (%): 596 (M+H$^+$, 100)

EXAMPLE 261

(2R,3S)-2-(3,5-Bis-trifluoromethyl-phenyl)-N-[6-(3-hydroxy-2-hydroxymethyl-pyrrolidin-1-yl)-4-o-tolyl-pyridin-3-yl]-N-methyl-isobutyramide a) (2R,3S)-[6-(3-Hydroxy-2-hydroxymethyl-pyrrolidin-1-yl)-4-iodo-pyridin-3-yl]-methyl-carbamic Acid tert-butyl Ester The title compound was obtained as a light yellow foam in 29% yield after flash chromatography according to the procedure described above for the preparation of (2S,4R)-[6-(4-hydroxy-2-hydroxymethyl-pyrrolidin-1-yl)-4-iodo-pyridin-3-yl]-methyl-carbamic acid tert-butyl ester using (2R,3S)-2-(hydroxymethyl)-3-hydroxypyrrolidine instead of (2S,4R)-2-(hydroxymethyl)-4-hydroxypyrrolidine.

MS m/e (%): 450 (M+H$^+$, 100)

b) (2R,3S)-2-(3,5-Bis-trifluoromethyl-phenyl)-N-[6-(3-hydroxy-2-hydroxymethyl-pyrrolidin-1-yl)-4-iodo-pyridin-3-yl]-N-methyl-isobutyramide The title compound was obtained as a light yellow foam in 53% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide using (2R,3S)-[6-(3-hydroxy-2-hydroxymethyl-pyrrolidin-1-yl)-4-iodo-pyridin-3-yl]-methyl-carbamic acid tert-butyl ester instead of (2S,4R)-[6-(4-hydroxy-2-hydroxymethyl-pyrrolidin-1-yl)-4-iodo-pyridin-3-yl]-methyl-carbamic acid tert-butyl ester.

MS m/e (%): 632 (M+H$^+$, 100)

c) (2R,3S)-2-(3,5-Bis-trifluoromethyl-phenyl)-N-[6-(3-hydroxy-2-hydroxymethyl-pyrrolidin-1-yl)-4-o-tolyl-pyridin-3-yl]-N-methyl-isobutyramide The title compound was obtained as a brown foam in 85% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-tolylboronic acid instead of 4-tolylboronic acid and (2R,3S)-2-(3,5-bis-trifluoromethyl-phenyl)-N-[6-(3-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.

MS m/e (%): 596 (M+H$^+$, 100)

EXAMPLE 262

(2R,3S)-2-(3,5-Bis-trifluoromethyl-phenyl)-N-[6-(3-hydroxy-2-hydroxymethyl-pyrrolidin-1-yl)-4-(2-trifluoromethyl-phenyl)-pyridin-3-yl]-N-methyl-isobutyramide The title compound was obtained as a light yellow foam in 58% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2-(trifluoromethyl)phenylboronic acid instead of 2-tolylboronic acid in step c).

MS m/e (%): 650 (M+H$^+$, 100)

EXAMPLE 263

(2R,3S)-2-(3,5-Bis-trifluoromethyl-phenyl)-N-[6-(3-hydroxy-2-hydroxymethyl-pyrrolidin-1-yl)-4-(2-methoxy-phenyl)-pyridin-3-yl]-N-methyl-isobutyramide The title compound was obtained as a brown foam in 89% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2-methoxyphenylboronic acid instead of 2-tolylboronic acid in step c).

MS m/e (%): 612 (M+H$^+$, 100)

EXAMPLE 264

(2R,3S)-2-(3,5-Bis-trifluoromethyl-phenyl)-N-[4-(2-fluoro-phenyl)-6-(3-hydroxy-2-hydroxymethyl-pyrrolidin-1-yl)-pyridin-3-yl]-N-methyl-isobutyramide The title compound was obtained as a brown foam in 70% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2-fluorophenylboronic acid instead of 2-tolylboronic acid in step c).

MS m/e (%): 600 (M+H$^+$, 100)

EXAMPLE 265

(2R,3S)-2-(3,5-Bis-trifluoromethyl-phenyl)-N-[6-(3-hydroxy-2-hydroxymethyl-pyrrolidin-1-yl)-4-phenyl-pyridin-3-yl]-N-methyl-isobutyramide The title compound was obtained as a brown foam in 79% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using phenylboronic acid instead of 2-tolylboronic acid in step c).

MS m/e (%): 582 (M+H$^+$, 100)

EXAMPLE 266

(2R,3S)-2-(3,5-Bis-trifluoromethyl-phenyl)-N-[4-(4-fluoro-phenyl)-6-(3-hydroxy-2-hydroxymethyl-pyrrolidin-1-yl)-pyridin-3-yl]-N-methyl-isobutyramide The title compound was obtained as a light yellow foam in 77% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 4-fluorophenylboronic acid instead of 2-tolylboronic acid in step c).

MS m/e (%): 600 (M+H$^+$, 100)

EXAMPLE 267

(2R,3S)-2-(3,5-Bis-trifluoromethyl-phenyl)-N-[6-(3-hydroxy-2-hydroxymethyl-pyrrolidin-1-yl)-4-p-tolyl-pyridin-3-yl]-N-methyl-isobutyramide The title compound was obtained as a light yellow foam in 53% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 4-tolylboronic acid instead of 2-tolylboronic acid in step c).

MS m/e (%): 596 (M+H$^+$, 100)

EXAMPLE 268

(2R,3S)-2-(3,5-Bis-trifluoromethyl-phenyl)-N-[4-(3,
4-dichloro-phenyl)-6-(3-hydroxy-2-hydroxymethyl-
pyrrolidin-1-yl)-pyridin-3-yl]-N-methyl-isobutyra-
mide The title compound was obtained as a light yellow foam in 45% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 3,4-dichlorophenylboronic acid instead of 2-tolylboronic acid in step c).

MS m/e (%): 650 (M+H$^+$, 100)

EXAMPLE 269

(2R,3S)-2-(3,5-Bis-trifluoromethyl-phenyl)-N-[4-(3-
chloro-phenyl)-6-(3-hydroxy-2-hydroxymethyl-pyr-
rolidin-1-yl)-pyridin-3-yl]-N-methyl-isobutyramide The title compound was obtained as a light yellow foam in 79% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 3-chlorophenylboronic acid instead of 2-tolylboronic acid in step c).

MS m/e (%): 616 (M+H$^+$, 100)

EXAMPLE 270

(2R,3S)-2-(3,5-Bis-trifluoromethyl-phenyl)-N-[4-(2,
5-dichloro-phenyl)-6-(3-hydroxy-2-hydroxymethyl-
pyrrolidin-1-yl)-pyridin-3-yl]-N-methyl-isobutyra-
mide The title compound was obtained as a light yellow foam in 50% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2,5 dichlorophenylboronic acid instead of 2-tolylboronic acid in step c).

MS m/e (%): 650 (M+H$^+$, 100)

EXAMPLE 271

(2R,3S)-2-(3,5-Bis-trifluoromethyl-phenyl)-N-[4-(2,
3-dichloro-phenyl)-6-(3-hydroxy-2-hydroxymethyl-
pyrrolidin-1-yl)-pyridin-3-yl]-N-methyl-isobutyra-
mide The title compound was obtained as a light yellow foam in 54% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2,3-dichlorophenylboronic acid instead of 2-tolylboronic acid in step c)

MS m/e (%): 650 (M+H$^+$, 100).

EXAMPLE 272

(2R,3S)-2-(3,5-Bis-trifluoromethyl-phenyl)-N-[4-(2-
chloro-4-fluoro-phenyl)-6-(3-hydroxy-2-hydroxym-
ethyl-pyrrolidin-1-yl)-pyridin-3-yl]-N-methyl-isobu-
tyramide The title compound was obtained as a light yellow foam in 77% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2-chloro-4-fluorobenzeneboronic acid instead of 2-tolylboronic acid in step c).

MS m/e (%): 634 (M+H$^+$, 100)

EXAMPLE 273

(2R,3S)-2-(3,5-Bis-trifluoromethyl-phenyl)-N-[4-(4-
fluoro-2-formyl-phenyl)-6-(3-hydroxy-2-hydroxym-
ethyl-pyrrolidin-1-yl)-pyridin-3-yl]-N-methyl-isobu-
tyramide The title compound was obtained as a light yellow foam in 60% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 4-fluoro-2-formylphenylboronic acid instead of 2-tolylboronic acid in step c).

MS m/e (%): 628 (M+H$^+$, 100)

EXAMPLE 274

(2R,3S)-2-(3,5-Bis-trifluoromethyl-phenyl)-N-[4-(4-
fluoro-2-hydroxymethyl-phenyl)-6-(3-hydroxy-2-
hydroxymethyl-pyrrolidin-1-yl)-pyridin-3-yl]-N-
methyl-isobutyramide The title compound was obtained as a white foam in 48% yield after flash chromatography according to the procedure described above for the preparation of (2S,4R)-2-(3,5-bis-trifluoromethyl-phenyl)-N-[4-(4-fluoro-2-hydroxymethyl-phenyl)-6-(4-hydroxy-2-hydroxymethyl-pyrrolidin-1-yl)-pyridin-3-yl]-N-methyl-isobutyramide using (2R,3S)-2-(3,5-bis-trifluoromethyl-phenyl)-N-[4-(4-fluoro-2-formyl-phenyl)-6-(3-hydroxy-2-hydroxymethyl-pyrrolidin-1-yl)-pyridin-3-yl]-N-methyl-isobutyramide instead of (2S,4R)-2-(3,5-bis-trifluoromethyl-phenyl)-N-[4-(4-fluoro-2-formyl-phenyl)-6-(4-hydroxy-2-hydroxymethyl-pyrrolidin-1-yl)-pyridin-3-yl]-N-methyl-isobutyramide.

MS m/e (%): 630 (M+H$^+$, 100)

EXAMPLE 275

(2R,3S)-2-(3,5-Bis-trifluoromethyl-phenyl)-N-[4-(3-
fluoro-2-methyl-phenyl)-6-(3-hydroxy-2-hydroxym-
ethyl-pyrrolidin-1-yl)-pyridin-3-yl]-N-methyl-isobu-
tyramide The title compound was obtained as a off white foam in 78% yield after flash chromatography according to the procedures described above for the preparation of (2R,3S)-2-(3, 5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 3-fluoro-2-methylphenylboronic acid instead of 2-tolylboronic acid in step c).
MS m/e (%): 614 (M+H+, 100)

EXAMPLE 276

(2R,3S)-2-(3,5-Bis-trifluoromethyl-phenyl)-N-[4-(5-fluoro-2-methyl-phenyl)-6-(3-hydroxy-2-hydroxymethyl-pyrrolidin-1-yl)-pyridin-3-yl]-N-methyl-isobutyramide The title compound was obtained as a light yellow foam in 83% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 5-fluoro-2-methylphenylboronic acid instead of 2-tolylboronic acid in step c).
MS m/e (%): 614 (M+H+, 100)

EXAMPLE 277

(2R,3S)-2-(3,5-Bis-trifluoromethyl-phenyl)-N-[4-(2,5-difluoro-phenyl)-6-(3-hydroxy-2-hydroxymethyl-pyrrolidin-1-yl)-pyridin-3-yl]-N-methyl-isobutyramide The title compound was obtained as a light yellow foam in 52% yield after flash chromatography according to the procedures described above for the preparation of (2R,3S)-2-(3,5-bis-trifluoromethyl-phenyl)-N-[6-(3-hydroxy-2-hydroxymethyl-pyrrolidin-1-yl)-4-o-tolyl-pyridin-3-yl]-N-methyl-isobutyramide using 2,5-difluorophenylboronic acid instead of 2-tolylboronic acid in step c).
MS m/e (%): 618 (M+H+, 100)

EXAMPLE 278

(2R,3S)-2-(3,5-Bis-trifluoromethyl-phenyl)-N-[6'-(3-hydroxy-2-hydroxymethyl-pyrrolidin-1-yl)-2-methyl-[3,4']bipyridinyl-3'-yl]-N-methyl-isobutyramide The title compound was obtained as a light brown solid in 46% yield after flash chromatography according to the procedures described above for the preparation of (2S,4R)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide using (2R,3S)-2-(3,5-bis-trifluoromethyl-phenyl)-N-[6-(3-hydroxy-2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.
MS m/e (%): 597 (M+H+, 100)

EXAMPLE 279

(S)-2-(3,5-Bis-trifluoromethyl-phenyl)-N-[6-(2-hydroxymethyl-pyrrolidin-1-yl)-4-o-tolyl-pyridin-3-yl]-N-methyl-isobutyramide a) (S)-[6-(2-Hydroxymethyl-pyrrolidin-1-yl)-4-iodo-pyridin-3-yl]-methyl-carbamic Acid tert-butyl Ester The title compound was obtained as a light yellow foam in 15% yield after flash chromatography according to the procedure described above for the preparation of (2S,4R)-[6-(4-hydroxy-2-hydroxymethyl-pyrrolidin-1-yl)-4-iodo-pyridin-3-yl]-methyl-carbamic acid tert-butyl ester using L-prolinol instead of (2S,4R)-2-(hydroxymethyl)-4-hydroxypyrrolidine.
MS m/e (%): 434 (M+H+, 100)

b) (S)-2-(3,5-Bis-trifluoromethyl-phenyl)-N-[6-(2-hydroxymethyl-pyrrolidin-1-yl)-4-iodo-pyridin-3-yl]-N-methyl-isobutyramide The title compound was obtained as a white foam in 74% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide using (S)-[6-(2-hydroxymethyl-pyrrolidin-1-yl)-4-iodo-pyridin-3-yl]-methyl-carbamic acid tert-butyl ester instead of (2S,4R)-[6-(4-hydroxy-2-hydroxymethyl-pyrrolidin-1-yl)-4-iodo-pyridin-3-yl]-methyl-carbamic acid tert-butyl ester.
MS m/e (%): 616 (M+H+, 100)

c) (S)-2-(3,5-Bis-trifluoromethyl-phenyl)-N-[6-(2-hydroxymethyl-pyrrolidin-1-yl)-4-o-tolyl-pyridin-3-yl]-N-methyl-isobutyramide The title compound was obtained as a white foam in 43% yield after flash chromatography according to the procedure described above for the preparation of (2S,4R)-2-(3,5-bis-trifluoromethyl-phenyl)-N-[6-(4-hydroxy-2-hydroxymethyl-pyrrolidin-1-yl)-4-p-tolyl-pyridin-3-yl]-N-methyl-isobutyramide using 2-tolylboronic acid instead of 4-tolylboronic acid and (S)-2-(3,5-bis-trifluoromethyl-phenyl)-N-[6-(2-hydroxymethyl-pyrrolidin-1-yl)-4-iodo-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.
MS m/e (%): 580 (M+H+, 100)

EXAMPLE 280

(S)-2-(3,5-Bis-trifluoromethyl-phenyl)-N-[6-(2-hydroxymethyl-pyrrolidin-1-yl)-4-(2-methoxy-phenyl)-pyridin-3-yl]-N-methyl-isobutyramide The title compound was obtained as a yellow foam in 28% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 2-methoxyphenylboronic acid instead of 2-tolylboronic acid in step c).
MS m/e (%): 596 (M+H+, 100)

EXAMPLE 281

(S)-2-(3,5-Bis-trifluoromethyl-phenyl)-N-[4-(2-bromo-phenyl)-6-(2-hydroxymethyl-pyrrolidin-1-yl)-pyridin-3-yl]-N-methyl-isobutyramide The title compound was obtained as a white foam in 23% yield after flash chromatography according to the procedures described above for the preparation of (S)-2-(3,5-bis-trifluoromethyl-phenyl)-N-[6-(2-hydroxymethyl-pyrrolidin-1-yl)-

4-o-tolyl-pyridin-3-yl]-N-methyl-isobutyramide using 2-bromophenylboronic acid instead of 2-tolylboronic acid in step c).

MS m/e (%): 644 (M+H$^+$, 100)

EXAMPLE 282

(S)-2-(3,5-Bis-trifluoromethyl-phenyl)-N-[4-(2-fluoro-phenyl)-6-(2-hydroxymethyl-pyrrolidin-1-yl)-pyridin-3-yl]-N-methyl-isobutyramide The title compound was obtained as a yellow foam in 68% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 2-fluorophenylboronic acid instead of 2-tolylboronic acid in step c).

MS m/e (%): 634 (M+H$^+$, 100)

EXAMPLE 283

(S)-2-(3,5-Bis-trifluoromethyl-phenyl)-N-[4-(2,4-dichloro-phenyl)-6-(2-hydroxymethyl-pyrrolidin-1-yl)-pyridin-3-yl]-N-methyl-isobutyramide The title compound was obtained as a white foam in 29% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 2,4-dichlorophenylboronic acid instead of 2-tolylboronic acid in step c).

MS m/e (%): 634 (M+H$^+$, 100)

EXAMPLE 284

(S)-2-(3,5-Bis-trifluoromethyl-phenyl)-N-[4-(2,5-dichloro-phenyl)-6-(2-hydroxymethyl-pyrrolidin-1-yl)-pyridin-3-yl]-N-methyl-isobutyramide The title compound was obtained as a yellow foam in 32% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 2,5-dichlorophenylboronic acid instead of 2-tolylboronic acid in step c).

MS m/e (%): 634 (M+H$^+$, 100)

EXAMPLE 285

(S)-2-(3,5-Bis-trifluoromethyl-phenyl)-N-[4-(2,3-dichloro-phenyl)-6-(2-hydroxymethyl-pyrrolidin-1-yl)-pyridin-3-yl]-N-methyl-isobutyramide The title compound was obtained as a white foam in 18% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 2,3-dichlorophenylboronic acid instead of 2-tolylboronic acid in step c).

MS m/e (%): 634 (M+H$^+$, 100)

EXAMPLE 286

(S)-2-(3,5-Bis-trifluoromethyl-phenyl)-N-[4-(3,4-dichloro-phenyl)-6-(2-hydroxymethyl-pyrrolidin-1-yl)-pyridin-3-yl]-N-methyl-isobutyramide The title compound was obtained as a orange foam in 34% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 3,4-dichlorophenylboronic acid instead of 2-tolylboronic acid in step c).

MS m/e (%): 634 (M+H$^+$, 100)

EXAMPLE 287

(S)-2-(3,5-Bis-trifluoromethyl-phenyl)-N-[4-(4-chloro-phenyl)-6-(2-hydroxymethyl-pyrrolidin-1-yl)-pyridin-3-yl]-N-methyl-isobutyramide The title compound was obtained as a yellow oil in 50% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 4-chlorophenylboronic acid instead of 2-tolylboronic acid in step c).

MS m/e (%): 600 (M+H$^+$, 100)

EXAMPLE 288

(S)-2-(3,5-Bis-trifluoromethyl-phenyl)-N-[4-(4-fluoro-phenyl)-6-(2-hydroxymethyl-pyrrolidin-1-yl)-pyridin-3-yl]-N-methyl-isobutyramide The title compound was obtained as a white foam in 45% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using 4-fluorophenylboronic acid instead of 2-tolylboronic acid in step c).

MS m/e (%): 644 (M+H$^+$, 100)

EXAMPLE 289

(S)-2-(3,5-Bis-trifluoromethyl-phenyl)-N-[6-(2-hydroxymethyl-pyrrolidin-1-yl)-4-phenyl-pyridin-3-yl]-N-methyl-isobutyramide The title compound was obtained as a white foam in 48% yield after flash chromatography according to the procedures described above for the preparation of (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide using phenylboronic acid instead of 2-tolylboronic acid in step c).

MS m/e (%): 566 (M+H$^+$, 100)

EXAMPLE 290

(S)-2-(3,5-Bis-trifluoromethyl-phenyl)-N-[6'-(2-hydroxymethyl-pyrrolidin-1-yl)-2-methyl-[3,4']bipyridinyl-3'-yl]-N-methyl-isobutyramide a) (6'-Chloro-2-methyl-[3,4']bipyridinyl-3'-yl)-methyl-amine

The title compound was obtained as a light yellow solid in 60% yield after flash chromatography according to the procedure described above for the preparation of (2S,4R)-2-(3,5-bis-trifluoromethyl-phenyl)-N-[6'-(4-hydroxy-2-hydroxymethyl-pyrrolidin-1-yl)-2-methyl-[3,4']bipyridinyl-3'-yl]-N-methyl-isobutyramide using (6-chloro-4-iodo-pyridin-3-yl)-methyl-amine instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide.

b) 2-(3,5-Bis-trifluoromethyl-phenyl)-N-(6'-chloro-2-methyl-[3,4]bipyridinyl-3'-yl)-N-methyl-isobutyramide To a solution of 2.77 g (11.9 mmol) (6'-chloro-2-methyl-[3,4']bipyridinyl-3'-yl)-methyl-amine in 120 ml tetrahydrofuran 7.8 ml (12 mmol) of a 1.6 M solution of n-butyllithium in hexanes was added dropwise at −78° C. After 30 min. 4.2 g (13 mmol) 2-(3,5-bis-trifluoromethyl-phenyl)-2-methyl-propionyl chloride were added. The reaction mixture was stirred at −78° C. for 5 min. and allowed to warm to room temperature during a period of 1 h. Dilution with 2 M aqueous sodium carbonate solution was followed by extraction with three portions of tert-butyl methyl ether. The combined organic layers were washed with 2 M aqueous sodium carbonate solution and brine, dried over sodium sulfate and concentrated in vacuo. Flash column chromatography gave 4.8 g (78%) of the title compound as an off-white solid.

MS m/e (%): 516 (M+H$^+$, 100)

c) (S)-2-(3,5-Bis-trifluoromethyl-phenyl)-N-[6'-(2-hydroxymethyl-pyrrolidin-1-yl)-2-methyl-[3,4']bipyridinyl-3'-yl]-N-methyl-isobutyramide The title compound was obtained as a white solid in 65% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-(6'-chloro-2-methyl-[3,4']bipyridinyl-3'-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 581 (M+H$^+$, 100)

EXAMPLE 291

N-{6'-[Bis-(2-hydroxy-ethyl)-amino]-2-methyl-[3,4']bipyridinyl-3'-yl}-2-(3,5-bis-trifluoromethyl-phenyl)-N-methyl-isobutyramide The title compound was obtained as an off-white solid in 43% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine and 2-(3,5-bis-trifluoromethyl-phenyl)-N-(6'-chloro-2-methyl-[3,4']bipyridinyl-3'-yl)-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 585 (M+H$^+$, 100)

EXAMPLE 292

(S)-2-(3,5-Bis-trifluoromethyl-phenyl)-N-[6'-(2-hydroxymethyl-pyrrolidin-1-yl)-4-methyl-[3,4']bipyridinyl-3'-yl]-N-methyl-isobutyramide a) (6'-Chloro-4-methyl-[3,4']bipyridinyl-3'-yl)-methyl-amine

The title compound was obtained as a light yellow solid in comparable yield after flash chromatography according to the procedure described above for the preparation of (2S,4R)-2-(3,5-bis-trifluoromethyl-phenyl)-N-[3-chloro-6'-(4-hydroxy-2-hydroxymethyl-pyrrolidin-1-yl)-[2,4']bipyridinyl-3'-yl]-N-methyl-isobutyramide using (6-chloro-4-iodo-pyridin-3-yl)-methyl-carbamic acid tert-butyl ester instead of (2S,4R)-2-(3,5-bis-trifluoromethyl-phenyl)-N-[6-(4-hydroxy-2-hydroxymethyl-pyrrolidin-1-yl)-4-iodo-pyridin-3-yl]-N-methyl-isobutyramide and 3-bromo-4-methylpyridine instead of 3-chloro-2-iodo-pyridine.

b) 2-(3,5-Bis-trifluoromethyl-phenyl)-N-(6'-chloro-4-methyl-[3,4]bipyridinyl-3'-yl)-N-methyl-isobutyramide The title compound was obtained as a light yellow solid in 65% yield after flash chromatography according to the procedure described above for the preparation of 2-(3,5-bis-trifluoromethyl-phenyl)-N-(6'-chloro-2-methyl-[3,4']bipyridinyl-3'-yl)-N-methyl-isobutyramide using (6'-chloro-4-methyl-[3,4']bipyridinyl-3'-yl)-methyl-amine instead of (6'-chloro-2-methyl-[3,4']bipyridinyl-3'-yl)-methyl-amine.

MS m/e (%): 585 (M+H$^+$, 100)

c) (S)-2-(3,5-Bis-trifluoromethyl-phenyl)-N-[6'-(2-hydroxymethyl-pyrrolidin-1-yl)-4-methyl-[3,4']bipyridinyl-3'-yl]-N-methyl-isobutyramide The title compound was obtained as a light yellow solid in 39% yield after flash chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using 2-(3,5-bis-trifluoromethyl-phenyl)-N-(6'-chloro-4-methyl-[3,4']bipyridinyl-3'-yl)-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide.

MS m/e (%): 581 (M+H$^+$, 100)

EXAMPLE 293

N-{6'-[Bis-(2-hydroxy-ethyl)-amino]-4-methyl-[3,4']bipyridinyl-3'-yl}-2-(3,5-bis-trifluoromethyl-phenyl)-N-methyl-isobutyramide The title compound was obtained as an off-white solid in 34% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using diethanolamine instead of ethanolamine and 2-(3,5-bis-trifluoromethyl-phenyl)-N-(6'-chloro-4-methyl-[3,4']bipyridinyl-3'-yl)-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 585 (M+H$^+$, 100)

EXAMPLE 294

2-(3,5-Bis-trifluoromethyl-phenyl)-N-{6'-[(2-hydroxy-ethyl)-methyl-amino]-4-methyl-[3,4']bipyridinyl-3'-yl}-N-methyl-isobutyramide The title compound was obtained as a light yellow solid in 66% yield after flash chromatography according to the procedure described above for the preparation of 2-(3,5-bis-trifluoromethyl-phenyl)-N-[4-(2-chloro-phenyl)-6-(2-hydroxy-ethylamino)-pyridin-3-yl]-N-methyl-isobutyramide using 2-(methylamino) ethanol instead of ethanolamine and 2-(3,5-bis-trifluoromethyl-phenyl)-N-(6'-chloro-4-methyl-[3,4']bipyridinyl-3'-yl)-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

MS m/e (%): 555 (M+H$^+$, 100)

EXAMPLE 295

(S)-2-(3,5-Bis-trifluoromethyl-phenyl)-N-[6-(2-hydroxymethyl-4-oxo-pyrrolidin-1-yl)-4-o-tolyl-pyridin-3-yl]-N-methyl-isobutyramide a) (2S,4R)-Acetic Acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl Ester To a solution of 1.5 g (2.4 mmol) (2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide and 0.4 ml (5 mmol) pyridine in 24 ml dichloromethane were added dropwise at room temperature 0.22 ml (2.4 mmol) acetic anhydride. After stirring at room temperature for 20 h the reaction mixture was diluted with a 0.1 M aqueous hydrochloric acid solution and extracted with 3 portions of dichloromethane. The combined organic extracts were washed with a 2 M aqueous sodium carbonate solution, dried over sodium sulfate and concentrated in vacuo. Flash column chromatography gave 1.1 g (71%) of the title compound as an off-white solid.

MS m/e (%): 638 (M+H$^+$, 100)

b) (S)-Acetic Acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl Ester To a solution of 0.08 ml (0.9 mmol) oxalyl chloride in 2 ml dichloromethane were added dropwise at −78° C. 0.13 ml (1.9 mmol) dimethyl sulfoxide and after a period of 3 min. a solution of 0.50 g (0.78 mmol) (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester in 2 ml dichloromethane. After stirring at −78° C. for 30 min. 0.7 ml (4 mmol) N,N-diisopropylethylamine were added. The reaction mixture was allowed to warm to room temperature during 1 h, diluted with tert-butyl methyl ether and washed with an aqueous ammonium chloride solution. The aqueous layer was extracted with two portions of tert-butyl methyl ether. The combined organic extracts were dried over sodium sulfate and concentrated in vacuo. Flash column chromatography gave 0.47 g (94%) of the title compound as a white solid.

MS m/e (%): 636 (M+H$^+$, 100)

c) (S)-2-(3,5-Bis-trifluoromethyl-phenyl)-N-[6-(2-hydroxymethyl-4-oxo-pyrrolidin-1-yl)-4-o-tolyl-pyridin-3-yl]-N-methyl-isobutyramide A solution of 60 mg (0.094 mmol) (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester and a catalytic amount of sodium methylate in 2 ml methanol was stirred at room temperature for 30 min. The reaction mixture was diluted with water and brine and extracted with three portions of dichloromethane. The combined organic extracts were dried over sodium sulfate and concentrated in vacuo. Flash column chromatography gave 13 mg (23%) of the title compound as a light brown solid.

MS m/e (%): 594 (M+H$^+$, 100)

EXAMPLE 296

(S)-2-(3,5-Bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide a) (2S,4R)-Acetic acid 1-[5-{[2-(3,5-bis-trifluoromethyl-phenyl)-2-methyl-propionyl]-methyl-amino}-4-(4-fluoro-2-methyl-phenyl)-pyridin-2-yl]-4-hydroxy-pyrrolidin-2-ylmethyl Ester The title compound was obtained as a white solid in 52% yield after flash chromatography according to the procedure described above for the preparation of (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester using (2S,4R)-2-(3,5-bis-trifluoromethyl-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide.

MS m/e (%): 656 (M+H$^+$, 100)

b) (S)-Acetic Acid 1-[5-{[2-(3,5-bis-trifluoromethyl-phenyl)-2-methyl-propionyl]-methyl-amino}-4-(4-fluoro-2-methyl-phenyl)-pyridin-2-yl]-4-oxo-pyrrolidin-2-ylmethyl Ester The title compound was obtained as a white solid in 77% yield after flash chromatography according to the procedure described above for the preparation of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester using (2S,4R)-acetic acid 1-[5-{[2-(3,5-bis-trifluoromethyl-phenyl)-2-methyl-propionyl]-methyl-amino}-4-(4-fluoro-2-methyl-phenyl)-pyridin-2-yl]-4-hydroxy-pyrrolidin-2-ylmethyl ester instead of (2S,4R)-acetic acid 1-(5-{[2-(3,5-bis-trifluoromethyl-phenyl)-2- methyl-propionyl]-methyl-amino}-4-o-tolyl-pyridin-2-yl)-4-hydroxy-pyrrolidin-2-ylmethyl ester.

MS m/e (%): 654 (M+H$^+$, 100)

c) (S)-2-(3,5-Bis-trifluoromethyl-phenyl)-N-[4-(4-fluoro-2-methyl-phenyl)-6-(2-hydroxymethyl-4-oxo-pyrrolidin-1-yl)-pyridin-3-yl]-N-methyl-isobutyramide The title compound was obtained as a light yellow solid in 37% yield after flash chromatography according to the procedure described above for the preparation of (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide using (S)-acetic acid 1-[5-{[2-(3,5-bis-trifluoromethyl-phenyl)-2-methyl-propionyl]-methyl-amino}-4-(4-fluoro-2-methyl-phenyl)-pyridin-2-yl]-4-oxo-pyrrolidin-2-ylmethyl ester instead of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester.

MS m/e (%): 612 (M+H$^+$, 100)

EXAMPLE 297

(2S,4S)-2-(3,5-Bis-trifluoromethyl-phenyl)-N-[6-(4-fluoro-2-hydroxymethyl-pyrrolidin-1-yl)-4-o-tolyl-pyridin-3-yl]-N-methyl-isobutyramide a) (2S,4S)-Acetic Acid 1-(5-{[2-(3,5-bis-trifluoromethyl-phenyl)-2-methyl-propionyl]-methyl-amino}-4-o-tolyl-pyridin-2-yl)-4-fluoro-pyrrolidin-2-ylmethyl Ester To a solution of 0.14 g (0.21 mmol) (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester in 2 ml dichloromethane were added dropwise at 0° C. 0.03 ml (0.2 mmol) (diethylamino)sulfur trifluoride. After 1 h the reaction mixture was diluted with a 0.5 M aqueous sodium hydroxide solution and extracted with four portions of dichloromethane. The combined organic extracts were dried over sodium sulfate and concentrated in vacuo. Flash column chromatography gave 47 mg (35%) of the title compound as a white solid.

MS m/e (%): 640 (M+H$^+$, 100)

b) (2S,4S)-2-(3,5-Bis-trifluoromethyl-phenyl)-N-[6-(4-fluoro-2-hydroxymethyl-pyrrolidin-1-yl)-4-o-tolyl-pyridin-3-yl]-N-methyl-isobutyramide The title compound was obtained as an off-white solid in 91% yield after flash chromatography according to the procedure described above for the preparation of (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide using (2S,4S)-acetic acid 1-(5-{[2-(3,5-bis-trifluoromethyl-phenyl)-2-methyl-propionyl]-methyl-amino}-4-o-tolyl-pyridin-2-yl)-4-fluoro-pyrrolidin-2-ylmethyl ester instead of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester MS m/e (%): 598 (M+H$^+$, 100) .

EXAMPLE 298

(2S,4S)-2-(3,5-Bis-trifluoromethyl-phenyl)-N-[6-(4-fluoro-2-hydroxymethyl-pyrrolidin-1-yl)-4-(4-fluoro-2-methyl-phenyl)-pyridin-3-yl]-N-methyl-isobutyramide The title compound was obtained as a white solid in comparable yields after flash chromatography according to the procedures described above for the preparation of (2S,4S)-2-(3,5-bis-trifluoromethyl-phenyl)-N-[6-(4-fluoro-2-hydroxymethyl-pyrrolidin-1-yl)-4-o-tolyl-pyridin-3-yl]-N-methyl-isobutyramide using (2S,4R)-acetic acid 1-[5-{[2-(3,5-bis-trifluoromethyl-phenyl)-2-methyl-propionyl]-methyl-amino}-4-(4-fluoro-2-methyl-phenyl)-pyridin-2-yl]-4-hydroxy-pyrrolidin-2-ylmethyl ester instead of (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester in step a).

MS m/e (%): 616 (M+H$^+$, 100)

EXAMPLE 299

(S)-2-(3,5-Bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide a) (S)-Acetic Acid 1-(5-{[2-(3,5-bis-trifluoromethyl-phenyl)-2-methyl-propionyl]-methyl-amino}-4-o-tolyl-pyridin-2-yl)-4,4-difluoro-pyrrolidin-2-ylmethyl Ester To a solution of 0.20 g (0.31 mmol) (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester in 3 ml dichloromethane were added at room temperature 0.19 ml (1.5 mmol) (diethylamino)sulfur trifluoride. After 36 h the reaction mixture was partitioned between water and tert-butyl methyl ether. The layers were separated and the organic layer was washed with 0.5 M aqueous sodium hydroxide solution. The combined aqueous layers were extracted with three portions of tert-butyl methyl ether. The combined organic extracts were dried over sodium sulfate and concentrated in vacuo. Flash column chromatography gave 93 mg (45%) of the title compound as an off-white solid.

MS m/e (%): 658 (M+H$^+$, 100)

b) (S)-2-(3,5-Bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide The title compound was obtained as a white solid in 83% yield after flash chromatography according to the procedure described above for the preparation of (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide using (S)-acetic acid 1-(5-{[2-(3,5-bis-trifluoromethyl-phenyl)-2-methyl-propionyl]-methyl-amino}-4-o-tolyl-pyridin-2-yl)-4,4-difluoro-pyrrolidin-2-ylmethyl ester instead of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester.

MS m/e (%): 616 (M+H$^+$, 100)

EXAMPLE 300

(S)-2-(3,5-Bis-trifluoromethyl-phenyl)-N-[6-(4,4-difluoro-2-hydroxymethyl-pyrrolidin-1-yl)-4-(4-fluoro-2-methyl-phenyl)-pyridin-3-yl]-N-methyl-isobutyramide The title compound was obtained as a light yellow solid in comparable yields after flash chromatography according to the procedures described above for the preparation of (S)-2-(3,5-bis-trifluoromethyl-phenyl)-N-[6-(4,4-difluoro-2-hydroxymethyl-pyrrolidin-1-yl)-4-o-tolyl-pyridin-3-yl]-N-methyl-isobutyramide using (S)-acetic acid 1-(5-{[2-(3,5-bis-trifluoromethyl-phenyl)-2-methyl-propionyl]-methyl-amino}-4-(4-fluoro-2-methyl-phenyl)-pyridin-2-yl)-4-oxo-pyrrolidin-2-ylmethyl ester instead of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester in step a).

MS m/e (%): 634 (M+H$^+$, 100)

EXAMPLE 301

(2S,4R)-2-(3,5-Bis-trifluoromethyl-phenyl)-N-[6-(4-fluoro-2-hydroxymethyl-pyrrolidin-1-yl)-4-o-tolyl-pyridin-3-yl]-N-methyl-isobutyramide a) (2S,4S)-Acetic Acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl Ester The title compound was obtained as a white solid in 60% yield after flash chromatography according to the procedure described above for the preparation of (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester using (2S,4S)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide instead of (2S,4R)-2-(3,5-bis-trifluoromethyl-phenyl)-N-[6-(4-hydroxy-2-hydroxymethyl-pyrrolidin-1-yl)-4-o-tolyl-pyridin-3-yl]-N-methyl-isobutyramide.

MS m/e (%): 638 (M+H$^+$, 100)

b) (2S,4R)-Acetic Acid 1-(5-{[2-(3,5-bis-trifluoromethyl-phenyl)-2-methyl-propionyl]-methyl-amino}-4-o-tolyl-pyridin-2-yl)-4-fluoro-pyrrolidin-2-ylmethyl Ester The title compound was obtained as an off-white solid in 69% yield after flash chromatography according to the procedure described above for the preparation of (2S,4S)-acetic acid 1-(5-{[2-(3,5-bis-trifluoromethyl-phenyl)-2-methyl-propionyl]-methyl-amino}-4-o-tolyl-pyridin-2-yl)-4-fluoro-pyrrolidin-2-ylmethyl ester using (2S,4S)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester instead of (2S,4R)-acetic acid 1-(5-{[2-(3,5-bis-trifluoromethyl-phenyl)-2-methyl-propionyl]-methyl-amino}-4-o-tolyl-pyridin-2-yl)-4-hydroxy-pyrrolidin-2-ylmethyl ester.

MS m/e (%): 640 (M+H$^+$, 100)

c) (2S,4R)-2-(3,5-Bis-trifluoromethyl-phenyl)-N-[6-(4-fluoro-2-hydroxymethyl-pyrrolidin-1-yl)-4-o-tolyl-pyridin-3-yl]-N-methyl-isobutyramide The title compound was obtained as a white solid in 78% yield after flash chromatography according to the procedure described above for the preparation of (S)-2-(3,5-bis-trifluoromethyl-phenyl)-N-[6-(2-hydroxymethyl-4-oxo-pyrrolidin-1-yl)-4-o-tolyl-pyridin-3-yl]-N-methyl-isobutyramide using (2S,4R)-acetic acid 1-(5-{[2-(3,5-bis-trifluoromethyl-phenyl)-2-methyl-propionyl]-methyl-amino}-4-o-tolyl-pyridin-2-yl)-4-fluoro-pyrrolidin-2-ylmethyl ester instead of (S)-acetic acid 1-(5-{[2-(3,5-bis-trifluoromethyl-phenyl)-2-methyl-propionyl]-methyl-amino}-4-o-tolyl-pyridin-2-yl)-4-oxo-pyrrolidin-2-ylmethyl ester.

MS m/e (%): 598 (M+H$^+$, 100)

EXAMPLE 302

(S)-N-[6-[2-(Acetylamino-methyl)-pyrrolidin-1-yl]-4-(4-fluoro-2-methyl-phenyl)-pyridin-3-yl]-2-(3,5-bis-trifluoromethyl-phenyl)-N-methyl-isobutyramide a) (S)-2-(3,5-Bis-trifluoromethyl-phenyl)-N-[6-[2-(1,3-dioxo-1,3-dihydro-isoindol-2-ylmethyl)-pyrrolidin-1-yl]-4-(4-fluoro-2-methyl-phenyl)-pyridin-3-yl]-N-methyl-isobutyramide To a solution of 0.20 g (0.33 mmol) (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide and 54 mg (0.37 mmol) phthalimide in 3 ml tetrahydrofuran were added 71 mg (0.37 mmol) diethyl azodicarboxylate (90%) and 97 mg (0.37 mmol) triphenylphosphine at 0° C. After stirring for 90 min. the reaction mixture was allowed to warm to room temperature over night. The mixture was diluted with a 0.1 M aqueous sodium hydroxide solution and extracted with three portions of tert-butyl methyl ether. The combined organic extracts were dried over sodium sulphate and concentrated. Flash column chromatography gave 70 mg (29%) of the title compound as a light yellow solid.

MS m/e (%): 727 (M+H$^+$, 100)

b) (S)-N-[6-[2-(Acetylamino-methyl)-pyrrolidin-1-yl]-4-(4-fluoro-2-methyl-phenyl)-pyridin-3-yl]-2-(3,5-bis-trifluoromethyl-phenyl)-N-methyl-isobutyramide A solution of 65 mg (0.089 mmol) (S)-2-(3,5-bis-trifluoromethyl-phenyl)-N-[6-[2-(1,3-dioxo-1,3-dihydro-isoindol-2-ylmethyl)-pyrrolidin-1-yl]-4-(4-fluoro-2-methyl-phenyl)-pyridin-3-yl]-N-methyl-isobutyramide and 7.0 mg (0.14 mmol) hydrazine hydrate in 1 ml ethanol was stirred at room temperature over night. The reaction mixture was diluted with a 1 M aqueous sodium hydroxide solution and extracted with three portions of tert-butyl methyl ether. The combined organic extracts were dried over sodium sulphate and concentrated to give 55 mg of crude (S)-N-[6-(2-aminomethyl-pyrrolidin-1-yl)-4-(4-fluoro-2-methyl-phenyl)-pyridin-3-yl]-2-(3,5-bis-trifluoromethyl-phenyl)-N-methyl-isobutyramide. This material was dissolved in 2 ml dichloromethane, followed by the addition of 0.013 ml (0.092 mmol) triethylamine and 0.009 ml (0.09 mmol) acetic anhydride at 0° C. The cooling bath was removed 5 min. after completed addition, and stirring was continued at room temperature over night. The reaction mixture was diluted with a 0.5 M aqueous sodium hydroxide solution and extracted with three portions of tert-butyl methyl ether. The combined organic extracts were dried over sodium sulphate and concentrated. Flash chromatography gave 44 mg (77%) of the title compound as an off-white solid.

MS m/e (%): 639 (M+H$^+$, 100)

EXAMPLE 303

(S)-Dimethyl-carbamic Acid 1-[5-{[2-(3,5-bis-trifluoromethyl-phenyl)-2-methyl-propionyl]-methyl-amino}-4-(4-fluoro-2-methyl-phenyl)-pyridin-2-yl]-pyrrolidin-2-ylmethyl Ester To a solution of 44 mg (0.33 mmol) 1,1,3,3-tetramethyl-2-thiourea in 1.5 ml N,N-dimethylformamide were added 0.027 ml iodomethane at room temperature. After stirring for 50 min. 0.20 g (0.33 mmol) (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide and a suspension of 45 mg (0.90 mmol) sodium hydride (ca. 50% dispersion in mineral oil) in 0.5 ml n-hexane were added. After stirring at room temperature for 1 h the reaction mixture was diluted with water and extracted with three portions of tert-butyl methyl ether. The combined organic extracts were dried over sodium sulphate and concentrated. Flash column chromatography gave 90 mg (40%) of the title compound as an off-white solid.
MS m/e (%): 669 (M+H$^+$, 100)

EXAMPLE 304

(3R,5S)-2-(3,5-Bis-trifluoromethyl-phenyl)-N-[4'-(4-fluoro-2-methyl-phenyl)-3,5-dihydroxy-3,4,5,6-tetrahydro-2H-[1,2']bipyridinyl-5'-yl]-N-methyl-isobutyramide a) (5R,3S)-1-Benzyl-5-(tert-butyl-dimethyl-silanyloxy)-piperidin-3-ol To a solution of 1.8 g (5.6 mmol) (3R,5R)-1-benzyl-5-(tert-butyl-dimethyl-silanyloxy)-piperidin-3-ol in 50 ml THF were consecutively added 0.75 g (6.2 mmol) benzoic acid, 1.1 g (6.2 mmol) diethyl azodicarboxylate and 1.6 g (6.2 mmol) triphenylphosphine at 0° C. After 6 h the reaction mixture was diluted with tert-butyl methyl ether washed with a 2N aqueous solution of sodium carbonate. The aqueous layer was extracted with 3 portions of tert-butyl methyl ether. The combined organic extracts were washed with a 2N aqueous solution of sodium carbonate and brine and dried over sodium sulfate. Flash chromatography gave 0.80 g (3S,5R)-benzoic acid 1-benzyl-5-(tert-butyl-dimethyl-silanyloxy)-piperidin-3-yl ester as a light brown oil. The ester was dissolved in a mixture of 50 ml dioxane and 18 ml 1N aqueous sodium hydroxide solution. The reaction mixture was heated at 70° C. for 5 h. After cooling to room temperature the mixture was extracted with tert-butyl methyl ether. The organic extract was washed with a 2N aqueous solution of sodium carbonate. The combined aqueous layers were extracted with two portions of tert-butyl methyl ether. The combined organic extracts were washed with brine and dried over sodium sulfate. Flash chromatography gave 0.10 g (17%) of the title compound as a light brown oil.
MS m/e (%): 322 (M+H$^+$, 100)

b) (3R,5S)-2-(3,5-Bis-trifluoromethyl-phenyl)-N-[4'-(4-fluoro-2-methyl-phenyl)-3,5-dihydroxy-3,4,5,6-tetrahydro-2H-[1,2']bipyridinyl-5'-yl]-N-methyl-isobutyramide The title compound was obtained as a light yellow solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (5R,3S)-1-benzyl-5-(tert-butyl-dimethyl-silanyloxy)-piperidin-3-ol instead of (R)-(4-benzyl-morpholin-3-yl)-methanol in step a).
MS m/e (%): 614.7 (M+H$^+$, 100)

EXAMPLE 305

(3S,5S)-2-(3,5-Bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide a) (3R,5R)-3,5-Bis-(tert-butyl-dimethyl-silanyloxy)-piperidine The title compound was obtained as a light brown solid in comparable yields after flash chromatography according to the procedures described above for the preparation of (S)-3-(tert-butyl-dimethyl-silanyloxymethyl)-morpholine (Example 174b)) using (3R,5R)-1-benzyl-piperidine-3,5-diol instead of (R)-(4-benzyl-morpholin-3-yl)-methanol in step a).
MS m/e (%): 346 (M+H$^+$, 100)

b) (3R,5R)-3,5-Bis-(tert-butyl-dimethyl-silanyloxy)-piperidine-1-carboxylic Acid Benzyl Ester To a solution of 0.50 g (1.4 mmol) (3R,5R)-3,5-bis-(tert-butyl-dimethyl-silanyloxy)-piperidine and 0.15 g (1.5 mmol) triethylamine in 30 ml of THF was added dropwise a solution of 0.26 g (1.5 mmol) benzyl chloroformate in 2 ml of THF at 0° C. After completed addition, the mixture was allowed to warm to room temperature during 30 min. Quenching with a saturated aqueous solution of sodium hydrogencarbonate was followed by extraction with three portions of dichloromethane. The combined organic extracts were washed with brine and dried over sodium sulfate. Flash chromatography gave 0.62 g (90%) of the title compound as a colorless oil.
MS m/e (%): 480 (M+H$^+$, 100)

c) (3R,5R)-3-(tert-Butyl-dimethyl-silanyloxy)-5-hydroxy-piperidine-1-carboxylic Acid Benzyl Ester To a solution of 8.7 g (18 mmol) (3R,5R)-3,5-bis-(tert-butyl-dimethyl-silanyloxy)-piperidine-1-carboxylic acid benzyl ester in 200 ml THF were added 18 ml (18 mmol) of a 1M solution of tetrabutyl ammoniumfluoride in THF at 0° C. After completed addition, the mixture was allowed to warm to room temperature over night. Addition of water was followed by extraction with three portions of tert-butyl methyl ether. The combined organic extracts were dried over sodium sulfate. Flash chromatography gave 1.1 g (16%) of the title compound as a pale yellow oil.
MS m/e (%): 366 (M+H$^+$, 98)

d) (3S,5R)-3-Benzoyloxy-5-(tert-butyl-dimethyl-silanyloxy)-piperidine-1-carboxylic Acid Benzyl Ester To a solution of 2.8 g (7.8 mmol) (3R,5R)-3-(tert-butyl-dimethyl-silanyloxy)-5-hydroxy-piperidine-1-carboxylic acid benzyl ester in 70 ml dry THF were consecutively added 1.0 g (8.5 mmol) benzoic acid, 1.7 g (8.5 mmol) diethyl azodicarboxylate and 2.2 g (8.5 mmol) triphenylphosphine at 0° C. After 6 h the reaction mixture was diluted with tert-butyl methyl ether washed with a 2N aqueous solution of sodium carbonate. The aqueous layer was extracted with 3 portions of tert-butyl methyl ether. The combined organic extracts were washed with a 2N aqueous solution of sodium carbonate and brine and dried over sodium sulfate. Flash chromatography gave 2.8 g (78%) of the title compound as a yellow oil.

MS m/e (%): 470 (M+H+, 100)

e) (3S,5R)-3-Benzoyloxy-5-hydroxy-piperidine-1-carboxylic Acid Benzyl Ester

To a solution of 2.3 g (5.0 mmol) (3S,5R)-3-benzoyloxy-5-(tert-butyl-dimethyl-silanyloxy)-piperidine-1-carboxylic acid benzyl ester in 20 ml dry THF were added 5.5 ml (5.5 mmol) of a 1M solution of tetrabutyl ammoniumfluoride in THF at 0° C. After completed addition, the mixture was allowed to warm to room temperature over 30 min. Addition of water was followed by extraction with three portions of tert-butyl methyl ether. The combined organic extracts were dried over sodium sulfate. Kugelrohr distillation gave 1.7 g (95%) of the title compound as a light yellow oil.

MS m/e (%): 356 (M+H+, 100)

f) (3S,5S)-3,5-Dihydroxy-piperidine-1-carboxylic Acid Benzyl Ester

The title compound was obtained as a light brown oil in 4% yield after flash chromatography according to the procedure described above for the preparation of (5R,3S)-1-benzyl-5-(tert-butyl-dimethyl-silanyloxy)-piperidin-3-ol (Example 304a)) using (3S,5R)-3-benzoyloxy-5-hydroxy-piperidine-1-carboxylic acid benzyl ester instead of (3R,5R)-1-benzyl-5-(tert-butyl-dimethyl-silanyloxy)-piperidin-3-ol.

MS m/e (%): 252 (M+H+, 63)

g) (3S,5S)-2-(3,5-Bis-trifluoromethyl-phenyl)-N-[4'-(2-chloro-phenyl)-3,5-dihydroxy-3,4,5,6-tetrahydro-2H-[1,2']bipyridinyl-5'-yl]-N-methyl-isobutyramide The title compound was obtained as a light brown solid in comparable yields after flash chromatography according to the procedures described above for the preparation of (R)-2-(3,5-bis-trifluoromethyl-phenyl)-N-[4-(4-fluoro-2-methyl-phenyl)-6-(3-hydroxymethyl-morpholin-4-yl)-pyridin-3-yl]-N-methyl-isobutyramide using (3S,5S)-3,5-dihydroxy-piperidine-1-carboxylic acid benzyl ester instead of (R)-(4-benzyl-morpholin-3-yl)-methanol in step a) and 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 616 (M+H+, 100)

EXAMPLE 306

(S)-2-(3,5-Bis-trifluoromethyl-phenyl)-N-[6-(2-formyl-pyrrolidin-1-yl)-4-o-tolyl-pyridin-3-yl]-N-methyl-isobutyramide The title compound was obtained as a colorless viscous oil in comparable yields after flash chromatography according to the procedures described above for the preparation of 2-(3,5-bis-trifluoromethyl-phenyl)-N-[4-(2-chloro-phenyl)-6-(2-oxo-propylamino)-pyridin-3-yl]-N-methyl-isobutyramide (Example 75a)) using (S)-2-(3,5-bis-trifluoromethyl-phenyl)-N-[6-(2-hydroxymethyl-pyrrolidin-1-yl)-4-o-tolyl-pyridin-3-yl]-N-methyl-isobutyramide instead of (RS)-2-(3,5-bis-trifluoromethyl-phenyl)-N-[4-(2-chloro-phenyl)-6-(2-hydroxy-propylamino)-pyridin-3-yl]-N-methyl-isobutyramide.

MS m/e (%): 578 (M+H+, 100)

EXAMPLE 307

(S)-2-(3,5-Bis-trifluoromethyl-phenyl)-N-[4-(4-fluoro-2-methyl-phenyl)-6-(2-methanesulfonylmethyl-pyrrolidin-1-yl)-pyridin-3-yl]-N-methyl-isobutyramide a) (S)-2-Methanesulfonylmethyl-pyrrolidine-1-carboxylic Acid Benzyl Ester To a suspension of 1.81 g (25.8 mmol) sodium methanethiolate in 25 ml methanol was added a solution of 1.35 g (4.31 mmol) 2-methanesulfonyloxymethyl-pyrrolidine-1-carboxylic acid benzyl ester in 25 ml methanol. Conversion was monitored by thin layer chromatography. After complete consumption of the starting material the reaction mixture was diluted with ethyl acetate and washed with two portions of water. The organic layer was dried over sodium sulfate. Flash chromatography gave 0.89 g (3.4 mmol, 78%) (S)-2-methylsulfanylmethyl-pyrrolidine-1-carboxylic acid benzyl ester as a light yellow oil.

This material was dissolved in 25 ml of methanol and treated with 3.1 g (5.1 mmol) Oxone at room temperature. Conversion was monitored by thin layer chromatography. After complete consumption of the starting material the reaction mixture was diluted with water and extracted with three portions of ethyl acetate. The combined organic extracts were dried over sodium sulfate and concentrated in vacuo to give 0.86 g (86%) of the crude title compound as a colorless oil.

MS m/e (%): 297 (M+, 3)

b) (S)-2-Methanesulfonylmethyl-pyrrolidine

A solution of 0.86 g (2.9 mmol) (S)-2-methanesulfonylmethyl-pyrrolidine-1-carboxylic acid benzyl ester in 15 ml ethanol was deoxygenated by three cycles of evacuation and flushing with argon. After addition of 0.15 g palladium on charcoal (10%) the reaction vessel was evacuated and filled with hydrogen gas. The reaction mixture was stirred at room temperature under an atmosphere of hydrogen over night. Filtration over decalite and evaporation of the solvent in vacuo gave 0.44 g (93%) of the crude title compound as a light yellow oil.

MS m/e (%): 164 (M+H+, 100)

c) (S)-2-(3,5-Bis-trifluoromethyl-phenyl)-N-[4-(4-fluoro-2-methyl-phenyl)-6-(2-methanesulfonylmethyl-pyrrolidin-1-yl)-pyridin-3-yl]-N-methyl-isobutyramide The title compound was obtained as an off-white solid after preparative thin layer chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide using (S)-2-methanesulfonylmethyl-pyrrolidine instead of L-prolinol.

MS m/e (%): 660 (M+H+, 100)

EXAMPLE 308

2-(3,5-Bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide

A mixture of 0.50 g (0.94 mmol) 2-(3,5-bis-trifluoromethyl-phenyl)-N-[6-chloro-4-(4-fluoro-2-methyl-phenyl)-pyridin-3-yl]-N-methyl-isobutyramide, 0.32 g (2.8 mmol) 4-(hydroxymethyl)piperidine, 0.12 g (2.8 mmol) lithium chloride and 0.39 g (2.8 mmol) potassium carbonate in 5 ml DMSO was heated at 140° C. for 24 h. After cooling to room temperature the reaction mixture was diluted with water and extracted with three portions of dichloromethane. The combined organic extracts were dried over sodium sulphate and concentrated. Flash column chromatography gave 0.42 g (74%) of the title compound as a white solid.

MS m/e (%): 612 (M+H$^+$, 100)

EXAMPLE 309

2-(3,5-Bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide a) Methanesulfonic acid 5'-{[2-(3,5-bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-ylmethyl Ester To a solution of 0.42 g (0.69 mmol) 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide in 7 ml dichloromethane were added 83 mg (0.72 mmol) methanesulfonyl chloride and 73 mg (0.72 mmol) triethylamine at 0° C. After 30 min the reaction mixture was diluted with water and extracted with three portions of dichloromethane. The combined organic extracts were dried over sodium sulphate and concentrated. Flash column chromatography gave 0.29 g (63%) of the title compound as a white solid.

MS m/e (%): 690 (M+H$^+$, 100)

b) 2-(3,5-Bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide A solution of 0.29 g (0.42 mmol) methanesulfonic acid 5'-{[2-(3,5-bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-ylmethyl ester and 44 mg (0.63 mmol) sodium methanethiolate in 8 ml DMF was heated at 80° C. for 30 min. After cooling to room temperature the reaction mixture was treated with a 1 N aqueous sodium hydroxide solution and extracted with three portions of tert-butyl methyl ether. The combined organic extracts were dried over sodium sulphate and concentrated. Flash column chromatography gave 0.25 g (92%) of the title compound as a white solid.

MS m/e (%): 642 (M+H$^+$, 100)

EXAMPLE 310

(RS)-2-(3,5-Bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide

To a solution of 0.25 g (0.39 mmol) 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide in 10 ml dichloromethane were added 95 mg (70%, 0.39 mmol) 3-chloroperbenzoic acid at 0° C. After completed addition, the reaction mixture was allowed to warm to room temperature and stirred over night. An aqueous solution of sodium hydrogensulfite was added and the mixture was stirred for 10 min. Basification with 1 N aqueous sodium hydroxide solution was followed by extraction with three portions of dichloromethane. The combined organic extracts were dried over sodium sulphate and concentrated. Flash column chromatography gave 0.23 g (89%) of the title compound as a white solid.

MS m/e (%): 658 (M+H$^+$, 100)

EXAMPLE 311

2-(3,5-Bis-trifluoromethyl-phenyl)-N-[4'-(4-fluoro-2-methyl-phenyl)-4-methanesulfonylmethyl-3,4,5,6-tetrahydro-2H-[1,2']bipyridinyl-5'-yl]-N-methyl-isobutyramide

To a solution of 0.22 g (0.33 mmol) (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide in 5 ml dichloromethane were added 142 mg (70%, 0.58 mmol) 3-chloroperbenzoic acid at 0° C. After completed addition, the reaction mixture was allowed to warm to room temperature and stirred over night. An aqueous solution of sodium hydrogensulfite was added and the mixture was stirred for 10 min. Basification with 1 N aqueous sodium hydroxide solution was followed by extraction with three portions of dichloromethane. The combined organic extracts were dried over sodium sulphate and concentrated. Flash column chromatography gave 0.13 g (55%) of the title compound as a white solid.

MS m/e (%): 674 (M+H$^+$, 100)

EXAMPLE 312

(RS)-2-(3,5-Bis-trifluoromethyl-phenyl)-N-[4-(4-fluoro-2-methyl-phenyl)-6-(3-hydroxymethyl-pyrrolidin-1-yl)-pyridin-3-yl]-N-methyl-isobutyramide

The title compound was obtained as a white solid in 70% yield after flash chromatography according to the procedure described above for the preparation of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide using (RS)-3-(hydroxymethyl)pyrrolidine instead of 4-(hydroxymethyl)piperidine.

MS m/e (%): 598 (M+H$^+$, 100)

EXAMPLE 313

(RS)-2-(3,5-Bis-trifluoromethyl-phenyl)-N-[4-(4-fluoro-2-methyl-phenyl)-6-(3-methylsulfanylmethyl-pyrrolidin-1-yl)-pyridin-3-yl]-N-methyl-isobutyramide The title compound was obtained as a white solid in 66% yield after flash chromatography according to the procedures described above for the preparation of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide using 2-(3,5-bis-trifluoromethyl-phenyl)-N-[4-(4-fluoro-2-methyl-phenyl)-6-(3-hydroxymethyl-pyrrolidin-1-yl)-pyridin-3-yl]-N-methyl-isobutyramide instead of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide in step a).

MS m/e (%): 628 (M+H$^+$, 100)

EXAMPLE 314

2-(3,5-Bis-trifluoromethyl-phenyl)-N-{4-(4-fluoro-2-methyl-phenyl)-6-[(RS)-3-((RS)-methanesulfinyl-methyl)-pyrrolidin-1-yl]-pyridin-3-yl}-N-methyl-isobutyramide The title compound was obtained as a white solid in 86% yield after flash chromatography according to the procedure described above for the preparation of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide using (RS)-2-(3,5-bis-trifluoromethyl-phenyl)-N-[4-(4-fluoro-2-methyl-phenyl)-6-(3-methylsulfanylmethyl-pyrrolidin-1-yl)-pyridin-3-yl]-N-methyl-isobutyramide instead of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide.

MS m/e (%): 644 (M+H$^+$, 100)

EXAMPLE 315

(RS)-2-(3,5-Bis-trifluoromethyl-phenyl)-N-[4-(4-fluoro-2-methyl-phenyl)-6-(3-methanesulfonylmethyl-pyrrolidin-1-yl)-pyridin-3-yl]-N-methyl-isobutyramide The title compound was obtained as a white solid in 31% yield after flash chromatography according to the procedure described above for the preparation of 2-(3,5-bis-trifluoromethyl-phenyl)-N-[4'-(4-fluoro-2-methyl-phenyl)-4-methanesulfonylmethyl-3,4,5,6-tetrahydro-2H-[1,2']bipyridinyl-5'-yl]-N-methyl-isobutyramide using 2-(3,5-bis-trifluoromethyl-phenyl)-N-{4-(4-fluoro-2-methyl-phenyl)-6-[(RS)-3-((RS)-methanesulfinylmethyl)-pyrrolidin-1-yl]-pyridin-3-yl}-N-methyl-isobutyramide instead of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide.

MS m/e (%): 660 (M+H$^+$, 100)

EXAMPLE 316

(R)-N-[6-(3-Amino-pyrrolidin-1-yl)-4-(4-fluoro-2-methyl-phenyl)-pyridin-3-yl]-2-(3,5-bis-trifluoromethyl-phenyl)-N-methyl-isobutyramide A mixture of 939 mg (1.76 mmol) 2-(3,5-bis-trifluoromethyl-phenyl)-N-[6-chloro-4-(4-fluoro-2-methyl-phenyl)-pyridin-3-yl]-N-methyl-isobutyramide, 1.22 g (8.81 mmol) potassium carbonate and 770 mg (3.52 mmol) (R)-3-(trifluoro-acetamido)pyrrolidine hydrochloride in 20 ml dimethyl sulfoxide was stirred at 130° C. for 52 h. After cooling to room temperature the reaction mixture was diluted with 30 ml tert-butyl methyl ether and washed with 20 ml of water and 10 ml of a saturated aqueous solution of sodium carbonate. The combined organic layers were dried over sodium sulfate, concentrated and dissolved in 25 ml of a 2 N solution of ammonia in ethanol. The solution was stirred at room temperature for 18 h. The reaction mixture was concentrated and purified by flash chromatography to give 670 mg (65%) of the title compound as a light brown foam.

MS m/e (%): 583 (M+H$^+$, 100)

EXAMPLE 317

(R)-2-(3,5-Bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide To a solution of 620 mg (1.06 mmol) (R)-N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide in 6 ml dichloromethane were added 7 mg (0.05 mmol) 4-(N,N-dimethylamino)pyridine, 275 mg (2.13 mmol) N,N-diisopropylethylamine and 158 mg (1.38 mmol) methanesulfonyl chloride at room temperature. After stirring for 18 h the reaction mixture was diluted with 20 ml dichloromethane and washed with 20 ml of a saturated aqueous solution of sodium carbonate. The combined organic layers were dried over sodium sulfate, concentrated and purified by flash chromatography to give 618 mg (88%) of the title compound as an off-white foam.

MS m/e (%): 659 (M+H$^+$, 66)

EXAMPLE 318

(R)-2-(3,5-Bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide To a solution of 150 mg (0.227 mmol) (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide in 1 ml dimethylformamide were added 15 mg (0.34 mmol) sodium hydride (55% dispersion in mineral oil) at room temperature. After stirring at room temperature for 30 min 39 mg (27 mmol) iodomethane were added. The reaction mixture was stirred at room temperature for 18 h, followed by dilution with 10 ml ethyl acetate and washing with 10 ml saturated sodium carbonate solution. The combined organic layers were dried over sodium sulfate, concentrated in vacuo and purified by flash chromatography to give 120 mg (78%) of the title compound as a white foam.

MS m/e (%): 675 (M+H$^+$, 100)

EXAMPLE 319

(R)-2-(3,5-Bis-trifluoromethyl-phenyl)-N-[6-[3-(ethyl-methanesulfonyl-amino)-pyrrolidin-1-yl]-4-(4-fluoro-2-methyl-phenyl)-pyridin-3-yl]-N-methyl-isobutyramide The title compound was obtained as a white foam in 84% yield after flash chromatography according to the procedure described above for the preparation of (R)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide using iodoethane instead of iodomethane.
MS m/e (%): 689 (M+H$^+$, 100)

EXAMPLE 320

2-(3,5-Bis-trifluoromethyl-phenyl)-N-[4'-(4-fluoro-2-methyl-phenyl)-4-methanesulfonylamino-3,4,5,6-tetrahydro-2H-[1,2']bipyridinyl-5'-yl]-N-methyl-isobutyramide The title compound was obtained as a white foam in 93% yield after flash chromatography according to the procedure described above for the preparation of (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide using N-[4-amino-4'-(4-fluoro-2-methyl-phenyl)-3,4,5,6-tetrahydro-2H-[1,2']bipyridinyl-5'-yl]-2-(3,5-bis-trifluoromethyl-phenyl)-N-methyl-isobutyramide (Example 114c)) instead of (R)-N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide.
MS m/e (%): 673 ([M−H$^+$]$^-$, 90)

EXAMPLE 321

2-(3,5-Bis-trifluoromethyl-phenyl)-N-[4'-(4-fluoro-2-methyl-phenyl)-4-(methanesulfonyl-methyl-amino)-3,4,5,6-tetrahydro-2H-[1,2']bipyridinyl-5'-yl]-N-methyl-isobutyramide The title compound was obtained as a white foam in 98% yield after flash chromatography according to the procedure described above for the preparation of (R)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide using 2-(3,5-bis-trifluoromethyl-phenyl)-N-[4'-(4-fluoro-2-methyl-phenyl)-4-methanesulfonylamino-3,4,5,6-tetrahydro-2H-[1,2']bipyridinyl-5'-yl]-N-methyl-isobutyramide instead of (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide.
MS m/e (%): 689 (M+H$^+$, 100)

EXAMPLE 322

2-(3,5-Bis-trifluoromethyl-phenyl)-N-[4-(ethyl-methanesulfonyl-amino)-4'-(4-fluoro-2-methyl-phenyl)-3,4,5,6-tetrahydro-2H-[1,2']bipyridinyl-5'-yl]-N-methyl-isobutyramide The title compound was obtained as a white foam in 95% yield after flash chromatography according to the procedure described above for the preparation of (R)-2-(3,5-bis-trifluoromethyl-phenyl)-N-{4-(4-fluoro-2-methyl-phenyl)-6-[3-(methanesulfonyl-methyl-amino)-pyrrolidin-1-yl]-pyridin-3-yl}-N-methyl-isobutyramide using 2-(3,5-bis-trifluoromethyl-phenyl)-N-[4'-(4-fluoro-2-methyl-phenyl)-4-methanesulfonylamino-3,4,5,6-tetrahydro-2H-[1,2']bipyridinyl-5'-yl]-N-methyl-isobutyramide instead of (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide and iodoethane instead of iodomethane.
MS m/e (%): 703 (M+H$^+$, 100)

EXAMPLE 323

2-(3,5-Bis-trifluoromethyl-phenyl)-N-[4'-(4-fluoro-2-methyl-phenyl)-4-trifluoromethyl-3,4,5,6-tetrahydro-2H-[1,2']bipyridinyl-5'-yl]-N-methyl-isobutyramide A mixture of 150 mg (0.28 mmol) 2-(3,5-bis-trifluoromethyl-phenyl)-N-[6-chloro-4-(4-fluoro-2-methyl-phenyl)-pyridin-3-yl]-N-methyl-isobutyramide and 0.16 g (0.84 mmol) 4-(trifluoromethyl)piperidine hydrochloride in 2 ml 1,8-diazabicyclo[5.4.0]undec-7-ene was heated at 140° C. for 20 h. After cooling to room temperature the reaction mixture was diluted with water and extracted with three portions of tert-butyl methyl ether. The combined organic layers were dried over sodium sulfate, concentrated in vacuo and purified by flash chromatography to give 62 mg (34%) of the title compound as a light yellow solid.
MS m/e (%): 650 (M+H$^+$, 100)

EXAMPLE 324

2-(3,5-Bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide a) 2-(3,5-Bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide The title compound was obtained as a white solid in 38% yield after flash chromatography according to the procedures described above for the preparation of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide (Example 309) using 2-(3,5-bis-trifluoromethyl-phenyl)-N-[4-(4-fluoro-2-methyl-phenyl)-6-(3-hydroxy-azetidin-1-yl)-pyridin-3-yl]-N-methyl-isobutyramide (Example 162) instead of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide in step a).
MS m/e (%): 600 (M+H$^+$, 100)

b) 2-(3,5-Bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide To a solution of 0.25 g (0.42 mmol) 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide in 10 ml dichloromethane were added 206 mg (70%, 0.84 mmol) 3-chloroperbenzoic acid at 0° C. After completed addition, the reaction mixture was allowed to warm to room temperature and stirred for 2 h. An aqueous solution of sodium hydrogensulfite was added and the mixture was stirred for 10 min. Basification with 1 N aqueous sodium hydroxide solution was followed by extraction with three portions of dichloromethane. The combined organic extracts were dried over sodium sulphate and concentrated. Flash column chromatography gave 0.16 g (60%) of the title compound as a white solid.

MS m/e (%): 632 (M+H$^+$, 100)

EXAMPLE 325

(RS)-2-(3,5-Bis-trifluoromethyl-phenyl)-N-[4'-(4-fluoro-2-methyl-phenyl)-3-methanesulfonyl-3,4,5,6-tetrahydro-2H-[1,2']bipyridinyl-5'-yl]-N-methyl-isobutyramide a) (RS)-2-(3,5-Bis-trifluoromethyl-phenyl)-N-[4'-(4-fluoro-2-methyl-phenyl)-3-hydroxy-3,4,5,6-tetrahydro-2H-[1,2']bipyridinyl-5'-yl]-N-methyl-isobutyramide The title compound was obtained as a white solid in 60% yield after flash chromatography according to the procedure described above for the preparation of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide using (RS)-3-hydroxypiperidine instead of 4-(hydroxymethyl)piperidine.

MS m/e (%): 598 (M+H$^+$, 100)

b) (RS)-2-(3,5-Bis-trifluoromethyl-phenyl)-N-[4'-(4-fluoro-2-methyl-phenyl)-3-methanesulfonyl-3,4,5,6-tetrahydro-2H-[1,2']bipyridinyl-5'-yl]-N-methyl-isobutyramide The title compound was obtained as a white solid in 5% yield after flash chromatography according to the procedures described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide (Example 324) using (RS)-2-(3,5-bis-trifluoromethyl-phenyl)-N-[4'-(4-fluoro-2-methyl-phenyl)-3-hydroxy-3,4,5,6-tetrahydro-2H-[1,2']bipyridinyl-5'-yl]-N-methyl-isobutyramide instead of 2-(3,5-bis-trifluoromethyl-phenyl)-N-[4-(4-fluoro-2-methyl-phenyl)-6-(3-hydroxy-azetidin-1-yl)-pyridin-3-yl]-N-methyl-isobutyramide in step a).

MS m/e (%): 660 (M+H$^+$, 100)

EXAMPLE 326

2-(3,5-Bis-trifluoromethyl-phenyl)-N-[4'-(4-fluoro-2-methyl-phenyl)-4-methanesulfonyl-3,4,5,6-tetrahydro-2H-[1,2']bipyridinyl-5'-yl]-N-methyl-isobutyramide The title compound was obtained as a white solid in 35% yield after flash column chromatography according to the procedures described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide using 2-(3,5-bis-trifluoromethyl-phenyl)-N-[4'-(4-fluoro-2-methyl-phenyl)-4-hydroxy-3,4,5,6-tetrahydro-2H-[1,2']bipyridinyl-5'-yl]-N-methyl-isobutyramide (Example 114a)) instead of 2-(3,5-bis-trifluoromethyl-phenyl)-N-[4-(4-fluoro-2-methyl-phenyl)-6-(3-hydroxy-azetidin-1-yl)-pyridin-3-yl]-N-methyl-isobutyramide in step a).

MS m/e (%): 660 (M+H$^+$, 100)

EXAMPLE 327

(1S,3R,5R)-2-(3,5-Bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide The title compound was obtained as a light brown solid in 57% yield after flash chromatography according to the procedure described above for the preparation of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide using nortropine instead of 4-(hydroxymethyl)piperidine.

MS m/e (%): 624 (M+H$^+$, 100)

EXAMPLE 328

(1R,3S,5S)-2-(3,5-Bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide The title compound was obtained as a white solid in 37% yield after flash chromatography according to the procedure described above for the preparation of (5R,3S)-1-benzyl-5-(tert-butyl-dimethyl-silanyloxy)-piperidin-3-ol (Example 304a)) using (1S,3R,5R)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide instead of (3R,5R)-1-benzyl-5-(tert-butyl-dimethyl-silanyloxy)-piperidin-3-ol.

MS m/e (%): 624 (M+H$^+$, 100)

EXAMPLE 329

(rac)-(1R,3R,5S)-2-(3,5-Bis-trifluoromethyl-phenyl)-N-[4-(4-fluoro-2-methyl-phenyl)-6-(3-methanesulfinyl-8-aza-bicyclo[3.2.1]oct-8-yl)-pyridin-3-yl]-N-methyl-isobutyramide a) (1R,3R,5S)-2-(3,5-Bis-trifluoromethyl-phenyl)-N-[4-(4-fluoro-2-methyl-phenyl)-6-(3-methylsulfanyl-8-aza-bicyclo[3.2.1]oct-8-yl)-pyridin-3-yl]-N-methyl-isobutyramide The title compound was obtained as a white solid in 45% yield after flash chromatography according to the procedures described above for the preparation of 2-(3,5-bis-trifluoromethyl-phenyl)-N-[4'-(4-fluoro-2-methyl-phenyl)-4-methyl-sulfanylmethyl-3,4,5,6-tetrahydro-2H-[1,2']bipyridinyl-5'-yl]-N-methyl-isobutyramide using (1R,3S,5S)-2-(3,5-bis-trifluoromethyl-phenyl)-N-[4-(4-fluoro-2-methyl-phenyl)-6-(3-hydroxy-8-aza-bicyclo[3.2.1]oct-8-yl)-pyridin-3-yl]-N-methyl-isobutyramide instead of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide in step a).

MS m/e (%): 654 (M+H$^+$, 100)

b) (rac)-(1R,3R,5S)-2-(3,5-Bis-trifluoromethyl-phenyl)-N-[4-(4-fluoro-2-methyl-phenyl)-6-(3-methanesulfinyl-8-aza-bicyclo[3.2.1]oct-8-yl)-pyridin-3-yl]-N-methyl-isobutyramide The title compound was obtained as a white solid in 78% yield after flash chromatography according to the procedure described above for the preparation of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide using (1R,3R,5S)-2-(3,5-bis-trifluoromethyl-phenyl)-N-[4-(4-fluoro-2-methyl-phenyl)-6-(3-methylsulfanyl-8-aza-bicyclo[3.2.1]oct-8-yl)-pyridin-3-yl]-N-methyl-isobutyramide instead of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide.

MS m/e (%): 670 (M+H$^+$, 100)

EXAMPLE 330

(1R,3R,5S)-2-(3,5-Bis-trifluoromethyl-phenyl)-N-[4-(4-fluoro-2-methyl-phenyl)-6-(3-methanesulfonyl-8-aza-bicyclo[3.2.1]oct-8-yl)-pyridin-3-yl]-N-methyl-isobutyramide The title compound was obtained as a white solid in 60% yield after flash chromatography according to the procedure described above for the preparation of 2-(3,5-bis-trifluoromethyl-phenyl)-N-[4'-(4-fluoro-2-methyl-phenyl)-4-methanesulfonylmethyl-3,4,5,6-tetrahydro-2H-[1,2']bipyridinyl-5'-yl]-N-methyl-isobutyramide using (rac)-(1R,3R,5S)-2-(3,5-bis-trifluoromethyl-phenyl)-N-[4-(4-fluoro-2-methyl-phenyl)-6-(3-methanesulfinyl-8-aza-bicyclo[3.2.1]oct-8-yl)-pyridin-3-yl]-N-methyl-isobutyramide instead of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide.

MS m/e (%): 686 (M+H$^+$, 100)

EXAMPLE 331

2-(3,5-Bis-trifluoromethyl-phenyl)-N-[4-dimethylsulfamoyl-4'-(4-fluoro-2-methyl-phenyl)-3,4,5,6-tetrahydro-2H-[1,2']bipyridinyl-5'-yl]-N-methyl-isobutyramide a) Thioacetic acid 5'-{[2-(3,5-bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-yl Ester A solution of 0.22 g (0.84 mmol) triphenylphosphine and 0.15 g (0.84 mmol) diethyl azodicarboxylate in 3.33 ml THF was stirred for 15 min at 0° C. This solution was added to a solution of 0.25 g (0.42 mmol) 2-(3,5-bis-trifluoromethyl-phenyl)-N-[4'-(4-fluoro-2-methyl-phenyl)-4-hydroxy-3,4,5,6-tetrahydro-2H-[1,2']bipyridinyl-5'-yl]-N-methyl-isobutyramide and 64 mg (0.84 mmol) thioacetic acid in 10 ml THF at 0° C. Conversion was monitored by thin layer chromatography. After complete consumption of the starting material a 2 N aqueous solution of sodium carbonate was added. The mixture was extracted with three portions of tert-butyl methyl ether. The combined organic extracts were dried over sodium sulphate and concentrated. Flash column chromatography gave 0.16 g (59%) of the title compound as a white solid.

MS m/e (%): 656 (M+H$^+$, 100)

b) 5'-{[2-(3,5-Bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-sulfonic Acid To a suspension of 0.16 g (0.24 mmol) thioacetic acid 5'-{[2-(3,5-bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-yl ester in 1 ml acetic acid were added 0.12 ml (1.2 mmol) of a 30% aqueous solution of hydrogen peroxide at room temperature. After heating to 60° C., a clear solution was obtained. Stirring was continued at this temperature for 20 h. After cooling to room temperature an aqueous solution of sodium hydrogensulfite was added and the mixture was stirred for 10 min. Acidification with 1 N aqueous hydrochloride solution to pH 1 was followed by extraction with three portions of dichloromethane. The combined organic extracts were dried over sodium sulphate and concentrated. Flash column chromatography gave 0.13 g (83%) of the title compound as a light yellow solid.

MS m/e (%): 660 ([M−H$^+$]$^-$, 100)

c) 2-(3,5-Bis-trifluoromethyl-phenyl)-N-[4-dimethylsulfamoyl-4'-(4-fluoro-2-methyl-phenyl)-3,4,5,6-tetrahydro-2H-[1,2']bipyridinyl-5'-yl]-N-methyl-isobutyramide To a solution of 0.13 g (0.19 mmol) 5'-{[2-(3,5-bis-trifluoromethyl-phenyl)-2-methyl-propionyl]-methyl-amino}-4'-(4-fluoro-2-methyl-phenyl)-3,4,5,6-tetrahydro-2H-[1,2']bipyridinyl-4-sulfonic acid in 2 ml dichloromethane were added 0.33 ml (0.39 mmol) oxalyl chloride and one drop of DMF at 0° C. After 30 min the reaction mixture was allowed to warm to room temperature during 2 h. To the yellow reaction mixture were added 1.8 ml (20 mmol) of an aqueous solution of dimethylamine (60%). After 1 h the reaction mixture was diluted with water and extracted with three portions of dichloromethane. The combined organic extracts were dried over sodium sulphate and concentrated. Flash column chromatography gave 92 mg (69%) of the title compound as a white solid.

MS m/e (%): 689 (M+H$^+$, 100)

EXAMPLE 332

2-(3,5-Bis-trifluoromethyl-phenyl)-N-[4'-(2-chloro-phenyl)-4-methylsulfanyl-3,4,5,6-tetrahydro-2H-[1,2']bipyridinyl-5'-yl]-N-methyl-isobutyramide The title compound was obtained as a white solid in 59% yield after flash chromatography according to the procedures described above for the preparation of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide using 2-(3,5-bis-trifluoromethyl-phenyl)-N-[4'-(2-chloro-phenyl)-4-hydroxy-3,4,5,6-tetrahydro-2H-[1,2']bipyridinyl-5'-yl]-N-methyl-isobutyramide (Example 51) instead of 2-(3,5-bis-trifluoromethyl-phenyl)-N-[4'-(4-fluoro-2-methyl-phenyl)-4-hydroxymethyl-3,4,5,6-tetrahydro-2H-[1,2']bipyridinyl-5'-yl]-N-methyl-isobutyramide in step a).

MS m/e (%): 630 (M+H$^+$, 100)

EXAMPLE 333

(RS)-2-(3,5-Bis-trifluoromethyl-phenyl)-N-[4'-(2-chloro-phenyl)-4-methanesulfinyl-3,4,5,6-tetrahydro-2H-[1,2']bipyridinyl-5'-yl]-N-methyl-isobutyramide The title compound was obtained as a white solid in 84% yield after flash chromatography according to the procedure described above for the preparation of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide using 2-(3,5-bis-trifluoromethyl-phenyl)-N-[4'-(2-chloro-phenyl)-4-methylsulfanyl-3,4,5,6-tetrahydro-2H-[1,2']bipyridinyl-5'-yl]-N-methyl-isobutyramide instead of 2-(3,5-bis-trifluoromethyl-phenyl)-N-[4'-(4-fluoro-2-methyl-phenyl)-4-methylsulfanylmethyl-3,4,5,6-tetrahydro-2H-[1,2']bipyridinyl-5'-yl]-N-methyl-isobutyramide.

MS m/e (%): 646 (M+H$^+$, 100)

EXAMPLE 334

2-(3,5-Bis-trifluoromethyl-phenyl)-N-[4'-(2-chloro-phenyl)-4-methanesulfonyl-3,4,5,6-tetrahydro-2H-[1,2']bipyridinyl-5'-yl]-N-methyl-isobutyramide The title compound was obtained as a white solid in 86% yield after flash chromatography according to the procedure described above for the preparation of 2-(3,5-bis-trifluoromethyl-phenyl)-N-[4'-(4-fluoro-2-methyl-phenyl)-4-methanesulfonylmethyl-3,4,5,6-tetrahydro-2H-[1,2']bipyridinyl-5'-yl]-N-methyl-isobutyramide using (RS)-2-(3,5-bis-trifluoromethyl-phenyl)-N-[4'-(2-chloro-phenyl)-4-methanesulfinyl-3,4,5,6-tetrahydro-2H-[1,2']bipyridinyl-5'-yl]-N-methyl-isobutyramide instead of (RS)-2-(3,5-bis-trifluoromethyl-phenyl)-N-[4'-(4-fluoro-2-methyl-phenyl)-4-methanesulfinylmethyl-3,4,5,6-tetrahydro-2H-[1,2']bipyridinyl-5'-yl]-N-methyl-isobutyramide.

MS m/e (%): 662 (M+H$^+$, 100)

EXAMPLE 335

2-(3,5-Bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide To a solution of 0.20 g (0.34 mmol) 2-(3,5-bis-trifluoromethyl-phenyl)-N-[4'-(4-fluoro-2-methyl-phenyl)-4-oxo-3,4,5,6-tetrahydro-2H-[1,2']bipyridinyl-5'-yl]-N-methyl-isobutyramide in 5 ml dichloromethane were added 0.03 g (0.4 mmol) 2-mercaptoethanol and 0.11 g (0.34 mmol) boron trifluoride etherate at 0° C. After 1 h the reaction mixture was allowed to warm to room temperature and stirred over night. Dilution with a 2 N aqueous sodium hydroxide solution was followed by extraction with 3 portions of dichloromethane. The combined organic extracts were dried over sodium sulfate and concentrated in vacuo. Flash column chromatography gave 0.22 g (98%) of the title compound as a white solid.

MS m/e (%): 656 (M+H$^+$, 100)

EXAMPLE 336

2-(3,5-Bis-trifluoromethyl-phenyl)-N-[6-(4,4-dioxo-1-oxa-4$\lambda^6$-thia-8-aza-spiro[4.5]dec-8-yl)-4-(4-fluoro-2-methyl-phenyl)-pyridin-3-yl]-N-methyl-isobutyramide The title compound was obtained as a white solid in 55% yield after flash chromatography according to the procedure described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide using 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide instead of 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide.

MS m/e (%): 688 (M+H$^+$, 100)

EXAMPLE 337

2-(3,5-Bis-trifluoromethyl-phenyl)-N-[4-(4-fluoro-2-methyl-phenyl)-6-(1-oxa-5-thia-9-aza-spiro[5.5]undec-9-yl)-pyridin-3-yl]-N-methyl-isobutyramide The title compound was obtained as a white solid in 84% yield after flash chromatography according to the procedure described above for the preparation of 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide using 3-mercapto-1-propanol instead of 2-mercaptoethanol.

MS m/e (%): 670 (M+H$^+$, 100)

EXAMPLE 338

2-(3,5-Bis-trifluoromethyl-phenyl)-N-[6-(5,5-dioxo-1-oxa-5$\lambda^6$-thia-9-aza-spiro[5.5]undec-9-yl)-4-(4-fluoro-2-methyl-phenyl)-pyridin-3-yl]-N-methyl-isobutyramide The title compound was obtained as a white solid in 70% yield after flash chromatography according to the procedure described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide using 2-(3,5-bis-trifluoromethyl-phenyl)-N-[4-(4-fluoro-2-methyl-phenyl)-6-(1-oxa-5-thia-9-aza-spiro[5.5]undec-9-yl)-pyridin-3-yl]-N-methyl-isobutyramide instead of 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide.

MS m/e (%): 702 (M+H$^+$, 100)

EXAMPLE 339

2-(3,5-Bis-trifluoromethyl-phenyl)-N-[4-(4-fluoro-2-methyl-phenyl)-6-(1,1,4,4-tetraoxo-1$\lambda^6$,4$\lambda^6$-dithia-8-aza-spiro[4.5]dec-8-yl)-pyridin-3-yl]-N-methyl-isobutyramide a) 2-(3,5-Bis-trifluoromethyl-phenyl)-N-[6-(1,4-dithia-8-aza-spiro[4.5]dec-8-yl)-4-(4-fluoro-2-methyl-phenyl)-pyridin-3-yl]-N-methyl-isobutyramide The title compound was obtained as a white solid in 41% yield after flash chromatography according to the procedure described above for the preparation of 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide using 1,2-ethanedithiol instead of 2-mercaptoethanol.

MS m/e (%): 672 (M+H$^+$, 100)

b) 2-(3,5-Bis-trifluoromethyl-phenyl)-N-[4-(4-fluoro-2-methyl-phenyl)-6-(1,1,4,4-tetraoxo-1$\lambda^6$,4$\lambda^6$-dithia-8-aza-spiro[4.5]dec-8-yl)-pyridin-3-yl]-N-methyl-isobutyramide The title compound was obtained as a white solid in 33% yield after flash chromatography according to the procedure described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide using 2-(3,5-bis-trifluoromethyl-phenyl)-N-[6-(1,4-dithia-8-aza-spiro[4.5]dec-8-yl)-4-(4-fluoro-2-methyl-phenyl)-pyridin-3-yl]-N-methyl-isobutyramide instead of 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide and 4 instead of 2 equivalents of 3-chloroperbenzoic acid.

MS m/e (%): 736 (M+H$^+$, 100)

EXAMPLE 340

2-(3,5-Bis-trifluoromethyl-phenyl)-N-[4-(4-fluoro-2-methyl-phenyl)-6-(1,1,5,5-tetraoxo-1$\lambda^6$,5$\lambda^6$-dithia-9-aza-spiro[5.5]undec-9-yl)-pyridin-3-yl]-N-methyl-isobutyramide a) 2-(3,5-Bis-trifluoromethyl-phenyl)-N-[6-(1,5-dithia-9-aza-spiro[5.5]undec-9-yl)-4-(4-fluoro-2-methyl-phenyl)-pyridin-3-yl]-N-methyl-isobutyramide The title compound was obtained as a white solid in 41% yield after flash chromatography according to the procedure described above for the preparation of 2-(3,5-bis-trifluoromethyl-phenyl)-N-[4-(4-fluoro-2-methyl-phenyl)-6-(1-oxa-4-thia-8-aza-spiro[4.5]dec-8-yl)-pyridin-3-yl]-N-methyl-isobutyramide using 1,3-propanedithiol instead of 2-mercaptoethanol.

MS m/e (%): 686 (M+H$^+$, 100)

b) 2-(3,5-Bis-trifluoromethyl-phenyl)-N-[4-(4-fluoro-2-methyl-phenyl)-6-(1,1,5,5-tetraoxo-1$\lambda^6$,5$\lambda^6$-dithia-9-aza-spiro[5.5]undec-9-yl)-pyridin-3-yl]-N-methyl-isobutyramide The title compound was obtained as an off-white solid in 4% yield after flash chromatography according to the procedure described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide using 2-(3,5-bis-trifluoromethyl-phenyl)-N-[6-(1,5-dithia-9-aza-spiro[5.5]undec-9-yl)-4-(4-fluoro-2-methyl-phenyl)-pyridin-3-yl]-N-methyl-isobutyramide instead of 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide and 4 instead of 2 equivalents of 3-chloroperbenzoic acid.

MS m/e (%): 750 (M+H$^+$, 100)

EXAMPLE 341

2-(3,5-Bis-trifluoromethyl-phenyl)-N-[4-(4-fluoro-2-methyl-phenyl)-6-(1-oxa-8-aza-spiro[4.5]dec-8-yl)-pyridin-3-yl]-N-methyl-isobutyramide The title compound was obtained as an off-white solid in 12% yield after flash chromatography according to the procedure described above for the preparation of 2-(3,5-bis-trifluoromethyl-phenyl)-N-[4'-(4-fluoro-2-methyl-phenyl)-4-trifluoromethyl-3,4,5,6-tetrahydro-2H-[1,2']bipyridinyl-5'-yl]-N-methyl-isobutyramide using 1-oxa-8-azaspiro[4.5]decane trifluoroacetic acid salt instead of 4-(trifluoromethyl)piperidine hydrochloride.

MS m/e (%): 638 (M+H$^+$, 100)

EXAMPLE 342

(RS)-2-(3,5-Bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide A mixture of 0.10 g (0.17 mmol) 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide (Example 142), 12 mg (0.39 mmol) paraformaldehyde and 61 mg (0.51 mmol) magnesium sulfate in 2 ml 1,2-dichloromethane was heated at 85° C. until complete consumption of starting material. After cooling to room temperature the reaction mixture was diluted with water and extracted with 3 portions of tert-butyl methyl ether. The combined organic extracts were dried over sodium sulfate and concentrated in vacuo. Flash column chromatography gave 60 mg (59%) of the title compound as an off-white solid.

MS m/e (%): 600 (M+H$^+$, 100)

EXAMPLE 343

2-(3,5-Bis-trifluoromethyl-phenyl)-N-[4-(4-fluoro-2-methyl-phenyl)-6-morpholin-4-yl-pyridin-3-yl]-N-methyl-isobutyramide The title compound was obtained as an off-white solid in 67% yield after flash chromatography according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide (Example 115) using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and morpholine instead of 2-(methylamino)ethanol.

MS m/e (%): 584 (M+H$^+$, 100)

EXAMPLE 344

2-(3,5-Bis-trifluoromethyl-phenyl)-N-[(1S,5R)-4-(4-fluoro-2-methyl-phenyl)-6-8-oxa-3-aza-bicyclo[3.2.1]oct-3-yl-pyridin-3-yl]-N-methyl-isobutyramide A mixture of 0.15 g (0.28 mmol) 2-(3,5-bis-trifluoromethyl-phenyl)-N-[6-chloro-4-(4-fluoro-2-methyl-phenyl)-pyridin-3-yl]-N-methyl-isobutyramide, 0.13 g (0.84 mmol) 8-oxa-3-aza-bicyclo[3.2.1]octane hydrochloride and 0.20 g (1.4 mmol) potassium carbonate in 1 ml dimethyl sulfoxide was heated at 150° C. under microwave irradiation in a sealed tube for 30 min. Another portion of 0.06 g (0.4 mmol) 8-oxa-3-aza-bicyclo[3.2.1]octane hydrochloride was added and the reaction mixture was heated at 150° C. under microwave irradiation in a sealed tube for 30 more minutes. After cooling to room temperature the reaction mixture was diluted with water and extracted with four portions of tert-butyl methyl ether. The combined organic extracts were dried over sodium sulfate and concentrated. Flash column chromatography gave 32 mg (18%) of the title compound as a light yellow solid.

MS m/e (%): 610 (M+H$^+$, 100)

EXAMPLE 345

2-(3,5-Bis-trifluoromethyl-phenyl)-N-[4-(4-fluoro-2-methyl-phenyl)-6-(2-methylsulfanyl-ethylamino)-pyridin-3-yl]-N-methyl-isobutyramide The title compound was obtained as light orange foam in 19% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide (Example 155) using 2-(methylthio)ethylamine instead of (2R,3S)-2-(hydroxymethyl)-3-hydroxypyrrolidine.

MS m/e (%): 588 (M+H$^+$, 100)

EXAMPLE 346

2-(3,5-Bis-trifluoromethyl-phenyl)-N-[4-(4-fluoro-2-methyl-phenyl)-6-(2-methanesulfonyl-ethylamino)-pyridin-3-yl]-N-methyl-isobutyramide The title compound was obtained as a white foam in 54% yield after flash chromatography according to the procedure described above for the preparation of (S)-2-methanesulfonylmethyl-pyrrolidine-1-carboxylic acid benzyl ester (Example 307a)) using 2-(3,5-bis-trifluoromethyl-phenyl)-N-[4-(4-fluoro-2-methyl-phenyl)-6-(2-methylsulfanyl-ethylamino)-pyridin-3-yl]-N-methyl-isobutyramide instead of (S)-2-methylsulfanylmethyl-pyrrolidine-1-carboxylic acid benzyl ester.

MS m/e (%): 620 (M+H$^+$, 100)

EXAMPLE 347

2-(3,5-Bis-trifluoromethyl-phenyl)-N-[4-(4-fluoro-2-methyl-phenyl)-6-thiazolidin-3-yl-pyridin-3-yl]-N-methyl-isobutyramide A mixture of 0.25 g (0.47 mmol) 2-(3,5-bis-trifluoromethyl-phenyl)-N-[6-chloro-4-(4-fluoro-2-methyl-phenyl)-pyridin-3-yl]-N-methyl-isobutyramide and 0.59 g (6.6 mmol) thiazolidine was heated three times at 180° C. for 30 minutes and once at 250° C. for 15 minutes under microwave irradiation in a sealed tube. The reaction mixture was diluted with a 0.2 M aqueous solution of sodium hydroxide and extracted with three portions of tert-butyl methyl ether. The combined organic extracts were dried over sodium sulfate and concentrated in vacuo. Flash column chromatography and drying in high vacuo (70-90° C./1-2 mbar) for three hours gave 33 mg (12%) of the title compound as a yellow oil MS m/e (%): 586 (M+H$^+$, 100).

EXAMPLE 348

(1RS,4RS)- or (1RS,4SR)-2-(3,5-Bis-trifluoromethyl-phenyl)-N-[4-(4-fluoro-2-methyl-phenyl)-6-(4-hydroxymethyl-1-oxo-1$\lambda^4$-thiazolidin-3-yl)-pyridin-3-yl]-N-methyl-isobutyramide (Diastereomeric Racemate of Example 349)

and

EXAMPLE 349

(1RS,4SR)- or (1RS,4RS)-2-(3,5-Bis-trifluoromethyl-phenyl)-N-[4-(4-fluoro-2-methyl-phenyl)-6-(4-hydroxymethyl-1-oxo-1$\lambda^4$-thiazolidin-3-yl)-pyridin-3-yl]-N-methyl-isobutyramide (Diastereomeric Racemate of Example 348)

a) (RS)-2-(3,5-Bis-trifluoromethyl-phenyl)-N-[6-[2-(tert-butyl-dimethyl-silanyloxy)-1-hydroxymethyl-ethylamino]-4-(4-fluoro-2-methyl-phenyl)-pyridin-3-yl]-N-methyl-isobutyramide The title compound was obtained as a white solid in 42% yield after flash chromatography according to the procedure described above for the preparation of (S)-4-benzyl-3-(tert-butyl-dimethyl-silanyloxymethyl)-morpholine (Example 174a)) using 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide (Example 142) instead of (R)-(4-benzyl-morpholin-3-yl)-methanol.

MS m/e (%): 702 (M+H$^+$, 100)

b) (RS)-Thioacetic Acid 2-[5-{[2-(3,5-bis-trifluoromethyl-phenyl)-2-methyl-propionyl]-methyl-amino}-4-(4-fluoro-2-methyl-phenyl)-pyridin-2-ylamino]-3-(tert-butyl-dimethyl-silanyloxy)-propyl Ester To a solution of 0.19 mg (0.71 mmol) triphenylphosphine in 10 ml dry THF were added 0.12 g (0.71 mmol) diethyl azodicarboxylate at 0° C. under argon. After 30 min a solution of 0.50 g (0.71 mmol) (RS)-2-(3,5-bis-trifluoromethyl-phenyl)-N-[6-[2-(tert-butyl-dimethyl-silanyloxy)-1-hydroxymethyl-ethylamino]-4-(4-fluoro-2-methyl-phenyl)-pyridin-3-yl]-N-methyl-isobutyramide in 5 ml dry THF and 0.06 g (0.9 mmol) thioacetic acid were added. The reaction mixture was allowed to warm to room temperature over night. Dilution with a saturated aqueous solution of sodium hydrogencarbonate was followed by extraction with three portions of tert-butyl methyl ether. The combined organic extracts were dried over sodium sulfate and concentrated in vacuo. Flash column chromatography gave 0.28 g (52%) of the title compound as a white solid.

MS m/e (%): 760 (M+H$^+$, 100)

c) (RS)-2-(3,5-Bis-trifluoromethyl-phenyl)-N-[4-(4-fluoro-2-methyl-phenyl)-6-(2-hydroxy-1-mercaptomethyl-ethylamino)-pyridin-3-yl]-N-methyl-isobutyramide A mixture of 0.28 mg (0.37 mmol) (RS)-thioacetic acid 2-[5-{[2-(3,5-bis-trifluoromethyl-phenyl)-2-methyl-propionyl]-methyl-amino}-4-(4-fluoro-2-methyl-phenyl)-pyridin- 2-ylamino]-3-(tert-butyl-dimethyl-silanyloxy)-propyl ester in 10 ml ethanol and 4 ml of a 2 N solution of ammonia in ethanol was heated at reflux for 4 h. After cooling to room temperature the reaction mixture was concentrated in vacuo to give 0.22 g of the crude title compound as a light brown amorphous residue, which was used in the next step without any further purification.

d) (RS)-2-(3,5-Bis-trifluoromethyl-phenyl)-N-[6-[2-(tert-butyl-dimethyl-silanyloxy)-1-mercaptomethyl-ethylamino]-4-(4-fluoro-2-methyl-phenyl)-pyridin-3-yl]-N-methyl-isobutyramide The crude title compound was obtained as a light brown amorphous residue in quantitative yield after extraction according to the procedure described above for the preparation of (S)-4-benzyl-3-(tert-butyl-dimethyl-silanyloxymethyl)-morpholine (Example 174a)) using (RS)-2-(3,5-bis-trifluoromethyl-phenyl)-N-[4-(4-fluoro-2-methyl-phenyl)-6-(2-hydroxy-1-mercaptomethyl-ethylamino)-pyridin-3-yl]-N-methyl-isobutyramide instead of (R)-(4-benzyl-morpholin-3-yl)-methanol.

e) (RS)-2-(3,5-Bis-trifluoromethyl-phenyl)-N-[6-[4-(tert-butyl-dimethyl-silanyloxymethyl)-thiazolidin-3-yl]-4-(4-fluoro-2-methyl-phenyl)-pyridin-3-yl]-N-methyl-isobutyramide The title compound was obtained as a white solid in 39% yield after flash chromatography according to the procedure described above for the preparation of (RS)-2-(3,5-bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide (Example 342) using (RS)-2-(3,5-bis-trifluoromethyl-phenyl)-N-[6-[2-(tert-butyl-dimethyl-silanyloxy)-1-mercaptomethyl-ethylamino]-4-(4-fluoro-2-methyl-phenyl)-pyridin-3-yl]-N-methyl-isobutyramide instead of 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide.
MS m/e (%): 730 (M+H$^+$, 100)

f) (1RS,4RS)-2-(3,5-Bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide and (1RS,4SR)-2-(3,5-Bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide To a solution of 50 mg (0.069 mmol) (RS)-2-(3,5-bis-trifluoromethyl-phenyl)-N-[6-[4-(tert-butyl-dimethyl-silanyloxymethyl)-thiazolidin-3-yl]-4-(4-fluoro-2-methyl-phenyl)-pyridin-3-yl]-N-methyl-isobutyramide in 2 ml dichloromethane were added 17 mg (70%, 0.069 mmol) 3-chloroperbenzoic acid at 0° C. After completed addition, the reaction mixture was allowed to warm to room temperature during 3 h. A saturated aqueous solution of sodium carbonate was added and the mixture was extracted with three portions of dichloromethane. The combined organic extracts were dried over sodium sulphate and concentrated. The residue, 80 mg of a brown oil, was dissolved in 2 ml THF and treated with 0.07 ml (0.07 mmol) of a 1 M solution of tetrabutylammonium fluoride in THF at room temperature. After stirring at room temperature over night the reaction mixture was diluted with a 2 N aqueous solution of sodium carbonate and extracted with three portions of tert-butyl methyl ether. The combined organic extracts were dried over sodium sulphate and concentrated. Preparative thin layer chromatography gave 24 mg (55%) of one diastereomeric racemate of 2-(3,5-bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide as a white solid and 11 mg (25%) of the second diastereomeric racemate of 2-(3,5-bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide as a white solid. The assignment of the relative configuration of the two diastereomeric racemates was not possible.
(1RS,4RS)- or (1RS,4SR)-2-(3,5-Bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide:MS m/e (%): 632 (M+H$^+$, 100)
(1RS,4SR)- or (1RS,4RS)-2-(3,5-Bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide:MS m/e (%): 632 (M+H$^+$, 100)

EXAMPLE 350

(RS)-2-(3,5-Bis-trifluoromethyl-phenyl)-N-[4-(4-fluoro-2-methyl-phenyl)-6-(4-hydroxymethyl-1,1-dioxo-1λ$^6$-thiazolidin-3-yl)-pyridin-3-yl]-N-methyl-isobutyramide The title compound was obtained as an off-white solid in 83% yield from (RS)-2-(3,5-bis-trifluoromethyl-phenyl)-N-[6-[4-(tert-butyl-dimethyl-silanyloxymethyl)-thiazolidin-3-yl]-4-(4-fluoro-2-methyl-phenyl)-pyridin-3-yl]-N-methyl-isobutyramide after flash chromatography according to the procedure described above for the preparation of (1RS,4RS)-2-(3,5-bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide and (1RS,4SR)-2-(3,5-bis-trifluoromethyl-phenyl)-N-[4-(4-fluoro-2-methyl-phenyl)-6-(4-hydroxymethyl-1-oxo-1λ$^4$-thiazolidin-3-yl)-pyridin-3-yl]-N-methyl-isobutyramide (step f)) using two instead of one molar equivalents of 3-chloroperbenzoic acid.
MS m/e (%): 648 (M+H$^+$, 100)

EXAMPLE 351

(1S,5R)-2-(3,5-Bis-trifluoromethyl-phenyl)-N-[6-(8,8-dioxo-8λ$^6$-thia-3-aza-bicyclo[3.2.1]oct-3-yl)-4-(4-fluoro-2-methyl-phenyl)-pyridin-3-yl]-N-methyl-isobutyramide a) (1S,5R)-2-(3,5-Bis-trifluoromethyl-phenyl)-N-[4-(4-fluoro-2-methyl-phenyl)-6-8-thia-3-aza-bicyclo[3.2.1]oct-3-yl-pyridin-3-yl]-N-methyl-isobutyramide The title compound was obtained as a light yellow viscous oil in 22% yield after flash chromatography according to the procedure described above for the preparation of (2R,3S)-2-(3,5-bis-trifluoromethyl-phenyl)-N-[4-(4-fluoro-2-methyl-phenyl)-6-(3-hydroxy-2-hydroxymethyl-pyrrolidin-1-yl)-pyridin-3-yl]-N-methyl-isobutyramide (Example 155) using (1S,5R)-8-thia-3-azabicyclo[3.2.1]octane hydrochloride instead of (2R,3S)-2-(hydroxymethyl)-3-hydroxypyrrolidine
MS m/e (%): 626 (M+H$^+$, 100).

b) (1S,5R)-2-(3,5-Bis-trifluoromethyl-phenyl)-N-[6-(8,8-dioxo-8λ⁶-thia-3-aza-bicyclo[3.2.1]oct-3-yl)-4-(4-fluoro-2-methyl-phenyl)-pyridin-3-yl]-N-methyl-isobutyramide The title compound was obtained as an off-white solid in 42% yield after flash chromatography according to the procedure described above for the preparation of (S)-2-methanesulfonylmethyl-pyrrolidine-1-carboxylic acid benzyl ester (Example 307a)) using (1S,5R)-2-(3,5-bis-trifluoromethyl-phenyl)-N-[4-(4-fluoro-2-methyl-phenyl)-6-8-thia-3-aza-bicyclo[3.2.1]oct-3-yl-pyridin-3-yl]-N-methyl-isobutyramide instead of (S)-2-methylsulfanylmethyl-pyrrolidine-1-carboxylic acid benzyl ester.
MS m/e (%): 658 (M+H⁺, 100)

EXAMPLE 352

(+)-2-(3,5-Bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide The title compound was obtained as a white solid by preparative HPLC separation of (RS)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide (Example 178) on a Chiralpak AD column (heptane/ethanol 85:15).
MS m/e (%): 644 (M+H⁺, 100)

EXAMPLE 353

(−)-2-(3,5-Bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide The title compound was obtained in 81% enantiomeric excess as a white solid by preparative HPLC separation of (RS)-2-(3,5-bis-trifluoromethyl-phenyl)-N-[6-(3-hydroxymethyl-1,1-dioxo-1λ⁶-thiomorpholin-4-yl)-4-o-tolyl-pyridin-3-yl]-N-methyl-isobutyramide (Example 178) on a Chiralpak AD column (heptane/ethanol 85:15).
MS m/e (%): 644 (M+H⁺, 100)

EXAMPLE 354

(RS)-2-(3,5-Bis-trifluoromethyl-phenyl)-N-[4-(4-fluoro-2-methyl-phenyl)-6-(1-oxo-1λ⁴-[1,4]thiazepan-4-yl)-pyridin-3-yl]-N-methyl-isobutyramide
and

EXAMPLE 355

2-(3,5-Bis-trifluoromethyl-phenyl)-N-[6-(1,1-dioxo-1λ⁶-[1,4]thiazepan-4-yl)-4-(4-fluoro-2-methyl-phenyl)-pyridin-3-yl]-N-methyl-isobutyramide a) 2-(3,5-Bis-trifluoromethyl-phenyl)-N-[4-(4-fluoro-2-methyl-phenyl)-6-[1,4]thiazepan-4-yl-pyridin-3-yl]-N-methyl-isobutyramide The title compound was obtained as a white solid in 41% yield after flash chromatography according to the procedure described above for the preparation of 2-(3,5-bis-trifluoromethyl-phenyl)-N-[4'-(4-fluoro-2-methyl-phenyl)-4-trifluoromethyl-3,4,5,6-tetrahydro-2H-[1,2']bipyridinyl-5'-yl]-N-methyl-isobutyramide (Example 323) using [1,4]thiazepane hydrochloride instead of 4-(trifluoromethyl)piperidine hydrochloride.
MS m/e (%): 614 (M+H⁺, 100)

b) (RS)-2-(3,5-Bis-trifluoromethyl-phenyl)-N-[4-(4-fluoro-2-methyl-phenyl)-6-(1-oxo-1λ⁴-[1,4]thiazepan-4-yl)-pyridin-3-yl]-N-methyl-isobutyramide and 2-(3,5-Bis-trifluoromethyl-phenyl)-N-[6-(1,1-dioxo-1λ⁶-[1,4]thiazepan-4-yl)-4-(4-fluoro-2-methyl-phenyl)-pyridin-3-yl]-N-methyl-isobutyramide To a solution of 0.11 g (0.18 mmol) 2-(3,5-bis-trifluoromethyl-phenyl)-N-[4-(4-fluoro-2-methyl-phenyl)-6-[1,4]thiazepan-4-yl-pyridin-3-yl]-N-methyl-isobutyramide in 2 ml dichloromethane were added 63 mg (70%, 0.27 mmol) 3-chloroperbenzoic acid at room temperature. The reaction mixture was stirred over night. Dilution with a 2 M aqueous solution of sodium carbonate was followed by extraction with three portions of dichloromethane. The combined organic extracts were dried over sodium sulphate and concentrated. Flash column chromatography gave 71 mg (66%) of (RS)-2-(3,5-bis-trifluoromethyl-phenyl)-N-[4-(4-fluoro-2-methyl-phenyl)-6-(1-oxo-1λ⁴-[1,4]thiazepan-4-yl)-pyridin-3-yl]-N-methyl-isobutyramide as a white solid and 32 mg (29%) of 2-(3,5-bis-trifluoromethyl-phenyl)-N-[6-(1,1-dioxo-1λ⁶-[1,4]thiazepan-4-yl)-4-(4-fluoro-2-methyl-phenyl)-pyridin-3-yl]-N-methyl-isobutyramide as a white solid.
(RS)-2-(3,5-Bis-trifluoromethyl-phenyl)-N-[4-(4-fluoro-2-methyl-phenyl)-6-(1-oxo-1λ⁴-[1,4]thiazepan-4-yl)-pyridin-3-yl]-N-methyl-isobutyramide: MS m/e (%): 630 (M+H⁺, 100)
2-(3,5-bis-trifluoromethyl-phenyl)-N-[6-(1,1-dioxo-λ⁶-[1,4]thiazepan-4-yl)-4-(4-fluoro-2-methyl-phenyl)-pyridin-3-yl]-N-methyl-isobutyramide: MS m/e (%): 646 (M+H⁺, 100)

EXAMPLE 356

2-(3,5-Bis-trifluoromethyl-phenyl)-N-[6-(1,1-dioxo-1λ⁶-[1,3]thiazinan-3-yl)-4-(4-fluoro-2-methyl-phenyl)-pyridin-3-yl]-N-methyl-isobutyramide a) 2-(3,5-Bis-trifluoromethyl-phenyl)-N-[4-(4-fluoro-2-methyl-phenyl)-6-(3-hydroxy-propylamino)-pyridin-3-yl]-N-methyl-isobutyramide A mixture of 2.0 g (3.8 mmol) 2-(3,5-bis-trifluoromethyl-phenyl)-N-[6-chloro-4-(4-fluoro-2-methyl-phenyl)-pyridin-3-yl]-N-methyl-isobutyramide and 5.6 g (75 mmol) 3-amino-1-propanol was heated at 180° C. under microwave irradiation for 40 min. Dilution with water was followed by extraction with three portions of tert-butyl methyl ether. The combined organic extracts were dried over sodium sulfate and concentrated in vacuo. Flash chromatography gave 1.9 g (87%) of the title compound as a white solid.
MS m/e (%): 572 (M+H⁺, 100)

b) Thioacetic Acid 3-[5-{[2-(3,5-bis-trifluoromethyl-phenyl)-2-methyl-propionyl]-methyl-amino}-4-(4-fluoro-2-methyl-phenyl)-pyridin-2-ylamino]-propyl Ester The title compound was obtained as a white solid in 69% yield after flash chromatography according to the procedure described above for the preparation of (RS)-thioacetic acid 2-[5-{[2-(3,5-bis-trifluoromethyl-phenyl)-2-methyl-propionyl]-methyl-amino}-4-(4-fluoro-2-methyl-phenyl)-pyridin-2-ylamino]-3-(tert-butyl-dimethyl-silanyloxy)-propyl ester (Example 349b)) using 2-(3,5-bis-trifluoromethyl-phenyl)-N-[4-(4-fluoro-2-methyl-phenyl)-6-(3-hydroxy-propylamino)-pyridin-3-yl]-N-methyl-isobutyramide instead of (RS)-2-(3,5-bis-trifluoromethyl-phenyl)-N-[6-[2-(tert-butyl-dimethyl-silanyloxy)-1-hydroxymethyl-ethylamino]-4-(4-fluoro-2-methyl-phenyl)-pyridin-3-yl]-N-methyl-isobutyramide.

MS m/e (%): 630 (M+H$^+$, 100)

c) 2-(3,5-Bis-trifluoromethyl-phenyl)-N-[4-(4-fluoro-2-methyl-phenyl)-6-(3-mercapto-propylamino)-pyridin-3-yl]-N-methyl-isobutyramide To a solution of 1.3 g (2.0 mmol) thioacetic acid 3-[5-{[2-(3,5-bis-trifluoromethyl-phenyl)-2-methyl-propionyl]-methyl-amino}-4-(4-fluoro-2-methyl-phenyl)-pyridin-2-ylamino]-propyl ester in 20 ml methanol were added 5 ml of a 25% aqueous solution of ammonium hydroxide. The reaction mixture was heated at 50° C. for 1 h. After cooling to room temperature the mixture was acidified with 1 N aqueous hydrochloric acid solution and extracted with three portions of tert-butyl methyl ether. The combined organic layers were dried over sodium sulfate and concentrated in vacuo to give the crude title compound in quantitative yield as a light yellow solid.

MS m/e (%): 588 (M+H$^+$, 100)

d) 2-(3,5-Bis-trifluoromethyl-phenyl)-N-[4-(4-fluoro-2-methyl-phenyl)-6-[1,3]thiazinan-3-yl-pyridin-3-yl]-N-methyl-isobutyramide The title compound was obtained as a white solid in 68% yield after flash chromatography according to the procedure described above for the preparation of (RS)-2-(3,5-bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide (Example 342) using 2-(3,5-bis-trifluoromethyl-phenyl)-N-[4-(4-fluoro-2-methyl-phenyl)-6-(3-mercapto-propylamino)-pyridin-3-yl]-N-methyl-isobutyramide instead of 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide.

MS m/e (%): 600 (M+H$^+$, 100)

e) 2-(3,5-Bis-trifluoromethyl-phenyl)-N-[6-(1,1-dioxo-1$\lambda^6$-[1,3]thiazinan-3-yl)-4-(4-fluoro-2-methyl-phenyl)-pyridin-3-yl]-N-methyl-isobutyramide The title compound was obtained as a white solid in 73% yield after flash chromatography according to the procedure described above for the preparation of 2-(3,5-bis-trifluoromethyl-phenyl)-N-[4-(4-fluoro-2-methyl-phenyl)-6-(3-methanesulfonyl-azetidin-1-yl)-pyridin-3-yl]-N-methyl-isobutyramide (Example 324b)) using 2-(3,5-bis-trifluoromethyl-phenyl)-N-[4-(4-fluoro-2-methyl-phenyl)-6-[1,3]thiazinan-3-yl-pyridin-3-yl]-N-methyl-isobutyramide instead of 2-(3,5-bis-trifluoromethyl-phenyl)-N-[4-(4-fluoro-2-methyl-phenyl)-6-(3-methylsulfanyl-azetidin-1-yl)-pyridin-3-yl]-N-methyl-isobutyramide.

MS m/e (%): 632 (M+H$^+$, 100)

EXAMPLE 357

N-[6-(2-Amino-ethylamino)-4-(4-fluoro-2-methyl-phenyl)-pyridin-3-yl]-2-(3,5-bis-trifluoromethyl-phenyl)-N-methyl-isobutyramide A mixture of 1.0 g (1.9 mmol) 2-(3,5-bis-trifluoromethyl-phenyl)-N-[6-chloro-4-(4-fluoro-2-methyl-phenyl)-pyridin-3-yl]-N-methyl-isobutyramide and 5.0 ml (75 mmol) ethylenediamine was heated at 130° C. for 6 h. After cooling to room temperature the reaction mixture was diluted with 20 ml tert-butyl methyl ether and washed with 20 ml of a saturated aqueous solution of sodium carbonate, 20 ml of water and 20 ml of a saturated aqueous solution of sodium carbonate. The combined organic layers were dried over sodium sulfate, concentrated in vacuo and purified by flash chromatography to give 0.92 g (88%) of the title compound as a white foam.

MS m/e (%): 557 (M+H$^+$, 100)

EXAMPLE 358

2-(3,5-Bis-trifluoromethyl-phenyl)-N-[4-(4-fluoro-2-methyl-phenyl)-6-(2-methanesulfonylamino-ethylamino)-pyridin-3-yl]-N-methyl-isobutyramide The title compound was obtained as a white foam in 89% yield after flash chromatography according to the procedure described above for the preparation of (R)-2-(3,5-bis-trifluoromethyl-phenyl)-N-[4-(4-fluoro-2-methyl-phenyl)-6-(3-methanesulfonylamino-pyrrolidin-1-yl)-pyridin-3-yl]-N-methyl-isobutyramide (Example 317) using N-[6-(2-amino-ethylamino)-4-(4-fluoro-2-methyl-phenyl)-pyridin-3-yl]-2-(3,5-bis-trifluoromethyl-phenyl)-N-methyl-isobutyramide instead of (R)-N-[6-(3-amino-pyrrolidin-1-yl)-4-(4-fluoro-2-methyl-phenyl)-pyridin-3-yl]-2-(3,5-bis-trifluoromethyl-phenyl)-N-methyl-isobutyramide.

MS m/e (%): 633 ([M−H$^+$]$^-$, 74)

EXAMPLE 359

2-(3,5-Bis-trifluoromethyl-phenyl)-N-[4-(4-fluoro-2-methyl-phenyl)-6-(3-methanesulfonyl-imidazolidin-1-yl)-pyridin-3-yl]-N-methyl-isobutyramide To a solution of 0.20 g (0.36 mmol) N-[6-(2-amino-ethylamino)-4-(4-fluoro-2-methyl-phenyl)-pyridin-3-yl]-2-(3,5-bis-trifluoromethyl-phenyl)-N-methyl-isobutyramide in 2 ml 1,2-dichloroethane were added 42 mg (0.48 mmol) paraformaldehyde and 0.13 g (1.1 mmol) magnesium sulfate. After stirring at room temperature for 18 h 0.14 g (1.1 mmol) N,N-diisopropylethylamine, 2 mg (0.02 mmol) 4-(N,N-dimethylamino)pyridine and 62 mg (0.54 mmol) methanesulfonyl chloride were added. The reaction mixture was heated to 80° C. and kept at this temperature for 4 h. After cooling to room temperature the reaction mixture was diluted with 20 ml tert-butyl methyl ether and washed with two 20-ml portions of a saturated aqueous solution of sodium carbonate. The combined organic layers were dried over sodium sulfate, concentrated in vacuo and purified by flash chromatography to give 93 mg (40%) of the title compound as a white foam.

MS m/e (%): 647 (M+H$^+$, 100)

EXAMPLE 360

N-[6-(2-Acetylamino-ethylamino)-4-(4-fluoro-2-methyl-phenyl)-pyridin-3-yl]-2-(3,5-bis-trifluoromethyl-phenyl)-N-methyl-isobutyramide The title compound was obtained as an off-white solid in 48% yield after flash chromatography according to the procedure described above for the preparation of 2-(3,5-bis-trifluoromethyl-phenyl)-N-[4-(4-fluoro-2-methyl-phenyl)-6-(3-hydroxy-propylamino)-pyridin-3-yl]-N-methyl-isobutyramide (Example 356a)) using N-acetylethylenediamine instead of 3-amino-1-propanol.

MS m/e (%): 599 (M+H$^+$, 100)

EXAMPLE 361

N-[6-(3-Acetyl-imidazolidin-1-yl)-4-(4-fluoro-2-methyl-phenyl)-pyridin-3-yl]-2-(3,5-bis-trifluoromethyl-phenyl)-N-methyl-isobutyramide To a solution of 50 mg (0.090 mmol) N-[6-(2-amino-ethylamino)-4-(4-fluoro-2-methyl-phenyl)-pyridin-3-yl]-2-(3,5-bis-trifluoromethyl-phenyl)-N-methyl-isobutyramide in 2 ml 1,2-dichloroethane were added 3 mg (0.1 mmol) paraformaldehyde and 32 mg (0.27 mmol) magnesium sulfate. After stirring at room temperature over night another 3 mg (0.1 mmol) paraformaldehyde were added and the reaction mixture was heated to 85° C. After 1 h the reaction mixture was cooled to room temperature and treated with 14 mg (0.13 mmol) triethylamine and 11 mg (0.13 mmol) acetyl chloride. Conversion was monitored by thin layer chromatography. After complete consumption of the starting material the reaction mixture was diluted with water and extracted with three portions of dichloromethane. The combined organic layers were dried over sodium sulfate, concentrated in vacuo and purified by flash chromatography to give 40 mg (73%) of the title compound as an off-white solid.

MS m/e (%): 611 (M+H$^+$, 100)

EXAMPLE 362

2-(3,5-Bis-trifluoromethyl-phenyl)-N-[6-(4-methanesulfonyl-piperazin-1-yl)-4-o-tolyl-pyridin-3-yl]-N-methyl-isobutyramide a) 2-(3,5-Bis-trifluoromethyl-phenyl)-N-methyl-N-(6-piperazin-1-yl-4-o-tolyl-pyridin-3-yl)-isobutyramide The crude title compound was obtained as an off-white solid in 98% yield after extraction according to the procedure described above for the preparation of 2-(3,5-bis-trifluoromethyl-phenyl)-N-{4-(4-fluoro-phenyl)-6-[(2-hydroxy-ethyl)-methyl-amino]-pyridin-3-yl}-N-methyl-isobutyramide (Example 115) using 2-(3,5-bis-trifluoromethyl-phenyl)-N-(6-chloro-4-o-tolyl-pyridin-3-yl)-N-methyl-isobutyramide instead of 2-(3,5-bis-trifluoromethyl-phenyl)-N-[6-chloro-4-(4-fluoro-phenyl)-pyridin-3-yl]-N-methyl-isobutyramide and piperazine instead of 2-(methylamino)ethanol.

MS m/e (%): 565 (M+H$^+$, 100)

b) 2-(3,5-Bis-trifluoromethyl-phenyl)-N-[6-(4-methanesulfonyl-piperazin-1-yl)-4-o-tolyl-pyridin-3-yl]-N-methyl-isobutyramide To a solution of 0.16 g (0.31 mmol) 2-(3,5-bis-trifluoromethyl-phenyl)-N-methyl-N-(6-piperazin-1-yl-4-o-tolyl-pyridin-3-yl)-isobutyramide and 38 mg (0.38 mmol) triethylamine in 4 ml dichloromethane were added 38 mg (0.33 mmol) methanesulfonyl chloride at 0° C. After completed addition the reaction mixture was allowed to warm to room temperature. Conversion was monitored by thin layer chromatography. After complete consumption of the starting material the reaction mixture was diluted with water and extracted with three portions of tert-butyl methyl ether. The combined organic layers were dried over sodium sulfate and concentrated in vacuo. Flash column chromatography gave 0.15 g (75%) of the title compound as a white solid.

MS m/e (%): 643 (M+H$^+$, 100)

EXAMPLE 363

2-(3,5-Bis-trifluoromethyl-phenyl)-N-[4-(2-chloro-phenyl)-6-(4-methanesulfonyl-piperazin-1-yl)-pyridin-3-yl]-N-methyl-isobutyramide The title compound was obtained as a white solid in 73% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide instead of 2-(3,5-bis-trifluoromethyl-phenyl)-N-(6-chloro-4-o-tolyl-pyridin-3-yl)-N-methyl-isobutyramide in step a).

MS m/e (%): 663 (M+H$^+$, 100)

EXAMPLE 364

2-(3,5-Bis-trifluoromethyl-phenyl)-N-[4-(3-chloro-2-methyl-phenyl)-6-(4-methanesulfonyl-piperazin-1-yl)-pyridin-3-yl]-N-methyl-isobutyramide The title compound was obtained as a white solid in 79% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(3-chloro-2-methyl-phenyl)-pyridin-3-yl]-N-methyl-isobutyramide (Intermediate 4K) instead of 2-(3,5-bis-trifluoromethyl-phenyl)-N-(6-chloro-4-o-tolyl-pyridin-3-yl)-N-methyl-isobutyramide in step a).

MS m/e (%): 677 (M+H$^+$, 100)

EXAMPLE 365

2-(3,5-Bis-trifluoromethyl-phenyl)-N-[4-(3-fluoro-2-methyl-phenyl)-6-(4-methanesulfonyl-piperazin-1-yl)-pyridin-3-yl]-N-methyl-isobutyramide The title compound was obtained as a white solid in 77% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(3-fluoro-2-methyl-phenyl)-pyridin-3-yl]-N-methyl-isobutyramide (Intermediate 4E) instead of 2-(3,5-bis-trifluoromethyl-phenyl)-N-(6-chloro-4-o-tolyl-pyridin-3-yl)-N-methyl-isobutyramide in step a).

MS m/e (%): 661 (M+H$^+$, 100)

EXAMPLE 366

2-(3,5-Bis-trifluoromethyl-phenyl)-N-[4-(4-fluoro-2-methyl-phenyl)-6-(4-methanesulfonyl-piperazin-1-yl)-pyridin-3-yl]-N-methyl-isobutyramide The title compound was obtained as a white solid in 83% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide (Intermediate 4D) instead of 2-(3,5-bis-trifluoromethyl-phenyl)-N-(6-chloro-4-o-tolyl-pyridin-3-yl)-N-methyl-isobutyramide in step a).

MS m/e (%): 661 (M+H$^+$, 100)

EXAMPLE 367

2-(3,5-Bis-trifluoromethyl-phenyl)-N-[6-(4-ethanesulfonyl-piperazin-1-yl)-4-(4-fluoro-2-methyl-phenyl)-pyridin-3-yl]-N-methyl-isobutyramide The title compound was obtained as a white solid in 78% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide (Intermediate 4D) instead of 2-(3,5-bis-trifluoromethyl-phenyl)-N-(6-chloro-4-o-tolyl-pyridin-3-yl)-N-methyl-isobutyramide in step a) and ethanesulfonyl chloride instead of methanesulfonyl chloride in step b).

MS m/e (%): 675 (M+H$^+$, 100)

EXAMPLE 368

2-(3,5-Bis-trifluoromethyl-phenyl)-N-[6-(4-chloromethanesulfonyl-piperazin-1-yl)-4-(4-fluoro-2-methyl-phenyl)-pyridin-3-yl]-N-methyl-isobutyramide The title compound was obtained as a white solid in 84% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide (Intermediate 4D) instead of 2-(3,5-bis-trifluoromethyl-phenyl)-N-(6-chloro-4-o-tolyl-pyridin-3-yl)-N-methyl-isobutyramide in step a) and chloromethylsulfonyl chloride instead of methanesulfonyl chloride in step b).

MS m/e (%): 695 (M+H$^+$, 100)

EXAMPLE 369

2-(3,5-Bis-trifluoromethyl-phenyl)-N-[6-(4-dimethylsulfamoyl-piperazin-1-yl)-4-(4-fluoro-2-methyl-phenyl)-pyridin-3-yl]-N-methyl-isobutyramide The title compound was obtained as a white solid in 84% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide using 2-(3,5-bis-trifluoromethyl-phenyl)-N-[6-chloro-4-(4-fluoro-2-methyl-phenyl)-pyridin-3-yl]-N-methyl-isobutyramide (Intermediate 4D) instead of 2-(3,5-bis-trifluoromethyl-phenyl)-N-(6-chloro-4-o-tolyl-pyridin-3-yl)-N-methyl-isobutyramide in step a) and dimethylsulfamoyl chloride instead of methanesulfonyl chloride in step b).

MS m/e (%): 695 (M+H$^+$, 100)

EXAMPLE 370

(R)-2-(3,5-Bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide a) (R)-2-(3,5-Bis-trifluoromethyl-phenyl)-N-[4-(4-fluoro-2-methyl-phenyl)-6-(3-methyl-piperazin-1-yl)-pyridin-3-yl]-N-methyl-isobutyramide A mixture of 0.20 g (0.38 mmol) 2-(3,5-bis-trifluoromethyl-phenyl)-N-[6-chloro-4-(4-fluoro-2-methyl-phenyl)-pyridin-3-yl]-N-methyl-isobutyramide, 0.11 g (1.1 mmol) (R)-2-methylpiperazine and 0.10 g (0.72 mmol) potassium carbonate in 0.3 ml dimethyl sulfoxide was heated at 180° C. under microwave irradiation in a sealed tube for 30 min. After cooling to room temperature the reaction mixture was diluted with a 0.3 M aqueous solution of sodium hydroxide and extracted with three portions of tert-butyl methyl ether. The combined organic extracts were dried over sodium sulfate and concentrated. Flash column chromatography gave 0.12 g (51%) of the title compound as an off-white solid.

MS m/e (%): 597 (M+H$^+$, 100)

b) (R)-2-(3,5-Bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide The title compound was obtained as a white solid in 87% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using (R)-2-(3,5-bis-trifluoromethyl-phenyl)-N-[4-(4-fluoro-2-methyl-phenyl)-6-(3-methyl-piperazin-1-yl)-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 675 (M+H$^+$, 100)

EXAMPLE 371

(R)-2-(3,5-Bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide a) (R)-1-Benzyl-3-methyl-piperazine A mixture of 1.0 g (10 mmol) (R)-2-methylpiperazine, 1.3 g (10 mmol) benzyl chloride and 4.1 g (30 mmol) potassium carbonate in 10 ml ethanol was heated at reflux over night. After cooling to room temperature the reaction mixture was diluted with a 0.5 M aqueous solution of sodium hydroxide and extracted with three portions of dichloromethane. The combined organic extracts were dried over sodium sulfate and concentrated. Flash column chromatography gave 0.93 g (49%) of the title compound as an off-white solid.

MS m/e (%): 191 (M+H$^+$, 100)

b) (R)-N-[6-(4-Benzyl-2-methyl-piperazin-1-yl)-4-(4-fluoro-2-methyl-phenyl)-pyridin-3-yl]-2-(3,5-bis-trifluoromethyl-phenyl)-N-methyl-isobutyramide A mixture of 0.20 g (0.38 mmol) 2-(3,5-bis-trifluoromethyl-phenyl)-N-[6-chloro-4-(4-fluoro-2-methyl-phenyl)- pyridin-3-yl]-N-methyl-isobutyramide, 93 mg (0.49 mmol) (R)-1-benzyl-3-methyl-piperazine, 0.01 g (0.03 mmol) cetyl-trimethyl-ammonium bromide, 0.038 g (0.074 mmol) bis(tri-t-butylphosphine)palladium(0), 0.05 ml NaOH 50% and 2 ml toluene was degassed by two freeze-thaw cycles. The reaction mixture was heated under argon at 90° C. for 48 h. After cooling to room temperature the mixture was diluted with water and brine and extracted with three portions of tert-butyl methyl ether. The combined organic layers were dried over sodium sulphate and concentrated in vacuo. Flash column chromatography gave 95 mg (37%) of the title compound as a light yellow solid.

MS m/e (%): 687 (M+H$^+$, 100)

c) (R)-2-(3,5-Bis-trifluoromethyl-phenyl)-N-[4-(4-fluoro-2-methyl-phenyl)-6-(2-methyl-piperazin-1-yl)-pyridin-3-yl]-N-methyl-isobutyramide A solution of 0.11 g (0.17 mmol) (R)-N-[6-(4-benzyl-2-methyl-piperazin-1-yl)-4-(4-fluoro-2-methyl-phenyl)-pyridin-3-yl]-2-(3,5-bis-trifluoromethyl-phenyl)-N-methyl-isobutyramide in 3 ml acetic acid was deoxygenated by three cycles of evacuation and flushing with argon. After addition of 0.02 g palladium on charcoal (10%) the reaction vessel was evacuated and filled with hydrogen gas. The reaction mixture was stirred at room temperature under an atmosphere of hydrogen for 3 h. The reaction mixture was filtered over decalite followed by washing with tert-butyl methyl ether. The filtrate was washed with a 2 M aqueous solution of sodium hydroxide. The aqueous layer was extracted with three portions of tert-butyl methyl ether. The combined organic layers were dried over sodium sulfate and concentrated in vacuo to give 98 mg (98%) of the crude title compound as an off-white solid, which was used in the next step without further purification.

MS m/e (%): 597 (M+H$^+$, 100)

d) (R)-2-(3,5-Bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide The title compound was obtained as a white solid in 87% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using (R)-2-(3,5-bis-trifluoromethyl-phenyl)-N-[4-(4-fluoro-2-methyl-phenyl)-6-(2-methyl-piperazin-1-yl)-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 675 (M+H$^+$, 100)

EXAMPLE 372

(R)-2-(3,5-Bis-trifluoromethyl-phenyl)-N-[4-(2-chloro-phenyl)-6-(4-methanesulfonyl-2-methyl-piperazin-1-yl)-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using 2-(3,5-bis-trifluoromethyl-phenyl)-N-[6-chloro-4-(2-chloro-phenyl)-pyridin-3-yl]-N-methyl-isobutyramide (Intermediate 4A) instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 677 (M+H$^+$, 100)

EXAMPLE 373

(R)-2-(3,5-Bis-trifluoromethyl-phenyl)-N-[6-(4-methanesulfonyl-2-methyl-piperazin-1-yl)-4-o-tolyl-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide (Intermediate 4G) instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 657 (M+H$^+$, 100)

EXAMPLE 374

(S)-2-(3,5-Bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide (Example 370) using (S)-2-methylpiperazine instead of (R)-2-methylpiperazine in step a).

MS m/e (%): 675 (M+H$^+$, 100)

EXAMPLE 375

(S)-2-(3,5-Bis-trifluoromethyl-phenyl)-N-[4-(2-chloro-phenyl)-6-(–4-methanesulfonyl-3-methyl-piperazin-1-yl)-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide (Example 370) using (S)-2-methylpiperazine instead of (R)-2-methylpiperazine in step a) and 2-(3,5-bis-trifluoromethyl-phenyl)-N-[6-chloro-4-(2-chloro-phenyl)-pyridin-3-yl]-N-methyl-isobutyramide (Intermediate 4A) instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 677 (M+H$^+$, 100)

EXAMPLE 376

(S)-2-(3,5-Bis-trifluoromethyl-phenyl)-N-[6-(−4-methanesulfonyl-3-methyl-piperazin-1-yl)-4-o-tolyl-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide (Example 370) using (S)-2-methylpiperazine instead of (R)-2-methylpiperazine in step a) and 2-(3,5-bis-trifluoromethyl-phenyl)-N-(6-chloro-4-o-tolyl-pyridin-3-yl)-N-methyl-isobutyramide (Intermediate 4G) instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 657 (M+H$^+$, 100)

EXAMPLE 377

(S)-2-(3,5-Bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide The title compound was obtained as a white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using (S)-2-methylpiperazine instead of (R)-2-methylpiperazine in step a).

MS m/e (%): 675 (M+H$^+$, 100)

EXAMPLE 378

(2RS,5SR)-2-(3,5-Bis-trifluoromethyl-phenyl)-N-[4-(4-fluoro-2-methyl-phenyl)-6-(4-methanesulfonyl-2,5-dimethyl-piperazin-1-yl)-pyridin-3-yl]-N-methyl-isobutyramide a) (2RS,5SR)-2-(3,5-Bis-trifluoromethyl-phenyl)-N-[6-(2,5-dimethyl-piperazin-1-yl)-4-(4-fluoro-2-methyl-phenyl)-pyridin-3-yl]-N-methyl-isobutyramide A mixture of 0.20 g (0.38 mmol) 2-(3,5-bis-trifluoromethyl-phenyl)-N-[6-chloro-4-(4-fluoro-2-methyl-phenyl)-pyridin-3-yl]-N-methyl-isobutyramide, 87 mg (0.75 mmol) (2RS,5SR)-dimethyl-piperazine, 0.01 g (0.03 mmol) cetyltrimethyl-ammonium bromide, 0.01 g (0.02 mmol) bis(tri-t-butylphosphine)palladium(0), 0.075 ml NaOH 50% and 3 ml toluene was degassed by two freeze-thaw cycles. The reaction mixture was heated under argon at 90° C. for 48 h. After cooling to room temperature the mixture was diluted with water and brine and extracted with three portions of tert-butyl methyl ether. The combined organic layers were dried over sodium sulphate and concentrated in vacuo. Flash column chromatography gave 96 mg (42%) of the title compound as a light yellow solid.

MS m/e (%): 611 (M+H$^+$, 100)

b) (2RS,5SR)-2-(3,5-Bis-trifluoromethyl-phenyl)-N-[4-(4-fluoro-2-methyl-phenyl)-6-(4-methanesulfonyl-2,5-dimethyl-piperazin-1-yl)-pyridin-3-yl]-N-methyl-isobutyramide The title compound was obtained as a white solid in 69% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using (2RS,5SR)-2-(3,5-bis-trifluoromethyl-phenyl)-N-[6-(2,5-dimethyl-piperazin-1-yl)-4-(4-fluoro-2-methyl-phenyl)-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 689 (M+H$^+$, 100)

EXAMPLE 379

(2S,6R)-2-(3,5-Bis-trifluoromethyl-phenyl)-N-[4-(4-fluoro-2-methyl-phenyl)-6-(4-methanesulfonyl-2,6-dimethyl-piperazin-1-yl)-pyridin-3-yl]-N-methyl-isobutyramide The title compound was obtained as a white solid in 1% overall yield after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using cis-2,6-dimethyl-piperazine instead of (R)-2-methylpiperazine in step a).

MS m/e (%): 689 (M+H$^+$, 100)

EXAMPLE 380

(3S,5R)-2-(3,5-Bis-trifluoromethyl-phenyl)-N-[4-(4-fluoro-2-methyl-phenyl)-6-(4-methanesulfonyl-3,5-dimethyl-piperazin-1-yl)-pyridin-3-yl]-N-methyl-isobutyramide The title compound was obtained as a white solid in 56% yield after flash chromatography according to the procedures described above for the preparation of (2RS,5SR)-2-(3,5-bis-trifluoromethyl-phenyl)-N-[4-(4-fluoro-2-methyl-phenyl)-6-(4-methanesulfonyl-2,5-dimethyl-piperazin-1-yl)-pyridin-3-yl]-N-methyl-isobutyramide using cis-2,6-dimethyl-piperazine instead of (2RS,5SR)-dimethyl-piperazine in step a).

MS m/e (%): 689 (M+H$^+$, 100)

EXAMPLE 381

(1S,4S)-2-(3,5-Bis-trifluoromethyl-phenyl)-N-[4-(4-fluoro-2-methyl-phenyl)-6-((1S,4S)-5-methanesulfonyl-2,5-diaza-bicyclo[2.2.1]hept-2-yl)-pyridin-3-yl]-N-methyl-isobutyramide a) (1S,4S)-N-[6-(5-Benzyl-2,5-diaza-bicyclo[2.2.1]hept-2-yl)-4-(4-fluoro-2-methyl-phenyl)-pyridin-3-yl]-2-(3,5-bis-trifluoromethyl-phenyl)-N-methyl-isobutyramide The title compound was obtained as an off-white solid in 85% yield after flash chromatography according to the procedure described above for the preparation of 2-(3,5-bis-trifluoromethyl-phenyl)-N-[4'-(4-fluoro-2-methyl-phenyl)-4-trifluoromethyl-3,4,5,6-tetrahydro-2H-[1,2']bipyridinyl- 5'-yl]-N-methyl-isobutyramide using (1S,4S)-(+)-2-benzyl-2,5-diazabicyclo[2.2.1]heptane dihydrobromide instead of 4-(trifluoromethyl)piperidine hydrochloride.
MS m/e (%): 685 (M+H$^+$, 100)

b) (1S,4S)-2-(3,5-Bis-trifluoromethyl-phenyl)-N-[4-(4-fluoro-2-methyl-phenyl)-6-(5-methanesulfonyl-2, 5-diaza-bicyclo F 2.2.1 hept-2-yl)-pyridin-3-yl]-N-methyl-isobutyramide The title compound was obtained as a white solid in 80% yield after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide (Example 371 steps c) and d)) using (1S,4S)-N-[6-(5-benzyl-2,5-diaza-bicyclo[2.2.1]hept-2-yl)-4-(4-fluoro-2-methyl-phenyl)-pyridin-3-yl]-2-(3,5-bis-trifluoromethyl-phenyl)-N-methyl-isobutyramide instead of (R)-N-[6-(4-benzyl-2-methyl-piperazin-1-yl)-4-(4-fluoro-2-methyl-phenyl)-pyridin-3-yl]-2-(3,5-bis-trifluoromethyl-phenyl)-N-methyl-isobutyramide in step c).
MS m/e (%): 673 (M+H$^+$, 100)

EXAMPLE 382

(1R,5S)-2-(3,5-Bis-trifluoromethyl-phenyl)-N-[4-(4-fluoro-2-methyl-phenyl)-6-(8-methanesulfonyl-3,8-diaza-bicyclo[3.2.1]oct-3-yl)-pyridin-3-yl]-N-methyl-isobutyramide The title compound was obtained as a white solid in comparable yields after flash chromatography according to the procedures described above for the preparation of (1S,4S)-2-(3,5-bis-trifluoromethyl-phenyl)-N-[4-(4-fluoro-2-methyl-phenyl)-6-(5-methanesulfonyl-2,5-diaza-bicyclo[2.2.1]hept-2-yl)-pyridin-3-yl]-N-methyl-isobutyramide using (1R,5S)-8-benzyl-3,8-diazabicyclo[3.2.1]octane dihydrochloride instead of (1S,4S)-(+)-2-benzyl-2,5-diazabicyclo[2.2.1]heptane dihydrobromide in step a).
MS m/e (%): 687 (M+H$^+$, 100)

EXAMPLE 383

(S)-2-(3,5-Bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide a) (S)-N-[6-(2-Benzyloxymethyl-piperazin-1-yl)-4-(4-fluoro-2-methyl-phenyl)-pyridin-3-yl]-2-(3,5-bis-trifluoromethyl-phenyl)-N-methyl-isobutyramide The title compound was obtained as a light brown solid in comparable yields according to the procedures described above for the preparation of (R)-2-(3,5-bis-trifluoromethyl-phenyl)-N-[4-(4-fluoro-2-methyl-phenyl)-6-(2-methyl-piperazin-1-yl)-pyridin-3-yl]-N-methyl-isobutyramide (Example 371c)) using (S)-1-benzyl-3-(benzyloxymethyl)piperazine (prepared as described in WO2001009111) instead of (R)-1-benzyl-3-methyl-piperazine in step b).
MS m/e (%): 703 (M+H$^+$, 100)

b) (S)-N-[6-(2-Benzyloxymethyl-4-methanesulfonyl-piperazin-1-yl)-4-(4-fluoro-2-methyl-phenyl)-pyridin-3-yl]-2-(3,5-bis-trifluoromethyl-phenyl)-N-methyl-isobutyramide The title compound was obtained as a white solid in 89% yield after flash chromatography according to the procedures described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using (S)-N-[6-(2-benzyloxymethyl-piperazin-1-yl)-4-(4-fluoro-2-methyl-phenyl)-pyridin-3-yl]-2-(3,5-bis-trifluoromethyl-phenyl)-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.
MS m/e (%): 781 (M+H$^+$, 100)

c) (S)-2-(3,5-Bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide The title compound was obtained as an off-white solid in 72% yield after flash chromatography according to the procedures described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide (Example 152b)) using (S) —N-[6-(2-benzyloxymethyl-4-methanesulfonyl-piperazin-1-yl)-4-(4-fluoro-2-methyl-phenyl)-pyridin-3-yl]-2-(3,5-bis-trifluoromethyl-phenyl)-N-methyl-isobutyramide instead of (1R,2R)-N-[6-(2-benzyloxy-cyclopentylamino)-4-(2-chloro-phenyl)-pyridin-3-yl]-2-(3,5-bis-trifluoromethyl-phenyl)-N-methyl-isobutyramide.
MS m/e (%): 691 (M+H$^+$, 100)

EXAMPLE 384

(S)-2-(3,5-Bis-trifluoromethyl-phenyl)-N-[4-(4-fluoro-2-methyl-phenyl)-6-(4-formyl-2-hydroxymethyl-piperazin-1-yl)-pyridin-3-yl]-N-methyl-isobutyramide A mixture of 0.35 ml (3.7 mmol) acetic anhydride and 0.17 ml (4.6 mmol) formic acid was heated at 50° C. for 2 h. After cooling to room temperature a portion of 0.08 ml of this mixture was added to 0.5 ml THF. A solution of 0.10 g (0.14 mmol) (S)-N-[6-(2-benzyloxymethyl-piperazin-1-yl)-4-(4-fluoro-2-methyl-phenyl)-pyridin-3-yl]-2-(3,5-bis-trifluoromethyl-phenyl)-N-methyl-isobutyramide (Example 383a)) in 1 ml THF was added dropwise at 0° C. Conversion was monitored by thin layer chromatography. After complete consumption of the starting material the reaction mixture was diluted with water and extracted with three portions of dichloromethane. The combined organic extracts were dried over sodium sulfate and concentrated in vacuo to give 0.11 g of crude (S)-N-[6-(2-benzyloxymethyl-4-formyl-piperazin-1-yl)-4-(4-fluoro-2-methyl-phenyl)-pyridin-3-yl]-2-(3,5-bis-trifluoromethyl-phenyl)-N-methyl-isobutyramide as a light yellow solid.

The title compound was obtained as a white solid in 58% yield after flash chromatography according to the procedure described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide (Example 152b)) using crude (S)-N-[6-(2-benzyloxymethyl-4-formyl-piperazin-1-yl)-4-(4-fluoro-2-methyl-phenyl)-pyridin-3-yl]-2-(3,5-bis-trifluoromethyl-phenyl)-N-methyl-isobutyramide instead of (1R,2R)-N-[6-(2-benzyloxy-cyclopentylamino)-4-(2-chloro-phenyl)-pyridin-3-yl]-2-(3,5-bis-trifluoromethyl-phenyl)-N-methyl-isobutyramide.
MS m/e (%): 641 (M+H$^+$, 100)

EXAMPLE 385

(S)-2-(3,5-Bis-trifluoromethyl-phenyl)-N-[6-(4-cyclopropanecarbonyl-2-hydroxymethyl-piperazin-1-yl)-4-(4-fluoro-2-methyl-phenyl)-pyridin-3-yl]-N-methyl-isobutyramide The title compound was obtained as an off-white solid in comparable yields after flash chromatography according to the procedures described above for the preparation of (S)-2-(3,5-bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide using cyclopropanecarboxylic acid chloride instead of methanesulfonyl chloride in step b).
MS m/e (%): 681 (M+H$^+$, 100)

EXAMPLE 386

(S)-N-[6-(4-Acetyl-2-hydroxymethyl-piperazin-1-yl)-4-(4-fluoro-2-methyl-phenyl)-pyridin-3-yl]-2-(3,5-bis-trifluoromethyl-phenyl)-N-methyl-isobutyramide The title compound was obtained as an off-white solid in comparable yields after flash chromatography according to the procedures described above for the preparation of (S)-2-(3,5-bis-trifluoromethyl-phenyl)-N-[4-(4-fluoro-2-methyl-phenyl)-6-(2-hydroxymethyl-4-methanesulfonyl-piperazin-1-yl)-pyridin-3-yl]-N-methyl-isobutyramide using acetic anhydride instead of methanesulfonyl chloride in step b).
MS m/e (%): 655 (M+H$^+$, 100)

EXAMPLE 387

(S)-2-(3,5-Bis-trifluoromethyl-phenyl)-N-[6-(4-ethyl-2-hydroxymethyl-piperazin-1-yl)-4-(4-fluoro-2-methyl-phenyl)-pyridin-3-yl]-N-methyl-isobutyramide a) (S)-N-[6-(2-Benzyloxymethyl-4-ethyl-piperazin-1-yl)-4-(4-fluoro-2-methyl-phenyl)-pyridin-3-yl]-2-(3,5-bis-trifluoromethyl-phenyl)-N-methyl-isobutyramide The title compound was obtained as a light brown solid in 5% yield in step c) according to the procedures described above for the preparation of (R)-2-(3,5-bis-trifluoromethyl-phenyl)-N-[4-(4-fluoro-2-methyl-phenyl)-6-(2-methyl-piperazin-1-yl)-pyridin-3-yl]-N-methyl-isobutyramide (Example 371c)) using (S)-1-benzyl-3-(benzyloxymethyl)piperazine (prepared as described in WO2001009111) instead of (R)-1-benzyl-3-methyl-piperazine in step b) and ethanol instead of acetic acid as a solvent in step c).
MS m/e (%): 731 (M+H$^+$, 100)

b) (S)-2-(3,5-Bis-trifluoromethyl-phenyl)-N-[6-(4-ethyl-2-hydroxymethyl-piperazin-1-yl)-4-(4-fluoro-2-methyl-phenyl)-pyridin-3-yl]-N-methyl-isobutyramide The title compound was obtained as a white solid in 58% yield after flash chromatography according to the procedure described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide (Example 152b)) using (S)-N-[6-(2-benzyloxymethyl-4-ethyl-piperazin-1-yl)-4-(4-fluoro-2-methyl-phenyl)-pyridin-3-yl]-2-(3,5-bis-trifluoromethyl-phenyl)-N-methyl-isobutyramide instead of (1R,2R)-N-[6-(2-benzyloxy-cyclopentylamino)-4-(2-chloro-phenyl)-pyridin-3-yl]-2-(3,5-bis-trifluoromethyl-phenyl)-N-methyl-isobutyramide.
MS m/e (%): 641 (M+H$^+$, 100)

EXAMPLE 388

2-(3,5-Bis-trifluoromethyl-phenyl)-N-[4-(2-chloro-phenyl)-6-(2-methylsulfamoyl-ethylamino)-pyridin-3-yl]-N-methyl-isobutyramide a) 2-[5-{[2-(3,5-Bis-trifluoromethyl-phenyl)-2-methyl-propionyl]-methyl-amino}-4-(2-chloro-phenyl)-pyridin-2-ylamino]-ethanesulfonic Acid The title compound was obtained as a light brown solid in 49% yield after flash column chromatography according to the procedure described above for the preparation of (S)-2-(3,5-bis-trifluoromethyl-phenyl)-N-[4-(4-fluoro-2-methyl-phenyl)-6-(2-hydroxymethyl-pyrrolidin-1-yl)-pyridin-3-yl]-N-methyl-isobutyramide (Example 165) using 2-(3,5-bis-trifluoromethyl-phenyl)-N-[6-chloro-4-(2-chloro-phenyl)-pyridin-3-yl]-N-methyl-isobutyramide (Intermediate 4A) instead of 2-(3,5-bis-trifluoromethyl-phenyl)-N-[6-chloro-4-(4-fluoro-2-methyl-phenyl)-pyridin-3-yl]-N-methyl-isobutyramide and taurine instead of L-prolinol.
MS m/e (%): 622 ([M−H$^+$]$^-$, 100)

b) 2-(3,5-Bis-trifluoromethyl-phenyl)-N-[4-(2-chloro-phenyl)-6-(2-methylsulfamoyl-ethylamino)-pyridin-3-yl]-N-methyl-isobutyramide The title compound was obtained as a white solid in 77% yield after flash column chromatography according to the procedure described above for the preparation of 2-(3,5-bis-trifluoromethyl-phenyl)-N-[4-dimethylsulfamoyl-4'-(4-fluoro-2-methyl-phenyl)-3,4,5,6-tetrahydro-2H-[1,2']bipyridinyl-5'-yl]-N-methyl-isobutyramide (Example 331 step c)) using a 12 M aqueous solution of N-methylamine instead of a solution of dimethylamine.
MS m/e (%): 637 (M+H$^+$, 100)

EXAMPLE 389

2-(3,5-Bis-trifluoromethyl-phenyl)-N-[4-(2-chloro-phenyl)-6-(2-methyl-1,1-dioxo-1$\lambda^6$-[1,2,4]thiadiazinan-4-yl)-pyridin-3-yl]-N-methyl-isobutyramide The title compound was obtained as a white solid in 31% yield after flash chromatography according to the procedure described above for the preparation of (RS)-2-(3,5-bis-trifluoromethyl-phenyl)-N-[4-(4-fluoro-2-methyl-phenyl)-6-(4-hydroxymethyl-oxazolidin-3-yl)-pyridin-3-yl]-N-methyl-isobutyramide (Example 342) using 2-(3,5-bis-trifluoromethyl-phenyl)-N-[4-(2-chloro-phenyl)-6-(2-methylsulfamoyl-ethylamino)-pyridin-3-yl]-N-methyl-isobutyramide instead of 2-(3,5-bis-trifluoromethyl-phenyl)-N-[4-(4-fluoro-2-methyl-phenyl)-6-(2-hydroxy-1-hydroxymethyl-ethylamino)-pyridin-3-yl]-N-methyl-isobutyramide
MS m/e (%): 649 (M+H$^+$, 100).

EXAMPLE 390

(RS)-2-(3,5-Bis-trifluoromethyl-phenyl)-N-[4-(2-chloro-phenyl)-6-(2-oxo-2$\lambda^4$-[1,2,3]oxathiazolidin-3-yl)-pyridin-3-yl]-N-methyl-isobutyramide To a solution of 0.20 g (0.36 mmol) 2-(3,5-bis-trifluoromethyl-phenyl)-N-[4-(2-chloro-phenyl)-6-(2-hydroxy-ethylamino)-pyridin-3-yl]-N-methyl-isobutyramide in a 5 ml dichloromethane were added consecutively 0.11 g (1.1 mmol) triethylamine and 0.05 g (0.4 mmol) thionyl chloride at room temperature. After 1 h the reaction mixture was diluted with water and extracted with three portions of dichloromethane. The combined organic extracts were dried over sodium sulfate and concentrated in vacuo. Flash column chromatography gave 0.17 g (77%) of the title compound as a white solid.

MS m/e (%): 606 (M+H$^+$, 100)

EXAMPLE 391

(S)-2-(3,5-Bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide a) (S)-4-Benzyl-2-benzyloxymethyl-1-methanesulfonyl-piperazine The crude title compound was obtained as a light brown oil in quantitative yield after extraction according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using (S)-1-benzyl-3-(benzyloxymethyl)piperazine instead of 2-(3,5-bis-trifluoromethyl-phenyl)-N-methyl-N-(6-piperazin-1-yl-4-o-tolyl-pyridin-3-yl)-isobutyramide.

MS m/e (%): 375 (M+H$^+$, 100)

b) (S)-2-Benzyloxymethyl-1-methanesulfonyl-piperazine

The crude title compound was obtained as a light brown oil in 60% yield after extraction according to the procedure described above for the preparation of (R)-2-(3,5-bis-trifluoromethyl-phenyl)-N-[4-(4-fluoro-2-methyl-phenyl)-6-(2-methyl-piperazin-1-yl)-pyridin-3-yl]-N-methyl-isobutyramide (Example 371c)) using (S)-4-benzyl-2-benzyloxymethyl-1-methanesulfonyl-piperazine instead of (R)-N-[6-(4-benzyl-2-methyl-piperazin-1-yl)-4-(4-fluoro-2-methyl-phenyl)-pyridin-3-yl]-2-(3,5-bis-trifluoromethyl-phenyl)-N-methyl-isobutyramide.

MS m/e (%): 285 (M+H$^+$, 100)

c) (S)-N-[6-(3-Benzyloxymethyl-4-methanesulfonyl-piperazin-1-yl)-4-(4-fluoro-2-methyl-phenyl)-pyridin-3-yl]-2-(3,5-bis-trifluoromethyl-phenyl)-N-methyl-isobutyramide The title compound was obtained as a white solid in 55% yield after flash chromatography according to the procedure described above for the preparation of (R)-N-[6-(4-benzyl-2-methyl-piperazin-1-yl)-4-(4-fluoro-2-methyl-phenyl)-pyridin-3-yl]-2-(3,5-bis-trifluoromethyl-phenyl)-N-methyl-isobutyramide (Example 371b)) using (S)-2-benzyloxymethyl-1-methanesulfonyl-piperazine instead of (R)-1-benzyl-3-methyl-piperazine.

MS m/e (%): 781 (M+H$^+$, 100)

d) (S)-2-(3,5-Bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide The title compound was obtained as a white solid in 96% yield after flash chromatography according to the procedure described above for the preparation of (1R,2R)-2-(3,5-bis-trifluoromethyl-phenyl)-N-[4-(2-chloro-phenyl)-6-(2-hydroxy-cyclopentylamino)-pyridin-3-yl]-N-methyl-isobutyramide (Example 152b)) using (S)-N-[6-(3-benzyloxymethyl-4-methanesulfonyl-piperazin-1-yl)-4-(4-fluoro-2-methyl-phenyl)-pyridin-3-yl]-2-(3,5-bis-trifluoromethyl-phenyl)-N-methyl-isobutyramide instead of (1R,2R)-N-[6-(2-benzyloxy-cyclopentylamino)-4-(2-chloro-phenyl)-pyridin-3-yl]-2-(3,5-bis-trifluoromethyl-phenyl)-N-methyl-isobutyramide.

MS m/e (%): 691 (M+H$^+$, 100)

EXAMPLE 392

(R)-2-(3,5-Bis-trifluoromethyl-phenyl)-N-[6-(3-hydroxymethyl-4-methanesulfonyl-piperazin-1-yl)-4-o-tolyl-pyridin-3-yl]-N-methyl-isobutyramide The title compound was obtained as white solid in comparable yields after flash column chromatography according to the procedures described above for the preparation of (S)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide using (R)-instead of (S)-1-benzyl-3-(benzyloxymethyl)piperazine in step a) and 2-(3,5-bis-trifluoromethyl-phenyl)-N-(6-chloro-4-o-tolyl-pyridin-3-yl)-N-methyl-isobutyramide (Intermediate 4G) instead of 2-(3,5-bis-trifluoromethyl-phenyl)-N-[6-chloro-4-(4-fluoro-2-methyl-phenyl)-pyridin-3-yl]-N-methyl-isobutyramide in step c).

MS m/e (%): 673 (M+H$^+$, 100)

EXAMPLE 393

(R)-2-(3,5-Bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide The title compound was obtained as white solid in comparable yields after flash column chromatography according to the procedures described above for the preparation of (S)-2-(3,5-bis-trifluoromethyl-phenyl)-N-[4-(4-fluoro-2-methyl-phenyl)-6-(3-hydroxymethyl-4-methanesulfonyl-piperazin-1-yl)-pyridin-3-yl]-N-methyl-isobutyramide using (R)-instead of (S)-1-benzyl-3-(benzyloxymethyl)piperazine in step a).

MS m/e (%): 691 (M+H$^+$, 100)

EXAMPLE 394

2-(3,5-Bis-trifluoromethyl-phenyl)-N-[4-(4-fluoro-2-methyl-phenyl)-6-(4-methanesulfonyl-3,3-dimethyl-piperazin-1-yl)-pyridin-3-yl]-N-methyl-isobutyramide a) 2-(3,5-Bis-trifluoromethyl-phenyl)-N-[6-(3,3-dimethyl-piperazin-1-yl)-4-(4-fluoro-2-methyl-phenyl)-pyridin-3-yl]-N-methyl-isobutyramide The title compound was obtained as a light brown amorphous resin in 27% yield after flash column chromatography according to the procedure described above for the preparation of 2-(3,5-bis-trifluoromethyl-phenyl)-N-[4'-(4-fluoro-2-methyl-phenyl)-4-trifluoromethyl-3,4,5,6-tetrahydro-2H-[1,2']bipyridinyl-5'-yl]-N-methyl-isobutyramide (Example 323) using 2,2-dimethyl-piperazine di-acetic acid salt instead of 4-(trifluoromethyl)piperidine hydrochloride.

MS m/e (%): 611 (M+H$^+$, 100)

b) 2-(3,5-Bis-trifluoromethyl-phenyl)-N-[4-(4-fluoro-2-methyl-phenyl)-6-(4-methanesulfonyl-3,3-dimethyl-piperazin-1-yl)-pyridin-3-yl]-N-methyl-isobutyramide The title compound was obtained as a white solid in 69% yield after flash column chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using 2-(3,5-bis-trifluoromethyl-phenyl)-N-[6-(dimethyl-piperazin-1-yl)-4-(4-fluoro-2-methyl-phenyl)-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 689 (M+H$^+$, 100)

EXAMPLE 395

2-(3,5-Bis-trifluoromethyl-phenyl)-N-[6-(4-methanesulfonyl-3,3-dimethyl-piperazin-1-yl)-4-o-tolyl-pyridin-3-yl]-N-methyl-isobutyramide The title compound was obtained as white solid in comparable yields after flash column chromatography according to the procedures described above for the preparation of 2-(3,5-bis-trifluoromethyl-phenyl)-N-[4-(4-fluoro-2-methyl-phenyl)-6-(4-methanesulfonyl-3,3-dimethyl-piperazin-1-yl)-pyridin-3-yl]-N-methyl-isobutyramide using 2-(3,5-bis-trifluoromethyl-phenyl)-N-(6-chloro-4-o-tolyl-pyridin-3-yl)-N-methyl-isobutyramide (Intermediate 4G) instead of 2-(3,5-bis-trifluoromethyl-phenyl)-N-[6-chloro-4-(4-fluoro-2-methyl-phenyl)-pyridin-3-yl]-N-methyl-isobutyramide in step a).

MS m/e (%): 671 (M+H$^+$, 100)

EXAMPLE 396

(S)-2-(3,5-Bis-trifluoromethyl-phenyl)-N-[4-(2-hydroxymethyl-phenyl)-6-(-4-methanesulfonyl-3-methyl-piperazin-1-yl)-pyridin-3-yl]-N-methyl-isobutyramide a) 2-(3,5-Bis-trifluoromethyl-phenyl)-N-[4-[2-(tert-butyl-dimethyl-silanyloxymethyl)-phenyl]-6-((S)-4-methanesulfonyl-3-methyl-piperazin-1-yl)-pyridin-3-yl]-N-methyl-isobutyramide The title compound was obtained as a white solid in comparable yields after flash column chromatography according to the procedures described above for the preparation of (R)-2-(3,5-bis-trifluoromethyl-phenyl)-N-[4-(4-fluoro-2-methyl-phenyl)-6-(4-methanesulfonyl-3-methyl-piperazin-1-yl)-pyridin-3-yl]-N-methyl-isobutyramide (Example 370) using (S)-2-methylpiperazine instead of (R)-2-methylpiperazine in step a) and 2-(3,5-bis-trifluoromethyl-phenyl)-N-{4-[2-(tert-butyl-dimethyl-silanyloxymethyl)-phenyl]-6-chloro-pyridin-3-yl}-N-methyl-isobutyramide (Intermediate 4L) instead of 2-(3,5-bis-trifluoromethyl-phenyl)-N-[6-chloro-4-(4-fluoro-2-methyl-phenyl)-pyridin-3-yl]-N-methyl-isobutyramide in step b).

MS m/e (%): 787 (M+H$^+$, 100)

b) (S)-2-(3,5-Bis-trifluoromethyl-phenyl)-N-[4-(2-hydroxymethyl-phenyl)-6-(-4-methanesulfonyl-3-methyl-piperazin-1-yl)-pyridin-3-yl]-N-methyl-isobutyramide A solution of 73 mg (0.093 mmol) 2-(3,5-bis-trifluoromethyl-phenyl)-N-[4-[2-(tert-butyl-dimethyl-silanyloxymethyl)-phenyl]-6-((S)-4-methanesulfonyl-3-methyl-piperazin-1-yl)-pyridin-3-yl]-N-methyl-isobutyramide in 5 ml of a 1 M solution of hydrochloric acid in methanol was stirred at room temperature. Conversion was monitored by thin layer chromatography. After complete consumption of the starting material the reaction mixture was diluted with a 1 M aqueous solution of sodium hydroxide and extracted with three portions of tert-butyl methyl ether. The combined organic extracts were dried over sodium sulfate and concentrated in vacuo. Flash column chromatography gave 62 mg (quantitative) of the title compound as a light yellow solid.

MS m/e (%): 673 (M+H$^+$, 100)

EXAMPLE 397

2-(3,5-Bis-trifluoromethyl-phenyl)-N-[4-(4-fluoro-2-methyl-phenyl)-6-(4-methanesulfonyl-2,2-dimethyl-piperazin-1-yl)-pyridin-3-yl]-N-methyl-isobutyramide The title compound was obtained as an off-white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using 2,2-dimethyl-piperazine di-acetic acid salt instead of (R)-2-methyl-piperazine in step a).

MS m/e (%): 689 (M+H$^+$, 100)

EXAMPLE 398

2-(3,5-Bis-trifluoromethyl-phenyl)-N-[6-(4-methanesulfonyl-2,2-dimethyl-piperazin-1-yl)-4-o-tolyl-pyridin-3-yl]-N-methyl-isobutyramide The title compound was obtained as an off-white solid in comparable yields after flash chromatography according to the procedures described above for the preparation of (R)-2-(3,5-bis-trifluoromethyl-phenyl)-N-[4-(4-fluoro-2-methyl-phenyl)-6-(4-methanesulfonyl-2-methyl-piperazin-1-yl)-pyridin-3-yl]-N-methyl-isobutyramide using 2,2-dimethyl-piperazine di-acetic acid salt instead of (R)-2-methyl-piperazine in step a) and 2-(3,5-bis-trifluoromethyl-phenyl)-N-(6-chloro-4-o-tolyl-pyridin-3-yl)-N-methyl-isobutyramide (Intermediate 4G) instead of 2-(3,5-bistrifluoromethyl-phenyl)-N-[6-chloro-4-(4-fluoro-2-methyl-phenyl)-pyridin-3-yl]-N-methyl-isobutyramide in step b).
MS m/e (%): 671 (M+H$^+$, 100)

EXAMPLE 399

(S)-2-(3,5-Dimethoxy-phenyl)-N-[6-(2-hydroxymethyl-pyrrolidin-1-yl)-4-o-tolyl-pyridin-3-yl]-N-methyl-isobutyramide a) N-(6-Chloro-4-o-tolyl-pyridin-3-yl)-2-(3,5-dimethoxy-phenyl)-N-methyl-isobutyramide The title compound was obtained in an analogous manner to that described in example 1a) from (6-chloro-4-o-tolyl-pyridin-3-yl)-methyl-amine and 2-(3,5-dimethoxy-phenyl)-2-methyl-propionyl chloride as a white solid.
MS m/e (%): 439 (M+H$^+$, 100).

b) (S)-2-(3,5-Dimethoxy-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from N-(6-chloro-4-o-tolyl-pyridin-3-yl)-2-(3,5-dimethoxy-phenyl)-N-methyl-isobutyramide and L-prolinol as a light yellow foam.
MS m/e (%): 504 (M+H$^+$, 100).

EXAMPLE 400

(2S,4R)-2-(3,5-Dimethoxy-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from N-(6-chloro-4-o-tolyl-pyridin-3-yl)-2-(3,5-dimethoxy-phenyl)-N-methyl-isobutyramide and (2S,4R)-4-hydroxy-2-hydroxymethyl-pyrrolidine as a light yellow foam.
MS m/e (%): 520 (M+H$^+$, 100).

EXAMPLE 401

2-(3,5-Dimethoxy-phenyl)-N-[4-(4-fluoro-2-methyl-phenyl)-6-(2-hydroxy-ethylamino)-pyridin-3-yl]-N-methyl-isobutyramide a) N-[6-Chloro-4-(4-fluoro-2-methyl-phenyl)-pyridin-3-yl]-2-(3,5-dimethoxy-phenyl)-N-methyl-isobutyramide The title compound was obtained in an analogous manner to that described in example 1a) from [6-chloro-4-(4-fluoro-2-methyl-phenyl)-pyridin-3-yl]-methyl-amine and 2-(3,5-dimethoxy-phenyl)-2-methyl-propionyl chloride as a white solid.
MS m/e (%): 457 (M+H$^+$, 100).

b) 2-(3,5-Dimethoxy-phenyl)-N-[4-(4-fluoro-2-methyl-phenyl)-6-(2-hydroxy-ethylamino)-pyridin-3-yl]-N-methyl-isobutyramide The title compound was obtained in an analogous manner to that described in example 1b) from N-[6-chloro-4-(4-fluoro-2-methyl-phenyl)-pyridin-3-yl]-2-(3,5-dimethoxy-phenyl)-N-methyl-isobutyramide and ethanolamine as an off-white foam.
MS m/e (%): 482 (M+H$^+$, 100).

EXAMPLE 402

(S)-2-(3,5-Dimethoxy-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from N-[6-chloro-4-(4-fluoro-2-methyl-phenyl)-pyridin-3-yl]-2-(3,5-dimethoxy-phenyl)-N-methyl-isobutyramide and L-prolinol as a white foam.
MS m/e (%): 522 (M+H$^+$, 100).

EXAMPLE 403

(2S,4R)-2-(3,5-Dimethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from N-[6-chloro-4-(4-fluoro-2-methyl-phenyl)-pyridin-3-yl]-2-(3,5-dimethoxy-phenyl)-N-methyl-isobutyramide and (2S,4R)-4-hydroxy-2-hydroxymethyl-pyrrolidine as a white foam.
MS m/e (%): 538 (M+H$^+$, 100).

EXAMPLE 404

(2S,4R)-N-[4-(2-Chloro-phenyl)-6-(4-hydroxy-2-hydroxymethyl-pyrrolidin-1-yl)-pyridin-3-yl]-2-(3,5-dimethoxy-phenyl)-N-methyl-isobutyramide a) N-[6-Chloro-4-(2-chloro-phenyl)-pyridin-3-yl]-2-(3,5-dimethoxy-phenyl)-N-methyl-isobutyramide The title compound was obtained in an analogous manner to that described in example 1a) from [6-chloro-4-(2-chloro-phenyl)-pyridin-3-yl]-methyl-amine and 2-(3,5-dimethoxy-phenyl)-2-methyl-propionyl chloride as a light yellow solid.
MS m/e (%): 459 (M+H$^+$, 100).

b) (2S,4R)-N-[4-(2-Chloro-phenyl)-6-(4-hydroxy-2-hydroxymethyl-pyrrolidin-1-yl)-pyridin-3-yl]-2-(3,5-dimethoxy-phenyl)-N-methyl-isobutyramide The title compound was obtained in an analogous manner to that described in example 3) from N-[6-chloro-4-(2-chloro-phenyl)-pyridin-3-yl]-2-(3,5-dimethoxy-phenyl)-N-methyl-isobutyramide and (2S,4R)-4-hydroxy-2-hydroxymethyl-pyrrolidine as a light yellow foam.
MS m/e (%): 540 (M+H$^+$, 100).

EXAMPLE 405

2-(3,5-Bis-difluoromethoxy-phenyl)-N-[6-(2-hydroxy-ethylamino)-4-o-tolyl-pyridin-3-yl]-N-methyl-isobutyramide a) N-(6-Chloro-4-o-tolyl-pyridin-3-yl)-2-(3,5-dihydroxy-phenyl)-N-methyl-isobutyramide To a solution of 2.8 g (6.4 mmol) N-(6-chloro-4-o-tolyl-pyridin-3-yl)-2-(3,5-dimethoxy-phenyl)-N-methyl-isobutyramide in 70 ml CH$_2$Cl$_2$ 19 ml (19 mmol) BBr$_3$ (1 M in CH$_2$Cl$_2$) were added at 0° C. The reaction mixture was allowed to reach ambient temperature and stirred for 15 h After addition of 50 ml water the mixture was extracted with three portions of dichloromethane. The combined organic extracts were dried (Na$_2$SO$_4$), filtered and evaporated. The residue was purified by flash-chromatography (SiO$_2$, CH$_2$Cl$_2$/methanol) to give 2.5 g (95%) of the title compound as a white foam.

MS m/e (%): 409 (M+H$^+$, 87).

b) 2-(3,5-Bis-difluoromethoxy-phenyl)-N-(6-chloro-4-o-tolyl-pyridin-3-yl)-N-methyl-isobutyramide To a solution of 2.5 g (6.1 mmol) N-(6-chloro-4-o-tolyl-pyridin-3-yl)-2-(3,5-dihydroxy-phenyl)-N-methyl-isobutyramide in 60 ml DMF 1.7 g (12 mmol) K$_2$CO$_3$ and 1.5 ml (12 mmol) ethyl chlordifluoroacetate were added and the resulting suspension heated at 65° C. for 15 h. After cooling to ambient temperature, the reaction mixture was poured into 250 ml water and extracted with three portions of CH$_2$Cl$_2$. The combined organic extracts were dried (Na$_2$SO$_4$), filtered and evaporated. The residue was purified by flash-chromatography (SiO$_2$, CH$_2$Cl$_2$/ethyl acetate) to give 0.71 g (23%) of the title compound as a colorless viscous oil.

MS m/e (%): 511 (M+H$^+$, 100).

c) 2-(3,5-Bis-difluoromethoxy-phenyl)-N-[6-(2-hydroxy-ethylamino)-4-o-tolyl-pyridin-3-yl]-N-methyl-isobutyramide The title compound was obtained in an analogous manner to that described in example 1b) from 2-(3,5-bis-difluoromethoxy-phenyl)-N-(6-chloro-4-o-tolyl-pyridin-3-yl)-N-methyl-isobutyramide and ethanolamine as an off-white foam.

MS m/e (%): 536 (M+H$^+$, 100).

EXAMPLE 406

(2S,4R)-2-(3,5-Bis-difluoromethoxy-phenyl)-N-[6-(4-hydroxy-2-hydroxymethyl-pyrrolidin-1-yl)-4-o-tolyl-pyridin-3-yl]-N-methyl-isobutyramide The title compound was obtained in an analogous manner to that described in example 3) from 2-(3,5-bis-difluoromethoxy-phenyl)-N-(6-chloro-4-o-tolyl-pyridin-3-yl)-N-methyl-isobutyramide and (2S,4R)-4-hydroxy-2-hydroxymethyl-pyrrolidine as a light yellow foam.

MS m/e (%): 592 (M+H$^+$, 100).

EXAMPLE 407

(S)-2-(3,5-Bis-difluoromethoxy-phenyl)-N-[6-(2-hydroxymethyl-pyrrolidin-1-yl)-4-o-tolyl-pyridin-3-yl]-N-methyl-isobutyramide The title compound was obtained in an analogous manner to that described in example 2) from 2-(3,5-bis-difluoromethoxy-phenyl)-N-(6-chloro-4-o-tolyl-pyridin-3-yl)-N-methyl-isobutyramide and L-prolinol as a white foam.

MS m/e (%): 576 (M+H$^+$, 100).

EXAMPLE 408

2-(3,5-Bis-difluoromethoxy-phenyl)-N-[4-(4-fluoro-2-methyl-phenyl)-6-(2-hydroxy-ethylamino)-pyridin-3-yl]-N-methyl-isobutyramide a) 2-(3,5-Bis-difluoromethoxy-phenyl)-N-[6-chloro-4-(4-fluoro-2-methyl-phenyl)-pyridin-3-yl]-N-methyl-isobutyramide The title compound was obtained in an analogous manner to that described in example 406a), b) from N-[6-chloro-4-(4-fluoro-2-methyl-phenyl)-pyridin-3-yl]-2-(3,5-dimethoxy-phenyl)-N-methyl-isobutyramide as a colorless oil.

MS m/e (%): 529 (M+H$^+$, 100).

b) 2-(3,5-Bis-difluoromethoxy-phenyl)-N-[4-(4-fluoro-2-methyl-phenyl)-6-(2-hydroxy-ethylamino)-pyridin-3-yl]-N-methyl-isobutyramide The title compound was obtained in an analogous manner to that described in example 1b) from 2-(3,5-bis-difluoromethoxy-phenyl)-N-[6-chloro-4-(4-fluoro-2-methyl-phenyl)-pyridin-3-yl]-N-methyl-isobutyramide and ethanolamine as a white foam.

MS m/e (%): 554 (M+H$^+$, 100).

EXAMPLE 409

(S)-2-(3,5-Bis-difluoromethoxy-phenyl)-N-[4-(4-fluoro-2-methyl-phenyl)-6-(2-hydroxymethyl-pyrrolidin-1-yl)-pyridin-3-yl]-N-methyl-isobutyramide The title compound was obtained in an analogous manner to that described in example 2) from 2-(3,5-bis-difluoromethoxy-phenyl)-N-[6-chloro-4-(4-fluoro-2-methyl-phenyl)-pyridin-3-yl]-N-methyl-isobutyramide and L-prolinol as a light brown foam.

MS m/e (%): 594 (M+H$^+$, 100).

EXAMPLE 410

(2S,4R)-2-(3,5-Bis-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide a) 2-(3,5-Bis-difluoromethoxy-phenyl)-N-[6-chloro-4-(2-chloro-phenyl)-pyridin-3-yl]-N-methyl-isobutyramide The title compound was obtained in an analogous manner to that described in example 406a), b) from N-[6-chloro-4-(2-chloro-phenyl)-pyridin-3-yl]-2-(3,5-dimethoxy-phenyl)-N-methyl-isobutyramide as a colorless oil.

MS m/e (%): 531 (M+H$^+$, 100).

b) (2S,4R)-2-(3,5-Bis-difluoromethoxy-phenyl)-N-[4-(2-chloro-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from 2-(3,5-bis-difluoromethoxy-phenyl)-N-[6-chloro-4-(2-chloro-phenyl)-pyridin-3-yl]-N-methyl-isobutyramide and (2S,4R)-4-hydroxy-2-hydroxymethyl-pyrrolidine as a light yellow foam.
MS m/e (%): 612 (M+H$^+$, 100).

EXAMPLE 411

(S)-2-(3,5-Bis-difluoromethoxy-phenyl)-N-[4-(2-chloro-phenyl)-6-(2-hydroxymethyl-pyrrolidin-1-yl)-pyridin-3-yl]-N-methyl-isobutyramide The title compound was obtained in an analogous manner to that described in example 2) from 2-(3,5-bis-difluoromethoxy-phenyl)-N-[6-chloro-4-(2-chloro-phenyl)-pyridin-3-yl]-N-methyl-isobutyramide and L-prolinol as a white foam.
MS m/e (%): 596 (M+H$^+$, 100).

EXAMPLE 412

2-(3,5-Bis-difluoromethoxy-phenyl)-N-[4-(2-chloro-phenyl)-6-(2-hydroxy-ethylamino)-pyridin-3-yl]-N-methyl-isobutyramide The title compound was obtained in an analogous manner to that described in example 1b) from 2-(3,5-bis-difluoromethoxy-phenyl)-N-[6-chloro-4-(2-chloro-phenyl)-pyridin-3-yl]-N-methyl-isobutyramide and ethanolamine as a white foam.
MS m/e (%): 556 (M+H$^+$, 100).

EXAMPLE 413

(2S,4R)-2-(3,5-Bis-difluoromethoxy-phenyl)-N-[4-(4-fluoro-2-methyl-phenyl)-6-(4-hydroxy-2-hydroxymethyl-pyrrolidin-1-yl)-pyridin-3-yl]-N-methyl-isobutyramide The title compound was obtained in an analogous manner to that described in example 3) from 2-(3,5-bis-difluoromethoxy-phenyl)-N-[6-chloro-4-(4-fluoro-2-methyl-phenyl)-pyridin-3-yl]-N-methyl-isobutyramide and (2S,4R)-4-hydroxy-2-hydroxymethyl-pyrrolidine as a light yellow foam.
MS m/e (%): 610 (M+H$^+$, 100).

EXAMPLE 414

(2S,4R)-N-[6-(4-Hydroxy-2-hydroxymethyl-pyrrolidin-1-yl)-4-o-tolyl-pyridin-3-yl]-N-methyl-2-(3-trifluoromethoxy-phenyl)-isobutyramide a) N-(6-Chloro-4-o-tolyl-pyridin-3-yl)-N-methyl-2-(3-trifluoromethoxy-phenyl)-isobutyramide The title compound was obtained in an analogous manner to that described in example 1a) from (6-chloro-4-o-tolyl-pyridin-3-yl)-methyl-amine and 2-methyl-2-(3-trifluoromethoxy-phenyl)-propionyl chloride (Intermediate 5I) as a light yellow oil.
MS m/e (%): 462 (M$^+$, 8).

b) (2S,4R)-N-[6-(4-Hydroxy-2-hydroxymethyl-pyrrolidin-1-yl)-4-o-tolyl-pyridin-3-yl]-N-methyl-2-(3-trifluoromethoxy-phenyl)-isobutyramide The title compound was obtained in an analogous manner to that described in example 3) from N-(6-chloro-4-o-tolyl-pyridin-3-yl)-N-methyl-2-(3-trifluoromethoxy-phenyl)-isobutyramide and (2S,4R)-4-hydroxy-2-hydroxymethyl-pyrrolidine as a white foam.
MS m/e (%): 544 (M+H$^+$, 100).

EXAMPLE 415

(2S,4R)-N-[4-(4-Fluoro-2-methyl-phenyl)-6-(4-hydroxy-2-hydroxymethyl-pyrrolidin-1-yl)-pyridin-3-yl]-N-methyl-2-(3-trifluoromethoxy-phenyl)-isobutyramide a) N-[6-Chloro-4-(4-fluoro-2-methyl-phenyl)-pyridin-3-yl]-N-methyl-2-(3-trifluoromethoxy-phenyl)-isobutyramide The title compound was obtained in an analogous manner to that described in example 1a) from [6-chloro-4-(4-fluoro-2-methyl-phenyl)-pyridin-3-yl]-methyl-amine and 2-methyl-2-(3-trifluoromethoxy-phenyl)-propionyl chloride (Intermediate 5I) as white solid.
MS m/e (%): 481 (M+H$^+$, 100).

b) (2S,4R)-N-[4-(4-Fluoro-2-methyl-phenyl)-6-(4-hydroxy-2-hydroxymethyl-pyrrolidin-1-yl)-pyridin-3-yl]-N-methyl-2-(3-trifluoromethoxy-phenyl)-isobutyramide The title compound was obtained in an analogous manner to that described in example 3) from N-[6-chloro-4-(4-fluoro-2-methyl-phenyl)-pyridin-3-yl]-N-methyl-2-(3-trifluoromethoxy-phenyl)-isobutyramide and (2S,4R)-4-hydroxy-2-hydroxymethyl-pyrrolidine as a white foam.
MS m/e (%): 562 (M+H$^+$, 100).

EXAMPLE 416

2-(3,5-Bis-difluoromethoxy-phenyl)-N-[4-(2-chloro-phenyl)-6-piperazin-1-yl-pyridin-3-yl]-N-methyl-isobutyramide The title compound was obtained in an analogous manner to that described in example 2) from 2-(3,5-bis-difluoromethoxy-phenyl)-N-[6-chloro-4-(2-chloro-phenyl)-pyridin-3-yl]-N-methyl-isobutyramide and piperazine instead of L-prolinol as a light yellow foam.
MS m/e (%): 581 (M+H$^+$, 100).

EXAMPLE 417

2-(3,5-Bis-difluoromethoxy-phenyl)-N-[4-(4-fluoro-2-methyl-phenyl)-6-piperazin-1-yl-pyridin-3-yl]-N-methyl-isobutyramide The title compound was obtained in an analogous manner to that described in example 2) from 2-(3,5-bis-difluoromethoxy-phenyl)-N-[6-chloro-4-(4-fluoro-2-methyl-phenyl)-pyridin-3-yl]-N-methyl-isobutyramide and piperazine instead of L-prolinol as an off-white foam.
MS m/e (%): 579 (M+H$^+$, 100).

EXAMPLE 418

2-(3,5-Bis-difluoromethoxy-phenyl)-N-[4-(2-chloro-phenyl)-6-(4-methanesulfonyl-piperazin-1-yl)-pyridin-3-yl]-N-methyl-isobutyramide The title compound was obtained as a white foam in 84% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using 2-(3,5-bis-difluoromethoxy-phenyl)-N-[4-(2-chloro-phenyl)-6-piperazin-1-yl-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 659 (M+H$^+$, 100)

EXAMPLE 419

2-(3,5-Bis-difluoromethoxy-phenyl)-N-[4-(4-fluoro-2-methyl-phenyl)-6-(4-methanesulfonyl-piperazin-1-yl)-pyridin-3-yl]-N-methyl-isobutyramide The title compound was obtained as a white foam in 88% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using 2-(3,5-bis-difluoromethoxy-phenyl)-N-[4-(4-fluoro-2-methyl-phenyl)-6-piperazin-1-yl-pyridin-3-yl]-N-methyl-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 657 (M+H$^+$, 100)

EXAMPLE 420

2-(3,5-Bis-difluoromethoxy-phenyl)-N-methyl-N-(6-piperazin-1-yl-4-o-tolyl-pyridin-3-yl)-isobutyramide The title compound was obtained in an analogous manner to that described in example 2) from N-(6-chloro-4-o-tolyl-pyridin-3-yl)-N-methyl-2-(3-trifluoromethoxy-phenyl)-isobutyramide and piperazine instead of L-prolinol as a light yellow foam.

MS m/e (%): 561 (M+H$^+$, 100).

EXAMPLE 421

2-(3,5-Bis-difluoromethoxy-phenyl)-N-[6-(4-methanesulfonyl-piperazin-1-yl)-4-o-tolyl-pyridin-3-yl]-N-methyl-isobutyramide The title compound was obtained as a white foam in 61% yield after flash chromatography according to the procedure described above for the preparation of 2-(3,5-bis-trifluoromethyl-phenyl)-N-[6-(4-methanesulfonyl-piperazin-1-yl)-4-o-tolyl-pyridin-3-yl]-N-methyl-isobutyramide (Example 362b)) using 2-(3,5-bis-difluoromethoxy-phenyl)-N-methyl-N-(6-piperazin-1-yl-4-o-tolyl-pyridin-3-yl)-isobutyramide instead of 2-(3,5-bis-trifluoromethyl-phenyl)-N-methyl-N-(6-piperazin-1-yl-4-o-tolyl-pyridin-3-yl)-isobutyramide.

MS m/e (%): 639 (M+H$^+$, 100)

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound selected from the group consisting of
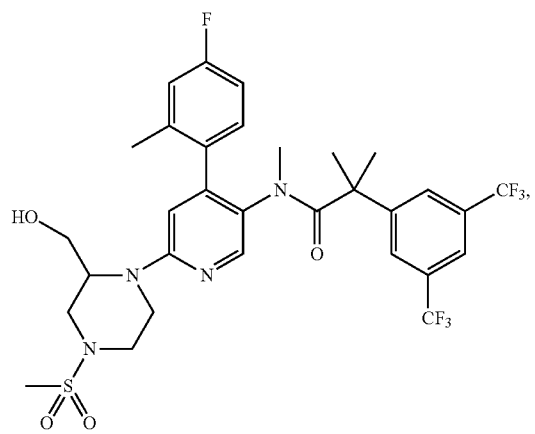
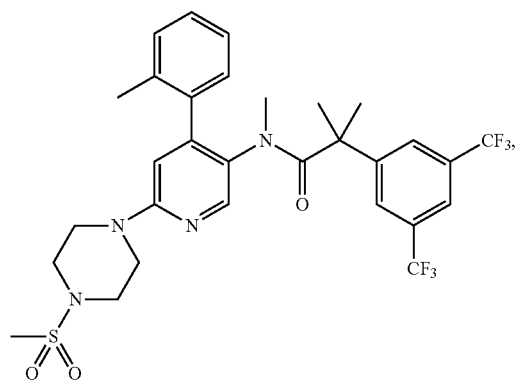
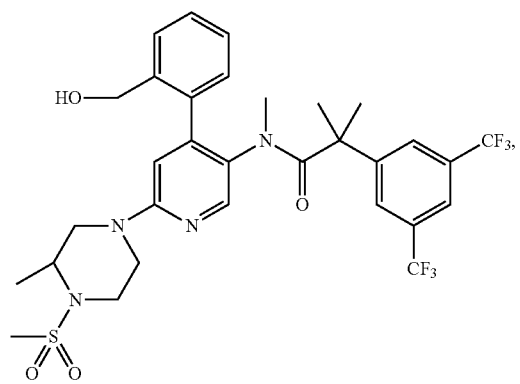
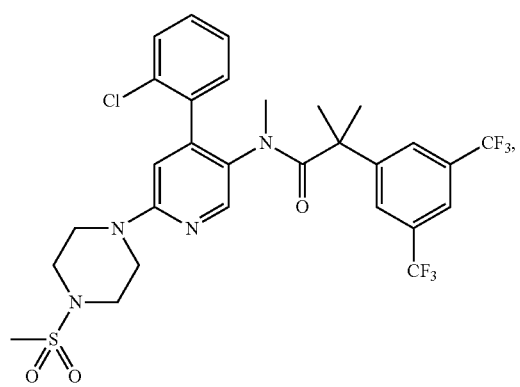
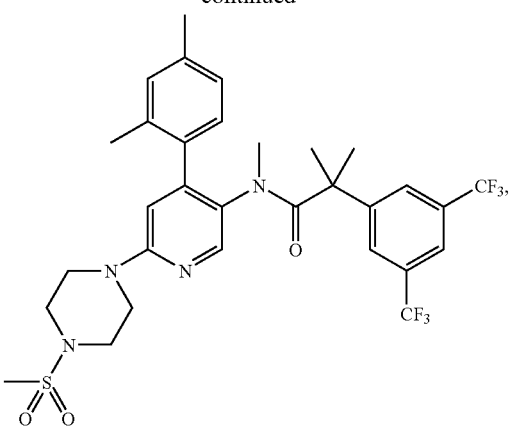
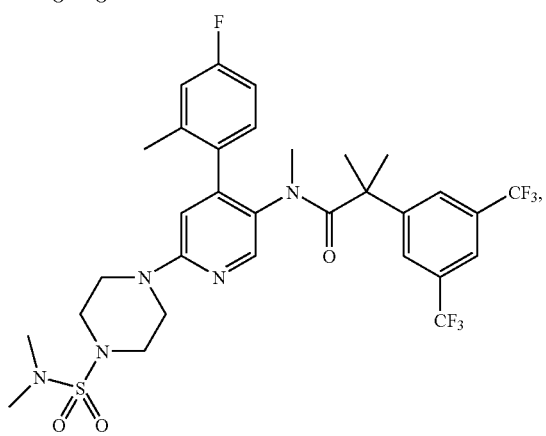
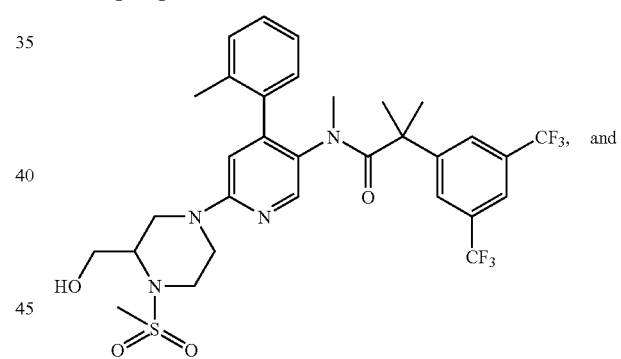 and
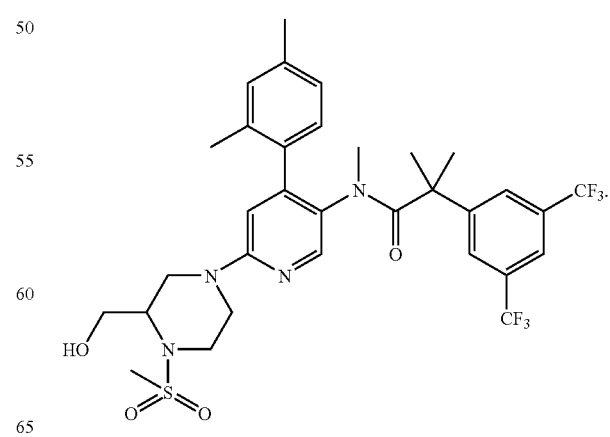

2. A compound of claim 1, which is
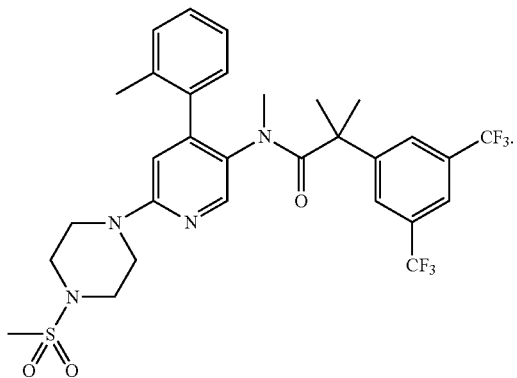
3. A compound selected from the group consisting of
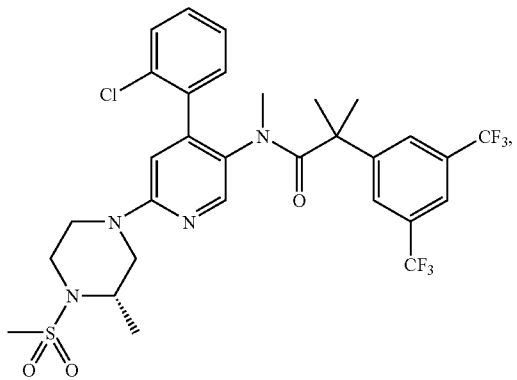
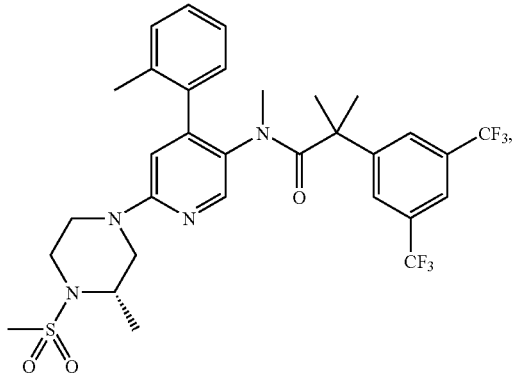
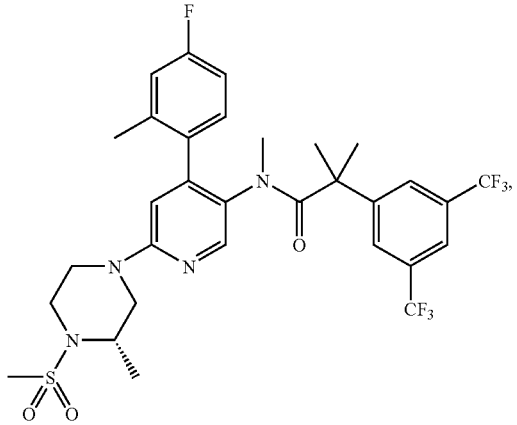
-continued
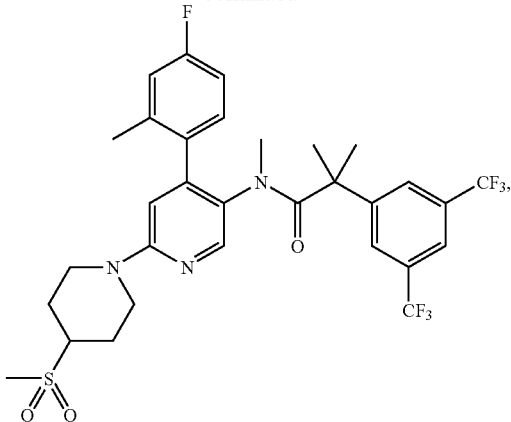
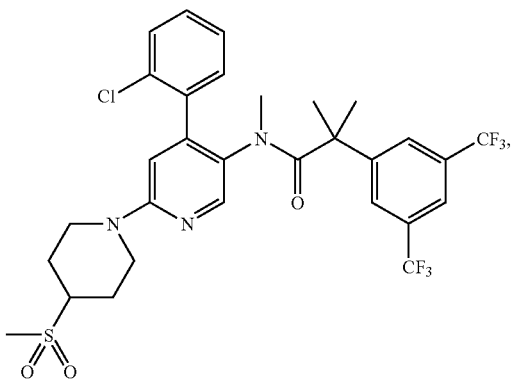
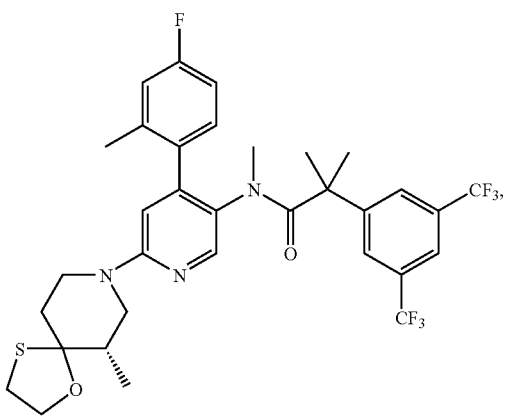
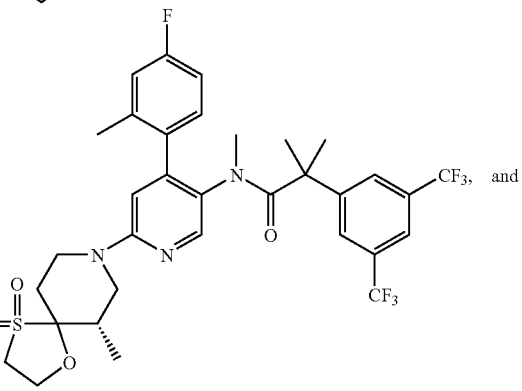

341
-continued
342
-continued
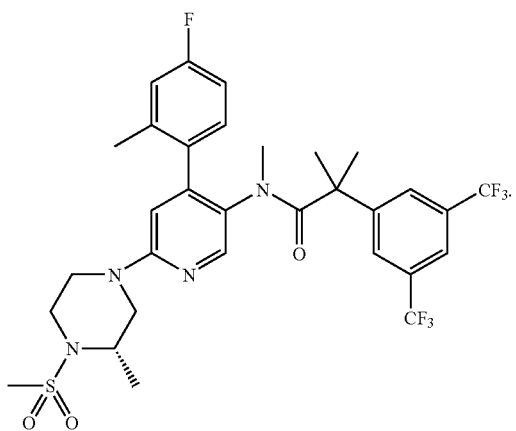
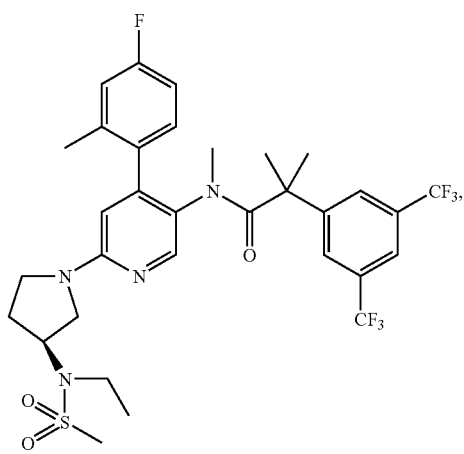
4. A compound selected from the group consisting of
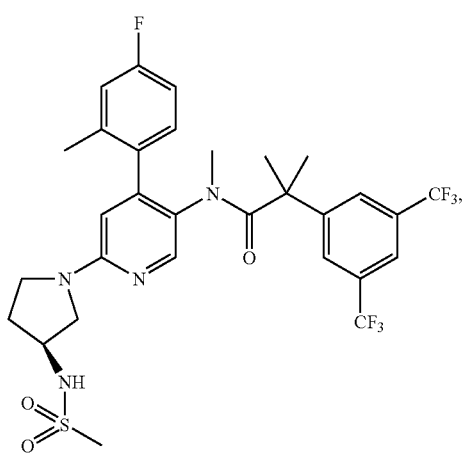
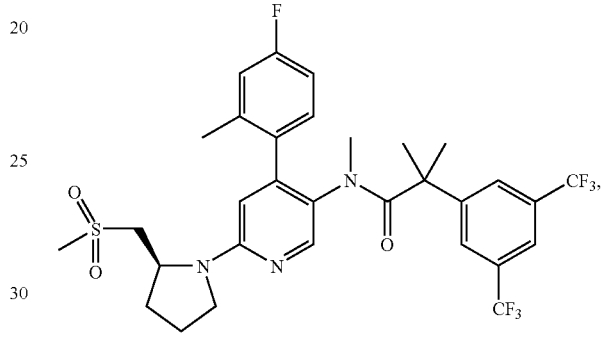
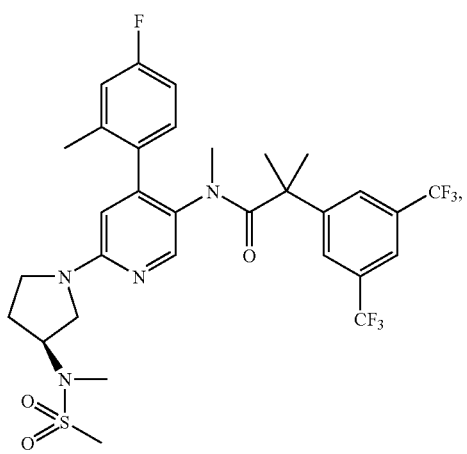
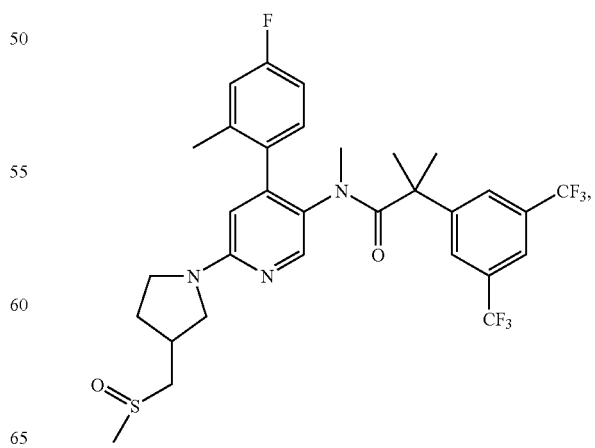

5. A compound selected from the group consisting of
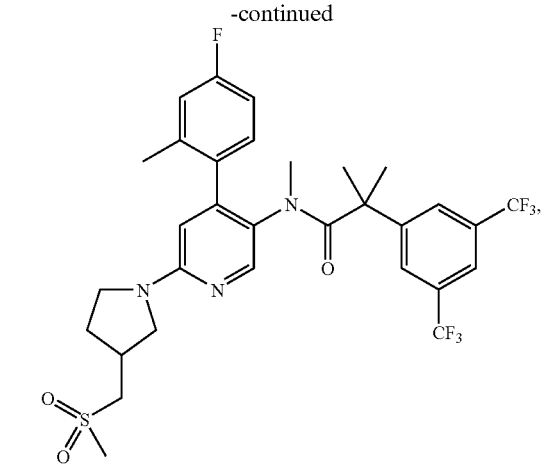

345
-continued
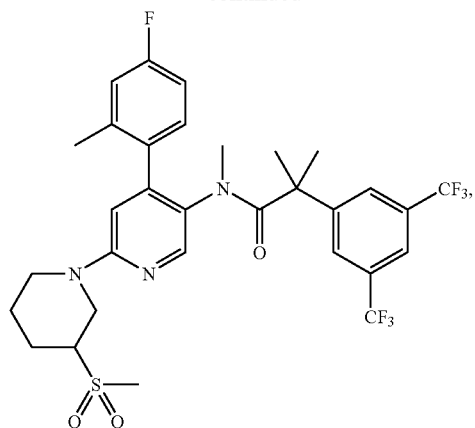
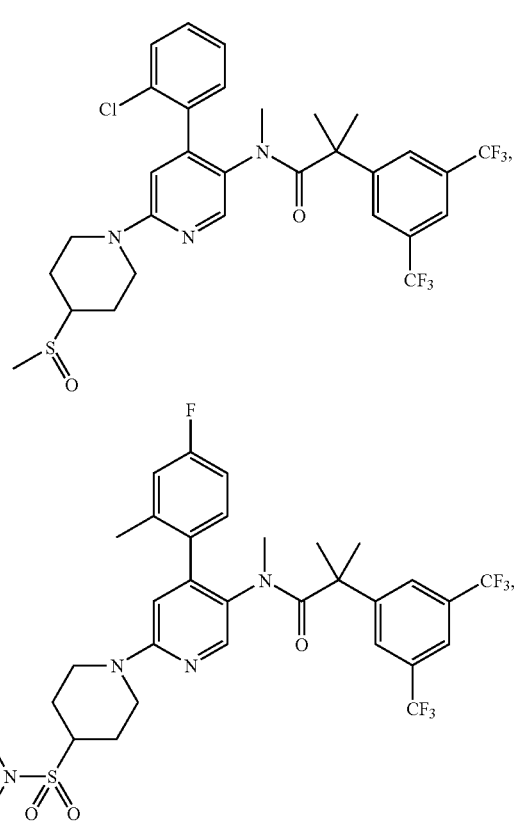
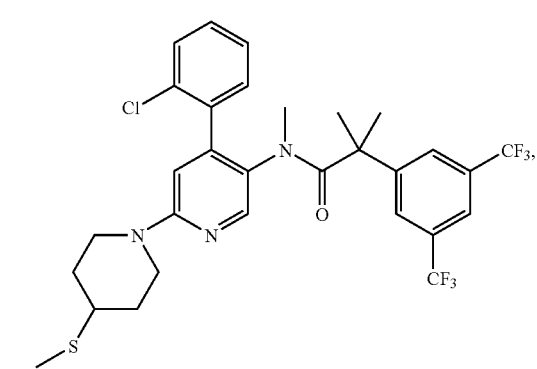
346
-continued
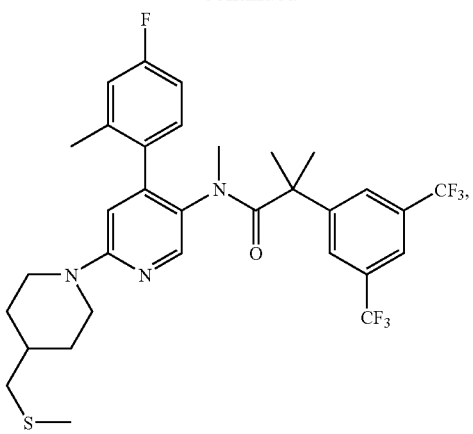
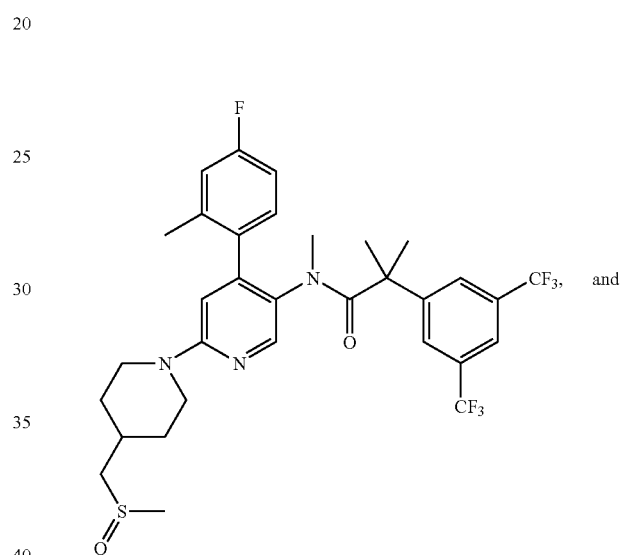
and
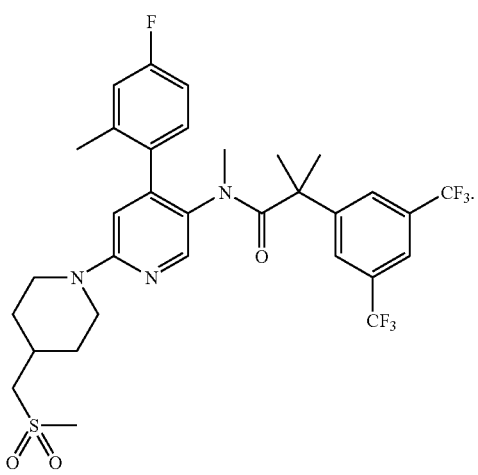

6. A compound selected from the group consisting of
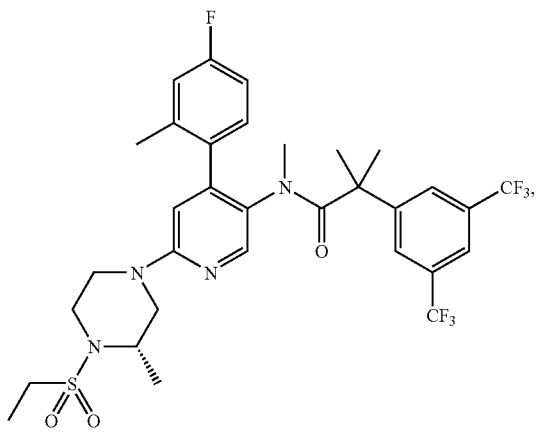
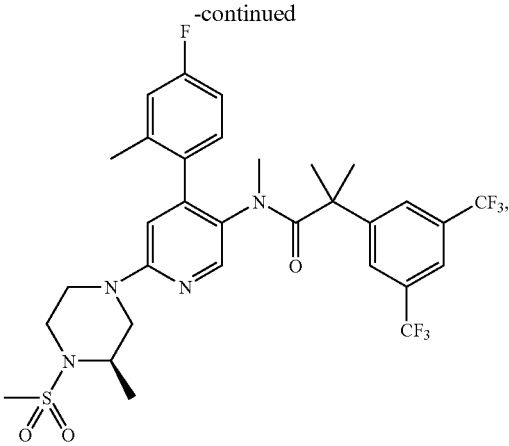

-continued
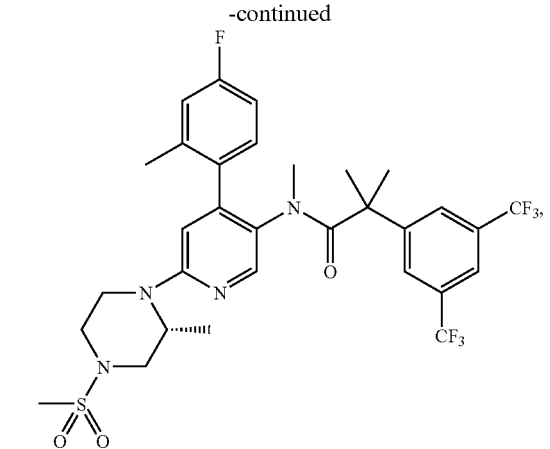
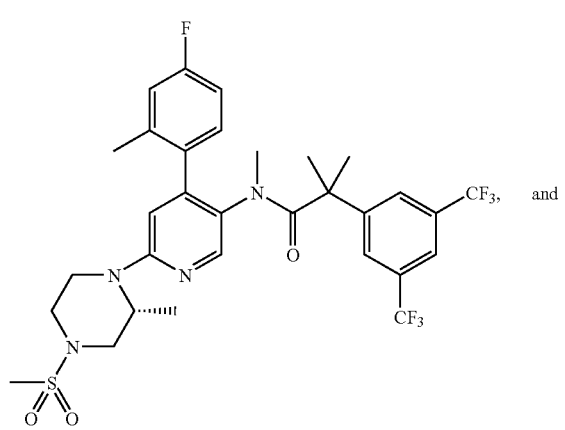
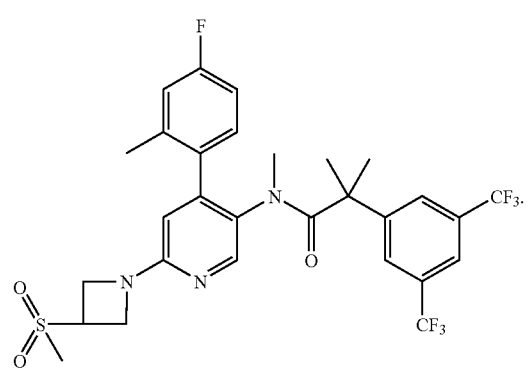
7. A compound selected from the group consisting of
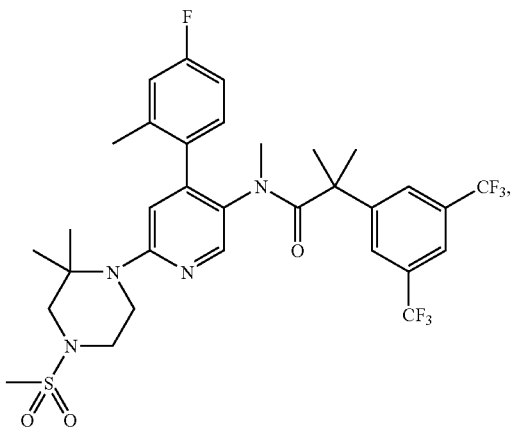
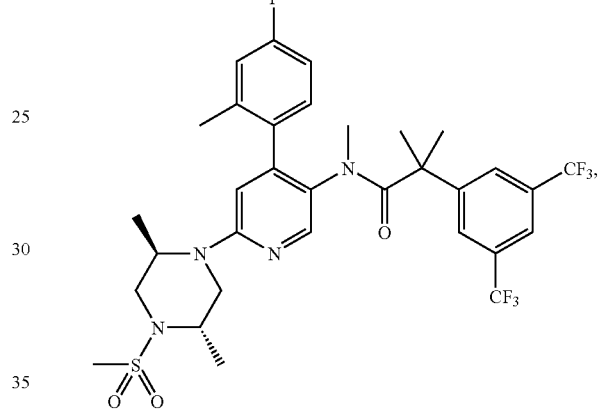
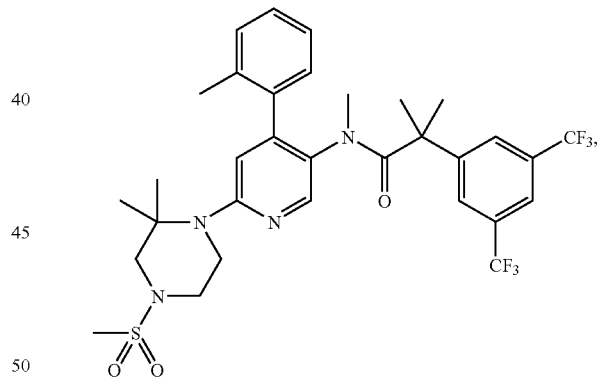
and
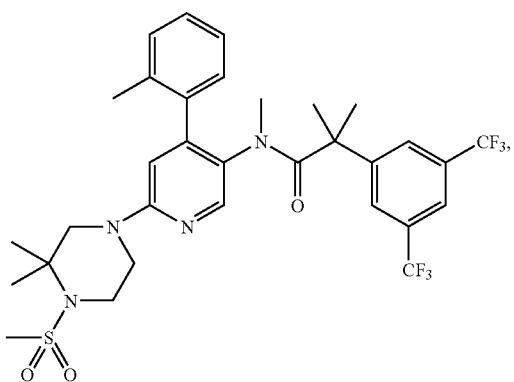

351
-continued
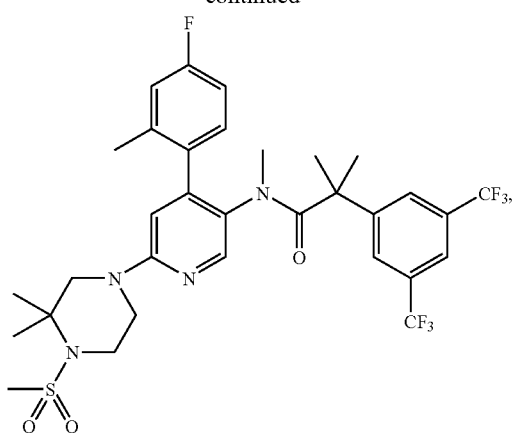
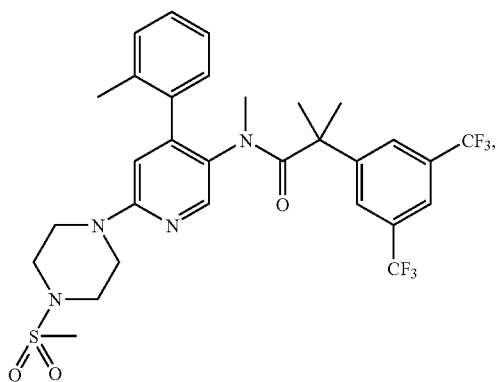
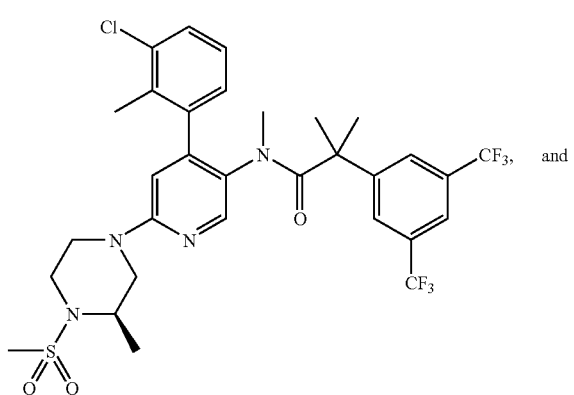
352
-continued
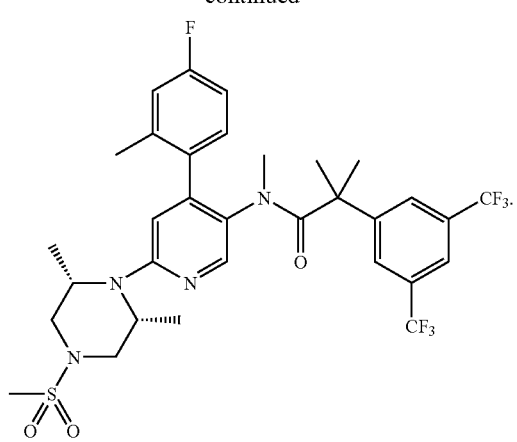
8. A compound selected from the group consisting of
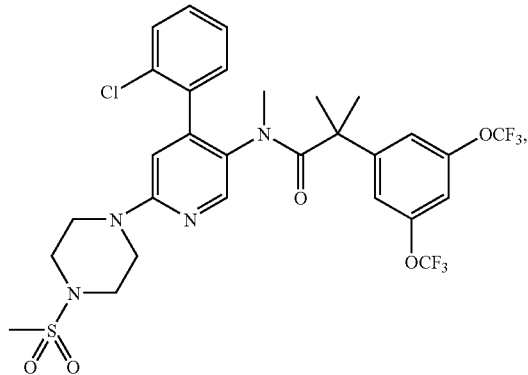
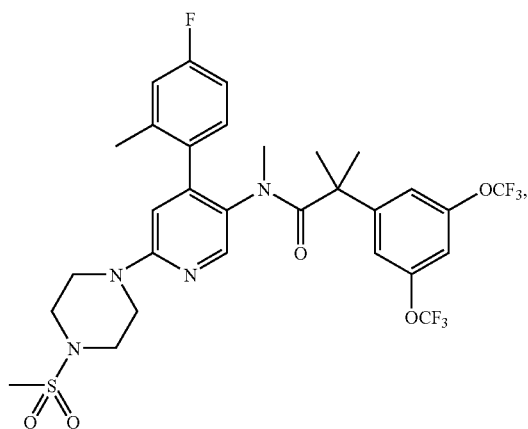
and 353
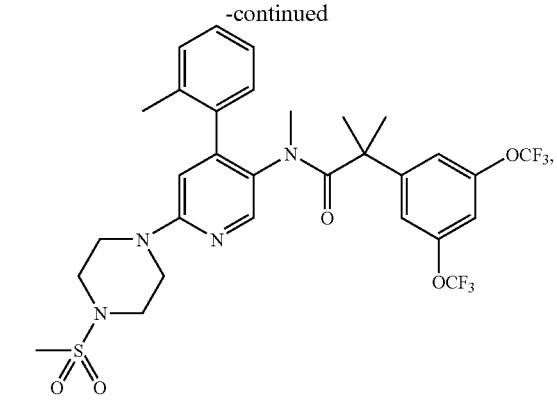
354
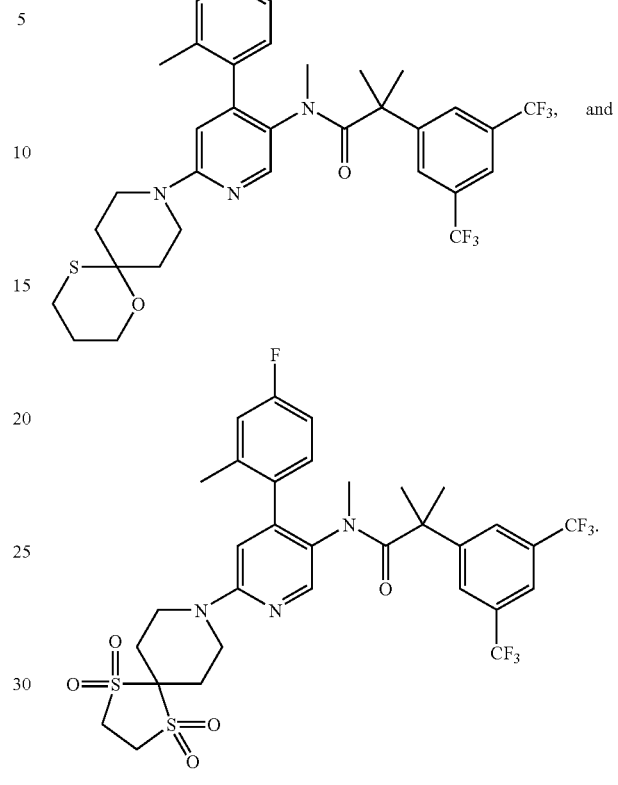
* * * * *